US009617600B2

(12) United States Patent
Dornan et al.

(10) Patent No.: US 9,617,600 B2
(45) Date of Patent: Apr. 11, 2017

(54) METHODS FOR ASSESSING RESPONSIVENESS OF B-CELL LYMPHOMA TO TREATMENT WITH ANTI-CD40 ANTIBODIES

(75) Inventors: David Dornan, San Mateo, CA (US); Bart Burington, Oakland, CA (US)

(73) Assignee: Genentech, Inc., South San Francisco, CA (US)

(*) Notice: Subject to any disclaimer, the term of this patent is extended or adjusted under 35 U.S.C. 154(b) by 173 days.

(21) Appl. No.: 13/264,973

(22) PCT Filed: Apr. 17, 2010

(86) PCT No.: PCT/US2010/031528
§ 371 (c)(1),
(2), (4) Date: Dec. 15, 2011

(87) PCT Pub. No.: WO2010/121231
PCT Pub. Date: Oct. 21, 2010

(65) Prior Publication Data
US 2012/0123695 A1 May 17, 2012

Related U.S. Application Data

(60) Provisional application No. 61/170,615, filed on Apr. 18, 2009.

(51) Int. Cl.
C12Q 1/68 (2006.01)
A61K 39/395 (2006.01)
A61K 39/00 (2006.01)

(52) U.S. Cl.
CPC ...... *C12Q 1/6886* (2013.01); *A61K 2039/505* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,016,043 A | 4/1977 | Schuurs et al. | |
| 4,018,653 A | 4/1977 | Mennen | |
| 4,275,149 A | 6/1981 | Litman et al. | |
| 4,318,980 A | 3/1982 | Boguslaski et al. | |
| 4,424,279 A | 1/1984 | Bohn et al. | |
| 4,737,456 A | 4/1988 | Weng et al. | |
| 4,816,567 A | 3/1989 | Cabilly et al. | |
| 5,182,368 A | 1/1993 | Ledbetter et al. | |
| 5,445,934 A | 8/1995 | Fodor et al. | |
| 5,500,362 A | 3/1996 | Robinson et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,591,669 A | 1/1997 | Krimpenfort et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,674,492 A | 10/1997 | Armitage et al. | |
| 5,700,637 A | 12/1997 | Southern | |
| 5,807,522 A | 9/1998 | Brown et al. | |
| 5,821,337 A | 10/1998 | Carter et al. | |
| 6,248,535 B1 * | 6/2001 | Danenberg et al. | 435/6.12 |
| 6,737,056 B1 | 5/2004 | Presta | |
| 6,838,261 B1 | 1/2005 | Siegall et al. | |
| 6,843,989 B1 | 1/2005 | Siegall et al. | |
| 6,946,129 B1 | 9/2005 | Siegall et al. | |
| 7,288,251 B2 | 10/2007 | Bedian et al. | |
| 2002/0197256 A1 | 12/2002 | Grewal | |
| 2005/0090434 A1 | 4/2005 | Morris et al. | |
| 2005/0164231 A1 | 7/2005 | Staudt et al. | |
| 2005/0260646 A1 | 11/2005 | Baker et al. | |
| 2007/0110754 A1 | 5/2007 | Long et al. | |
| 2011/0104671 A1 | 5/2011 | Dornan et al. | |

FOREIGN PATENT DOCUMENTS

| | | |
|---|---|---|
| CN | 1582165 A | 2/2005 |
| JP | 2006-342173 A | 12/2006 |
| JP | 2008-539794 A | 11/2008 |
| JP | 2008-544223 A | 12/2008 |
| WO | WO-91/10741 A1 | 7/1991 |
| WO | WO-96/18413 A1 | 6/1996 |
| WO | WO-96/33735 A1 | 10/1996 |
| WO | WO-96/34096 A1 | 10/1996 |
| WO | WO-97/17852 A1 | 5/1997 |
| WO | WO-97/31025 A1 | 8/1997 |
| WO | WO-98/24893 A2 | 6/1998 |
| WO | WO-98/24893 A3 | 6/1998 |
| WO | WO-00/75348 A1 | 12/2000 |
| WO | WO-00/75348 C1 | 12/2000 |
| WO | WO-01/75166 A2 | 10/2001 |
| WO | WO-01/75166 A3 | 10/2001 |

(Continued)

OTHER PUBLICATIONS

Nutt et al. Gene Expression-based Classification of Malignant Gliomas Correlates Better with Survival than Histological Classification Cancer Research vol. 63, pp. 1602-1607 (2003).*
Forero-Torres et al. A humanized antibody against CD40 (SGN-40) is well tolerated and active in non-Hodgkin's lymphoma (NHL: Results of a phase I study Journal of Clinical Oncology vol. 24, No. 18S Abstract 7534 (2006).*
Coleman, R. (Mar. 6, 2003). "Of Mouse and Man—What is the value of the Mouse in Predicting Gene Expression in Humans?" *Drug Discovery Today* 8:233-235.
Dermer, G.B. (Mar. 12, 1994). "Another Anniversary for the War on Cancer," *Bio/Technology* 12:320.
GeneCards. (2012). "USP-N-acteylglucosamine pyrophosphorylase 1 for BCL6," located at www:// genecards.org/cgi-bin/carddisp.pl?gene=UAPI&rf-/home/gencards/current/w . . . >, last visited on Oct. 3, 2012, 11 pages.
GeneCards. (2013). "B-Cell CLL/Lymphoma 6," located at www:// genecards.org/cgi-bin/carddisp.pl?gene=BCl6,>, last visited on Mar. 28, 2013, 11 pages.

(Continued)

*Primary Examiner* — John S Brusca
(74) *Attorney, Agent, or Firm* — Morrison & Foerster LLP

(57) ABSTRACT

The invention provides methods and kits useful for predicting or assessing responsiveness of a patient having B-cell lymphoma to treatment with anti-CD40 antibodies.

16 Claims, 30 Drawing Sheets

(56) References Cited

FOREIGN PATENT DOCUMENTS

| WO | WO-01/83755 A2 | 11/2001 |
|---|---|---|
| WO | WO-01/83755 A3 | 11/2001 |
| WO | WO-03/040170 A2 | 5/2003 |
| WO | WO-03/040170 A3 | 5/2003 |
| WO | WO-2004/071572 A2 | 8/2004 |
| WO | WO-2004/071572 A3 | 8/2004 |
| WO | WO-2005/044294 A2 | 5/2005 |
| WO | WO-2005/044294 A3 | 5/2005 |
| WO | WO-2006/125117 A2 | 11/2006 |
| WO | WO-2006/125117 A3 | 11/2006 |
| WO | WO-2006/125143 A2 | 11/2006 |
| WO | WO-2006/125143 A3 | 11/2006 |
| WO | WO-2006/128103 A2 | 11/2006 |
| WO | WO-2006/128103 A3 | 11/2006 |
| WO | WO-2006/133420 A2 | 12/2006 |
| WO | WO-2006/133420 A3 | 12/2006 |
| WO | WO-2007/032743 A2 | 3/2007 |
| WO | WO-2007/032743 A3 | 3/2007 |
| WO | WO-2007/066230 A2 | 6/2007 |
| WO | WO-2007/066230 A3 | 6/2007 |
| WO | WO-2007/075326 A2 | 7/2007 |
| WO | WO-2007/075326 A3 | 7/2007 |
| WO | WO-2007/075348 A1 | 7/2007 |
| WO | WO 2007/082379 * | 7/2007 |
| WO | WO-2008/079269 A2 | 7/2008 |
| WO | WO-2008/079269 A3 | 7/2008 |
| WO | WO-2009/062125 A1 | 5/2009 |

OTHER PUBLICATIONS

GeneAnnot. (2013). "GeneAnnot for BCL6," located at www://genecards.org/cgi-bin'carddisp.pi?gene=UAP1> last visited on Mar. 28, 2013, located at http://www.genecards.wizmann.ac.il/cgi-bin/geneannot/GA_Seach.pl?array=HG-U133&arrary=HG-U133_Plus_2&keywood_type-gene_symbol&keyword-bci6*target-integrated&_submit_Submit+Query,> last visited on Mar. 28, 2013.

Gökmen-Polar, Y. et al. (Feb. 15, 2001). "Elevated Protein Kinase C βII is an Early Promotive Event in Colon Carcinogenesis," *Cancer Research* 61:1375-1381.

Haynes, P.A. et al. (1998). "Proteome Analysis: Biological Assay or Data Archive?" *Electrophoresis* 19:1862-1871.

Liu, Z. et al. (2004). "Comparison of Differentially Expressed Genes in T Lymphocytes Between Human Autoimmune Disease and Murine Models of Autommune Disease," *Clinical Immunology* 112:225-230.

Saetre, P. et al. (2004). "From Wild Wolf to Domestic Dog: Gene Expression Changes in the Brain," *Molecular Brain Research* 126:198-206.

Singh, K. et al. (2004). "The Use of cDNA Microarrays to Investigate Changes to Gene Expression in the Involuting bovine Mammary Gland," *Proceedings of the New Zealand Society of Animal Production* 64:8-10.

Smiraglia, D.J. et al. (2001). "Excessive CpG Island Hypermethylation in Cnacer Cell Lines Versus Primary Human Malignancies," *Human Molecular Genetics* 10(13):1413-1419.

Advani, R. et al. (2009). "Evaluation of a Gene Signature to Predict Single Agent Dacetuzumab (SGN-40) Activity in Patients with DLBCL," Abstract No. 11063 *presented at 2009 ASCO Annual Meeting*, three pages, located at <http://www.asco.org/ASCOv2/Meetings/Abstracts?&vmview=abst_detail_view&confID=65&abstractIDS=32462>, last visited on Nov. 9, 2011, *J. Clin. Oncol.* 27:15s, three pages.

Anonoymous. (2012). "The R Project for Statistical Computing," located at <http://www.r-project.org/main.shtml>, last visited on Jun. 19, 2012, one page.

Anonoymous. (Nov. 7, 2003). "Affymetrix GenoChip Human Genome U133 Plus 2.0 Array," *Geo Expression*, two pages.

Ausubel, F.M. et al. eds. (1995). *Short Protocols in Molecular Biology, Current Protocols in Molecular Biology*, pp. iii-xxii. (Table of Contents Only.).

Ausubel, F.M. (1987). *Current Protocols in Molecular Biology*, New York, New York, five pages. (Table of Contents Only.).

Barbas, C.F. et al. (Apr. 26, 1994). "In Vitro Evolution of a Neutralizing Human Antibody to Human Immunodeficiency Virus Type 1 to Enhance Affinity and Broaden Strain Cross-Reactivity," *Proc. Nat. Acad. Sci USA* 91(9):3809-3813.

Basso, K. et al. (Dec. 15, 2004, e-pub. Aug. 26, 2004). "Tracking CD40 Signaling During Germinal Center Development," *Blood* 104:4088-4096.

Bohen, S.P. et al. (Feb. 18, 2004). "Variation in Gene Expression Patterns in Follicular Lymphoma and the Response to Rituximab," *Proceedings of the National Academy of Sciences of the United States of American* 100(4):1926-1930.

Bruggemann, M. et al. (1993). "Designer Mice: the Production of Human Antibody Repertoires in Transgenic Animals," *Year in Immuno.* 7:33-40.

Canellos G.P. et al. (1998). *The Lymphomas*. W.B.Saunders Company, Philadelphia, Pennsylvania, pp. xi-xiii. (Table of Contents Only.).

Cheung, V.G. et al. (Jan. 1999). "Making and Reading Microarrays," *Nature Genetics* 21(Suppl):15-19.

Clackson, T. et al. (Aug. 15, 1991). "Making Antibody Fragments Using Phage Display Libraries," *Nature* 352(6336):624-628.

Clynes, R. et al. (Jan. 20, 1998). "Fc Receptors are Required in Passive and Active Immunity to Melanoma," *PNAS USA* 95(2):652-656.

Coligan et al. (1991). *Current Protocols in Immunology*, vols. 1 and 2, Ed. Wiley-Interscience, New York, New York, Pubs, one page. (Table of Contents Only.).

Dogan, A. et al. (2000). "CD10 and BCL-6 Expression in Paraffin Sections of Normal Lymphoid Tissue and B-Cell Lymphomas," *American Journal of Surgical Pathology* 24(6):846-852.

Dornan, D. et al. (Nov. 20, 2009). "CD40 Pathway Activation Status Predicts Response to CD40 Targeted Therapy in Diffuse Large b-Cell Lymphoma," *51st Annual Meeting of the American Society of Hematology*, New Orleans, Louisiana, Dec. 5-8, 2009, two pages, *Blood* 114(22):1065.

Fellouse, F.A. (Aug. 24, 2004, e-pub. Aug. 11, 2004). "Synthetic Antibodies From a Four-Amino-Acid Code: A Dominant Role for Tyrosine in Antigen Recognition," *Proc. Nat. Acad. Sci. USA* 101(34):1246712472.

Fishwild, D.M et al., (Jul. 1996). "High-Avidity Human IgG Kappa Monoclonal Antibodies from a Novel Strain of Minilocus Transgenic Mice," *Nature Biotechnology* 14(7):845-851.

Forero-Torres, A. et al. (Nov. 20, 2009). "A Phase 1b Clinical Trial of Dacetuzumab in Combination with Rituximab and Gemcitabine: Multiple Responses Observed in Patients with Relapsed Diffuse Large B-Cell Lymphoma," *51st Annual Meeting of the American Society of Hematology*, New Orleans, Louisiana, Dec. 5-9, 2009, three pages. *Blood* 114(22):243-244.

Francisco, J.A. et al. (Jun. 15, 2000). "Agonistic Properties and in Vivo Antitumor Activity of the Anti-CD40 Antibody SGN-14," *Cancer Res.* 60(12):3225-3231.

Freshney, R.I. ed. (1987). *Animal Cell Culture*, Oxford, England, pp. ix-xiv. (Table of Contents.).

Friedman, J.et al. (2010). "Regularization Paths for Generalized Linear Models via Coordinate Descent," *J Stat Softw.* 33(1):1-20.

Gait, M.J. ed. (1984). *Oligonucleotide Synthesis*, Oxford, England, pp. vii-xii. (Table of Contents Only.).

GenBank Accession No. AY143166, last updated Dec. 5, 2003, located at <http://www.ncbi.nlm.nih.gov/nuccore/AY143166>, last visited May 15, 2011, two pages.

GenBank Accession No. BC019297, last updated Jul. 15, 2006, located at <http://www.ncbi.nlm.nih.gov/nuccore/BC019297>, last visited May 15, 2011, one page.

GenBank Accession No. BC062723, last updated Sep. 1, 2006, located at <http://www.ncbi.nlm.nih.gov/nuccore/BC062723>, last visited May 15, 2011, three pages.

(56) References Cited

OTHER PUBLICATIONS

GenBank Accession No. NM_000344, last updated May 1, 2011, located at <http://www.ncbi.nlm.nih.gov/nuccore/NM_000344>, last visited May 15, 2011, five pages.
GenBank Accession No. NM_000610.3, last updated Aug. 5, 2012, located at <http://www.ncbi.nlm.nih.gov/nuccore/NM-000610>, last visited Aug. 31, 2012, eight pages.
GenBank Accession No. NM_000626, last updated on Jun. 26, 2012, located at <http://www.ncbi.nlm.nih.gov/nuccore/NM_000626>, last visited Aug. 31, 2012, four pages.
GenBank Accession No. NM_000875, last updated May 15, 2011, located at <http://www.ncbi.nlm.nih.gov/nuccore/NM_000875>, last visited May 15, 2011, one page.
GenBank Accession No. NM_001250, last updated May 14, 2011, located at <http://www.ncbi.nlm.nih.gov/nuccore/nm_001250>, last visited May 15, 2011, three pages.
GenBank Accession No. NM_001706, last updated Apr. 30, 2011, located at <http://www.ncbi.nlm.nih.gov/nuccore/NM_001706>, last visited May 15, 2011, three pages.
GenBank Accession No. NM_001771, last updated Mar. 13, 2011, located at <http://www.ncbi.nlm.nih.gov/nuccore/NM_001771>, last visited May 15, 2011, four pages.
GenBank Accession No. NM_001814.4, last updated Aug. 18, 2012, located at <http://www.ncbi.nlm.nih.gov/nuccore/NM_001814>, last visited Aug. 31, 2012, four pages.
GenBank Accession No. NM_002737, last updated Oct. 7, 2008, located at <http://www.ncbi.nlm.nih.gov/nuccore/NM_002737>, last visited May 15, 2011, seven pages.
GenBank Accession No. NM_002767, last updated Mar. 11, 2011, located at <http://www.ncbi.nlm.nih.gov/nuccore/NM_002767>, last visited May 15, 2011, one page.
GenBank Accession No. NM_002927, last updated Mar. 20, 2011, located at <http://www.ncbi.nlm.nih.gov/nuccore/NM_002927>, last visited May 15, 2011, four pages.
GenBank Accession No. NM_003115.4, last updated Jun. 27, 2012, located at http://www.ncbi.nlm.nih.gov/nuccore/NM_003115, last visited on Aug. 31, 2012, four pages.
GenBank Accession No. NM_003641, last updated May 14, 2011, located at <http://www.ncbi.nlm.nih.gov/nuccore/AJ132100>, last visited May 15, 2011, one page.
GenBank Accession No. NM_004665, last updated Mar. 11, 2011, located at <http://www.ncbi.nlm.nih.gov/nuccore/NM_004665>, last visited May 15, 2011, one page.
GenBank Accession No. NM_005574, last updated Apr. 10, 2011, located at <http://www.ncbi.nlm.nih.gov/nuccore/NM_005574>, last visited May 15, 2011, three pages.
GenBank Accession No. NM_006763 last updated Mar. 13, 2011, located at <http://www.ncbi.nlm.nih.gov/nuccore/NM_006763>, last visited May 15, 2011, three pages.
GenBank Accession No. NM_015388, last updated Jul. 21, 2012, located at <http://www.ncbi.nlm.nih.gov/nuccore/NM_015388 >, last visited Sep. 6, 2012, three pages.
GenBank Accession No. NM_017549, last updated Mar. 11, 2011, located at <http://www.ncbi.nlm.nih.gov/nuccore/NM_017549>, last visited May 15, 2011, three pages.
GenBank Accession No. NM_019042, last updated Feb. 11, 2008, located at <http://www.ncbi.nlm.nih.gov/nuccore/NM_019042>, last visited Aug. 31, 2012, three pages.
Hammerling, G.J. et al. eds. (1981). "Monoclonal Antibodies and T-Cell Hybridomas," Elsevier, N.Y., pp. 563-587.
Harlow, E. et al. (1988). *Antibodies: A Laboratory Manual*, Cold Spring Harbor Laboratory Press, pp. iii-ix. (Table of Contents Only.).
Hawkins, R.E. et al. (1992). "Selection of Phage Antibodies by Binding Affinity. Mimicking Affinity Maturation," *J. Mol. Biol.* 226(3):889-896.
International Search Report mailed on Mar. 11, 2009, for PCT Application No. PCT/US2008/082920, filed on Nov. 7, 2008, three pages.
International Search Report mailed on Aug. 24, 2010, for PCT Application No. PCT/US2010/031528, filed on Apr. 17, 2010, four pages.
Jackson, J.R. et al. (Apr. 1995). "In Vitro Antibody Maturation Improvements of High Affinity, Neutralizing Antibody Against IL-1β," *J. Immunol.* 154(7):3310-3319.
Jakobovits, A. et al. (1993). "Analysis of Homozygous Mutant Chimeric Mice: Deletion of the Immunoglobulin Heavy-Chain Joining Region Blocks B-Cell Development and Antibody Production," *Proc. Natl. Acad. Sci. USA* 90(6):2551-2555.
Jakobovits, A. et al. (Mar. 18, 1993). "Germ-Line Transmission and Expression of a Human-Derived Yeast Artificial Chromosome," *Nature* 362(6417):255-258.
Jones, P.T. et al. (May 29, 1986). "Replacing the Complementarity-Determining Regions in a Human Antibody with Those from a Mouse," *Nature* 321(6069):522-525.
Köhler, G. et al. (Aug. 7, 1975). "Continuous Cultures of Fused Cells Secreting Antibody of Predefined Specificity," *Nature* 256(5517):495-497.
Lee, C.V. et al. (2004). "High-Affinity Human Antibodies From Phage-Displayed Synthetic Fab Libraries with a Single Framework Scaffold," *J. Mol. Biol.* 340(5):1073-1093.
Lee, C.V. et al. (2004). "Bivalent Antibody Phage Display Mimics Natural Immunoglobulin," *J. Immunol. Methods* 284(1-2):119-132.
Leong, A.S.Y. et al. (1996). "Epitope Retrieval with Microwaves. A Comparison of Citrate Buffer and EDTA with Three Commercial Retrieval Solutions," *Appl. Immunohistochem.* 4(3):201-207.
Lockhart, D.J. (Dec. 1996). "Expression Monitoring by Hybridization to High-Density Oligonucleotide Arrays," *Nature Biotechnology* 14(13):1675-1680.
Lonberg, N. et al. (Apr. 28, 1994). "Antigen-Specific Human Antibodies From Mice Comprising Distinct Genetic Modifications," *Nature* 368(6474):856-859.
Lonberg, N. et al. (1995). "Human Antibodies From Transgenic Mice," *Intern. Rev. Immunol.* 13:65-93.
Lossos, I.S. et al. (Aug. 15, 2001). "Expression of a Single Gene, BCL-6, Strongly Predicts Survival in Patients With Diffuse Large B-Cell Lymphoma," 98(4):945-951.
Luna, L.G. (1960). "Manual of Histological Staining Method of the Armed Forces Institute of Pathology," 3rd edition, The Blakiston Division McGraw-Hill Book Company, pp. xi-xii. (Table of Contents Only.).
Marks, J.D. et al. (Jul. 1992). "By-Passing Immunization: Building High Affinity Human Antibodies by Chain Shuffling," *Biotechnology* 10(7):779-783.
Marks, J.D. et al. (Dec. 5, 1991). "By-Passing Immunization. Human Antibodies From V-Gene Libraries Displayed on Phage," *J. Mol. Biol.* 222(3):581-597.
Mikel, U.V. ed. (1994). "The Armed Forces Institute of Pathology Advanced Laboratory Methods in Histology and Pathology," Armed Forces Institute of Pathology, American Registry of Pathology, Washington, D.C.
Morrison, S.L. et al. (Nov. 1984). "Chimeric Human Antibody Molecules: Mouse Antigen-Binding Domains with Human Constant Region Domains," *Proc. Natl. Acad. Sci. USA* 81(21):6851-6855.
Morrison, S.L. (Apr. 28, 1994). "Immunology. Success in Specification," *Nature* 368:(6474)812-813.
Mullis, K.B. et al. eds. (1994). "PCR: The Polymerase Chain Reaction" Birkäuser, Boston, MA, pp. xv-xvii. (Table of Contents Only.).
Neuberger, M. (Jul. 1996). "Generating High-Avidity Human Mabs in Mice," *Nature Biotechnology* 14(7):826.
Presta, L.G. (Aug. 1992). "Antibody Engineering," *Curr. Op. Struct. Biol.* 2(4):593-596.
O'Sullivan, M.J. et al. (1981). "Methods for the Preparation of Enzyme-Antibody Conjugates for use in Enzyme Immunoassay," Chap. 73 in *Methods in Enzym.* J. Langone et al eds., Academic Press, New York, New York, pp. 147-166.
Overbergh, L. et al. (Mar. 2003). "The Use of Real-Time Reverse Transcriptase PCR for the Quantification of Cytokine Gene Expression," *J. Biomolecular Techniques* 14(1):33-43.

(56) References Cited

OTHER PUBLICATIONS

Rai, K.R. et al. (2000). "Chronic Lymphocytic Leukemia," Chap. 72 in *Hematology, Basic Principles and Practice*, Hoffman et al. eds., 3rd ed., Churchill Livingstone, Philadelphia, PA, pp. 1350-1362.
Ravetch, J.V. et al. (1991). "FC Receptors," *Annu. Rev. Immunol.* 9:457-492.
Reichmann, L. et al. (Mar. 24, 1988). "Reshaping Human Antibodies for Therapy," *Nature* 332(6162):323-329.
Sambrook, J. et al. (1989). "Molecular Cloning: A Laboratory Manual", second edition. Cold Spring Harbor Laboratory, pp. v-xxxii. (Table of Contents Only.).
Schier, R. et al. (1996). "Identification of Functional and Structural Amino-Acids Residues by Parsimonious Mutagenesis," *Gene* 169(2):147-155.
Shi, X. et al. (Nov. 16, 2008). "Identification of a Diagnostic Gene Signature for SGN-40, Anti-CD40 Monoclonal Antibody, in Pre-Clinical NHL Models and the Role of FAS in SGN-40 Mediated Apoptosis," *50th Annual Meeting of the American Society of Hematology*, San Francisco, California, Dec. 6-9, 2008, two pages, *Blood* 112(11):565.
Sidhu, S.S. et al. (Apr. 2004). "Phage-Displayed Antibody Libraries of Synthetic Heavy Chain Complementarity Determining Regions," *J. Mol. Biol.* 338(2):299-310.
Singleton, P. et al., (1994). *Dictionary of Microbiology and Molecular Biology*, 2nd ed., J. Wiley & Sons, Chichester, United Kingdom, pp. vii-xiii. (Preface and Notes to the User Only.).
Smith, M.B. et al. (2007). "March's Advanced Organic Chemistry Reactions, Mechanisms and Structure," 6th ed., John Wiley & Sons, New York, N.Y, pp. xiii, xiv. (Table of Contents Only.).
Thomas, P.S. (Sep. 1980). "Hybridization fo Denatured RNA and Small DNA Fragments Transferred to Nitrocellulose," *Proc. Natl. Acad. Sci. USA* 77(9):5201-5205.
Turner, J.G. et al. (Jan. 1, 2001). "Anti-CD40 Antibody Induces Antitumor and Antimetastatic Effects: The Role of NK Cells," *Journal of Immunology, American Association of Immunologist* 166(1):89-94.
Tzankov, A. et al. (2003). "Prognostic Significance of CD44 Expression in Diffuse Large B Cell Lymphoma of Activated and Germinal Centre B Cell-Like Types: A Tissue Microarray Analysis of 90 Cases," *J. Clin. Pathol.* 56:747-752.
Van Besien, K. et al. (2000). "Clinical Manifestations, Staging and Treatment of Non-Hodgkin Lymphoma," Chapter 70 in *Hematology, Basic Principles and Practice*, 3rd ed. Hoffman et al. eds., Churchill Livingstone, Philadelphia, PA, pp. 1293-1338.
Written Opinion mailed on Mar. 11, 2009, for PCT Application No. PCT/US2008/082920, filed on Nov. 7, 2008, five pages.
Written Opinion mailed on Aug. 24, 2010, for PCT Application No. PCT/US2010/031528, filed on Apr. 17, 2010, nine pages.
Yelton, D.E. et al. (Aug. 15, 1995). "Affinity Maturation of the BR96 Anti-Carcinoma Antibody by Codon-Based Mutagenesis," *J. Immunol.* 155(4):1994-2004.
Zhou, H. et al. (2005)"Regularization and Variable Selection Via the Elastic Net," *J. R. Statist. Soc. B.* 67(2):301-320.
Kimura, H. et al. (Jun. 2005, e-pub. Sep. 8, 2005). "Plasma MIP-1β levels and skin toxicity in Japanese non-small cell lung cancer patients treated with the EGFR-targeted tyrosine kinase inhibitor, gefitinib," *Lung Cancer* 50(3):393-399.
Ramaswamy, S. et al. (Dec. 18, 2001, e-pub. Dec. 11, 2001). "Multiclass cancer diagnosis using tumor gene expression signatures," *Proc. Natl. Acad. Sci. U.S.A.* 98(26):15149-15154.
The Free Dictionary, definition for "measuring", last visited on Mar. 18, 2014, located at http:www.thefreedictonary.com/measuring >, three pages.
The Free Dictionary, definition for "determining,", last visited on Mar. 4, 2014, located at http://www.thefreedictionary.com/determining>, two pages.
Definition for "Assay", printed on Dec. 1, 2014, available via. url:<http://www.google.com/search?q=assaying+definition>.

\* cited by examiner

VNN2

```
LOCUS       NM_004665               2034 bp    mRNA    linear   PRI 03-SEP-2007
DEFINITION  Homo sapiens vanin 2 (VNN2), transcript variant 1, mRNA.
ACCESSION   NM_004665
VERSION     NM_004665.2  GI:17865813

1 aaaccttggc catggtcact tcctctttc caatctctgt ggcagttttt gcctaataa
   61 ccctgcaggt tggtactcag gacagtttta tagctgcagt gtatgaacat gctgtcattt
  121 tgccaaataa aacagaaaca ccagtttctc aggaggatgc cttgaatctc atgaacgaga
  181 atatagacat tctggagaca gcgatcaagc aggcagctga gcagggtgct cgaatcattg
  241 tgactccaga agatgcactt tatggatgga aatttaccag ggaaactgtt tcccttatc
  301 tggaggatat cccagaccct caggtgaact ggattccgtg tcaagaccc cacagatttg
  361 gtcacacacc agtacaagca agactcagct gcctggccaa ggacaactct atctatgtct
  421 tggcaaattt gggggacaaa aagccatgta attcccgtga ctccacatgt cctcctaatg
  481 gctactttca atacaataac aatgtggtgt ataatacaga aggaaaactc gtggcacgtt
  541 accataagta ccacctgtac tctgagcctc agtttaatgt ccctgaaaag ccggagttgg
  601 tgacttcaa cacggnattt ggaaggtttg gnatttcac gtgcttgat atattcttct
  661 atgatcctgg tgttaccctg gtgaaagatt tccatgtgga caccatactg tttcccacag
  721 cttggatgaa cgttttgccc cttttgacag ctattgaatt ccattcagct tgggcaatgg
  781 gaatgggagt taatcttctt gtggccaaca cagatcatgt cagctaaat atgacaggaa
  841 gtggtatta tgcaccaaat ggtcccaaag tgtatcatta tgacatgaag acagagttgg
  901 gaaaacttct cctttcagag gtggattcac atccctatc ctgcttgcc tacccaacag
  961 ctgttaattg gaatgcctac gccaccacca tcaaaccatt tccagtacag aaaaacactt
 1021 tcaggggatt tatttccagg gatgggttca acttcacaga acttttgaa aatgcaggaa
 1081 acttacagt ctgtcaaaag gagctttgct gtcatttaag ctacagaatg ttacaaaaag
 1141 aagagaatga agtatacgtt ctaggagctt tacaggatt acatggccga aggagaagag
 1201 agtactggca ggtctgcaca atgctgaagt gcaaaactac taattgaca acttgtggac
 1261 ggccagtaga aactgcttct acaagattg aaatgtttctc cctcagtggc acatttggaa
 1321 cagagtatga ttttcctgaa gtgctactta ccgaattca tctgtcacct ggaaaatttg
 1381 aggtgctgaa agatgggcgt ttggtaaaca agaatggatc atctgggcct atactaacag
 1441 tgtcactctt tgggaggtgg tacacaaagg actaacttta cagctcatgt gggaccagca
 1501 attcagtaat aacttacctg ctaatattca tattattaat gatcatagct ttgcaaaata
 1561 ttgtaatgtt atagggcgtc tctttatcac tcagcttctg catdatatgc ttggctgaat
 1621 gtgtttatcg gcttcccaag ttactaaga aacttgaag ggctatttca gtagtataga
 1681 ccagtgagtc ctaaatattt tttctcatca ataattattt ttaagtatt atgataatgt
 1741 tgtccatttt tttggctact ctgaaatgtt gcagtgtgga acaatggaaa gagcctgggt
 1801 gtttgggtca gataaatgaa gatcaaactc cagctccagc ctcattgct tgagactttg
 1861 tgtgtatggg ggcttgtat gtatgggagt gaggagtttc agggccattg caaacatagc
 1921 tgtgcccttg aagagaatag taatgatggg aattagagg tttatgactg aattcccttt
 1981 gacattaaag actatttgaa ttcaaaaaaa aaaaaaaaa aaaaaaaaaa aaaa
```

FIG. 1A

RGS13

```
LOCUS       NM_002927               1498 bp    mRNA    linear   PRI 24-AUG-2007
DEFINITION  Homo sapiens regulator of G-protein signaling 13 (RGS13),
            transcript variant 1, mRNA.
ACCESSION   NM_002927
VERSION     NM_002927.3  GI:21464137
KEYWORDS    
SOURCE      Homo sapiens (human)

ORIGIN
        1 gaggccagag tgccatcgaa ggtaattata gagacagtaa aatccttta ctctgggaaa
       61 aataaaatgc tgggtgtctc acaaaattc agaactgat ttcaaacgga tcataacaaa
      121 gaggagatca aatttagcat ggtggactgc tcgacaggat atatttgtca atggaatgtt
      181 tccacatatt ataccaccaa catgagaaaa aaatgatcat tgtttatttg aagcttgatg
      241 atattctaac gctgacttt ctcttctcat tttagagaaa aatgagcagg cggaattgtt
      301 ggatttgtaa gatgtgcaga gatgaatcta agaggcccc ttcaaacctt acttggagg
      361 aagtattaca gtgggccag tcttttgaaa atttaatggc tacaaaatat ggtccagtag
      421 tctatgcagc atattaaaa atggagcaca gtgacgagaa tattcaattc tggatggcat
      481 gtgaaaccta taagaaatt gcctcacggt ggagcagaat ttctagggca aagaagcttt
      541 ataagattta catccagcca cagtcccta gagagattaa cattgacagt tcgacaagag
      601 agactatcat caggaacatt caggaaccca ctgaaacatg tttgaagaa gctcagaaaa
      661 tagtctatat gcatatggaa agggattcct acccccgatt tctaaagtca gaaatgtacc
      721 aaaaactttt gaaaactatg cagtccaaca acagtttgtg actacaactc aaaagtttaa
      781 atagaaaaca gtatattgaa agtggtgggt tgatctttt tatttagaaa cccacaaaat
      841 cagaaacaca gtacaaataa aacagaaatc aaactataag ttgacttta gttcctaaaa
      901 agaaacatat ttcaaaagca atggaatcta gaattcttat aacatgaata acaaaatgta
      961 cagcaagcct atgtagttca attaatatat aaggaaaagg aaggtcttc tcatgatac
     1021 aagcattata aagttttac tgtagtagtc aattaatgga tatttcttg ttaataaaat
     1081 tttgtgtcat aatttacaaa ttagttcttt aaaaattgtt gttatatgaa tgtgttct
     1141 agcatgaatg tcctatagag tactctaaat aacttgaatt tatagacaaa tgctactcac
     1201 agtacaatca attgtattat accatgagaa aatcaaaaag gtgttcttca gagacatttt
     1261 atctataaaa tttcctact attatgttca ttaacaaact tcttatcac atgtatcttc
     1321 tacatgtaaa acattctga tgattttta acaaaaaata tatgaattc ttcatttgct
     1381 cttgcatcta cattgctata aggatataaa atgtggtttc tatattttga gatgtttttt
     1441 ccttacaatg tgaactcatc gtgatcttgg aaatcaataa agtcaaatat caactaaa
```

```
LOCUS       NM_001771               3260 bp    mRNA    linear   PRI 03-SEP-2007
DEFINITION  Homo sapiens CD22 molecule (CD22), mRNA.
ACCESSION   NM_001771
VERSION     NM_001771.1  GI:4502650
KEYWORDS
SOURCE      Homo sapiens (human)

ORIGIN
        1 ccatcccata gtgagggaag acacgcggaa acaggcttgc acccagacac gacaccatgc
       61 atctcctgg  ccctggctc  ctgctcctgg ttctagaata cttggctttc tctgactcaa
      121 gtaaatgggt ttttgagcac cctgaaaccc tctacgcctg ggagggggcc tgcgtctgga
      181 tccctgcac  ctacagagcc ctagatggtg acctggaaag cttcatcctg ttccacaatc
      241 ctgagtataa caagaacacc tgaagtttg  atgggacaag actctatgaa agcacaaggg
      301 atgggaagt  tcctctgag  cagaaaaggg tgcaattcct gggagacaag aataagaact
      361 gcacactgag tatccaaccg gtgcacctca atgacagtgg tcagctgggg ctgaggatgg
      421 agtccaagac tgagaaatgg atggaacgaa tacacctcaa tgtctctgaa aggccttttc
      481 cagctcatat ccagtcctc  ccagaaattc aagagtccca ggaagtcact ctgacctgct
      541 tgctgaattt ctcctgctat gggtatccga tccaattgca gtggctccta gaggggttc
      601 caatgaggca ggctgctgtc acctcgacct cctgaccat caagtctgtc ttcacccgga
      661 gcgagctcaa gttctcccca cagtggagtc accatgggaa gattgtgacc tgcagcttc
      721 aggatgcaga tgggaagttc ctctccaatg acacggtgca gctgaacgtg aagcacaccc
      781 cgaagttgga gatcaaggtc actcccagtg atgccatagt gagggagggg gactctgtga
      841 ccatgacctg cgaggtcagc agcagcaacc cggagtacac gacggtatcc tggctcaagg
      901 atgggacctc gctgaagaag cagaatacat tcacgctaaa cctgcgcgaa gtgaccaagg
      961 accagagtgg gaagtactgc tgtcaggtcc gcaatgacgt gggccggga  aggtcggaag
     1021 aagtgttcct gcaagtgcag tatgcccgg  aaccttcac  ggttcagatc tccactcac
     1081 cggctgtgga gggaagtcaa gtgagtttc  tttgcatgtc actggccaat cctctcttcaa
     1141 caaattcac  gtggtaccac aatgggaaag aaatgcaggg aaggacagag gagaaagtcc
     1201 acatcccaaa gatcctccc  tgcacgctg  ggacttattc ctgtgtggca gaaacattc
     1261 ttggtactgg acagagggc  ccggagctg  agctggatgt ccagtatcct cccaagaagg
     1321 tgaccacagt gattcaaaac cccatgccga ttcgagaagg agacacagtg acccttctt
     1381 gtaactacaa ttccagtaac cccagtgtta cccggtatga atggaaaccc catggcgct
     1441 gggaggagcc atcgcttggg gtgctgaaga tcaaaacgt  tggctgggac aacacaacca
     1501 tcgcctgcg  acgttgtaat agttggtgct cgtgggcctc ccctgtcgcc ctgaatgtcc
     1561 agtatgccc  ccgagacgtg aggtccgga aaatcaagcc cctttccgag attcactctg
     1621 gaaactggt  cagctccaa tgtgacttct caggcagcca ccaaagaa  gtccagttct
     1681 tctgggagaa aaatggaagg cttctgggga agaaagca  gctgaatttt gactccatct
     1741 ccccagaaga tgctgggagt tatagctgct gggtgaacaa ctcatagga cagacagcgt
     1801 ccaaggcctg gacactgaa gtgctgtatg caccagaag  gctgatgtg tccatgagcc
     1861 cggggacca agtgatggag gggaagagtg caacctgac  ctgtgagagt gacgccacc
     1921 ctccgtctc  ccactacacc tggtttgact ggaataacca aagcctccc  caccacagcc
     1981 agaagctgag attggagccg gtgaaggtcc agcactgg  tgcctactgg tgcagggga
     2041 ccaacagtgt gggcaagggc cgttcgctc  tcagcaccct tactgtctac tatagccgga
     2101 agaccatcgg caggcgagtg gctgtgggac tcgggtcctg cctcgccatc ctcatcctgg
     2161 caatctgtgg gctcaagctc cagacgtt  ggaagaggac acagagccag caggggcttc
     2221 aggagaattc cagcggcag agcttctttg tgaggaataa aaaggttaga agggcccacc
     2281 tctctgaagg ccccactcc ctggatgct acaatcaat gatggaagat ggcattagct
     2341 acaccaccct gcgctttccc gagatgaaca taccacgaac tggagatgca gagtcctcag
```

FIG. 1C

```
2401 agatgcagag acctcccgg acctgcgatg acacggtcac ttattcagca ttgcacaagc
2461 gccaagtggg cgactatgag aacgtcattc cagattttcc agaagatgag gggattcatt
2521 actcagagct gatccagttt ggggtcgggg agcggcctca ggcacaagaa aatgtggact
2581 atgtgatcct caaacattga cactggatgg gctgcagcag aggcactggg ggcagcgggg
2641 gccagggaag tcccgagtt tcccagaca ccgccacatg gcttcctcct gcgtgcatgt
2701 gcgcacacac acacacacac gcacacacac acacacacac tcactgcgga gaaccttgtg
2761 cctggctcag agccagtctt tttggtgagg gtaacccaa acctccaaaa ctcctgcccc
2821 tgttctcttc cactctcctt gctacccaga aatcatctaa ataactgccc tgacatgcac
2891 acctccctg cccaccagc ccactggcca tctccacccg gagctgctgt gtcctctgga
2941 tctgctcgtc attttccttc ccttctccat ctctctggcc ctctacccct gatctgacat
3001 ccccactcac gaatattacg cccagtttct gcctctgagg gaaagccag aaaaggacag
3061 aaacgaagta gaaaggggcc cagtcctggc ctggcttctc ctttggaagt gaggcattgc
3121 acggggagac gtacgtatca gcggcccctt gactctgggg actcggggtt tgagatggac
3181 acactggtgt ggattaacct gccagggaga cagagctcac aataaaatg gctcagatgc
3241 cacttcaag aaaaaaaaa
```

```
LOCUS       NM_001250               1616 bp    mRNA    linear   PRI 30-SEP-2007
DEFINITION  Homo sapiens CD40 molecule, TNF receptor superfamily member 5
            (CD40), transcript variant 1, mRNA.
ACCESSION   NM_001250
VERSION     NM_001250.4  GI:91105420
KEYWORDS    
SOURCE      Homo sapiens (human)

ORIGIN
        1 gccaaggctg gggcagggga gtcagtagag gcctcgctcg gggcccagt ggtcctgccg
       61 cctggtctca cctcgctatg gttcgtctgc ctctgcagtg cgtcctctgg ggctgcttgc
      121 tgaccgctgt ccatccagaa ccaccactg catgcagaga aaacagtac ctaataaaca
      181 gtcagtgctg ttctttgtgc cagccaggac agaaactggt gagtgactgc acagagttca
      241 ctgaaacgga atgccttcct tggggtgaaa gcgaattcct agacacctgg aacagagaga
      301 cacactgcca ccagcaaaa tactgcgacc ccaacctagg gcttcgggtc cagcagaagg
      361 gcacctcaga aacagacacc atctgcacct gtgaagaagg ctggcactgt acgagtgagg
      421 cctgtgagag ctgtgtcctg caccgctcat gctcgccgg ctttgggctc aagcagatcg
      481 ctacaggggt ttctgatacc atctgcgagc cctgccagt cggcttcttc tccaatgtgt
      541 catctgcttt cgaaaatgtc caccttggga caagctgtga gacaaagac ctggttgtgc
      601 aacagccagg cacaacaag actgatgttg tctgtggtcc ccaggatcgg ctgagacccc
      661 tggtggtgat ccccatcatc ttcgggatcc tgtttgccat cctcttgggc ctggtcttta
      721 tcaaaaggt ggccaagaag ccaaccaata aggccccca cccaagcag gaacccccagg
      781 agatcaattt ccccgacgat cttcctggct ccaacactga tgctccagtg caggagactt
      841 tacatggatg ccaaccggtc accccaggagg atggcaaaga gagtcgcatc tcagtcagg
      901 agagacagtg aggctgcacc aaccaggag tgtggtcaag tggcaaaca ggagtggc
      961 cagagagcct ggtgctgctg ctgctgtggc gtgagggtga ggggctggca ctgactgggc
     1021 atagctccc gcttctgctg gcaccctgc agtttgagac aggagacctg gcactggatg
     1081 cagaaacagt tcaccttgaa gaacctctca ctcaccctg gagccatcc agtctccaa
     1141 cttgtattaa agacagaggc agaagtttgg tggtggtggt gttgggtat ggttagtaa
     1201 tatccaccag agcttccgat ccagcagttt ggtgccaga gaggcatcat ggtggcttcc
     1261 ctgcgccag gaagccatat acacagatgc ccatgcagc attgtttgtg atagtgaaca
     1321 actggaagct gcttaactgt ccatcagcag gagactggct aaataaatt agaatatatt
     1381 tatacaacag aatctcaaaa acactgttga gtaaggaaaa aaggcatgc tgctgaatga
     1441 tgggtatgga acttttaaa aagtacatg cttttatgta tgtatattgc ctatggatat
     1501 atgtataaat acaatatgca tcatatattg atataacaag ggttctggaa gggtacacag
     1561 aaaacccaca gctcgaagag tggtgacgtc tggggtgggg aagaagggtc tgggag
```

FIG. 1E

IFITM1

```
LOCUS       NM_003641               733 bp    mRNA    linear   PRI 03-SEP-2007
DEFINITION  Homo sapiens interferon induced transmembrane protein 1 (9-27)
            (IFITM1), mRNA.
ACCESSION   NM_003641
VERSION     NM_003641.3  GI:150010588
KEYWORDS
SOURCE      Homo sapiens (human)

ORIGIN
        1 aaacagcagg aaatagaaac ttaagagaaa tacacactto tgagaaactg aaacgacagg
       61 ggaaggagg  tctcactgag cacgtccca  gcatccggac accacagcgg ccctt cgctc
      121 cacgcagaaa accacacttc tcaaaccttc actcaacact tccttcccca aagccagaag
      181 atgcacaagg aggaacatga ggtggtgtg  ctggggcac  cccccagcac catccttcca
      241 aggtccaacg tgatcaaaat ccacagcgag acctcgtgc  ccgaccatgt cgtctggtcc
      301 ctgttcaaca ccctcttctt gaactggtgc tgtctgggct tcatagcatt cgcctactcc
      361 gtgaagtcta gggacaggaa gatggttggc gacgtgaccg gggccaggc  ctatgcctcc
      421 accgccaagt gcctgaacat ctgggccctg attctgggca tcctcatgac cattggattc
      481 atcctgttac tggtattgg  ctctgtgaca gtctaccata ttatgttaca gataatacag
      541 gaaaacgg   gttactagta gccgccata  gcctgcaacc tttgcactcc actgtgcaat
      601 gctggccctg cacgctgggg ctgttgcccc tgccccttg  gtcctgcccc tagatacagc
      661 agtttatacc cacacacctg tctacagtgt cattcaataa agtgcacgtg cttgtgaaaa
      721 aaaaaaaaa  aaa
```

FIG. 1F

BCL6

```
LOCUS       NM_001706               3537 bp    mRNA    linear   PRI 30-SEP-2007
DEFINITION  Homo sapiens B-cell CLL/lymphoma 6 (zinc finger protein 51)
            (BCL6), transcript variant 1, mRNA.
ACCESSION   NM_001706
VERSION     NM_001706.2  GI:21040323
KEYWORDS
SOURCE      Homo sapiens (human)

ORIGIN
        1 ggcccctcga gcctcgaacc ggaacctcca aatccgagac gctctgatta tgaggacctc
       61 gaaatatgcc ggccagtgaa aaaatcttgt ggctttgagg gcttttggtt ggccaggggc
      121 agtaaaaatc tcggagagct gacaccaagt cctccctgc cacgtagcag tggtaaagtc
      181 cgaagctcaa attccgagaa ttgagctctg ttgattctta gaactggggt tcttagaagt
      241 ggtgatgcaa gaagtttcta ggaaaggccg gacaccaggt tttgagcaaa attttggact
      301 gtgaagcaag gcattggtga agacaaaatg gcctcgccgg ctgacagttg tatccagttc
      361 acccgccatg ccagtgatgt tcttctcaac cttaatcgtc tcggagtcg agacatcttg
      421 actgatgttg tcattgttgt gagccgtgag cagtttagag cccataaaac ggtcctcatg
      481 gcctgcagtg gcctgttcta tagcatcttt acagaccagt tgaaatgcaa ccttagtgtg
      541 atcaatctag atcctgagat caacccctgag ggatctgca tctcctgga cttcatgtac
      601 acatctggc tcaatttgcg ggagggcaaa atcatggtg tgatggccac ggctatgtac
      661 ctgcagatgg agcatgttgt ggacacttgc ggaagttta ttaaggccag tgaagcagag
      721 atggttttctg cctccaagcc tcctcgtgaa gagttcctca acagccggat gctgatgccc
      781 caagacatca tggcctatcg gggtcgtgag gtggtggaga caaacctgcc actgaggagc
      841 gccctgggt gtgagcag agcctttgcc cccagcctgt acagtggcct gtccacaccg
      901 ccagcctctt attccatgta cagtcaccttc cctgtcagca gcctcctctt ctccgatgag
      961 gagttcggga tgtccggat gctgtcagca aaccccttcc ccaaggacgg ggcactccca
     1021 tgtgatagtg caggccaagt ccctggtgga tacagccgg cgactttgga ggtgtcccca
     1081 aatgtgtgcc acagcaatat ctattcaccc aaggaaaaca tccagaaga ggcacgaagt
     1141 gatatgcact acagtgtggc tgaggcctc aaacctgtg cccctctcagc ccgaaatgcc
     1201 ccctacttcc cttgtgacaa ggcagcaaa gaagaagaga gacctcctc ggaagatgag
     1261 attgccctgc atttcgagcc cccaatgca ccctgaaacc ggaagggtct ggttagtcca
     1321 cagagccccc agaaatctga ctgcagcct aactcgccca cagagtcctg cagcagtaag
     1381 aatgctgca tcctccaggc tctggctcc cctcagcca agagcccacc tgacccaaaa
     1441 ggctgcaact ggaagaaata caagttcatc gtgctcaaca gctcaaccca gaatgccaaa
     1501 ccagaggggc ctgagcaggc tgagctgggc cgcttttcc cacgagctga caggcccca
     1561 cctgcctgcc agccacccat ggagcttgag aacttgacc tcagtcccca aaccaagctg
     1621 agtgccagcg gggaggactc caccatccca caagcagcc ggctcaataa catgttaaac
     1681 aggtccatga ggggctctcc ccgagcagc agcgagagcc actcaccact ctacatgcac
     1741 acccgaagt gcagtcacg ggctctcag tcccacagc atgagagat gtgcctccac
     1801 aacgctgggc ccacgttccc tgaggagatg ggagagaccc agtctgagta ctagagattct
     1861 agctgtgaga acggggccgt tttctgcaat gagtgtgact gccgctttcc tgaggaggcc
     1921 tcactcccaa ggaacacgct gcagaaccac agtgacaaac cctacaagtg tgaccgctgc
     1981 caggcctcct tcggctacaa gggcaacctc gccagccaca gaccgtcca tacggtgaag
     2041 aaacctatc gttgcaacat ctgtggggc cagttcaac ggcagccaa cctgaaaacc
     2101 cacactcgaa ttcactctgg agagaagcc tacaaatgcg aaacctgcgg agccagattt
     2161 gtacaggtgg cccactctgg tgccatgtg ctatcaaca ctggtgagaa gccctatccc
     2221 tgtgaaatct gtggcacccg tttcgggcac cttcagacta tgaagagcca cctgcgaatc
     2281 cacacaggag agaaacctta ccattgtgag aagtgtaacc tgcatttcgg tcacaaaagc
     2341 cagctgcgac tcacttgcg ccagaagcat ggggcatca ccaacaccaa ggtgcaatac
```

FIG. 1G

```
2401 cgcgtgtcag ccactgacct gcctccggag ctccccaaag cctgctgaag catggagtg
2461 tgatgctttc gtctccagcc ccttctcaga atctacccaa aggatactgt aacacttta
2521 aatgttcatc ccatgatgta gtgcctcttt catccactag tgcaaatcat agctggggg
2581 tgggggtggt ggggtcggg gcctggggga ctgggagccg cagcagctcc cctccccc
2641 ctgccataaa acattaagaa aatcatattg cttcttctcc tatgtgtaag gtgaaccat
2701 tcagcaaaaa gcaaaatcat tttatatgtc aaagcagggg agtatgcaaa agttctgac
2761 tgacttagt ctgcaaaatg aggaatgtat atgttttgtg ggaacagatg tttcttttg
2821 atgtaaatgt gcattctttt aaaagacaag acttcagtat gttgtcaaag agagggctt
2881 aatttttta accaaggtg aaggaatata tggcagagtt gtaaatatat aaatatata
2941 atatataaaa taaatatata taaagctaac aaagatatat taaaaatata aaactgcgt
3001 aaaggctga ttttgtatct gcaggcagac acggatctga gaatctttat tgagaaaga
3061 cacttaagag aatattttaa gtattgcatc tgtataagta agaaaatatt ttgtctaaa
3121 tgcctcagtg tatttgtatt ttttgcaag tgaaggttta caatttacaa agtgtgtat
3181 aaaaaaaca aaagaacaa aaaaatctgc agaaggaaaa atgtgtaatt ttgttctag
3241 tttcagtttg tatataccg tacaacgtgt cctcacggtg cctttttca cggaagttt
3301 caatgatggg cgagcgtgca ccatcccttt ttgaagtgta ggcagacaca gggacttga
3361 gttgttacta actaaactct cttgggaat gtttgtctca tcccattctg cgtcatgct
3421 gtgttataac tactccggag acagggtttg gctgtgtcta aactgcatta ccgcgttgt
3481 aaatatagct gtacaaatat aagaataaaa tgttgaaaag tcaaactgga aaaaaa
```

FIG. 1H

EPDR1

```
LOCUS       NM_017549               2613 bp    mRNA    linear   PRI 26-JUN-2007
DEFINITION  Homo sapiens ependymin related protein 1 (zebrafish) (EPDR1),
            mRNA.
ACCESSION   NM_017549
VERSION     NM_017549.3  GI:116009437
SOURCE      Homo sapiens (human)

ORIGIN
        1 tcccccctct taaaacacga tgcctcccag gatgctagtg gcaccactgc cactgcattt
       61 cctgttggca gcagtgagca gtgaaaaccg aagcggcaga aggcagtggc agcaggcagt
      121 ggcagcaggc agtggcccag gcagaaatag ctcccgcgcg attcactgga gccttcccg
      181 ggccctggtc ccggctaccg ggactgcgc gtccggatct caaaagcggc agaggccacc
      241 gaagggacag gaagcacttt ggtccagacc acactcccgg cacagtgcgg aaagagccgg
      301 cggagccac tctgatcccg gacgcctcag cgccccttg ggcttgggct tgccctcggg
      361 ccggggaagg ctgaccgcga tgccaggacg cggtcccctc cgcaccgtcc cgggcgccct
      421 gggtgcctgg ctgctgggcg gcctctgggc ctggaccctg tcggcctgt gcagcctggg
      481 ggcggtggga gccccgcgcc cgtgccaggc gccgcagcag tgggagggc gccaggttat
      541 gtaccagcaa agtacgcggc gcaaccgccg cgccctgctc tcctacgatc ggctcaacca
      601 gcgcgtgcgg gtgctggacg agaggaaggc gctgatcccc tgcaagagat tatttgaata
      661 tattttgctg tataaggatg gagtgatgtt tcagattgac caagccacca agcagtgctc
      721 aaagatgacc ctgacacagc cctgggatcc tcttgacatt cctcaaaact ccacctttga
      781 agatcagtac tccatcgggg ggctcaggac gtgatcacc gtccaggagt ggtcggacag
      841 aaagtcagct agatcctatg aaacctggat tggcatctat acagtcaagg attgctatcc
      901 tgtccaggaa acttttacca taaactacag tgtgatattg tctacgcggt ttttgacat
      961 ccagctgggt attaagacc cctcggtgtt tacccctcaa agcacgtgcc agatgcccca
     1021 actggagaag atgagcgaag actgctcctg gtgagcctgt gcatagggaa gggcagcat
     1081 cggatgtcag cccctgcgg ccccagctgg agatggatat gagactagtc aagatgtgaa
     1141 tgctaattgg agagaaaatat aattttagga agatgacat tgatgtgggg ttttgatgtg
     1201 tctgattttg actactcaag ctctgtttac agaagaaaat tgaatggcga gggtgtggcc
     1261 atatgaactg actagatggc taatatggac acttgggta tttctaatgc ctgttcaggg
     1321 ctggttttct gcatgcacgg gtatacacat aatgcagtgc catgcacata gggaagggtc
     1381 agtaagagaa gtttgccttg gcagcaagta tttattgtt acattattca gaattagtga
     1441 taataaaaag cagagtgatt ttggtcaatt ttattattaa ttcttaaatt cctgcagag
     1501 aatgcccct ttaatgctgc accaggggttg gcattgctcc cactgagccc cactccacc
     1561 tgtccctgca ctcccttggt tgccaaaaaa atgataactt aaatccttc cagacttaag
     1621 aattttatgg catggcccaa ttgatataaa cattagaag gaaatgaaaa gctaaaatag
     1681 gaagtaatta ttcctctaaa gaaacatttt gagcaaggca gtttagagaa tcctaatgtc
     1741 tacactggca tagcacgagc catgtaagct tcttttttt ctatgcaaga gtatgatgt
     1801 atgtgctgaa tcttcacaga cttgtcaata cacaggcagt attctaaaat agcactgaac
     1861 agggagtcag gagactatg tctcctaaac ccaggactag agttccttcg tactgtcact
     1921 cctttggtca ttaaatgcac tgggttgcc cgcacttgg ccttcctaga acactgcttc
     1981 ataacctctc tgtctgactt ctgcatctcc ttcaggtca gctcattac aagagttgct
     2041 cccaagcctg gatgagttgc accttgcatc ttgagcatgc atttctcaca ataattatta
     2101 agcrgtgtga taattttctgc tttcaggaca ctcarccatt atcttggctg tgagctcctt
     2161 gggtacgggt accttgtatg tttacttta tatccctagc acaaagcaag tgcctggcac
     2221 atagtcagtg cctaagtat tctgtagagtg aagaatgcca gcctctcttg tccctggttt
     2281 cctatgtgt tgaatgtggt tgagtttgtc cattgctagg gagagactc cagtaataaa
     2341 atttactatt ctagatgctt ctactgttat gttttatctg cccattatc ttcttagtt
     2401 accaggagaa atgtgtgaca cctatattat aatgaaaaca atctcattac ttatagttta
     2461 tctatattaa acaaatttaa ttgcatttta aagcattctt tgatactgtt gcttttgcaa
     2521 taaatatgga taatcttggt tataagggag ttaaacaat gctgtaataa ataaagtgct
     2581 tcatgtgatc aaaatcaaaa aaaaaaaaa aaa
```

FIG. 1I

IGF1R

```
LOCUS       NM_000875              11242 bp    mRNA    linear   PRI 22-OCT-2007
DEFINITION  Homo sapiens insulin-like growth factor 1 receptor (IGF1R),
            mRNA.
ACCESSION   NM_000875 NM_015883
VERSION     NM_000875.3  GI:119220593
KEYWORDS    
SOURCE      Homo sapiens (human)

ORIGIN
        1 tttttttttt tttttttga gaaaggggaa tttcatccca aataaaagga atgaagtctg
       61 gctccggagg agggtcccg actcgctgt ggggctcct gttttctctcc gccgcgctct
      121 cgctctggcc gacgagtgga gaaatctgcg ggccaggcat cgacatccgc aacgactatc
      181 agcagctgaa gcgcctggag aactgaacgg tgatcgaggg ctacctccac atcctgctca
      241 tctccaaggc cgaggactac cgcagctacc gattcccaa gctcacggtc attaccgagt
      301 acttgctgct gttccgagtg gctggactcg agagcctcgg agaccctttc cccaacctca
      361 cggtcatccg cggctggaaa ctcttctaca actaacgccc ggtcatcttc gagatgacca
      421 atctcaagga tattgggctt tacaacctga ggaacattac tcggggggcc atcaggattg
      481 agaaaaatgc tgacctctgt taccttctca ctgtggactg gtccctgatc ctggatgcgg
      541 tgtccaataa ctacattgtg gggaataagc cccaaagga atgtggggac ctgtgtccag
      601 ggaccatgga ggagaagccg atgtgtgaga agaccaccat caacaatgag tacaactacc
      661 gctgctggac cacaaatcgc tgccagaaaa tgtgcccaag cacgtgtggg aagcgggctg
      721 gcaccgagaa caatgagtgc tgcaccccg agtgcctggg cagtgcagc gcgcctgaca
      781 acgacacggc ctgtgtagct tgccgccact actactatgc cggtgtctgt gtgcctgcct
      841 gccgccccaa cacctacagg tttgagggct ggcgctgtgt ggaccgtgac ttctgcgcca
      901 acatcctcag cgccgagagc agcgactcgg aggggttgt gatccacgac ggcgagtgca
      961 tgcaggagtg cccctcgggc ttcatccgca acggcagcca gagcatgtac tgcatcccct
     1021 gtgaaggtcc ttgccccaag gtctgtgagg aagaaaagaa aacaaagacc attgattctg
     1081 ttacttctgc tcagatgctc caaggatgca ccatcttcaa gggcaatttg ctcattaaca
     1141 tccgacgggg gaataacatt gcttcagagc tggagaactt catgggctc atcgaggtgg
     1201 tgacgggcta cgtgaagatc cgccattctc atgccttggt ctccttgtcc ttcctaaaaa
     1261 accttcgcct catcctagga gaggagcagc tagaagggaa ttactccttc tacgtcctcg
     1321 acaaccagaa cttgcagcaa ctgtgggact gggaccaccg caactgacc atcaaagcag
     1381 ggaaaatgta cttcgcttc aatcccaat tatgtgtttc cgaaatttac cgcatggagg
     1441 aagtgacggg gactaagggg cgccaaagca aagggacat aaacacgagg aacaacgggg
     1501 agagagcctc ctgtgaaagt gacgtactgc atttcacctc caccaccacg tgaagaatc
     1561 gcatcatcat aacctggcac cggtacggc cccctgacta cagggatctc atcagcttca
     1621 ccgttacta caaggaagca cccttaaga atgtcacaga gtatgatggg caggatgcct
     1681 gggctccaa cagctgaac atggtgacg tgacctccc gcccaacaag gacgtggagg
     1741 ccggatctt actacatggg ctgaagcct ggactcagta gccgttcac gtcaaggctg
     1801 tgaccctcac catgtggag aacgaccata tcgtggggca agagtgag atcttgtaca
     1861 ttcgcacaa tgcttcagtt cctccatc cctggaacgt tcttcagca tcgaactcct
     1921 cttctcagtt aaatctgaag tggaacccta ctctctgcc caaaggcaac ctgagtacc
     1981 acattgtgcg ctggcaggg cagcctcagg acggtacct ttacggaac aattactgct
     2041 ccaaagacaa aatcccatc aggaagtatg ccgacggac catgacatt gaggaggtca
     2101 cagagaaccc aagactgag gtgtgtggtg gggagaagg gcttgctgc gcctgccca
     2161 aaactgaagc cgagaagcag gcgagaagg aggaggctga ataccgcaaa gtctttgaga
     2221 atttctgca caactccatc ttcgtgccca gactgaaag gaaggggaga atgtcatgc
     2281 aagtggcaa caccaccatg tcagcagaa gcaggaacac cacggccgca gacacctaca
     2341 acatcaccga ccggaagag ctggagacag agtacccttt cttgagagc agagtggata
     2401 acaaggagag aactgtcatt tctaacctc ggccttcac attgtaccga atcgatatcc
```

FIG. 1J

```
2461 acagctgcaa ccacgaggct gagaagctgg gctgcagcgc ctccaacttc gtctttgcaa
2521 ggactatgcc cgcagaagga gcagatgaca ttcctgggcc agtgacctgg gagccaaggc
2581 ctgaaaactc catctttta aagtggccgg aacctgagaa tcccaatgga ttgattctaa
2641 tgtatgaaat aaaatacgga tcacaagttg aggatcagcg agaatgtgtg tccagacagg
2701 aatacaggaa gtatggaggg gccaagctaa acggctaaa ccggggaac tacacagccc
2761 ggattcaggc cacatctctc tctgggaatg ggtcgtggac agatcctgtg ttcttctatg
2821 tccaggccaa aacaggatat gaaaacttca tccatctgat catcgctctg cccgtgctg
2881 tcctgttgat cgtgggaggg ttggtgtatg tgctgtacgt cttccataga aagagaaata
2941 acagcaggct gggaatgga gtgctgtatg cctctgtgaa cccggagtac ttcagccgtg
3001 ctgatgtgta cgttcctgat gagtgggagg tggctcggga gaagatcacc atgagccggg
3061 aacttgggca gggtgtgtt gggatggtct atgaaggagt tgccaagggt gtggtgaaag
3121 atgaacctga aaccagagtg gccattaaaa cagtgaacga ggccgcaagc atggtgaga
3181 ggattgagtt tctcaaggaa gcttctgtga tgaaggagtt caattgtcac catgtggtgc
3241 gattgctggg tgtggtgtcc caaggccagc caacactggt catcatggaa ctgatgacac
3301 ggggcgatct caaaagttat ctccggtctc tgaggccaga aatggagaat aatccagtcc
3361 tagcacctcc aagcctgagc aagatgattc agatggccgg agagattgca gacggcatgg
3421 catacctcaa cgccaataag ttcgtccaca gagaccttgc tgcccggaat tgcatggtag
3481 ccgaagattt cacagtcaaa atcggagatt ttggtatgac gcgagatatc tatgagacag
3541 actattaccg gaaaggaggg aaaggctgc tgccgtgcg ctggatgtct cctgagtccc
3601 tcaaggatgg agtcttcacc acttactgg acgtctggtc cttcgggtc gtcctctggg
3661 agatcgccac actggccgag cagcctacc agggcttgtc caacgagcaa gtccttcgct
3721 tcgtcatgga gggcggcctt ctggacaagc cagacaactg tcctgacatg ctgtttgaac
3781 tgatgcgcat gtgctggcag tataaccca agatgaggcc ttccttcctg gagatcatca
3841 gcagcatcaa agaggagatg gagcctggct tcgggaggt ctcttctac tacagcgagg
3901 agaacaagct gcccgagccc gaggagctgg acctggagcc agaaacatg gagagcgtcc
3961 cctggaccc ctcggcctcc tcgtcctccc tgccactgcc cgacagcac tcaggacaca
4021 aggccgagaa cggcccgggc cctgggtgc tggtcctccg cgccagttc gacgagagac
4081 agcttatgc ccacatgaac ggggcgca agaacgagcg ggcttgccg ctgccagt
4141 cttcgacctg ctgatcctg gatcctgaat ctgtgcaaac agtaacgtgt gcgcacgcg
4201 agcggggtgg gggggagag agagttttaa caatccattc acaagcctcc tgtacctcag
4261 tggatcttca gaactgccct tgctgcccgc gggagacagc ttctgcag taaaacacat
4321 ttgggatgtt ccttttttca atatgcaagc agcttttat tccctgccca aaccttaac
4381 tgacatgggc ctttaagaac cttaatgaca acattaata gcaagagagc acttgagaac
4441 cagtctcctc actctgtccc tgtccttccc tgttctcccct ttctctctcc tctctgcttc
4501 ataacggaaa aataattgcc acaagtccag ctggaagcc cttttatca gtttgaggaa
4561 gtggctgtcc ctgtggcccc atccaaccac tgtacacacc cgcctgacac cgtgggtcat
4621 tacaaaaaaa cacgtggaga tggaaatttt tacctttatc tttcacctt ctagggacat
4681 gaaatttaca aagggccatc gttcatccaa ggctgttacc attttaagc tgcctaattt
4741 tgccaaaatc ctgaactttc tccttcatcg gccggcgct gattcctgt gtcggaggc
4801 atgggtgagc atggcagctg gttgctccat ttgagagaca cgctgggac acactccgtc
4861 catccgactg cccctgctgt gctgctcaag gccacaggca cacaggtctc attgcttctg
4921 actagattat tatttggggg aactggacac aataggtctt tctctcagtg aaggtgggga
4981 gaagctgaac cggcttcct gcctgcctc ccagccccc tgccaaccc caagaatct
5041 ggtggccatg ggccccgaag cagcctggcg gacaggcttg gagtcaaggg gcccatgcc
5101 tgcttctctc ccagcccag ctccccgcc cgcccaag gacacagatg ggaagggtt
5161 tccagggact cagcccact gttgatcag gttgcaagg aaagaaattc aaacaccaca
5221 acagcagtaa gaagaaaagc agtcaatgga ttcaagcatt ctaagcttg ttgacatttt
5281 ctctgttcct aggacttctt catgggtctt acagttctat gttagccat gaaacattg
5341 catcacatc gtctttaaatg tcactttat aacttttta cggttcagat attcatctat
5401 acgtctgtac agaaaaaaaa aagtgctat ttttttgtt cttgatcttt gtggatttaa
5461 tctatgaaaa ccttcaggtc caccctctcc cctttctgct cactccaaga aacttcttat
5521 gctttgtact agagtgcgtg actttcttcc tcttttccg gtaatggata cttctatcac
5581 ataatttgcc atgaactgtt ggatgccttt ttataaatac atccccatc cctgctccca
```

FIG. 1K

```
5641 cctgcccctt tagttgtttt ctaacccgta ggctctctgg gcacgaggca gaaagcaggc
5701 cgggcaccca tcctgagagg gccgcgctcc tctcccagc ctgcctcac agcattggag
5761 cctgttacag tgcaagacat gatacaaact caggtcagaa aaacaaggt taaatattc
5821 acacgtcttt gttcagtgtt tccactcacc gtggttgaga agctcaccc tctcttccc
5881 ttgcctttgc ttaggttgtg acacacatat atatatattt ttttaattct tgggtacaac
5941 agcagtgtta acgcagaca ctaggcatt ggattactat tttcttaat ggctatttaa
6001 tccttccatc ccacgaaaaa cagctgctga gtccaaggga gcagcagc gtggtccggc
6061 agggcctgtt gtggccctcg ccacccct caccggaccg actgacctgt ctttggaacc
6121 agaacatccc aagggaactc cttcgcactg gtgttgagtg ggaccccggg atccaggctg
6181 gccaggggtg gcacccctcag ggtgtgccc gctggagtgc taggtggagg tagcacagac
6241 gccacggtgg cccaagagcc ccttgcttc ttgctggggg accagggctg tggtgctggc
6301 ccactttccc tcggccagga atccaggtcc ttgggccca ggggtcttgt cttgttcat
6361 tttagcact tctcagcaga gagatgacag cacaagagtt gctctggga tagaaatgtt
6421 taggagtaag aacaaagctg ggatacggtg attgctagtt gtgactgaag attcaacaca
6481 gaaagaaag ttataccggc ttttttgctg gtcagcagtt tgtcccacctg ctttctctag
6541 tctctatccc atagcgtgtt ccctttaaaa aaaaaaaaaa ggtattatat gtaggagttt
6601 tcttttaatt tattttgtga taaattacca gtttcaatca ctgtagaaaa gcccattat
6661 gaattaaat ttcaaggaaa gggtgtgtgt gtgtgtatgt gtgggtgtg tgtgtgtgag
6721 agtgatggga cagttcttga ttttttgggt tttttttccc ccaaacattt atctacctca
6781 ctcttatttt ttatatgtgt atatagacaa aagaatacat ctcaccttc tcagcacctg
6841 acaataggcc gtgatactg gtaacctcat ccacgccaca gggccacac ccaggtgatg
6901 caggggaag ccaggctgta ttccggggtc aaagcaacac taactcacct ctctgctcat
6961 ttcagacagc ttgcttttt ctgagatgtc ctgttttgtg ttgcttttt tgtttttgttt
7021 tctatcttgg ttccaccaa ggtgttagat ttctcctcct cctagccagg tggcctgtg
7081 aggcaacga gggcaccaga gcacacctgg gggagccac aggctgtccc tggctggttg
7141 tctttggaac aaaactgttc tgtgcagatg gaatgaccaa cacatttgt ccttaagaga
7201 gcagtggttc ctcaggttct gaggagagga aggtgtccag gcagcaccat ctctgtgcga
7261 atcccaggg taaaggcgtg gggtattggg tttgctcccc ttgctgctgc tccatcccgt
7321 caggaggctc gcgctgaggc aggaccgtgc ggccatggct gctgcattca ttgagcacaa
7381 aggtgcagtt gcagcagcag ctggagagca agagtcaccc agctgtgcg ccagaatgca
7441 gaggctcctg acctcacagc cagtccctga taaacacac gcaggagcag agtccctcc
7501 ccctccaggc tgccctctca agttctccct cacctcctc cctagggta gacagagatg
7561 taccaaacct tcgggtgga aagccagtg gccggcgcc aggctgtgg cgtcacgcc
7621 ccccgccag ggctgtacct ccgtctccct ggtcctgatg ctcacaggac agacggctcg
7681 ctccctctt ccagcagctg ctcttacagg cactgatgat ttcgctggga agtgtggcgg
7741 gcagttgc ctaagcgtgg atggctcctc ggcaattcca gctaagtga aggcgctcag
7801 gagcctcctg ctggaacgcg accatctct cccaggacc cgggatctt aaggtcattg
7861 agaaatactg ttggatcagg gttttgttct tccacctgt aggtgaccc ttggaataac
7921 ggctctctt ctcgtgcaca tacttaccgg tttccacaac tggatttcta cagatcattc
7981 agctggttat aagggttttg ttaaactgt ccgagttact gatgtcatt tgttttgtt
8041 ttatgtaggt agcttttaag tagaaaacac taacagtgta gtgccatca tagcaaatgc
8101 ttcagaaaca cctcaataaa agagaaaact tggcttgtgt gatggtgcag tcacttact
8161 ggaccaacc acccaccttg actataccaa ggcatcatct atccacagtt ctagcctaac
8221 ttcatgctga ttttctgcc tcttgatttt tctctgtgtg ttccaaataa tcttaagctg
8281 agttgtggca ttttccatgc aacctccttc tgccagcagc tcacactgct tgaagtcata
8341 tgaaccactg aggcacatca tggaattgat gtgagcatta agacgttctc ccacacagcc
8401 cttccctgag gcagcaggag ctggtgtgta ctggagacac tgttgaactt gatcaagacc
8461 cagaccaccc caggtctcct tgtgtggatg tcatgacgtt tgacataccc ttggaacgag
8521 cctcctcctt ggaagatgga agaccgtgtt cgtggccgac ctggcctctc ctggcctgtt
8581 tcttaagatg cgggagtcaca tttcaatggt acgaaaagtg gcttgtaaa atagaagagc
8641 agtcactgtg gaactaccaa atggcagat gtcggtgca cattgggtg ctttgggata
8701 aaagatttat gagccaacta ttctctggca ccagattcta ggcagtttg ttccactgaa
8761 gcttttccca cagcagtcca cctctgcagg ctggcagccg aatggcttgc cagtggctct
```

FIG. 1L

```
8821 gtggcaagat cacactgaga tcgatgggtg agaaggctag gatgcttgcc tagtgttctt
8881 agctgtcacg ttggctcctt ccagggtggc cagacggtgt tggccattcc cttctaaaac
8941 acaggcgcca tcctggtgac agtgaccgc cgtggtatgc cttggcccat tccagcagtc
9001 ccagttatgc atttcaagtt tggggttgt tcttttcgtt aatgttcctc tgtgttgtca
9061 gctgtcttca ttcctgggc taagagcat tgggagatgt ggaccagaga tccactcctt
9121 aagaaccagt ggcgaaagac actttcttc ttcactctga agtagctggt ggtacaaatg
9181 agaacttcaa gagaggatgt tattagact gaacctctgt tgccagagat gctgaagata
9241 cagaccttgg acaggtcaga gggttcatt tttggcctt atcttagatg actggttgcg
9301 tcattggag aagtgagtgc tccttgatgg tggaatgacc gggtggtggg tacagaacca
9361 ttgtcacagg gatcctggca cagagaagag ttacgagcag cagggtgcag ggcttggaag
9421 gaatgtgggc aaggttttga acttgattgt tcttgaagct atcagaccac atcgaggctc
9481 agcagtcatc cgtgggcatt tggttcaac aaagaaacct aacatcctac tctggaaact
9541 gatctggag ttaaggcgaa ttgttcaaga acacaaacta catcgacctc gtcagttgtc
9601 agttctgggg catgacttta ggttttgtt tctgcgagaa cataacgatc actcattttt
9661 atgtccacg tgtgtgtc cgcatcttc tggtcaacat tgtttaact agtcactcat
9721 tagcgttttc aatagggctc ttaagtccag tagattacgg gtagtcagtt gacgaagatc
9781 tggtttacaa gaactaatta aatgtttcat tgcattttg taagaacaga ataattttat
9841 aaaatgtttg tagtttataa ttgccgaaaa taatttaaag acacttttt tttctctgtg
9901 tgtgcaaatg tgtgtctgtg atccatttt ttttttttt ttaggacac ctgtttacta
9961 gctagcttta caatatgcca aaaaggatt tctccctgac cccatccgtg gttcaccctc
10021 tttccccct atgctttg ccctagttta taacaaagga atgatgatga tttaaaagt
10081 agttctgtat cttcagtatc ttggtcttc agaaccctct ggttggaag gggatcattt
10141 tttactggtc atttccttt ggagtgtagc tactttaaca gatggaaaga acctcattgg
10201 ccatggaaac agccgaggtg ttggagcca gcagtgcatg gcacgttcg gcatctggct
10261 tgattggtct ggctgccgtc attgtcagca cagtgccatg gacatgggaa gacttgactg
10321 cacagccaat ggttttcatg atgattacag cacacacagt gatcacataa acgatgacag
10381 ctatggggca cacaggccat ttgcttacat gctctgtatc atgactgatt actgctttgt
10441 tagaacacag aagagccct attttattta aggcagaacc ccgaagatac gtatttcgaa
10501 tacgaaaaag aatttttaat aaaactata acatacacaa aaattggttt taaagttgac
10561 tccacttcct ctaactccag tggattgttg gccatgtctc ccaactcca caatatctct
10621 atcatgggaa acacctgggg ttttgcgct acataggaga aagatctgga aactatttgg
10681 gttttgtttt caacttttca tttggatgtt tggcgttgca cacacacatc caccggtgga
10741 agagcgcc ggtgaaaaca cctgtctgct ttataagcca gtgaggttga ggtgagagt
10801 ttgccagagt ttgtctacct ctgggtatcc ctttgtctgg gataaaaaaa atgaaaccag
10861 aaggcgggat ggaatggatg caccgcaaat aatgcatttt ctgagttttc ttgttaaaaa
10921 aaaatttttt taagtaagaa aaaaaaaggt aataacatgc ccaatttgtt acataaaatg
10981 acttctgtgt tataaattat tcctaaaaaa tcctgtttat ataaaaaatc agtagatgaa
11041 aaaaatttca aagtgttttt gtatattctg ttgtaagaat ttattcctgt tattgcgata
11101 tactctggat tcttacata atggaaaaaa gaaactgtct attgaatg gctgaagcta
11161 aggcaacgtt agttctctt actctgcttt ttctagtaa agtactacat ggttaagtt
11221 aaataaaata attctgtatg ca
```

FIG. 1M

BTG2

```
LOCUS       NM_006763               2718 bp    mRNA    linear   PRI 25-SEP-2007
DEFINITION  Homo sapiens BTG family, member 2 (BTG2), mRNA.
ACCESSION   NM_006763
VERSION     NM_006763.2  GI:28872718
KEYWORDS
SOURCE      Homo sapiens (human)

ORIGIN
        1 cagggtaacg ctgtcttgtg gacccgcact tcccacccga gacctctcac tgagcccgag
       61 ccgcgcgcga catgagccac gggaagggaa ccgacatgct cccggagatc gccgccgccg
      121 tgggcttcct ctccagcctc ctgaggaccc ggggctgcgt gagcgagcag aggcttaagg
      181 tcttcagcgg ggcgctcgag gaggcactca gagcacta caaacaccac tggttttccg
      241 aaaagccgtc caagggctcc ggctaccgct gcattcgcat caaccacaag atggacccca
      301 tcatcagcag ggtggccagc cagatcggac tcagcagcc ccagtgcac cagtgctgc
      361 ccagcgagct gacctgtgg gtggacccc atgaggtgtc ctaccgcatt ggggaggacg
      421 gatccatctg cgtcttgtac gaggaggccc cactgccgc ctgctgtggg ctcctcacct
      481 gcaagaaccc agtgctgctg ggcggagca gccctcgaa gaactacgtg atggcagtct
      541 ccagctaggc cctccgcc ccgcctggg cgcgccgtg ctatgctgc cgtgacaaca
      601 ggccaccaca taccctcaacc tggggaactg tattttaaa tgaagagcta tttatatata
      661 ttattttttt ttaagaaagg aggaaaagaa accaaaagtt ttttttaaga aaaaaatcc
      721 ttcaagggag ctgcttggaa gtggcctcc caggtgctt tggagagaac tgttgcgtgc
      781 ttgagtctgt gagccagtgt ctgcctatag gaggggagc tgttagggg tagacctagc
      841 caaggagaag tgggagacgt ttggctagca cccaggaag atgtgagagg gagcaagcaa
      901 ggttagcaac tgtgaacaga gaggtcggga tttgccctgg ggaggaaga gaggccaagt
      961 tcagagctct ctgtctcccc cagccagaca cctgcatccc tggtcctct attactcagg
     1021 ggcattcatg cctggactta aacaatacta tgttatcttt ttttatttt ttctaatgag
     1081 gtcctgggca gagagtgaaa aggcctctcc tgattcctac tgtcctaagc tgcttttctt
     1141 gaaatcatga cttgtttcta attctaccct caggggcctg tagatgttgc ttttcagcca
     1201 ggaatctaaa gctttgggtt ttctgagggg ggggaggagg gaactgagg ttattggggt
     1261 taggatggaa gggaactctg cacaaaaacct ttgctttgct agtgctgctt tgtgtgtatg
     1321 tgtggcaaat aattttgggg tgattttgcaa tgaaattttg ggacccaaag agtatccact
     1381 gggatggttt tttggccaaa actcttcctt ttggaaccac atgaaagtcc tgatgctgct
     1441 gccatgatcc cttgagagg tggctcaaaa gctacaggga actccaggtc ctttattact
     1501 gccttcttt caaaagcaca actctctctct aacctcccc tcccttcc cttctggtcg
     1561 ggtcatagag ctaccgtatt ttctaggaca agagttctca gtcactgtgc aatatgccc
     1621 ctggtcccca ggagggtctg gaggaaaact ggctatcaga acctcctgat gccctggtgg
     1681 gcttagggaa ccatctctcc tgctctcctt gggatgatgg ctgctagtc agccttgcat
     1741 gtattccttg gctgaatggg agagtgccc atgttctgca agactacttg gtattcttgt
     1801 agggccgaca ctaaataaag gccaaacctt gggcactgtt ttttctccct ggtgctcaga
     1861 gcacctgtgg gaaaggttgc tgtctgtctc agtacaatcc aaatttgtcg tagactgtg
     1921 caatatatac tgttgtgggt tggagaaaag tggaaagcta cactgggaag aaactccctt
     1981 ccttcaattt ctcagtgaca ttgatgaggg gtcctcaaaa gacctgagt ttcccaaacc
     2041 gaatcacctt aagaaggaca gggctagggc attggccag gatggcacc ctcctgctgt
     2101 tgccccttag tgaggaatct tcacccact tcctctaccc ccaggttctc ctcccacag
     2161 ccagtcccct ttcctggatt tctaaactgc taatttga ctcaaaggtg ctatttacca
     2221 aacactctcc ctaccatte ctgccagctc tgcctccttt tcaactctcc acatttgta
     2281 ttgcttccc agacctgctt ccagtcttta ttgctttaaa gttcactttg ggcccacaga
     2341 cccagagct aatttctgg tttgtgggtt gaaacaaagc tgtgaatcac tgcaggctgt
     2401 gttcttgcat cttgtctgca aacaggtccc tgcttttta gaagcagct catggtctca
```

FIG. 1N

```
2461 tgcttaatct tgtctctctt ctcttcttta tgatgttcac tttaaaaaca acaaaacccc
2521 tgagctggac tgttgagcag gcctgtctct cctattaagt aaaaataaat agtagtagta
2581 tgtttgtaag ctattctgac agaaaagaca aaggttacta attgtatgat agtgttttta
2641 tatggaagaa tgtacagctt atggacaaat gtacaccttt ttgttacttt aataaaaatg
2701 tagtaggata aaaaaaaa
```

FIG. 10

LMO2

```
LOCUS       NM_005574               2304 bp    mRNA    linear   PRI 30-SEP-
2007
DEFINITION  Homo sapiens LIM domain only 2 (rhombotin-like 1) (LMO2), mRNA.
ACCESSION   NM_005574
VERSION     NM_005574.2  GI:6633806
KEYWORDS
SOURCE      Homo sapiens (human)

ORIGIN
        1 gaattcgtcc aaactgagga tcacaagtct ccacattctg agtaggagga tgagggtctg
       61 agttaggatt tgggtcctgc agggcttgct aaggaatccc ctgatggcct aggattccac
      121 gcagagcaca tctggtgtga gagagctcgc tgcaagggtg aaggctccgc cctatcagat
      181 agacaaccag gccaccaaga ggccagccc tccaaactct ggattgcaa catcctcaaa
      241 gaacagcaac gggccttgag cagaattgag aaggaaatac ccccaccctgc cctcagccgt
      301 taagtgggct ttgctattca caagggcctc tggtgtcct ggcagagagg ggagatggca
      361 caggcaccag gtgctagggt gccagggcct ccgagaagg aacaggtgca aagcaggcaa
      421 ttagcccaga aggtatccgt ggggcaggca gctagatct gatggggaa gccaccagga
      481 ttacatcatc tgctgtaaca actgctctga aagaagata tttttcaacc tgaacttgca
      541 gtagctagtg gagaggtagg aaaaaggaaa tgaaacagag acagagggaa gcctgagcca
      601 aaatagacct tcccgagaga ggaggaagcc cggagagaga cgcacggtcc cctccccgcc
      661 cctaggccgc cgccccctct ctgccctcgg cggcgagcag ggcgctgca cccggggccg
      721 gaaaggtgcc aggggctccg ggcggccggg cggcgcaca ccatcccgcc gggcggcgcg
      781 gagccggcga cagcgcgca gaggaccgg gcggtggcgg cggcgggacc gggatggaag
      841 ggagcgcggt gactgtcctt gagcgcggag gggcgagctc gccggcggag gccgagcaag
      901 cggaggcagg agggcggcg acggcggcgg cggcggcggc gccgagcac ccgaggggt
      961 ccgaagcggc agccggcgc acaaagggga gcgccccgc gcgccccgc cgccccgcac
     1021 ccgcctccc tccccaatgt cctcggccat cgaaaggaag agcctggacc ctcagagga
     1081 accagtggat gaggtgctgc agatccccc atccctgctg acatgcggcg gctgccagca
     1141 gaacatcggg gacgctact tcctgaaggc catgaccag tactggcacg aggactgcct
     1201 gagctgcgac ctctgtggct gccggctggg tgaggtggg cggcgcttct actacaaact
     1261 gggcggaag ctctgccgga gagactattct caggcttttt gggcagacg gtctctgcgc
     1321 atcctgtgac aagcggatcc gtgcctatga gatgacaatg cgggtgaaag acaaagtgta
     1381 tcacctggaa tgtttcaagt gtgccgcctg tcagaagcat ttctgtgtag gtgacagata
     1441 cctcctcatc aactctgaca tagtgtgcga acaggacatc tacgagtgga ctaagatcaa
     1501 tgggatgata taggcccgag tccgggca tctttgggga ggtgttcact gaagacgccg
     1561 tctccatggc atcttgtct tcactcttag gcacttggg ggtttgaggg tgggtaagg
     1621 gattcttag gggatggtag acctttattg ggtatcaaga catagcatcc aagtggcata
     1681 attcagggcc tgacacttca aagtgacaga aggacagcc cttgggaagg aacttatggc
     1741 cacagcccat ccatagtaac tgacatgatt agcagaagaa aggaacattt aggggcaagc
     1801 aggcgctgtg ctatcatgat ggaatttcat atctacagat agagagttgt tgtgtacaga
     1861 cttgttgtga cttgacgct tgcgaactag agatgtgcaa ttgatttctt ttcttcctgg
     1921 cttttaact ccctgttttc aatcactgtc ctcacacaaa gggaaggaca gaaggagag
     1981 tggccattct ttttctttg gcccccttcc caaggcctta agctttggac ccaagggaaa
     2041 actcatgga gacgcatttc ggttgagaat ggaaaccaca acttttaacc aaagaattat
     2101 ttaaagcaat gctgatgaat cactgttttt agacacctc attttgaggg gaggagttcc
     2161 acagattgtt tctatacaaa tataaatctt aaaagttgt tcaactattt tattatccta
     2221 gattatatca aagtatttgt cgtgtgtaga aaaaaaaac agctctgcag gcttaataaa
     2281 aatgacagac tgaaaaaaaa aaaa
```

```
LOCUS       NM_000626              1300 bp    mRNA    linear   PRI 21-SEP-2008
DEFINITION  Homo sapiens CD79b molecule, immunoglobulin-associated beta
            (CD79B), transcript variant 1, mRNA.
ACCESSION   NM_000626
VERSION     NM_000626.2  GI:90193589

1 ctgcagccgg tgcagttaca cgttttcctc caaggagcct cggacgttgt cacgggtttg
   61 gggtcgggga cagagtggtg accatggcca ggctggcgtt gtctcctgtg cccagccact
  121 ggatggtggc gtgctgctg ctgctctcag ctgagccagt accagcagcc agatcggagg
  181 acggtaccg gaatccaaa ggtagtgctt gttcgcggat ctggcagagc ccacgtttca
  241 tagccaggaa acggggcttc acggtgaaaa tgcactgcta catgaacagc gcctcaggca
  301 atgtgagctg gtctctggaag caggagatgg acgagaatcc ccagcagctg aagctggaaa
  361 agggccgcat ggaagagtcc cagaacgaat ctctggccac cctcaccatc caaggcatcc
  421 ggtttgagga caatggcatc tacttctgtc agcagaagtg caacaacacc tggagggtct
  481 accagggctg cggcacagag ctgcgagtca tgggattcag caccttggca cagctgaagc
  541 agaggaacac gctgaaggat ggtatcatca tgatccagac gctgctgatc atcctcttcc
  601 tcatcgtgcc tatcttcctg ctgctggaca aggatgacag caaggctggc atggaggaag
  661 atcacaccta cgagggctg gacattgacc agacagccac ctatgaggac atagtgacgc
  721 tgcggacagg ggaagtgaag tggtctgtag gtgagcacc aggccaggag tgagagccag
  781 gtcgcccat gacctgggtg caggtccct ggcctcagtg actgttcgg agctgctgg
  841 ctcatggccc aaccagtttc ctggacccc cagctggcct ctgaagctgg cccaccagag
  901 ctgccatttg tctccagccc ctggtcccca gctcttgcca agggcctgg agtagaagga
  961 caacagggca gcaacttgga gggagttctc tggggatgga cgggaccag ccttctgggg
 1021 gtgctatgag gtgatccgtc cccacacatg ggatgggga ggcagagact gatccagagc
 1081 ccgcaaatgg actcggagcc gagggcctcc cagcagagct tgggaagggc catggaccca
 1141 actgggcccc agaagagcca caggaacatc attcctctcc cgcaaccact cccacccag
 1201 ggaggccctg gcctccagtg ccttccccg tggaataaac ggtgtgtcct gagaaaccac
 1261 aaaaaaaaa aaaaaaaaa aaaaaaaaa aaaaaaaaa
```

```
LOCUS       NM_000610               5748 bp    mRNA    linear   PRI 23-OCT-2008
DEFINITION  Homo sapiens CD44 molecule (Indian blood group) (CD44),
            transcript variant 1, mRNA.
ACCESSION   NM_000610
VERSION     NM_000610.3  GI:48255934

1 gagaagaaag ccagtgcgtc tctgggcgca ggggccagtg gggctggag gcacaggcac
   61 ccgcgacac tccaggttcc ccgacccacg tcctggcag cccgattat ttacagcctc
  121 agcagagcac ggggcggggg cagggggcc cgcccgggag ggctgctact tcttaaaacc
  181 tctgcgggct gcttagtcac agdcccctt gcttgggtgt gtccttcgct cgctccctcc
  241 ctccgtctta ggtcactgtt ttcaactcg aataaaact gcagccaact tccgaggcag
  301 cctcattgcc cagcgcacc cagcctctgc caggttcggt ccgccatcct cgtccgtcc
  361 tccgccggcc cctgcccgc gccagggat cctccagcta cttcgccg cgcctccgt
  421 tgctccgga caccatggac aagtttggt ggcaccgagc ctgggcactg tgcctgtgc
  481 cgctgagcct ggcgcagatc gattgaata taacctgccg cttgcaggt gtattccacg
  541 tggagaaaaa tggtcgctac agcatctctc ggacggaggc cgctgacctc tgcaaggctt
  601 tcaatagcac cttgccaca atggccaga tggagaaagc tctgagcatc ggatttgaga
  661 cctgcaggta tgggttcata gaagggcacg tggtgattcc ccggatccac cccaactca
  721 tctgtgcagc aaacaacaca ggggtgtaca tcctcacatc caacacctcc cagtatgaca
  781 catattgctt caatgcttca gctccacctg aagaagattg tacatcagtc acagcctgc
  841 ctaatgcctt tgatggacca attaccataa ctattgttaa ccgtgatggt accgctatg
  901 tccagaaagg agaatacaga acgaatcctg aagacatcta cccagcaac cctactgatg
  961 atgacgtgag cagcggtcc tccagtgaaa ggagcagcac ttcaggaggt tacatcttt
 1021 acacctttc tactgtaacc cccatcgcc acggaagaca tcctggaac accgacagca
 1081 cagacagaat ccctgctacc actttgatga gaactagtgc tacagcaact gagacagcaa
 1141 ccaagaggca agaaactgg gattggtttc catggttgtt tctaccatca gagtcaaaga
 1201 atcatctcca cacacaca caatggctg gtacgtcttc aaatacate tcagcaggct
 1261 gggagccaaa tgaagaaat gaagatgaaa gagacagaca cctcagtttt tctggatcag
 1321 gcattgatga tgatgaagat tttatctca gcaccatttc aaccaacca cgggcttttg
 1381 accacacaaa acagaaccag gacggaccc agtggaacc aagccattca aatcggaag
 1441 tgctacttca gacaaccaca aggatgactg atgtagacag aaatggcacc actgttatg
 1501 aaggaaactg gaacccagaa gcacaccctc cctcattca ccatgagcat catgaggaag
 1561 aagagcccac acattctaca agcaaatcc aggcaactcc tagtagtaca acggaagaa
 1621 cagctaccca gaaggaacag tggtttggca cagatgggca tgagggatat gccaaacac
 1681 ccaaagaaga ctccattcg acaacaggga cagtgcagc ctcagctcat accagccatc
 1741 caatgcaagg aaggacaaca ccagcccag ggacagttc ctggactgat ttcttcaacc
 1801 caatgtcaca cccatggga cgaggtcatc aagcaggaag aaggatggat atggactcca
 1861 gtcatagtat aacgcttcag cctactgcaa atccaacac aggtttggtg gaagatttgg
 1921 acaggacagg acctctttca atgacaacgc agcagagtaa ttctcagagc ttctctacat
 1981 cacatgaagg gttggaagaa gataaagacc atccaacaac ttctactctg acatcaagca
 2041 ataggaatga tgtcacaggt ggaagaagag accaaatca ttctgaaggc tcaactactt
 2101 tactggaagg ttatacctct cattaccac acacaaggga aagcaggacc ttcatccag
 2161 tgacctgaac taagactggg tcctttggag ttactgcagt tactgttgga gattccaact
 2221 ctaatgtcaa tcgttcctta tcaggagacc aagacactt ccaccccag ggggggtcc
 2281 ataccactca tggatctgaa tcagatgac actcacatgg gagtcaagaa ggtgggagcaa
 2341 acacaacctc tggtcctata aggatgggcc aaattccaga atggctgatc atcttggcat
 2401 ccctcttggc cttggcttg attcttgcag ttgcattgc agtcaacagt cgaagaggt
 2461 gtgggcagaa gaaaagcta gtgatcaaca gtggcaatgg agctgtggag gacagaaagc
 2521 caagtggact caacggagag gccagcaagt ctcaggaaat ggtgcattg gtgaacaagg
 2581 agtgtcaga aactccagac cagtttatga cagctgatga gacaaggaac ctgcagaatg
 2641 tggacatgaa gattggggtg taaaacctac accattatct tggaagaaa caacgttgg
```

FIG. 1R

```
2701 aaacataacc attacaggga gctgggacac ttaacagatg caatgtgcta ctgattgttt
2761 cattgcgaat cttttttagc ataaatttt ctactcttt tgtttttgt gttttgttct
2821 ttaaagtcag gtccaattg taaaacagc attgctttct gaaattaggg cccaattaat
2881 aatcagcaag aatttgatcg ttccagttcc cactggagg ccttcatcc ctgggtgtg
2941 ctatggatgg cttctaacaa aaactacaca tatgtattcc tgatcgccaa ccttcccc
3001 accagctaag gacatttccc agggttaata gggcctggtc cctgggagga aatttgaatg
3061 ggtccatttt gcccttccat agcctaatcc ctgggcattg cttccactg aggttggggg
3121 ttggggtgta ctagttacac atcttcaaca gaccccctct agaaattttt cagatgcttc
3181 tgggagacac ccaaagggtg aagctattta tctgtagtaa actatttatc tgtgtttttg
3241 aaatattaaa ccctggatca gtcctttgat cagtataatt tttaaagtt actttgtcag
3301 aggcacaaaa gggtttaaac tgattcataa taaatatctg tacttcttcg atcttcactt
3361 tttgtgctgt gattcttcag tttctaaacc agcactgtct gggtccgtac aatgtatcag
3421 gaagagctga gaatggtaag gagactcttc taagtcttca tctcagagac cctgagttcc
3481 cactcagacc cactcagcca aatctcatgg aagacaagg aggggcagcac tgttttttgtt
3541 ttttgttttt tgttttttt ttttgacact gtccaaggt tttccatcct gtcctggaat
3601 cagagttgaa agctgaggag cttcagcctc ttttatggtt taatggccac ctgttctctc
3661 ctgtgaaagg cttgcaaag tcacattaag tttgcatgac ctgttatccc tggggcccta
3721 tttcatagag gctggcccta ttagtgattt ccaaaaacaa tatggaagtg cctttgatg
3781 tcttacaata agagaagaag ccaatggaaa tgaaagagat tggcaaaggg gaaggatgat
3841 gccatgtaga tcctgtttga catttttatg gtgtattg taaacttaaa cacacagtg
3901 tctgttcttg atgcagttgc tatttaggat gagttaagtg cctggggagt ccctcaaaag
3961 gttaaaggga ttccatcat tggaatctta tcaccagata ggcaagttta tgaccaaaca
4021 agagagtact ggctttatcc tctaacctca tattttctcc cacttggcaa gtccttgtg
4081 gcatttattc atcagtcagg gtgtccgatt ggtcctagaa cttccaaagg ctgcttgtca
4141 tagaagccat tgcatctata aagcaacggc tcctgttaaa tggtatctcc tttctgaggc
4201 tcctactaaa agtcatttgt tacctaaact tatgtgctta acaggcaatg cttctcagac
4261 cacaaagcag aaagaagaag aaagctcct gactaaatca gggctgggct tagacagagt
4321 tgatctgtag aatatcttta aaggagagat gtcaacttc tgcactattc ccagcctatg
4381 ctcctccctg tctaccttct ccctccctc ttcccctca cttcaccca caatcttgaa
4441 aaacttcctt tcttcttgt gaacatcatt ggcagatcc attttcagtg gtctggattt
4501 ctttttattt tcttttcaac ttgaaagaaa ctggacatta ggccactatg tgttgttact
4561 gccactagtg ttcaagtcc tcttgtttc ccagagattt cctgggtctg ccagaggcc
4621 agacaggctc actcaagctc tttaactgaa aagcaacaag ccactcagg acaaggttca
4681 aaatggttac aacagcctct acctgtcgcc ccagggagaa agggtagtg ataacagtct
4741 catagccaga gatggttttc cactccttct agatattccc aaaaagaggc tgagacagga
4801 ggttattttc aatttattt tggaattaaa tacttttttc cctttattac tgttgtagtc
4861 cctcacttgg atatccctct gtttccaaga tagaaataag ggaggtctag agcttctatt
4921 ccttggccat tgtcaacgga gagctggcca agtcttcaca aaccttgta acattgcctg
4981 aagtttatgg aataagatgt atttcactc ccttgatctc aagggcgtaa ctctggaagc
5041 acagcttgac tacacgtcat ttttaccaat gatttcagg tgacctgggc taagtcattt
5101 aaactgggtc tttataaag taaaggcca acatttaatt attttgcaaa gcaactaag
5161 agctaaagat gtaattttc ttgcaattgt aaatctttg tgtctcctga agacttcct
5221 taaaattagc tctgagtgaa aaatcaaag agacaaaga catcttcgaa tccatattc
5281 aagcctggta gaattggctt ttctagcaga acctttccaa aagttttata ttgagattca
5341 taacaacacc aagaattgat tttgtagcca acattcattc aatactgtta tatcagagga
5401 gtaggagaga ggaaacattt gactatctg gaaagcaaa atgtacttaa gaataagaat
5461 aacatggtcc attcacctt atgttataga tatgtcttg tgtaaatcat ttgttttgag
5521 ttttcaaaga atagcccatt gttcattctt gtgctgtaca atgaccactg ttattgttac
5581 tttgactttt cagagcacac cctcctctg gttttgtat atttattgat ggatcaataa
5641 taatgaggaa agcatgatat gtatattgct gagttgaaag cacttattgg aaaatattaa
5701 aaggctaaca ttaaagact aaggaaaca gaaaaaaaaa aaaaaaa
```

FIG. 1S

CTSC

```
LOCUS       NM_001814               1924 bp    mRNA    linear   PRI 06-APR-2008
DEFINITION  Homo sapiens cathepsin C (CTSC), transcript variant 1, mRNA.
ACCESSION   NM_001814
VERSION     NM_001814.3  GI:167000478

1 cgtagctatt ccaaggcgcg cgcacgtgg tggactcacc gctagccgc agcgctggc
   61 tcctggtaa ttcttcact cttttctcag ctccctgcag catgggtgct gggccctcct
  121 tgctgctcgc cgccctcctg ctgctctct ccggcgacgg cgccgtgcgc tgcgacacc
  181 ctgccaactg cacctatctt gacctgctgg gcacctgggt cttccaggtg ggctccagcg
  241 gttccagcg cgatgtcaac tgctcggtta tgggaccaca agaaaaaaa gtagtggtgt
  301 acctttcagaa gctggataca gcatatgatg acttggcaa ttctggccat ttcaccatca
  361 tttacaacca aggctttgag attgtgttga tgactacaa gtggtttgcc tttttaagt
  421 ataaagaaga gggcagcaag gtgaccactt actgcaacga gacaatgact gggtgggtgc
  481 atgatgtgtt gggccggaac tggcttgtt tcacggaaa gaaggtggga actgcctctg
  541 agaatgtgta tgtcaacata gcacaccta agaattctca ggaaaagtat tctaataggc
  601 tctacaagta tgatcacaac tttgtgaaag ctatcaatgc cattcagaag tcttggactg
  661 caactacata catggaatat gagactctta cctgggaga tatgattagg agaagtggtg
  721 gccacagtcg aaaaatccca aggcccaaac ctgacccct gactgctgaa atacagcaaa
  781 agatttgca tttgccaaca tcttgggact ggagaaatgt tcatgtatc aattttgtca
  841 gtcctgttcg aaaccaagca tcctgtggca gctgctactc atttgcttct atgggtatgc
  901 tagaagcgag aatccgtata ctaaccaaca atttctagac cccaatccta agccctcagg
  961 aggttgtgtc tgtagccag tatgctcaag gctgtgaagg cggcttccca taccttattg
 1021 caggaaagta cgcccaagat tttggctgg tggaagaagc ttgcttccc tacacaggca
 1081 ctgattctcc atgcaaaatg aaggaagact gctttcgtta ttactcctct gagtaccact
 1141 atgtaggagg tttctatgga ggctgcaatg aagccctgat gaagcttgag ttggtccatc
 1201 atgggccaat ggcagttgct ttgaagtat atgatgactt cctccactac aaaaagggga
 1261 tctaccacca cactggtcta agagaccctt tcaacccctt tgagctgact aatcatgctg
 1321 ttctgcttgt gggctatggc actgactcag cctctggat ggattactgg attgttaaaa
 1381 acagctgggg cacggctgg ggtgagaatg gctacttccg gatccgcaga ggaactgatg
 1441 agtgtgcaat tgagagcata gcagtggcag ccaccaat tcctaattg tagggtatgc
 1501 cttccagtat ttcataatga tctgcatcag ttgtaaaggg gaattggtat attcacagac
 1561 tgtagacttt cagcagcaat ctcagaagct tacaaataga tttccatgaa gatatttgtc
 1621 ttcagaatta aaactgccct taattttaat ataccttca atgggcaact ggccatttt
 1681 ttctaagtat tcattaagt gggattttc tggaagatgg tcagctatga agtaatagag
 1741 tttgcttaat cattgtaat tcaaacatgc tatatttttt aaaatcaatg tgaaaacata
 1801 gacttatttt taaattgtac caatcacaag aaaataatgg caataattat caaaactttt
 1861 aaaatagatg ctcatatttt taaaataaag ttttaaaaat aactgcaaaa aaaaaaaaaa
 1921 aaaa
```

FIG. 1T

UAP1

```
LOCUS       NM_003115               2344 bp    mRNA    linear   PRI 22-OCT-
2008
DEFINITION  Homo sapiens UDP-N-acteylglucosamine pyrophosphorylase 1
(UAP1), mRNA.
ACCESSION   NM_003115
VERSION     NM_003115.4  GI:156627574
```

```
   1 cggccgcctc cgcgtccgcg tcgtcgtctg tgctcccggc gctgacgtgt ctgggcggtc
  61 ggcttccact ccttcaggcg tcggcagcca ctagtcgtgg cgagagggc gggtgccgc
 121 gggctggagc tccacttggc ccccgctccc ggccgccgcc ggcgccgcc ccccccggat
 181 gagggtatat attcggagcg agcgcgggac gccgatgagt ggccgcgcgg aaggagctgg
 241 agacggtcgt agctgcggtc gcgccgagaa aggtttacag gtacatacat tacaccccta
 301 tttctacaaa gcttggctat tagagtatta tgaacattaa tgacctcaaa ctcacgttgt
 361 ccaaagctgg gcaagagcac ctactacgtt tctggaatga gcttgaagaa gcccaacagg
 421 tagaacttta tgcagagctc caggctatga actttgagga gctgaacttc ttttttccaaa
 481 aggccattga aggtttaaac cagtcttctc accaaaagaa tgtggatgca cgaatggaac
 541 ctgtgcctcg agaggtatta ggcagtgcta caagggatca agatcagctc caggcctggg
 601 aaagtgaagg acttttacag atttctcaga ataaagtagc agttcttctt ctagctggtg
 661 ggcaggggac aagactcggc gttgcatatc ctaaggggat gtatgatgtt ggtttgccat
 721 ccgtaagac actttttcag attcaagcag agcgtatcct gaagctacag caggttgctg
 781 aaaaatatta tggcaacaaa tgcattattc catggatat aatgaccagt ggcagaacaa
 841 tggaatctac aaaggagttc ttcaccaagc acaagtactt tggtttaaaa aagagaatg
 901 taatctttt tcagcaagga atgctcccg ccatgagttt tgatgggaaa attattttgg
 961 aagagaagaa caaagtttct atggctccag atgggaatgg tggtcttat cgggcacttg
1021 cagccagaa tattgtggag gatatggagc aaagaggcat ttggagcatt catgtctatt
1081 gtgttgacaa catattagta aaagtggcag acccacggtt cattggattt tgcattcaga
1141 aaggagcaga ctgtggagca aaggtggtag agaaaacgaa ccctacagaa ccagttggag
1201 tggtttgccg agtggatgga gttaccaggg tgctagaata tagtgagatt tccctggcaa
1261 cagctcaaaa acgaagctca gacggacgac tgctgttcaa tgcgggaac attgccaacc
1321 atttcttcac tgtaccattt ctgagagatg ttgtcaatgt tatgaacct cagtgcagc
1381 accatgtggc tcaaaagaag attccttatg tggataccca aggacagtta attaagcag
1441 acaaaccaa tggaataaag atggaaaaat ttgtcttga catcttccag ttgcaaaga
1501 agtttgtggt atatgaagta ttgcgagaag atgagttttc ccactaaag aatgctgata
1561 gtcagaatgg gaaagacaac cctactactg caaggcatgc tttgatgtcc ttcatcatt
1621 gctgggtcct caatgcaggg ggcattca tagatgaaaa tggctctgc cttccagcaa
1681 ttccccgctt gaaggatgcc aatgatgtac caatccatg tgaaatctct ctcttatct
1741 cctatgctgg agaaggatta gaaagttatg tggcagataa agaattccat gcacctctaa
1801 tcatcgatga gaatggagtt catgagctgg tgaaaaatgg tatttgaacc agataccaag
1861 ttttgtttgc cacgatagga atagttttta ttttgatag accaactgtg aacctacaag
1921 acgtcttgga caactgaagt ttaaatatcc acagggtttt atttgcttg ttgaactctt
1981 agagtattg caaacttccc aagatccaga tgactgaatt tcagatagca ttttatgat
2041 tcccaactca ttgaaggtct tatttatata atttttcca agccaaggag accattggcc
2101 atccaggaaa tttcgtacag ctgaaatata ggaggatgt tcaacatcag tttacttgca
2161 gctggaagca tttgttttg aagttgtaca tagtaataat atgtcattgt acatgttgaa
2221 aggttctat ggtactaaaa gtttgtttta tttatcaaa cattaagctt tttaagaaa
2281 ataattgggc agtgaaataa atgtatcttc ttgtctctgg agtgtcaaaa aaaaaaaaaa
2341 aaaa
```

FIG. 1U

PUS7

```
LOCUS       NM_019042               3484 bp    mRNA    linear   PRI 11-FEB-2008
DEFINITION  Homo sapiens pseudouridylate synthase 7 homolog (S. cerevisiae)
            (PUS7), mRNA.
ACCESSION   NM_019042 XM_496914 XM_499357
VERSION     NM_019042.3  GI:50727001

1 gtgcgagccc ggccgccggt gagtcggctg gagcgcatct ggtcctccgc gcggaaagcg
   61 ctgctttttgc ctggccgccc tagcgctgg ctcatccaag tggccttcgc cgctctcttg
  121 cgtcccaacc agagcgctgg ccacctcgcc gccagctca cgccgcgcc gcgctccag
  181 gctccgggtt ttcttaaatg tttcttgga gcttaaaga tggagatgac agaaatgact
  241 ggtgtgtcgc tgaaacgtgg ggcactggtt gtgaagata atgacagtgg agtcccagtt
  301 gaagagacaa aaaaacagaa gctgtcggaa tgcgtctaa ccaaaggtca agatgggcta
  361 cagaatgact ttctgtccat cagtgaagac gtgcctcggc ctcctgacac tgtcagtact
  421 gggaaaggtg gaaagaattc tgaggctcag ttggaagatg aggaagaaga ggaggaagat
  481 ggactttcag aggagtgcga ggaggaggaa tcagagagtt ttgcagcat gatgaagcat
  541 ggctcactg aggctgacgt aggcatcacc aagtttgtga gttctcatca agggttctcg
  601 ggaatcttaa aagaaagata ctcggactc gttgttcatg aaataggaaa agatggacgg
  661 atcagccatt tgaatgactt gtcattcca gtggatgagg aggaccttg agaagacata
  721 tttacagttt tgacagctga agaaaagcag cgattggaag agctccagct gttcaaaaat
  781 aaggaaacca gtgttgccat tgaggttatc gaggacacca agagaaaag aaccatcatc
  841 catcaggcta tcaaatctct gtttccagga ttagagacaa aaacagagga taggaggggg
  901 aagaaataca ttgtagccta ccacgcagct gggaaaaagg ctttggcaaa tccaagaaaa
  961 cattcttggc caaaatctag gggaagttac tgtccacttcg tactatataa ggaaaacaaa
 1021 gacaccatgg atgctattaa tgtactctcc aaatacttaa gagtcaagcc aaatatattc
 1081 tcctacatgg gaaccaaaga taaagggct ataacagttc aagaaattgc tgttctcaaa
 1141 ataactgcac aaagacttgc ccacctgaat aagtgcttga tgaactttaa gctagggaat
 1201 tccagctatc aaaaaaaccc actgaaattg ggagagcttc aaggaaaccc cttcactgtt
 1261 gttctcagaa atataacagg aacgatgac caagtacagc aagctatgaa ctctctcaag
 1321 gagattggat ttattaacta ctatggaatg caaagatttg gaaccacagc tgtccctacg
 1381 tatcaggttg gaagagctat actacaaaat tcctggacag aagtcatgga tttaatattg
 1441 aaaccctgct ctggagctga aaagggctac ttggttaaat gcagagaaga atgggcaaag
 1501 accaagacc caactgctgc cctcagaaaa ctacctgtca aaggtgtgt ggaagggcag
 1561 ctgcttcgag gactttcaaa atatggaatg aagaatatag ttctgtcatt tggcataata
 1621 cccagaaata atcgcttaac gtatattcat agctaccaaa gctatgtgtg gaataacatg
 1681 gtaagcaaga ggatagaaga ctatggacta aaacctgttc caggggacct cgttctcaaa
 1741 ggagccacag ccacctatat tgaggaagat gatgttaata attactctat ccatgatgtg
 1801 gtaatgccct tgctggttt cgatgttatc tacccaaaga taaaattca agaagcctac
 1861 agggaaatgc tcagagctga ccatcttgat attgacaaca tgagacacaa aattcgagat
 1921 tattccttgt caggggccta ccgaaagatc attattcgtc ctcagaatgt tagctgggaa
 1981 gtcgttgcat atgatgatcc caaaattcca cttttcaaca cagatgtgga ccacctagaa
 2041 gggaagacac caccagtttt tgcttctgaa ggcaaataca gggctctgaa aatggatttt
 2101 tctctacccc cttctacta cgctaccatg gccattcgag aagtgctaaa aatggatacc
 2161 agtatcaaga accagacgca gctgaaataca actggcttc gctgagcagt acctgtcca
 2221 cagattagaa aacgtacaca agtgttgct tcctggctca ctgtcgcatt ttgtcttagt
 2281 tcagctcat atatggattc caaatctttg taataaaaat tatttgtatt ttaagtttt
 2341 tattagctta aagaaataat ttgcaatatt tgtacatgta cacaaatcct gaggttctta
 2401 attttagctc agaatataaa ttagtcaaaa tacacttcag gtgcttaaat cagagtaaaa
 2461 tgtcagttt acaataataa aaaaaggact ttggttaaaa gtagcaggtt taggttttgc
 2521 tacattctca aaagacagca ggagtatttg acacatctgt gatggagtat acaacaatgc
 2581 attttaagag caaatgcaac aaaacaaatc tggactatgg ataaataatt tgagagctgc
 2641 cacccacaaa tataaataca gtactcatgc tgactgaaat aataagacat ctacaaattt
```

FIG. 1V

```
2701 ataaacaaaa agtgattgtc attatcctgc ttatgtacta gattcaggca agcattatag
2761 actttttggt tgcggtggct tttgcattta tattatcaat gccttgcagg aacgttgcat
2821 tgataggcac attttatttt tttatttttt ttttcgagac aggatctcac tctgtagcac
2881 aggctggatt gcagtgcaat cctgcaattc tcaatcttgc actgcagcct cgacctccta
2941 ggctccagtg actctcccac ctcagcctcc taagtagctg ggagtacagg cgcgcaccac
3001 cacgcctagc tgattttgt attttttgt agagacgggg gttggccat gttgccgagg
3061 ctaactcctg ggattacagg catgagctgt gctggccggg ttttttttc ttgatgtaaa
3121 cgtgtacagt tgtttatta gttaaggtct aatttttact ctaggtgcct tttatgttca
3181 gaactcttc cactggactg gtatttgctc aaaataaat aatggtagag aagaaaacta
3241 taaaaatgga caaggctttc tttatcagt agcgtttacc cttgtcacc agtggcttg
3301 gtattccat gtctggcatt gcataaactt ctctggtgtg aaaggataaa tatgcctttc
3361 taaagttgta tatcaaaatt gtatcaattt ttattttcta tgatttctag aaacaaatgt
3421 aataaatatt tttaaaatct cctttctact ggttatgtaa ataaatcaaa taaatatatc
3481 aaaa
```

```
LOCUS       NM_001771               3293 bp    mRNA    linear   PRI 16-MAR-2008
DEFINITION  Homo sapiens CD22 molecule (CD22), mRNA.
ACCESSION   NM_001771
VERSION     NM_001771.2  GI:157168354

1 cttttgctct cagatgctgc cagggtcact gaagagggaa gacacgcgga aacaggcttg
   61 cacccagaca cgacaccatg catctcctcg gccctggct cctgctcctg gttctagaat
  121 acttggcttt ctctgactca agtaaatggg ttttgagca ccctgaaacc ctctacgct
  181 gggaggggc ctgcgtctgg atccctgca cctacagagc cctagatggt gacctggaaa
  241 gcttcatcct gttccacaat cctgagtata caagaacac ctgaagtttt gatgggacaa
  301 gactctatga aagcacaaag gatgggaagg ttccttctga gcagaaaagg gtgcaattcc
  361 tgggagacaa gaataagaac tgcacactga gtatccaccc ggtgcacctc aatgacagtg
  421 gtcagctggg gctgaggatg gagtccaaga ctgagaaatg gatggaacga atacacctca
  481 atgtctctga aaggccttt ccacctcata tccagctccc tccagaaatt caagagtccc
  541 aggaagtcac tctgacctgc ttgctgaatt tctcctgcta tgggtatccg atccaattgc
  601 agtggctcct agaggggtt ccaatgaggc aggctgctgt cacctcgacc tccttgacca
  661 tcaagtctgt cttcacccgg agcgagctca gttctccc acagtggagt caccatggga
  721 agattgtgac ctgccagtt caggatgcag atgggaagtt cctctccaat gacacggtgc
  781 agctgaacgt gaagcacacc ccgaagtggg agatcaaggt cactcccagt gatgccatag
  841 tgagggaggg ggactctgtg accatgacct gcgaggtcag cagcagcaac ccggagtaca
  901 cgacggtatc ctggctcaag gatggaccct ctgaagaa gcagaataca ttcacgctaa
  961 acctgcgcga agtgaccaag gaccagagtg ggaagtactg ctgtcaggtc tccaatgacg
 1021 tgggccgggg aagtcggaa gaagtgttcc tgcaagtgca gtatgcccg gaacctcca
 1081 cggttcagat cctccactca ccggctgtgg agggaagtca agtcgagttt ctttgcatgt
 1141 cactggccaa tcctctttga acaaattaca cgtggtacca caatggaaaa gaaatgcagg
 1201 gaaggacaga ggagaaagtc cacattccaa agatcctccc ctggcacgct gggacttatt
 1261 cctgtgtggc agaaaacatt ctggctactg gacagaggag cccggagttt gagctggatg
 1321 tccagtatcc tccaagaag gtgaccacag tgattcaaaa cccatgccgg attcgagaag
 1381 gagacacagt gaccctttcc tgtaactaca attccagtaa cccagtgtct acccggtatg
 1441 aatggaaacc ccatggcgcc tgggaggagc catcgttgg ggtgctgaag atccaaaacg
 1501 tggctggga aaacacaacc atgctgcg cagcttgtaa tagttggtgc tgtgggcct
 1561 cccctgtcga cctgaatgtc cagtatgccc ccgagacgt gagggtccgg aaaatcaagc
 1621 cccttttcga gattcactct ggaaactgg tcagcctcca atgtgactc tcagcagcc
 1681 accccaaaga agtccagttc tctgggaga aaatggcag gcttctggga aagaaagcc
 1741 agctgaattt tgactccatc tccccagaag atgctgggag ttacagctgc tgggtgaaca
 1801 actcatagg acagacagcg tccaaggcct ggacacttga agtgtgtat gcacccagga
 1861 agctgcgtgt gtccatgagc ccggggacc aagtgatgga ggggaagagt gcaacctga
 1921 cctgtgagag cgacgccaag cctccgtct ccaactacac ctggtttgac tggaataacc
 1981 aaagcctccc ctaccacagc cagaagctga gattggagcc ggtgaaggtc cagcactggg
 2041 gtgcctactg gtgcaggg accaacagtg tgggcaaggg ccgttcgcct ctcagcaccc
 2101 tcacgtgta ctatagcccg gagaccatcg gcaggcgagt ggctgtggga ctgggtcct
 2161 gcctcgccat cctgatcctg gcaatctgtg ggctcaagct ccagcgacgt tggaagagga
 2221 cacagagca gcaggggccct tcaggaatt ccagcggca gagcttcttt gtgaggaata
 2281 aaaaggttag aagggcccc ctctctgaag gccccactc cctgggatgc tacaatccaa
 2341 tgatggaaga tggcattagc tacaccacc tgtgctttcc cagatgaaac ataccgaa
 2401 ctggagatgc agagtcctca gagatgcaga gacctccccc ggactgcgat gacacggtca
 2461 cttattcagc attgcagaag cgccaagtgg gcgactatga aacgtcatt ccagatttc
 2521 cagaagatga ggggattcat tactcagagc tgatccagtt tggggtgggg agagggcct
 2591 aggacaagaa aaatgtggac tatgtgatcc tcaaacattg acactggatg ggctgcagca
 2641 gaggactgg gggcagcggg ggcagggaa gtcccgagt tcccccagac acgccacat
```

FIG. 1X

```
2701 ggcttcctcc tgcgcgcatg tgcgcacaca cacacacaca cgcacacaca cacacacaca
2761 ctcactgcgg agaaccttgt gcctggctca gagccagtct ttttggtgag ggtaacccca
2821 aacctcaaaa actcctgccc ctgttatctt ccactctcct tgctacccag aaatcgatct
2881 aaatacctgc cctgacatgc acacctcccc ctgccccac cagggcact ggccatctcc
2941 accccagct gcttgtgtcc ctcctgggat ctgctcgtca tcattttcc ttccttctc
3001 catctctctg gccctctacc cctgatctga catccccact cacgaatatt atgcccagtt
3061 tctgctctg agggaaagcc cagaaaagga cagaaacgaa gtagaaaggg gcccagtcct
3121 ggcctggctt ctcctttgga agtgaggcat tgcacgggga gacgtacgta tcagcggcc
3181 ctgactctg gggactccgg gtttgagatg gacacactgg tgtggattaa cctgccaggg
3241 agacagagct cacaataaaa atggctcaga tgccacttca aagaaaaaaa aaa
```

FIG. 1Y

RGS13

```
LOCUS       NM_144766               1458 bp    mRNA    linear   PRI 31-JAN-2010
DEFINITION  Homo sapiens regulator of G-protein signaling 13 (RGS13),
            transcript variant 2, mRNA.
ACCESSION   NM_144766
VERSION     NM_144766.1  GI:21464138
KEYWORDS
SOURCE      Homo sapiens (human)

ORIGIN
        1 gaggccagag tgccatcgaa ggtaattata gagacagtaa aatcctttta ctctgggaaa
       61 aatasaatgc tgggtgtctc acaaaattc agaacctgat ttcaaacgga tcataacaaa
      121 gaggagatca aatttagcat ggtggactgc tcgacaggat atatttgtca atggaatgtt
      191 tccacatatt ataccaccaa catgagaaaa aaatgatcat tgtttattg aagcttgaaa
      241 aatgagcagg cggaattgtt ggatttgtaa gatgtgcaga gatgaatcta agaggcccc
      301 ttcaaacctt actctggagg aagtattaca gtgggccag tcttttgaaa atttaatggc
      361 tacaaaatat ggtccagtag tctatgcagc atatttaaaa atggagcaca gtgacgagaa
      421 tattcaattc tggatggcat gtgaaacta taagaaaatt gcctcacggt ggagcagaat
      481 ttctaggca aagaagtttt ataagattta catcagcca cagtcctta gagagattaa
      541 cattgcagt tcgacagag agactatcac caggaacatt caggaaccca ctgaaacatg
      601 tttgaagaa gctcagaaa tagtctatat tgatatggaa agggattcc accccagatt
      661 tctaaagtca gaaatgtacc aaaaactttt gaaactatg cagtccaaca acagttctg
      721 actacaactc aaaagtttaa atagaaaada gtatattgaa agtggtgggt ttgatctttt
      781 tatttagaaa cccacaaaat cagaaacaca gtacaaataa aacagaaatc aaactataag
      841 ttgactttta gttcctaaaa agaaacatat ttcaaaagca atggaatcta gaattcttat
      901 aacatgaata acaaatgta cagcaagcct atgtagttca attaatatat aaggaaaagg
      961 aaggtctttc tcatgataca aagcattata aagttttac tgtagtagtc aattaatgga
     1021 tattccttg ttaataaaat ttgtgtcat aatttacaaa ttagttcttt aaaaattgtt
     1081 gttatatgaa tgtgttctct agcatgaatg ttctatagag tactctaaat aacttgaatt
     1141 tatagacaaa tgctactcac agtacaatca atgtattat accatgagaa aatcaaaaag
     1201 gtgttcttca gagacatttt atctataaaa tttcctact attatgtca ttaacaaact
     1261 tctttatcac atgtatcttc tacatgtaaa acatttctga tgatttttta acaaaaaata
     1321 tatgaatttc ttcatttgct cttgcatcta cattgctata aggatataaa atgtggttc
     1381 tatattttga gatgttttt ccttacaatg tgaactcatc gtgatcttgg aaatcaataa
     1441 agtcaaatat caactaaa
```

FIG. 1Z

METHODS FOR ASSESSING RESPONSIVENESS OF B-CELL LYMPHOMA TO TREATMENT WITH ANTI-CD40 ANTIBODIES

CROSS-REFERENCE TO RELATED APPLICATIONS

This application is a National Phase application under 35 U.S.C. §371 of International Application No. PCT/US2010/031528, having an International Filing Date of Apr. 17, 2010, which claims priority benefit of U.S. provisional application Ser. No. 61/170,615, filed Apr. 18, 2009, all of which are incorporated herein by reference in their entirety.

TECHNICAL FIELD

The present invention relates generally to the fields of predicting, assessing, aiding assessment of responsiveness of a patient with B-cell lymphoma to treatment with anti-CD40 antibodies, and methods for treating individuals identified as candidates for the anti-CD40 antibody treatment.

BACKGROUND

CD40 is a type I transmembrane protein of the tumor necrosis receptor superfamily. CD40 is an important molecule involved in B-cell proliferation and differentiation, immunoglobulin isotype switching, and cell viability. Receptor signaling is initiated by the binding of CD40 to the CD40 ligand (CD40L or CD154), which is primarily expressed on activated CD4+ T cells.

On normal cells, CD40 is expressed on cells with high proliferative potential, including hematopoietic progenitors, epithelial and endothelial cells, and all antigen-presenting cells (dendritic cells, activated B lymphocytes, and activated monocytes). CD40 is highly expressed on several types of B-cell hematologic malignancies including multiple myeloma, non-Hodgkin's lymphoma (NHL), and chronic lymphocytic leukemia (CLL). The high prevalence of CD40 expression on B-cell malignancies makes it an attractive potential tumor target for antibody-based cancer therapy. CD40 is also expressed on a majority of bladder cancers and a significant percentage of other solid tumors, including head and neck cancers, renal cell carcinomas, ovarian and lung cancer.

Anti-CD40 antibodies and their uses for treating B cell hematologic malignancies have been described. See, e.g., U.S. Pat. Nos. 6,946,129; 6,843,989; 6,838,261; WO 2000/075348; US-2002-0197256; WO 2006/128103; and WO 2007/075326. It has been shown that a humanized anti-CD40 antibody induces growth inhibition and apoptosis of CD40-positive cells in a subset of hematologic tumor cell lines through direct signal transduction. WO 2006/128103; WO 2007/075326. Furthermore, the humanized anti-CD40 antibody kills tumor cells via immune effector functions, including antibody-dependent cellular cytotoxicity (ADCC) and antibody-dependent cellular phagocytosis (ADCP). In vivo, using xenograft models of multiple myeloma (MM) and non-Hodgkin's lymphoma (NHL), the anti-CD40 antibody suppresses tumor growth and improves survival in severe combined immunodeficient (SCID) mice. Comparison of the anti-CD40 antibody to rituximab (Genentech, Inc.) in several models revealed anti-tumor activity of the anti-CD40 antibody was at least as effective as rituximab. Clinical trials were initiated to test the humanized anti-CD40 antibody in patients with relapsed and refractory multiple myeloma (MM), relapsed non-Hodgkin's lymphoma (NHL), chronic lymphocytic lymphoma (CLL), or in relapsed diffuse large B cell lymphoma (DLBCL).

Although it has been shown anti-CD40 antibodies can induce growth inhibition and apoptosis of CD40-positive cells and may have anti-tumor activity in various types of B cell lymphoma patients, not all B lymphoma cells are sensitive to anti-CD40 antibody mediated cell death. There remains a need to identify one or more predictive markers for the responsiveness of B-cell lymphoma patients to an anti-CD40 antibody therapy.

All references cited herein, including patent applications and publications, are incorporated by reference in their entirety.

SUMMARY OF THE INVENTION

The invention provides methods and compositions for predicting, assessing or aiding assessment of responsiveness of a subject having a type of B-cell lymphoma to treatment with an anti-CD40 antibody.

In one aspect, the invention provides methods for assessing or aiding assessment of responsiveness of a subject having a B-cell lymphoma to treatment with an anti-CD40 antibody, comprising comparing a measured expression level of at least one marker gene selected from the group consisting of UAP1, BTG2, CD40, VNN2, RGS13, CD22, LMO2, IFITM1, CTSC, CD44, PUS7, BCL6, EPDR1, IGF1R and CD79B in a B-cell lymphoma sample from the subject to a reference level.

In another aspect, the invention provides methods for predicting responsiveness or monitoring treatment/responsiveness to an anti-CD40 antibody treatment in a subject having a B-cell lymphoma, comprising comparing a measured expression level of at least one marker gene selected from the group consisting of UAP1, BTG2, CD40, VNN2, RGS13, CD22, LMO2, IFITM1, CTSC, CD44, PUS7, BCL6, EPDR1, IGF1R and CD79B in a B-cell lymphoma sample from the subject to a reference level.

In another aspect, the invention provides methods for predicting, assessing or aiding assessment of responsiveness of a subject having a B-cell lymphoma to an anti-CD40 antibody treatment, comprising the steps of: (a) measuring the expression level of one or more marker genes in a sample comprising B lymphoma cells obtained from said subject, wherein said one or more marker genes are selected from the group consisting of IFITM1, CD40, RGS13, VNN2, LMO2, CD79B, CD22, BTG2, IGF1R, CD44, CTSC, EPDR1, UAP1, PUS7, and BCL6; and (b) predicting whether the subject is likely to respond to the anti-CD40 antibody treatment based on the measured expression level of said one or more marker genes from step (a). In some embodiments, expression levels of at least two, at least three, at least four, at least five, at least six, at least seven, at least eight, at least nine, at least ten, at least eleven, at least twelve, at least thirteen, at least fourteen, or fifteen maker genes from the group are measured and used for the prediction, assessment, or aiding assessment. In some embodiments, the prediction, assessment, or aiding assessment is determined by comparing the measured expression level of one or more marker genes to a reference level. In some embodiments, a reference level is a value or a range determined based on the measured expression level of the corresponding marker gene in samples comprising the B lymphoma cells from subjects having tumor volume increased or decreased after the anti-CD40 antibody treatment. In some embodiments, samples from subjects for reference level determination comprise the same type of B lymphoma cells as the sample from the subject whose responsiveness to the anti-CD40 antibody treatment is predicted. In some embodiments, the responsiveness is predicted or assessed using the sensitivity index value determined based on the measured expression level of one or more of the marker genes. In some embodiments, the responsiveness is predicted or assessed by classifying the subject using a K-nearest neighbors analysis described herein.

In another aspect, the invention provides methods for preparing a personalized genomics profile for a subject having B-cell lymphoma comprising the steps of: (a) determining the expression level of one or more marker genes selected from the group consisting of IFITM1, CD40, RGS13, VNN2, LMO2, CD79B, CD22, BTG2, IGF1R, CD44, CTSC, EPDR1, UAP1, PUS7, and BCL6 in a sample comprising B lymphoma cells obtained from the subject; and (b) generating a report summarizing the expression level of one or more marker genes obtained in step (a). In some embodiments, expression levels of at least two, at least three, at least four, at least five, at least six, at least seven, at least eight, at least nine, at least ten, at least eleven, at least twelve, at least thirteen, at least fourteen, or fifteen marker genes from the group are measured and used for generating the report for the personalized genomics profile. In some embodiments, the report includes a recommendation for an anti-CD40 antibody treatment for the subject. In some embodiments, the recommendation is determined by comparing the measured expression level of the marker genes to a reference level. In some embodiments, a reference level is a value or a range determined based on the measured expression level of the corresponding marker gene in samples comprising the B lymphoma cells from subjects having tumor volume increased or decreased after the anti-CD40 antibody treatment. In some embodiments, the recommendation is determined by the sensitivity index value determined based on the measured expression level of the marker genes. In some embodiments, the recommendation is determined by classifying the subject using a K-nearest neighbors analysis described herein.

In another aspect, the invention provides methods for predicting, assessing or aiding assessment of responsiveness of a subject having a B-cell lymphoma to an anti-CD40 antibody treatment, comprising the steps of: (a) measuring the expression level at least two marker genes selected from the group consisting of IFITM1, CD40, RGS13, VNN2, LMO2, CD79B, CD22, BTG2, IGF1R, CD44, CTSC, EPDR1, UAP1, PUS7, and BCL6 in a sample comprising B lymphoma cells from the subject; (b) calculating sensitivity index value (SI) based on the measured expression level of the marker genes in step (a) by the following equation:

$$SI = \sum_{j=1}^{p} \beta_j \frac{x_j - \hat{\mu}_j}{\sqrt{\hat{\sigma}_j^2}}$$

wherein the expression level of at least one marker gene having a positive correlation value and at least one marker gene having a negative correlation value shown in Table 4 is measured;

wherein (i) $\beta_j$ is the coefficient value for each marker genes measured; (ii) p is the number of marker genes measured; (iii) $x_j$ is transformed, normalized expression level for the sample from the subject for the expression level of each marker measured; and (iv) $\mu_j$ and $\sigma_j$ are means and standard deviations for each marker gene measured; wherein $\beta_j$, $\mu_j$ and $\sigma_j$ are determined from patient samples comprising the B lymphoma cells. In some embodiments, a value equals or greater than zero for the sensitivity index indicates that the subject is likely to respond to the anti-CD40 antibody treatment, or wherein a value less than zero for the sensitivity index indicates that the subject is less likely to respond to the anti-CD40 antibody treatment. In some embodiments, the expression levels of at least three, at least four, at least five, at least six, at least seven, at least eight, at least nine, at least ten, at least eleven, at least twelve, at least thirteen, at least fourteen, or fifteen marker genes are measured and used for the sensitivity index calculation. In some embodiments, the expression level of IFITM1, RGS13, CD79B, CD22, BTG2, CD44, EPDR1, and UAP1 are measured and used for the sensitivity index calculation. In some embodiments, $\beta_j$, $\mu_j$ and $\sigma_j$ are determined from patient samples have the same type of B lymphoma cells as the sample from subject whose responsiveness to the anti-CD40 treatment is predicted.

In another aspect, the invention provides methods for predicting responsiveness of a subject having B-cell lymphoma to an anti-CD40 antibody treatment, comprising the steps of (a) measuring the expression level of one or more marker genes in a sample comprising B lymphoma cells obtained from the subject, wherein said one or more marker genes are selected from the group consisting of BCL6, IFITM1, CD40, RGS13, VNN2, LMO2, CD79B, CD22, BTG2, IGF1R, CD44, CTSC, EPDR1, UAP1, and PUS7; and (b) classifying the subject as a responsive or a non-responsive subject using a K-nearest neighbors analysis based on the expression level of said one or more marker genes in the sample from the subject and reference samples with known classes. In some embodiments, said classification is determined using a weighted K-nearest neighbors analysis. In some embodiments, said classification is determined using an unweighted K-nearest neighbors analysis. In some embodiments, the classification of the subject in step (b) is carried out by (1) determining parameter K (i.e., number of nearest neighbors); (2) calculating the difference between the measured expression level of the marker genes in the sample from the subject and the expression level of the respective marker genes in each reference sample; (3) determining the nearest reference samples by selecting those samples with the smallest weighted average of the absolute differences (WAAD) between the sample from the subject and the reference sample; and (4) determining the class of the subject based on the known classes of the K-nearest reference samples. In some embodiments, K is determined using cross-validation with clinical trial samples. In some embodiments, K is 4, 5, 6, 7, 8, 9, 10, 11, 12, or 13. In some embodiments, the reference samples are samples comprising B lymphoma cells obtained from subjects whose responsiveness to the anti-CD40 antibody treatment has been tested or is known. In some embodiments, the reference samples comprise the same type of B lymphoma cells as the sample from the subject whose responsiveness to the anti-CD40 antibody treatment is predicted or assessed. In some embodiments, expression levels of at least two, at least three, at least four, at least five, at least six, at least seven, at least eight, at least nine, at least ten, at least eleven, at least twelve, at least thirteen, at least fourteen, or all fifteen marker genes of BCL6, IFITM1, CD40, RGS13, VNN2, LMO2, CD79B, CD22, BTG2, IGF1R, CD44, CTSC, EPDR1, UAP1, and PUS7 are measured and used for classifying the subject. In some embodiments, expression levels of BCL6, IFITM1, CD22, IGF1R, CD44, EPDR1, and UAP1 are measured and used in classifying the subject. In some embodiments, the measured expression level is normalized.

In another aspect, the invention provides methods for treating a subject having B-cell lymphoma, comprising administering an effective amount of an anti-CD40 antibody to the subject, wherein the responsiveness of the B-cell lymphoma in the subject has been assessed by the methods described herein. In another aspect, the invention provides methods for treating a subject having B-cell lymphoma, comprising a) selecting a subject for an anti-CD40 antibody treatment by comparing a measured expression level of at least one marker gene selected from the group consisting of UAP1, BTG2, CD40, VNN2, RGS13, CD22, LMO2, IFITM1, CTSC, CD44, PUS7, BCL6, EPDR1, IGF1R and CD79B in a B-cell lymphoma sample from the subject to a reference level to assess if the B-cell lymphoma in the subject is suitable for the anti-CD40 antibody treatment; and administering an effective amount of the anti-CD40 antibody to the subject. In another aspect, the invention provides methods for treating a subject having B-cell lymphoma, comprising a) selecting a subject for an anti-CD40 antibody treatment if the subject is classified as a responsive subject using a K-nearest neighbors analysis based on the measured expression level of one or more marker genes selected from the group consisting of UAP1, BTG2, CD40, VNN2, RGS13, CD22, LMO2, IFITM1, CTSC, CD44, PUS7, BCL6, EPDR1, IGF1R and CD79B in a B-cell lymphoma sample from the subject and reference samples with known classes; and administering an effective amount of the anti-CD40 antibody to the subject.

In some embodiments, the reference level is a measured expression level of the marker gene in a different B-cell lymphoma sample. In some embodiments, said different B cell lymphoma sample comprises B lymphoma cells that are resistant to an anti-CD40 antibody induced cell death.

In some embodiments, the measured expression level of the marker gene and/or the reference level are normalized.

In some embodiments, measured expression levels of at least two, at least three, at least four, at least five, at least six, at least seven, at least eight, at least nine, at least ten, at least eleven, at least twelve, at least thirteen, at least fourteen, or fifteen genes selected from the group consisting of UAP1, BTG2, CD40, VNN2, RGS13, CD22, LMO2, IFITM1, CTSC, CD44, PUS7, BCL6, EPDR1, IGF1R and CD79B in the B-cell lymphoma sample from the subject are compared to one or more reference levels.

In some embodiments, the expression level is measured by detecting mRNA expression (e.g., real time quantitative reverse transcription PCR (qRT-PCR)) and/or by detecting protein expression (e.g., immunohistochemistry (IHC)). Probes and primers shown in Table 1 may be used in qRT-PCR.

In some embodiments, B-cell lymphoma is non-Hodgkin's lymphoma (NHL), including, but is not limited to, follicular lymphoma, relapsed follicular lymphoma, small lymphocytic lymphoma, mantle cell lymphoma, marginal zone lymphoma, lymphoplasmacytic lymphoma, mycosis fungoides/Sezary syndrome, splenic marginal zone lymphoma, and diffuse large B-cell lymphoma (DLBCL). In some embodiments, B-cell lymphoma is selected from the group consisting of indolent lymphoma, aggressive lymphoma, and highly aggressive lymphoma. In some embodiments, B-cell lymphoma is relapsed and/or refractory lymphoma. In some embodiments, B-cell lymphoma is relapsed/refractory DLBCL.

In some embodiments, the anti-CD40 antibody treatment is a treatment with an agonist anti-CD40 antibody. In some embodiments, the agonist anti-CD40 antibody stimulates CD40 and enhances the interaction between CD40 and CD40 ligand. In some embodiments, the agonist anti-CD40 antibody stimulates CD40 but does not enhance or inhibits the interaction between CD40 and CD40 ligand. In some embodiments, the agonist anti-CD40 antibody comprises the heavy chain amino acid sequence shown in SEQ ID NO:1 and the light chain amino acid sequence shown in SEQ ID NO:2.

In a further aspect, the invention provides kits comprising reagents for measuring expression levels of at least one marker gene selected from the group consisting of UAP1, BTG2, CD40, VNN2, RGS13, CD22, LMO2, IFITM1, CTSC, CD44, PUS7, BCL6, EPDR1, IGF1R and CD79B. In some embodiments, the kits comprise at least a pair of primers for amplifying by PCR at least one marker gene. For example, forward and reverse primers shown in Table 1 may be used. The kits may further comprise a surface having attached thereof probes for detecting the amplified gene products, such as a microarray and the invention contemplates and includes such surfaces. In some embodiments, the kits comprise at least a pair of primers and a probe for detecting expression level of one marker gene (such as UAP1, BTG2, CD40, VNN2, RGS13, CD22, LMO2, IFITM1, CTSC, CD44, PUS7, BCL6, EPDR1, IGF1R and CD79B) by qRT-PCR. The kits may further comprise a pair of primers and a probe for detecting expression level of a reference gene by qRT-PCR. In some embodiments, the kits comprise one or more antibodies that specifically recognize one or more proteins encoded by the marker gene. The kits may further comprise other reagents and/or instructions for carrying out any of the methods described herein.

It is to be understood that one, some, or all of the properties of the various embodiments described herein may be combined to form other embodiments of the present invention. These and other aspects of the invention will become apparent to one of skill in the art.

BRIEF DESCRIPTION OF THE FIGURES

FIGS. 1A to 1Z. GenBank sequences for some of the genes listed in Table 1. Nucleic acid sequences encoding mRNA of VNN2 (FIG. 1A: SEQ ID NO:258), RGS13 (FIG. 1B: SEQ ID NO:259), CD22 (FIGS. 1C and 1D: SEQ ID NO:260), CD40 (FIG. 1E: SEQ ID NO:261), IFITM1 (FIG. 1F: SEQ ID NO:262), BCL6 (FIGS. 1G and 1H: SEQ ID NO:263), EPDR1 (FIG. H: SEQ ID NO:264), IGF1R (FIGS. 1J to 1M: SEQ ID NO:265), BTG2 (FIGS. 1N and 1O: SEQ ID NO:266), LMO2 (FIG. 1P: SEQ ID NO:267), CD79B (FIG. 1Q SEQ ID NO:268), CD44 (FIGS. 1R and 1S: SEQ ID NO:269), CTSC (FIG. 1T: SEQ ID NO:270), UAP1 (FIG. 1U: SEQ ID NO:271), PUS7 (FIGS. 1V and 1W: SEQ ID NO:272), CD22 (FIGS. 1X and 1Y: SEQ ID NO:273), and RGS13 (FIG. 1Z: SEQ ID NO:274).

DETAILED DESCRIPTION

Figure 2:
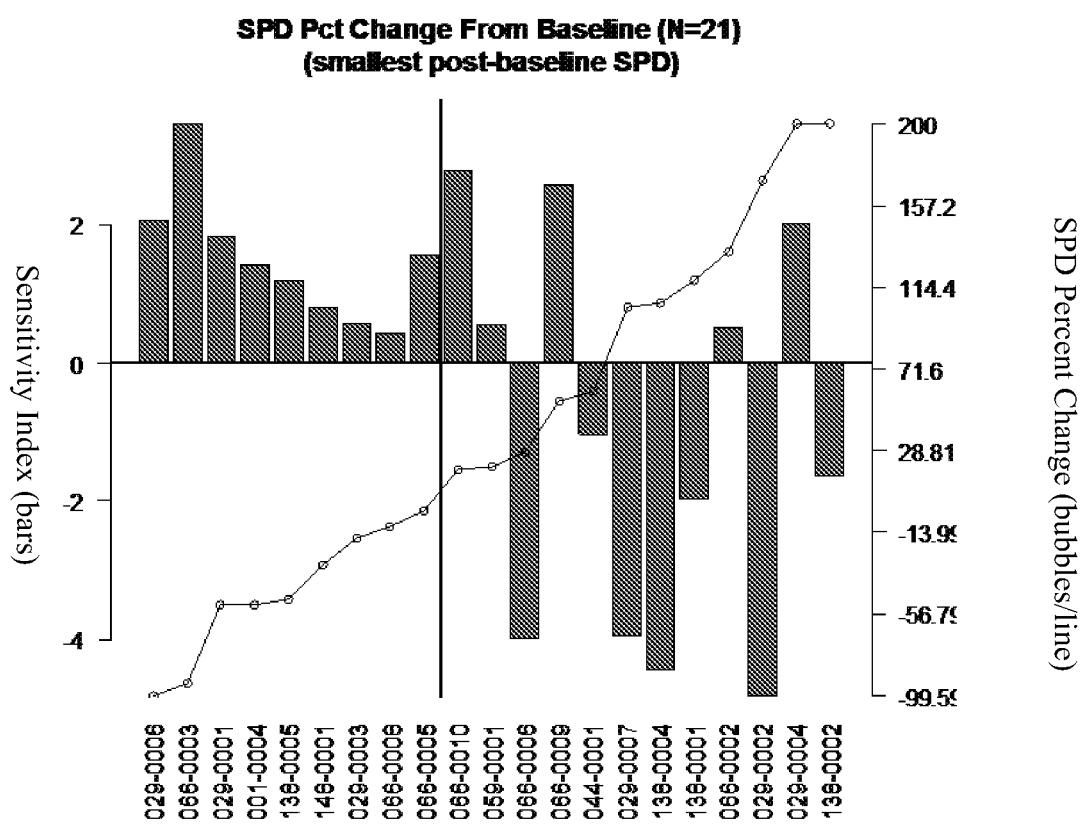
FIG. 2. Association of multivariate sensitivity index and percent change in tumor sum of the product of diameters (SPD) measurements for 21 patients in Clinical Trial 001. SPD percent change is determined by comparing the smallest post-baseline SPD to baseline SPD. Positive change indicates tumor volume increases, and negative change indicates tumor volume decreases. Weights (coefficients) used for the sensitivity index calculation are shown in Table 5. Larger multivariate sensitivity index values are associated with SPD decreases post-baseline (Sperman's Rho=−0.58; P=0.006).

The present invention is based on the discovery that certain genes are differentially expressed between B lymphoma cells that are sensitive to anti-CD40 antibody induced cell death and B lymphoma cells that are resistant to anti-CD40 induced cell death. Data from clinical trials described in Examples 1 and 2 indicate that the expression level of one or more of the fifteen genes UAP1, BTG2, CD40, VNN2, RGS13, CD22, LMO2, IFITM1, CTSC, CD44, PUS7, BCL6, EPDR1, IGF1R and CD79B can be used to predict, assess or aid assessment of responsiveness to anti-CD40 antibody treatment (such as anti-CD40 Ab.1 treatment). Some of the differentially expressed genes between sensitive B lymphoma cells and resistant B lymphoma cells are the CD40 ligand downregulated pathway genes; and some are in the B-cell receptor signaling pathway. Accordingly, expression levels of one or more of these differentially expressed genes can be used for assessing or aiding assessment of responsiveness of a subject having B-cell lymphoma to treatment with anti-CD40 antibodies, predicting responsiveness of the subject to treatment with anti-CD40 antibodies, and monitoring treatment/responsiveness in the subject.

A. GENERAL TECHNIQUES

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Primers, oligonucleotides and polynucleotides employed in the present invention can be generated using standard techniques known in the art.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

B. DEFINITIONS

As used herein, the terms "a subject having a B-cell lymphoma" and "B-cell lymphoma patient" refer to a subject who has been diagnosed with a type of B-cell lymphoma or has been given a probable diagnosis of a type of B-cell lymphoma.

The term "biomarker" or "marker" as used herein refers generally to a molecule, including a gene, protein, carbohydrate structure, or glycolipid, the expression of which in or on a mammalian tissue or cell or secreted can be detected by known methods (or methods disclosed herein) and is predictive or can be used to predict (or aid prediction) for a mammalian cell's or tissue's sensitivity to, and in some embodiments, to predict (or aid prediction) an individual's responsiveness to treatment regimes based on anti-CD40 antibodies.

The term "sample", as used herein, refers to a composition that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized.

By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis according to the present invention, provided that it is understood that the present invention comprises a method whereby the same section of tissue sample is analyzed at both morphological and molecular levels, or is analyzed with respect to both protein and nucleic acid.

As used herein, a "B-cell lymphoma sample" or a "sample comprising B lymphoma cells" is a tissue or cell sample containing B lymphoma cells from a subject or a patient that have been diagnosed with a type of B-cell lymphoma.

As used herein, method for "aiding assessment" refers to methods that assist in making a clinical determination (e.g., responsiveness of a B-cell lymphoma to treatment with anti-CD40 antibodies), and may or may not be conclusive with respect to the definitive assessment.

A "subject" or an "individual" is a mammal, more preferably a human. Mammals include, but are not limited to, humans, primates, farm animal, sport animals, rodents, and pets (e.g., dogs and cats).

As used herein, a "reference value" can be an absolute value; a relative value; a value that has an upper and/or lower limit; a range of values; an average value; a median value; a mean value; or a value as compared to a particular control or baseline value.

The term "array" or "microarray", as used herein refers to an ordered arrangement of hybridizable array elements, such as polynucleotide probes (e.g., oligonucleotides) and antibodies, on a substrate. The substrate can be a solid substrate, such as a glass slide, or a semi-solid substrate, such as nitrocellulose membrane. The nucleotide sequences can be DNA, RNA, or any permutations thereof.

"Amplification," as used herein, generally refers to the process of producing multiple copies of a desired sequence. "Multiple copies" means at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

Expression/amount of a gene or biomarker in a first sample is at a level "greater than" the level in a second sample if the expression level/amount of the gene or biomarker in the first sample is at least about 1.5×, 1.75×, 2×, 3×, 4×, 5×, 6×, 7×, 8×, 9× or 10× the expression level/amount of the gene or biomarker in the second sample. Expression levels/amounts can be determined based on any suitable criterion known in the art, including but not limited to mRNA, cDNA, proteins, protein fragments and/or gene copy. Expression levels/amounts can be determined qualitatively and/or quantitatively.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR $_2$ ("amidate"), P(O)R, P(O)OR', CO or CH $_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

A "primer" is generally a short single stranded polynucleotide, generally with a free 3'-OH group, that binds to a target potentially present in a sample of interest by hybridizing with a target sequence, and thereafter promotes polymerization of a polynucleotide complementary to the target. A "pair of primers" refer to a 5' primer and a 3' primer that can be used to amplify a portion of a specific target gene.

The term "3'" generally refers to a region or position in a polynucleotide or oligonucleotide 3' (downstream) from another region or position in the same polynucleotide or oligonucleotide. The term "5'" generally refers to a region or position in a polynucleotide or oligonucleotide 5' (upstream) from another region or position in the same polynucleotide or oligonucleotide.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

"Detection" includes any means of detecting, including direct and indirect detection.

The term "prediction" is used herein to refer to the likelihood that a patient will respond either favorably or unfavorably to a drug or set of drugs. In one embodiment, the prediction relates to the extent of those responses. In one embodiment, the prediction relates to whether and/or the probability that a patient will survive or improve following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc., or whether long-term survival of the patient, following a therapeutic regimen is likely.

The term "long-term" survival is used herein to refer to survival for at least 1 year, 5 years, 8 years, or 10 years following therapeutic treatment.

"Patient response" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e. reduction, slowing down or complete stopping) of disease spread; (6) relief, to some extent, of one or more symptoms associated with the disorder; (7) increase in the length of disease-free presentation following treatment; and/or (8) decreased mortality at a given point of time following treatment.

The term "antibody" is used in the broadest sense and specifically covers monoclonal antibodies (including full length monoclonal antibodies), multispecific antibodies (e.g., bispecific antibodies), and antibody fragments so long as they exhibit the desired biological activity or function.

"Antibody fragments" comprise a portion of a full length antibody, generally the antigen binding or variable region thereof. Examples of antibody fragments include Fab, Fab', $F(ab')_2$, and Fv fragments; diabodies; linear antibodies; single-chain antibody molecules; and multispecific antibodies formed from antibody fragments.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

The term "monoclonal antibody" as used herein refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., *Nature,* 256:495 (1975); Harlow et al., *Antibodies: A Laboratory Manual,* (Cold Spring Harbor Laboratory Press, 2nd ed. 1988); Hammerling et al., in: *Monoclonal Antibodies and T-Cell Hybridomas* 563-681, (Elsevier, N.Y., 1981)), recombinant DNA methods (see, e.g., U.S. Pat. No. 4,816,567), phage display technologies (see, e.g., Clackson et al., *Nature,* 352:624-628 (1991); Marks et al., *J. Mol. Biol.,* 222:581-597 (1991); Sidhu et al., *J. Mol. Biol.* 338(2):299-310 (2004); Lee et al., *J. Mol. Biol.* 340(5):1073-1093 (2004); Fellouse, *Proc. Nat. Acad. Sci. USA* 101(34):12467-12472 (2004); and Lee et al. *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA,* 90:2551 (1993); Jakobovits et al., *Nature,* 362:255-258 (1993); Bruggemann et al., *Year in Immuno.,* 7:33 (1993); U.S. Pat. Nos. 5,545,806; 5,569,825; 5,591,669 (all of GenPharm); U.S. Pat. No. 5,545,807; WO 1997/17852; U.S. Pat. Nos. 5,545,807; 5,545,806; 5,569, 825; 5,625,126; 5,633,425; and 5,661,016; Marks et al., *Bio/Technology,* 10: 779-783 (1992); Lonberg et al., *Nature,* 368: 856-859 (1994); Morrison, *Nature,* 368: 812-813 (1994); Fishwild et al., *Nature Biotechnology,* 14: 845-851 (1996); Neuberger, *Nature Biotechnology,* 14: 826 (1996); and Lonberg and Huszar, *Intern. Rev. Immunol.,* 13: 65-93 (1995).

The monoclonal antibodies herein specifically include "chimeric" antibodies. "Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816, 567; and Morrison et al., *Proc. Natl. Acad. Sci. USA* 81:6851-6855 (1984)). Humanized antibody as used herein is a subset of chimeric antibodies.

"Humanized" forms of non-human (e.g., murine) antibodies are chimeric antibodies which contain minimal sequence derived from non-human immunoglobulin. For the most part, humanized antibodies are human immunoglobulins (recipient or acceptor antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR are typically no more than 6 in the H chain, and in the L chain, no more than 3. The humanized antibody optionally also will comprise at least a portion of an immunoglobulin constant region (Fc), typically that of a human immunoglobulin. For further details, see Jones et al., *Nature* 321:522-525 (1986); Reichmann et al., *Nature* 332:323-329 (1988); and Presta, *Curr. Op. Struct. Biol.* 2:593-596 (1992).

A "human antibody" is one which possesses an amino acid sequence which corresponds to that of an antibody produced by a human and/or has been made using any of the known techniques for making human antibodies. This definition of a human antibody specifically excludes a humanized antibody comprising non-human antigen-binding residues.

An "affinity matured" antibody is one with one or more alterations in one or more CDRs/HVRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR/HVR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain. By "Fc region chain" herein is meant one of the two polypeptide chains of an Fc region.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or Presta U.S. Pat. No. 6,737,056 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Treating" or "treatment" or "alleviation" refers to therapeutic treatment wherein the object is to slow down (lessen) if not cure the targeted pathologic condition or disorder or prevent recurrence of the condition. A subject is successfully "treated" for the B cell malignancy if, after receiving a therapeutic amount of a CD40 binding antibody, the subject shows observable and/or measurable reduction in or absence of one or more signs and symptoms of the particular disease. For example, significant reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues. Reduction of the signs or symptoms of a disease may also be felt by the patient. Treatment can achieve a complete response, defined as disappearance of all signs of cancer, or a partial response, wherein the size of the tumor is decreased, preferably by more than 50 percent, more preferably by 75%. A patient is also considered treated if the patient experiences stable disease. In one criterion, the antibodies of the invention achieve >95% peripheral blood B cell depletion and the B cells return to 25% of baseline. In some embodiments, treatment with the anti-CD40 antibodies is effective to result in the cancer patients being progression-free in the cancer 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

The term "non-Hodgkin's lymphoma" or "NHL", as used herein, refers to a cancer of the lymphatic system other than Hodgkin's lymphomas. Hodgkin's lymphomas can generally be distinguished from non-Hodgkin's lymphomas by the presence of Reed-Sternberg cells in Hodgkin's lymphomas and the absence of said cells in non-Hodgkin's lymphomas.

An "effective amount" refers to an amount effective, at dosages and for periods of time necessary, to achieve the desired therapeutic or prophylactic result. A "therapeutically effective amount" of a therapeutic agent may vary according to factors such as the disease state, age, sex, and weight of the individual, and the ability of the antibody to elicit a desired response in the individual. A therapeutically effective amount is also one in which any toxic or detrimental effects of the therapeutic agent are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "housekeeping gene" refers to a group of genes that codes for proteins whose activities are essential for the maintenance of cell function. These genes are typically similarly expressed in all cell types.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of gene expression analysis or protocol, one may use the results of the gene expression analysis or protocol to determine whether a specific therapeutic regimen should be performed.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

As used herein, "a", "an", and "the" can mean singular or plural (i.e., can mean one or more) unless indicated otherwise.

It is understood that aspect and embodiments of the invention described herein include "comprising," "consisting," and "consisting essentially of" aspects and embodiments.

C. METHODS OF THE INVENTION

The invention provides methods for assessing or aiding assessment of responsiveness of a subject having B-cell lymphoma to treatment with an anti-CD40 antibody. The invention also provides methods for predicting responsiveness or monitoring treatment/responsiveness to an anti-CD40 antibody treatment in a subject having B-cell lymphoma. The invention provides methods for selecting a subject having B-cell lymphoma for treatment with an anti-CD40 antibody and treating the subject with an anti-CD40 antibody treatment. In some embodiments, the methods comprise measuring the expression level of one or more marker genes selected from the group consisting of UAP1, BTG2, CD40, VNN2, RGS13, CD22, LMO2, IFITM1, CTSC, CD44, PUS7, BCL6, EPDR1, IGF1R and CD79B in a sample comprising B lymphoma cells obtained from the subject; and predicting, assessing, or aiding assessment of responsiveness of the subject to an anti-CD40 antibody treatment based on the measure expression level of said one or more marker genes. In some embodiments, the methods comprise comparing the measured expression level of at least one marker gene selected from UAP1, BTG2, CD40, VNN2, RGS13, CD22, LMO2, IFITM1, CTSC, CD44, PUS7, BCL6, EPDR1, IGF1R and CD79B in a B-cell lymphoma sample from the subject to a reference level for the respective marker gene. In some embodiments, the responsiveness is predicted or assessed using the sensitivity index value determined based on the measured expression level of one or more of the marker genes. In some embodiments, the responsiveness is predicted or assessed by classifying the subject using a K-nearest neighbors analysis described herein.

The methods of the present invention are useful for clinicians to identify patients with B-cell lymphoma for treatment with an anti-CD40 antibody, aid in patient selection during the course of development of anti-CD40 antibody therapy, predict likelihood of success when treating an individual patient with a particular treatment regimen, assess and monitor disease progression, monitor treatment efficacy, and determine prognosis for individual patients. Any of these embodiments are included in this invention.

In some embodiments, B-cell lymphoma is non-Hodgkin's lymphoma (NHL), including, but is not limited to, follicular lymphoma, relapsed follicular lymphoma, small lymphocytic lymphoma, mantle cell lymphoma, marginal zone lymphoma, lymphoplasmacytic lymphoma, mycosis fungoides/Sezary syndrome, splenic marginal zone lymphoma, and diffuse large B-cell lymphoma.

In some embodiments, B-cell lymphoma is indolent. In some embodiments, B-cell lymphoma is aggressive. In some embodiments, B-cell lymphoma is highly aggressive. In some embodiments, indolent B-cell lymphoma is follicular lymphoma, marginal zone lymphoma, or small lymphocytic lymphoma. In some embodiments, indolent B-cell lymphoma is follicular lymphoma.

Marker Genes

The expression level of one or more of the marker genes in a B-cell lymphoma sample may be used in the methods of the invention, such as to predict, assess or aid assessment of responsiveness of the B-cell lymphoma to treatment with an anti-CD40 antibody. In some embodiments, the expression level of one or more of the marker genes relative to a reference level is used in the methods of the invention.

Using the expression level of UAP1, BTG2, CD40, VNN2, RGS13, CD22, LMO2, IFITM1, CTSC, CD44, PUS7, BCL6, EPDR1, IGF1R and CD79B for predicting, assessing or aiding assessment of responsiveness to an anti-CD40 antibody treatment is shown in Examples 1 and 2. Expression levels of one or more of these genes are used in the methods of the invention. In some embodiments, expression levels of at least two, at least three, at least four, at least five, at least six, at least seven, at least eight, at least nine, at least ten, at least eleven, at least twelve, at least thirteen, at least fourteen, or fifteen genes selected from UAP1, BTG2, CD40, VNN2, RGS13, CD22, LMO2, IFITM1, CTSC, CD44, PUS7, BCL6, EPDR1, IGF1R and CD79B are measured and used in the methods of the invention.

Genes (including sequences) used as markers herein are known in the art. For example, examples of GenBank accession numbers for human genes are VNN2 (NM_004665; NM_078488; AJ132100; D89974; BC064641; CR609799; BC126145; BC126147; and AB026705); RGS13 (NM_002927; NM_144766; BT006929; BC056866; AY562947; CR536532; CR610389; CR599001; BC016667; AF493935; BC036950; and AF030107); CD22 (NM_001771; AK026467; BC109306; BC109307; AK225694; AK225625; X52785; and X59350); LRRC8A (AY143166; BC051322; AK123611; AY358286; NM_019594; XM_026998; AK001199; AB037858; CR619692; CR619448; AK024649; BC000775; AK027495; and AK074723); CD40 (NM_001250; NM_152854; BC064518; AY225405; CR619622; CR608994; CR605787; AB209660; AK222896; AJ300189; BT019901; and BC012419); IFITM1 (NM_003641; BC000897; BT007173;

BT009859; CR456894; CR541874; CR604902; X57351; X84958; NM_006435; BC009696; X02490; and J04164); SMN1 (NM_000344; BC062723; CR611445; CR593735; BC000908; NM_022874; BC015308; and U18423); PRKCA (NM_002737; AB209475; BC109274; BC109273; AF035594; BC053321; BX648954; AK125425; BC062759; BC071767; BC103691; BC101403; BC107592; AY633609; BC122530; BC015855; AF086287; AF035595; M22199; and X52479); EPDR1 (DQ914439; AY027862; NM_017549; AJ250475; AF202051; CR624676; CR596656; NM_016616; BC000686; BC018299; AF305596; and BC036816); PRPSAP2 (NM_002767; AB007851; BX648850; AK126398; CR457082; BC101672; BC101670; and BC106050); IGF1R (NM_000875; NM_015883; AY429545; CR624013; BC078157; BC088377; BC107089; BC111046; BC113610; BC113612; BC010607; X04434 M24599; and U09023); BTG2 (NM_006763; CR606002; CR604962; CR595352; CR591042; BC105948; BC105949; U72649; and Y09943); LMO2 (BC042426; NM_005574; BC073973; AK127915; CR625714; CR614368; CR604507; AF257211; BCO34041; BCO35607; and X61118); YIPF3 (AL050274; AK000946; CR533541; CR623137; CR622890; CR622532; CR621993; CR619816; CR619437; CR619054; CR618212; CR616987; CR616384; CR615623; CR615153; CR615118; CR612415; CR611748; CR611260; CR610983; CR610470; CR607768; CR606024; CR603408; CR603202; CR602267; CR601987; CR599615; CR598162; CR597677; CR596581; CR596249; CR595236; CR592266; CR590752; CR590349; NM_015388; AK021433; AK021655; AK022757; BC019297; and AF162672); and BCL6 (NM001706; NM_138931; BX649185; U00115; BC142705; BC146796; BC150184; AL713713; AK090890; AL832990; and Z21943). GenBank accession numbers for marker genes are also listed in Table 1.

The nucleic acid sequence of some of the genes are shown in FIGS. 1A to 1Z.

Reference Levels

The measured expression level of one or more marker genes in a B-cell lymphoma sample is compared to a reference level. In some embodiments, the reference level is the expression level of a gene the expression level of which does not change (does not change significantly) among different type of B-cell lymphomas, for example, between B-cell lymphoma sensitive to anti-CD40 antibody and B-cell lymphoma resistant to anti-CD40 antibody. In some embodiments, expression levels of one or more housekeeping genes (such as genes shown in Tables 8 and 9 of WO 2009/062125) are used as reference levels.

In some embodiments, the measured expression level of the marker gene is normalized using the reference level. In some embodiments, the normalized expression level of the marker gene is calculated as a ratio of or difference between the marker gene and reference expression levels, on the original or on a log scale, respectively.

The reference genes may be selected as specific normalizing counterparts to the marker genes. Reference genes were selected for high mean expression and low variance in B cell lymphoma samples. In addition, reference genes were selected to have similar variance between replicated expression measurements of individual cell lines relative to variance between expression measurements of biologically distinct cell lines. In addition, reference genes were selected to have low statistical association with one or more markers.

In some embodiments, the reference level is a measured expression level of the marker gene in a different B-cell lymphoma sample. In some embodiments, the different B cell lymphoma sample comprises B lymphoma cells that are resistant to an anti-CD40 antibody induced cell death.

In some embodiments, the reference level is determined based on the expression level of the corresponding marker gene in samples comprising B lymphoma cells from subjects having tumor volume increased after the anti-CD40 antibody treatment and/or having tumor volume decreased after the anti-CD40 antibody treatment. In some embodiments, the samples from subjects for reference level determination comprise the same type of B lymphoma cells as the sample from the subject whose responsiveness to the anti-CD40 antibody treatment is predicted or assessed. In some embodiments, the same method (e.g., qRT-PCR) and/or reagents (e.g., primers and probes) are used for measuring expression level of the marker genes in the sample and measuring expression level of the corresponding marker genes in the reference samples.

Measuring Expression Levels

The methods disclosed herein provide methods to examine the expression level of one or more of these marker genes in a lymphoma sample (e.g., B-cell lymphoma sample). In some embodiments, the expression level relative a reference level is examined for one or more marker genes. The methods and assays include those which examine expression of marker genes such as one or more of UAP1, BTG2, CD40, VNN2, RGS13, CD22, LMO2, IFITM1, CTSC, CD44, PUS7, BCL6, EPDR1, IGF1R and CD79B. Expression levels may be measured at mRNA level and/or protein level.

The invention provides methods for measuring levels of expression from a mammalian tissue or cells sample (such as cells and/or tissues associated with B-cell lymphoma). For example, for obtaining patient samples, H&E staining is carried out and used as a guide for tissue macrodissection to enrich for tumor content. The sample can be obtained by a variety of procedures known in the art including, but is not limited to surgical excision, aspiration or biopsy. The sample may be fresh or frozen. In some embodiments, the sample is fixed and embedded in paraffin or the like. In the methods, a mammalian tissue or cell sample is obtained and examined for expression of one or more biomarkers. The methods may be conducted in a variety of assay formats, including assays detecting mRNA expression, enzymatic assays detecting presence of enzymatic activity, and immunohistochemistry assays. Determination of expression of such biomarkers in said tissues or cells will be predictive that such tissues or cells will be sensitive/responsive to treatment with an anti-CD40 antibody.

As discussed below, expression of various biomarkers in a sample can be analyzed by a number of methodologies, many of which are known in the art and understood by the skilled artisan, including but are not limited to, microarray (gene and/or tissue array analysis), in situ hybridization, Northern analysis, PCR analysis of mRNAs, immunohistochemical and/or Western analysis, FACS, protein arrays, mass spectrometry, quantitative blood based assays (as for example Serum ELISA) (to examine, for example, levels of protein expression), and/or biochemical enzymatic activity assays. Typical protocols for evaluating the status of genes and gene products are found, for example in Ausubel et al. eds., 1995, Current Protocols In Molecular Biology, Units 2 (Northern Blotting), 4 (Southern Blotting), (Immunoblotting) and 18 (PCR Analysis). The protocols below relating to detection of particular biomarkers, such as expression level of one or more of UAP1, BTG2, CD40, VNN2, RGS13, CD22, LMO2, IFITM1, CTSC, CD44, PUS7, BCL6, EPDR1, IGF1R and CD79B, in a sample are provided for illustrative purposes.

In some embodiments, the methods of the invention further include protocols which examine the presence and/or expression of mRNAs, such as mRNAs of at least one, at least two, at least three, at least four, at least five, at least six, at least seven, at least eight, at least nine, at least ten, at least eleven, at least twelve, at least thirteen, at least fourteen, or fifteen genes from UAP1, BTG2, CD40, VNN2, RGS13, CD22, LMO2, IFITM1, CTSC, CD44, PUS7, BCL6, EPDR1, IGF1R and CD79B, in a tissue or cell sample. In some embodiments, expression of various biomarkers in a sample may be analyzed by microarray technologies, which examine or detect mRNAs, in a tissue or cell sample. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment. (See, e.g., WO 01/75166 published Oct. 11, 2001; see also, for example, U.S. Pat. No. 5,700,637, U.S. Pat. No. 5,445,934, and U.S. Pat. No. 5,807,522, Lockart, *Nature Biotechnology*, 14:1675-1680 (1996); Cheung, V. G. et al., *Nature Genetics* 21(Suppl):15-19 (1999) for a discussion of array fabrication). DNA microarrays are miniature arrays containing gene fragments that are either synthesized directly onto or spotted onto glass or other substrates. Thousands of genes are usually represented in a single array. A typical microarray experiment involves the following steps: 1) preparation of fluorescently labeled target from RNA isolated from the sample, 2) hybridization of the labeled target to the microarray, 3) washing, staining, and scanning of the array, 4) analysis of the scanned image and 5) generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ).

The Affymetrix GeneChip® system is a commercially available microarray system which comprises arrays fabricated by direct synthesis of oligonucleotides on a glass surface. Probe/Gene Arrays: Oligonucleotides, usually 25 mers, are directly synthesized onto a glass wafer by a combination of semiconductor-based photolithography and solid phase chemical synthesis technologies. Each array contains up to 400,000 different oligos and each oligo is present in millions of copies. Since oligonucleotide probes are synthesized in known locations on the array, the hybridization patterns and signal intensities can be interpreted in terms of gene identity and relative expression levels by the Affymetrix Microarray Suite software. Each gene is represented on the array by a series of different oligonucleotide probes. Each probe pair consists of a perfect match oligonucleotide and a mismatch oligonucleotide. The perfect match probe has a sequence exactly complimentary to the particular gene and thus measures the expression of the gene. The mismatch probe differs from the perfect match probe by a single base substitution at the center base position, disturbing the binding of the target gene transcript. This helps to determine the background and nonspecific hybridization that contributes to the signal measured for the perfect match oligo. The Microarray Suite software subtracts the hybridization intensities of the mismatch probes from those of the perfect match probes to determine the absolute or specific intensity value for each probe set. Probes are chosen based on current information from GenBank and other nucleotide repositories. The sequences are believed to recognize unique regions of the 3' end of the gene. A GeneChip Hybridization Oven ("rotisserie" oven) is used to carry out the hybridization of up to 64 arrays at one time. The fluidics station performs washing and staining of the probe arrays. It is completely automated and contains four modules, with each module holding one probe array. Each module is controlled independently through Microarray Suite software using preprogrammed fluidics protocols. The scanner is a confocal laser fluorescence scanner which measures fluorescence intensity emitted by the labeled cRNA bound to the probe arrays. The computer workstation with Microarray Suite software controls the fluidics station and the scanner. Microarray Suite software can control up to eight fluidics stations using preprogrammed hybridization, wash, and stain protocols for the probe array. The software also acquires and converts hybridization intensity data into a presence/absence call for each gene using appropriate algorithms. Finally, the software detects changes in gene expression between experiments by comparison analysis and formats the output into .txt files, which can be used with other software programs for further data analysis.

In some embodiments, expression of various biomarkers in a sample may also be assessed by examining gene deletion or gene amplification. Gene deletion or amplification may be measured by any one of a wide variety of protocols known in the art, for example, by conventional Southern blotting, Northern blotting to quantitate the transcription of mRNA (Thomas, *Proc. Natl. Acad. Sci. USA*, 77:5201-5205 (1980)), dot blotting (DNA analysis), or in situ hybridization (e.g., FISH), using an appropriately labeled probe, cytogenetic methods or comparative genomic hybridization (CGH) using an appropriately labeled probe. By way of example, these methods may be employed to detect deletion or amplification of genes.

In some embodiments, expression of various biomarkers in a sample may be assessed by hybridization assays using complementary DNA probes (such as in situ hybridization using labeled riboprobes, Northern blot and related techniques) and various nucleic acid amplification assays (such as RT-PCR using complementary primers, such as primers specific for one or more genes of UAP1, BTG2, CD40, VNN2, RGS13, CD22, LMO2, IFITM1, CTSC, CD44, PUS7, BCL6, EPDR1, IGF1R and CD79B, and other amplification type detection methods, such as, branched DNA, SISBA, TMA and the like).

Tissue or cell samples from mammals can be conveniently assayed for, e.g., mRNAs of any one or more of UAP1, BTG2, CD40, VNN2, RGS13, CD22, LMO2, IFITM1, CTSC, CD44, PUS7, BCL6, EPDR1, IGF1R and CD79B genes, using Northern, dot blot or PCR analysis. In some embodiments, expression of one or more biomarkers may be assayed by RT-PCR. In some embodiments, RT-PCR is quantitative RT-PCR (qRT-PCR). In some embodiments, RT-PCR is real-time RT-PCR. In some embodiments, RT- PCR is quantitative real-time RT-PCR. RT-PCR assays such as quantitative PCR assays are well known in the art. In an illustrative embodiment of the invention, a method for detecting a mRNA in a biological sample comprises producing cDNA from the sample by reverse transcription using at least one primer; amplifying the cDNA so produced using a polynucleotide as sense and antisense primers to amplify cDNAs therein; and detecting the presence of the amplified cDNA of interest. In some embodiments, real-time RT-PCR is quantitative RT-PCR. In some embodiments, real-time RT-PCR may be performed using TaqMan® chemistry (Applied Biosystems). In some embodiments, real-time RT-PCR may be performed using TaqMan® chemistry (Applied Biosystems) and the ABI Prism® 7700 Sequence Detection System (Applied Biosystems). Real-time RT-PCR combines the principles that Taq polymerase has a 5'-3; exonuclease activity and dual-labeled fluorogenic oligonucleotide problems have been created which emit a fluorescent signal only upon cleavage, based on the principle of fluorescence resonance energy transfer. See, e.g., Overbergh, L. et al., *J. Biomolecular Techniques* 14(1): 33-43 (2003). In addition, such methods can include one or more steps that allow one to determine the levels of mRNA, in a biological sample (e.g., by simultaneously examining the levels a comparative control mRNA sequence of a "housekeeping" gene such as an actin family member and/or one or more genes listed in Tables 8 and 9 in WO 2009/062125). Examples of primers and probes that may be used for conducting qRT-PCR are provided in Table 1.

In some embodiments, the expression of proteins encoded by UAP1, BTG2, CD40, VNN2, RGS13, CD22, LMO2, IFITM1, CTSC, CD44, PUS7, BCL6, EPDR1, IGF1R and CD79B in a sample is examined using immunohistochemistry and staining protocols. Immunohistochemical staining of tissue sections has been shown to be a reliable method of assessing or detecting presence of proteins in a sample. Immunohistochemistry ("IHC") techniques utilize an antibody to probe and visualize cellular antigens in situ, generally by chromogenic or fluorescent methods.

For sample preparation, a tissue or cell sample from a mammal (typically a human patient) may be used. Examples of samples include, but are not limited to, tissue biopsy, blood, lung aspirate, sputum, lymph fluid, etc. The sample can be obtained by a variety of procedures known in the art including, but not limited to surgical excision, aspiration or biopsy. The tissue may be fresh or frozen. In some embodiments, the sample is fixed and embedded in paraffin or the like.

The tissue sample may be fixed (i.e. preserved) by conventional methodology (See e.g., "Manual of Histological Staining Method of the Armed Forces Institute of Pathology," $3^{rd}$ edition (1960) Lee G. Luna, HT (ASCP) Editor, The Blakston Division McGraw-Hill Book Company, New York; *The Armed Forces Institute of Pathology Advanced Laboratory Methods in Histology and Pathology* (1994) Ulreka V. Mikel, Editor, Armed Forces Institute of Pathology, American Registry of Pathology, Washington, D.C.). One of skill in the art will appreciate that the choice of a fixative is determined by the purpose for which the sample is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a sample.

Generally, the sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De7 (CMS, Houston, Tex.) may be used.

In some embodiments, subsequent to the sample preparation, a tissue section may be analyzed using IHC. IHC may be performed in combination with additional techniques such as morphological staining and/or fluorescence in-situ hybridization. Two general methods of IHC are available; direct and indirect assays. According to the first assay, binding of antibody to the target antigen (e.g., a protein or fragment thereof encoded by any of UAP1, BTG2, CD40, VNN2, RGS13, CD22, LMO2, IFITM1, CTSC, CD44, PUS7, BCL6, EPDR1, IGF1R and CD79B) is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting.

(b) Colloidal gold particles.

(c) Fluorescent labels including, but are not limited to, rare earth chelates (europium chelates), Texas Red, rhodamine, fluorescein, dansyl, Lissamine, umbelliferone, phycocrytherin, phycocyanin, or commercially available fluorophores such SPECTRUM ORANGE7 and SPECTRUM GREEN7 and/or derivatives of any one or more of the above. The fluorescent labels can be conjugated to the antibody using the techniques disclosed in *Current Protocols in Immunology, supra*, for example. Fluorescence can be quantified using a fluorimeter.

(d) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed. J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase).

Numerous other enzyme-substrate combinations are available to those skilled in the art. For a general review of these, see U.S. Pat. Nos. 4,275,149 and 4,318,980. Sometimes, the label is indirectly conjugated with the antibody. The skilled artisan will be aware of various techniques for achieving this. For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten and one of the different types of labels mentioned above is conjugated with an anti-hapten antibody. Thus, indirect conjugation of the label with the antibody can be achieved.

Aside from the sample preparation procedures discussed above, further treatment of the tissue section prior to, during or following IHC may be desired. For example, epitope retrieval methods, such as heating the tissue sample in citrate buffer may be carried out (see, e.g., Leong et al. *Appl. Immunohistochem.* 4(3):201 (1996)).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. Preferably, the label is an enzymatic label (e.g. HRPO) which catalyzes a chemical alteration of the chromogenic substrate such as 3,3'-diaminobenzidine chromogen. Preferably the enzymatic label is conjugated to antibody which binds specifically to the primary antibody (e.g. the primary antibody is rabbit polyclonal antibody and secondary antibody is goat anti-rabbit antibody).

In some embodiments, the antibodies employed in the IHC analysis to detect expression of one or more biomarkers are antibodies generated to bind primarily to the one or more biomarkers of interest, such as one or more proteins encoded by UAP1, BTG2, CD40, VNN2, RGS13, CD22, LMO2, IFITM1, CTSC, CD44, PUS7, BCL6, EPDR1, IGF1R and CD79B. In some embodiments, the antibody is a monoclonal antibody. Antibodies are readily available in the art, including from various commercial sources, and can also be generated using routine skills known in the art.

Specimens thus prepared may be mounted and coverslipped. Slide evaluation is then determined, e.g. using a microscope, and staining intensity criteria, routinely used in the art, may be employed. As one example, staining intensity criteria may be evaluated as follows:

TABLE A

| Staining Pattern | Score |
| --- | --- |
| No staining is observed in cells. | 0 |
| Faint/barely perceptible staining is detected in more than 10% of the cells. | 1+ |
| Weak to moderate staining is observed in more than 10% of the cells. | 2+ |
| Moderate to strong staining is observed in more than 10% of the cells. | 3+ |

In alternative methods, the sample may be contacted with an antibody specific for said biomarker under conditions sufficient for an antibody-biomarker complex to form, and then detecting said complex. The presence of the biomarker may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labeled antibody to a target biomarker.

Sandwich assays are among the most useful and commonly used assays. A number of variations of the sandwich assay technique exist, and all are intended to be encompassed by the present invention. Briefly, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g., 2-40 minutes or overnight if more convenient) and under suitable conditions (e.g., from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

In some embodiments, the methods involves immobilizing the target biomarkers in the sample and then exposing the immobilized target to specific antibody which may or may not be labeled with a reporter molecule. Depending on the amount of target and the strength of the reporter molecule signal, a bound target may be detectable by direct labeling with the antibody. Alternatively, a second labeled antibody, specific to the first antibody is exposed to the target-first antibody complex to form a target-first antibody-second antibody tertiary complex. The complex is detected by the signal emitted by the reporter molecule. By "reporter molecule", as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, -galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample. Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art. However, other reporter molecules, such as radioisotope, chemiluminescent or bioluminescent molecules, may also be employed.

In some embodiments, expression of a selected biomarker in a tissue or cell sample may be examined by way of functional or activity-based assays. For instance, if the biomarker is an enzyme, one may conduct assays known in the art to determine or detect the presence of the given enzymatic activity in the tissue or cell sample.

In any of the above methods of assessing level of expression of one or more biomarkers, a sample comprising a target molecule can be obtained by methods well known in the art, and that are appropriate for the particular type and location of the disease of interest. Tissue biopsy is often used to obtain a representative piece of disease tissue. Alternatively, cells can be obtained indirectly in the form of tissues/fluids that are known or thought to contain the disease cells of interest. For instance, samples of disease lesions may be obtained by resection, bronchoscopy, fine needle aspiration, bronchial brushings, or from sputum, pleural fluid or blood. Genes or gene products can be detected from disease tissue or from other body samples such as urine, sputum or serum. The same techniques discussed above for detection of target genes or gene products in disease samples can be applied to other body samples. By screening such body samples, a simple early diagnosis can be achieved for these diseases. In addition, the progress of therapy can be monitored more easily by testing such body samples for target genes or gene products.

Means for enriching a tissue preparation for disease cells are known in the art. For example, the tissue may be isolated from paraffin or cryostat sections. Cells of interest may also be separated from normal cells by flow cytometry or laser capture microdissection. These, as well as other techniques for separating disease from normal cells, are well known in the art. If the disease tissue is highly contaminated with normal cells, detection of signature gene expression profile may be more difficult, although techniques for minimizing contamination and/or false positive/negative results are known, some of which are described herein below. For example, a sample may also be assessed for the presence of a biomarker (including a mutation) known to be associated with a disease cell of interest but not a corresponding normal cell, or vice versa.

Subsequent to the determination that the tissue or cell sample expresses one or more of the biomarkers indicating the tissue or cell sample will be sensitive to treatment with anti-CD40 antibodies, it is contemplated that an effective amount of the anti-CD40 antibody may be administered to the mammal, such as a human to treat a disorder, such as a B-cell lymphoma which is afflicting the mammal. Diagnosis in mammals, such as humans, of the various pathological conditions described herein can be made by the skilled practitioner.

Comparing Expression Levels and Predicting, Assessing or Aiding Assessment of Responsiveness of B-Cell Lymphoma to an Anti-CD40 Antibody Treatment The methods described herein comprise a process of comparing a measured expression level of a marker gene and a reference level. The reference level may be a measured expression level of a reference gene different from the marker gene or a measured expression level of the same marker gene in a different sample.

In some embodiments, a measured expression level of a marker gene in a B cell lymphoma sample from a subject is compared to a measured expression level of a reference gene in the sample. In some embodiments, the expression level of the reference gene does not substantially change among various types of B lymphoma cells, including anti-CD40 antibody sensitive and resistant cells. In some embodiments, the ratio of the measured expression level of the marker gene to the measured expression level of the reference is calculated, and the ratio may be used for assessing or aiding assessment of responsiveness of the B cell lymphoma to an anti-CD antibody treatment.

In some embodiments, a measured expression level of a marker gene in a B cell lymphoma sample from a subject is compared to a measured expression level of the marker gene in a reference sample. In some embodiments, the reference sample comprises B lymphoma cells that are resistant or not responsive to an anti-CD40 antibody. For example, the comparison is performed to determine the magnitude of the difference between the measured expression levels of the marker gene in the sample from the subject and in the reference sample (e.g., comparing the fold or percentage difference between the expression levels of the marker gene in the sample from the subject and the reference sample). In some embodiments, an increase or decreased expression of a marker gene in the sample from the subject as compared to the expression of the marker gene in the reference sample comprising B lymphoma cells that are resistant or not responsive to an anti-CD40 antibody suggests or indicates responsiveness of the B-cell lymphoma to treatment with an anti-CD40 antibody. In some embodiments, a fold of increase in the expression level of the sample from the subject can be at least about any of 1.5×, 1.75×, 2×, 3×, 4×, 5×, 6×, 7×, 8×, 9×, or 10× the expression level of the reference sample. In some embodiments, a fold of decrease in the expression level of the sample from the subject can be less than about any of 0.01, 0.05, 0.1, 0.2, 0.3, 0.4, 0.5, 0.6, 0.7, 0.8 of the expression level of the reference sample.

In some embodiments, the expression levels of one or more marker genes selected from the group consisting of IFITM1, CD40, RGS13, VNN2, LMO2, CD79B, CD22, BTG2, IGF1R, CD44, CTSC, EPDR1, UAP1, and PUS7 are compared to a reference level.

In some embodiments, an increased expression level of one or more of IFITM1, CD79B, IGF1R, CD44, CTSC, EPDR1, and PUS7 as compared to a reference level indicates that said subject is less likely to respond to an agonist anti-CD40 antibody treatment. In some embodiments, the reference level is a value or a range determined by expression levels of the corresponding marker gene in samples comprising B lymphoma cells from subjects having tumor volume increased after an agonist anti-CD40 antibody treatment.

In some embodiments, an increased expression of one or more of CD40, RGS13, VNN2, LMO2, CD22, BTG2, and UAP1 as compared to a reference level indicates that said subject is likely to respond to the agonist anti-CD40 antibody treatment. In some embodiments, the reference level is a value or a range determined by expression levels of the corresponding marker gene in samples comprising B lymphoma cells from subjects having tumor volume decreased after an agonist anti-CD40 antibody treatment.

In some embodiments, the expression level BCL6 is measured and compared to a reference level. The expression level of BCL6 is used for predicting, assessing, or aiding assessment of responsiveness of the subject to an anti-CD40 antibody treatment. As shown in Example 1, BCL6 expression trends lower in those subjects with tumor increases after an agonist anti-CD40 antibody treatment. In some embodiments, an increased expression of BCL6 as compared to a reference level determined by expression level of BCL6 in samples from subjects having tumor volume decreased after an agonist anti-CD40 antibody treatment may indicate the subject is likely to respond to the agonist anti-CD40 antibody treatment.

In some embodiments, the expression levels of one or more of IFITM1, CD40, RGS13, VNN2, LMO2, CD79B, CD22, BTG2, IGF1R, CD44, CTSC, EPDR1, UAP1, PUS7, and BCL6 are measured, and a sensitivity index is calculated based on the measured expression level of the marker genes. For example, the following equation may be used for determining sensitivity index (SI):

$$SI = \sum_{j=1}^{p} \beta_j \frac{x_j - \hat{\mu}_j}{\sqrt{\hat{\sigma}_j^2}}$$

wherein expression level of at least one marker gene having a positive correlation value and at least one marker gene having a negative correlation value shown in Table 4 are measured; wherein (i) $\beta_j$ is the coefficient value for each marker genes measured; (ii) p is the number of marker genes measured; (iii) $x_j$ is transformed, normalized expression level for the sample from the subject for expression level of each marker measured; and (iv) $\mu_j$ and $\sigma_j$ are means and standard deviations for each marker gene measured; wherein $\beta_j$, $\mu_j$ and $\sigma_j$ are determined from patient samples comprising B lymphoma cells from a clinical trial. In some embodiments, a value equals or greater than zero for the sensitivity index indicates that the subject is likely to respond the anti-CD40 antibody treatment, or wherein a value less than zero for the sensitivity index indicates that the subject is less likely to respond the anti-CD40 antibody treatment. Examples 1 described in detail how to analyze and determine parameters for reference samples and new samples. In some embodiments, the expression levels of IFITM1, RGS13, CD79B, CD22, BTG2, CD44, EPDR1, and UAP1 are measured and used for the sensitivity index calculation. In some embodiments, equal number of positive correlated marker genes and negative correlated marker genes are measured and used for the sensitivity index calculation.

Methods for determining sensitivity index are known in the art. See Zhou H. and Hastie T. (2005) *Regularization and*

*variable selection via the elastic net*; J. R. Statist. Soc. B. 67(2). pp. 301-320; Friedman J., Hastie T. and Tibshirani R. 2008. *Regularization Paths for Generalized Linear Models via Coordinate Descent*. Technical Report, Department of Statistics, Stanford University (World Wide Web-stat.stanford.edu/~hastie/Papers/glmnet.pdf) R package glmnet; R Development Core Team (2008). R: A language and environment for statistical computing. R Foundation for Statistical Computing, Vienna, Austria. ISBN 3-900051-07-0, URL World Wide Web at R-project.org.

An alternative method using weighted K-nearest neighbors (WKNN) to classify a patient sample as responsive to an anti-CD40 antibody treatment is described in Example 2. The qRT-PCR is used to measure expression of 15 genes, UAP1, BTG2, CD40, VNN2, RGS13, CD22, LMO2, IFITM1, CTSC, CD44, PUS7, BCL6, EPDR1, IGF1R and CD79B. Tumor size reduction of at least 10% is defined as being responsive to the anti-CD40 antibody treatment. Weights for the 15 genes are determined using penalized regression (GLMNET).

In some embodiments, the methods of the invention comprise classifying the subject as a responsive or non-responsive subject using a K-nearest neighbors analysis based on the expression level of said one or more marker genes of UAP1, BTG2, CD40, VNN2, RGS13, CD22, LMO2, IFITM1, CTSC, CD44, PUS7, BCL6, EPDR1, IGF1R and CD79B in the sample from the subject and reference samples with known classes. In some embodiments, classifying the subject using a K-nearest neighbors analysis is carried out by (1) determining parameter K (i.e., number of nearest neighbors); (2) calculating the difference between the measured expression level of the marker genes in the new sample to be classified and the expression level of the respective marker genes in each reference sample; (3) determining the nearest reference samples by selecting those samples with the smallest weighted average of the absolute differences (WAAD) between the new sample and the reference sample; and (4) determining class of the new sample based on the known classes of the K nearest reference samples. The weights and/or parameter K are determined using cross-validation with clinical trial samples with known classes. For example, 5-fold (such as 5-fold, 6-fold, 7-fold, 8-fold, 9-fold, or 10-fold) to N-fold cross-validation may be used to minimize the weighted K-nearest neighbors classification error, wherein N is the size of the samples. In some embodiments, K is an integer between 4 and 13 (e.g., 4, 5, 6, 7, 8, 9, 10, 11, 12, and 13). In some embodiments, the nearest reference samples (nearest neighbors) are those with the smallest weighted average of the absolute differences (WADD) between the expression level of the new sample to be classified and the expression level of each reference sample for each of the 15 marker genes UAP1, BTG2, CD40, VNN2, RGS13, CD22, LMO2, IFITM1, CTSC, CD44, PUS7, BCL6, EPDR1, IGF1R and CD79B. In some embodiments, the weights for the WAAD are the absolute values of the coefficients from an elastic net penalized regression of reference sample tumor shrinkage on the expression levels of the 15 maker genes. In some embodiments, the magnitude of the penalty is chosen by 10 fold cross-validation to minimize the WKNN classification error. Weights for the 15 genes may be determined using penalized regression (GLMNET). In some embodiments, qRT-PCR is used to measure expression levels of the 15 genes, UAP1, BTG2, CD40, VNN2, RGS13, CD22, LMO2, IFITM1, CTSC, CD44, PUS7, BCL6, EPDR1, IGF1R and CD79B. In some embodiments, the K nearest reference samples contribute to the inverse of their WADD (i.e., 1 divided by the WAAD) in the manner of a vote for their known class label, and the class label with the largest total inverse WAAD contributions is assigned to the new sample. In some embodiments, a patient is considered as being responsive to an anti-CD40 antibody treatment if the patient has at least 10% tumor size reduction after the anti-CD40 antibody treatment. Tumor size reduction may be determined by the sum of the product of diameters (SPD). Example 2 provides a detailed description of using the weighted K-nearest neighbors method with 39 DLBCL patient samples as reference samples.

The comparisons and/or calculations for predicting, assessing or aiding assessment can be carried out in any convenient manner appropriate to the type of measured value and/or reference value for the gene markers at issue. The process of comparing or calculating may be manual or it may be automatic (such as by a machine including computer-based machine). In some embodiments, measured expression levels are normalized values. For example, the expression level may be normalized based on the equation under Transformed, Normalized Assay Values described in Example 1. As will be apparent to those of skill in the art, replicate measurements may be taken for the expression levels of marker genes and/or reference genes. In some embodiments, replicate measurements are taking into account for the measured values. The replicate measurements may be taken into account by using either the mean or median of the measured values as the "measured value". Statistical analysis known in the art may be used to verify the significance of the difference between the two values compared.

Anti-CD40 Antibody Treatment

The marker genes identified in the invention may be used for predicting, assessing, or aiding assessment of responsiveness of B-cell lymphoma to treatment with one or more anti-CD40 antibodies. The anti-CD40 antibodies may be one or more agonist antibodies (i.e., bind and stimulate CD40). Stimulatory antibodies can be of different types, such as: (1) those that deliver a stimulatory signal through CD40 but do not increase the interaction between CD40 and CD40L (e.g., antibody G28-5 and antibodies derived from G28-5 described in U.S. Pat. No. 5,182,368; and PCT WO 96/18413), or decrease the interaction between CD40 and CD40L (e.g., antibodies HuCD40-M2 and HuCD40-M3 and humanized antibodies described in U.S. Pat. No. 5,674,492; and (2) those that deliver a stimulatory signal through CD40 and can increase the interaction between CD40 and CD40L, e.g., S2C6 (Francisco et al., 2000, *Cancer Res.* 60:3225-31) and antibodies derived from S2C6. Agonists antibodies are also described in U.S. Pat. No. 7,288,251. The anti-CD40 antibodies may be one or more antagonist antibodies (i.e., bind CD40 and inhibit activities induced by CD40L). Examples of antagonist anti-CD40 antibodies include human antibody CHIR-12.12 described in U.S. Pub. No. 2007/0110754, and anti-CD40 antibodies described in WO 97/31025. In some embodiments, the anti-CD40 antibody comprises the heavy chain amino acid sequence of SEQ ID NO:1 and the light chain amino acid sequence of SEQ ID NO:2.

The methods of the invention may further comprise administering an effective amount of an anti-CD40 antibody to a subject having a B-cell lymphoma after the subject has been identified as a candidate for treatment based on the assays/methods described herein. One or more anti-CD40 antibodies may be administered. In some embodiments, the anti-CD40 antibody is administered in conjunction with one or more other therapeutic agents. For example, the anti- CD40 antibody is administered in conjunction with one or more of the following therapeutic agents: rituximab, gemzar, and ICE. For example, an anti-CD40 antibody can be administered to the patient in conjunction with rituximab therapy; with rituximab plus gemzar; with rituximab plus ICE (ifosfamide, carboplatin, etoposide) (R-ICE); or with rituximab plus chemotherapy.

As used herein, administration "in conjunction" includes simultaneous administration and/or administration at different times. Administration in conjunction also encompasses administration as a co-formulation (i.e., different drugs are present in the same composition) or administration as separate compositions, administration at different dosing frequencies or intervals, and administration using the same route or different routes.

The anti-CD40 antibodies or functional fragments can be used for the treatment of patients with NHL that are non-responsive or have an inadequate response to treatment with any one of the following drugs: rituximab (Genentech); ocrelizumab (Genentech, Inc.); ibritumomab tiuxetan (Zevalin™, Biogen Idec); tositumomab (Bexxar™, GlaxoSmithKline); HuMAX-CD20™ (GenMab); IMMU-106 (which is a humanized anti-CD20 a.k.a. hA20 or 90Y-hLL2, Immunomedics); AME-133 (Applied Molecular Evolution/Eli Lilly); gentuzumab ozogamicin (Mylotarg™, a humanized anti-CD33 antibody, Wyeth/PDL); alemtuzumab (Campath™, an anti-CD52 antibody, Schering Plough/Genzyme); epratuzumab (IMMU-103™, a humanized anti-CD22 antibody, Immunomedics), or have relapsed after treatment with these drugs.

The following references describe lymphomas and CLL, their diagnoses, treatment and standard medical procedures for measuring treatment efficacy. Canellos G P, Lister, T A, Sklar J L: The Lymphomas. W.B. Saunders Company, Philadelphia, 1998; van Besien K and Cabanillas, F: Clinical Manifestations, Staging and Treatment of Non-Hodgkin's Lymphoma, Chap. 70, pp 1293-1338, in: *Hematology, Basic Principles and Practice*, 3rd ed. Hoffman et al. (editors). Churchill Livingstone, Philadelphia, 2000; and Rai, K and Patel, D:Chronic Lymphocytic Leukemia, Chap. 72, pp 1350-1362, in: *Hematology, Basic Principles and Practice*, 3rd ed. Hoffman et al. (editors). Churchill Livingstone, Philadelphia, 2000.

Anti-CD40 antibodies for use in the treatment include chimeric, humanized and human antibodies. Any agonist or antagonist antibodies described herein or known in the art may be used in the treatment. For example, humanized anti-CD40 antibodies described in WO 2006/128103 may be used for the anti-CD40 antibody treatment, and these antibodies and their amino acid sequences are incorporated herein by reference. In some embodiments, the anti-CD40 antibody for use in the treatment described herein binds to CD40 (such as human CD40) expressed on B lymphoma cells and induces apoptosis of the B lymphoma cells. The anti-CD40 antibody may also have the characteristics of killing B lymphoma cells in vivo via immune effector functions, such as ADCC, CDC, and/or ADCP. In some embodiments, the anti-CD40 antibody binds to CD40 with a $K_d$ value of no higher than about $1 \times 10^{-8}$ or no higher than $1 \times 10^{-9}$. In some embodiments, the anti-CD40 antibody binds to CD40 and stimulates CD40 (i.e., an agonist antibody). In some embodiments, the anti-CD40 antibody increases the binding of CD40 ligand to CD40, for example, by at least 45%, by at least 50%, by at least 60%, or by at least 75%. A method of determining increases in binding of CD40 ligand to CD40 are disclosed in U.S. Pat. No. 6,838,261 (the disclosure of which is incorporated by reference herein). In some embodiments, the anti-CD40 is a humanized antibody derived from murine monoclonal antibody S2C6 described in WO 00/75348 (including antibodies provided in Tables 3 and 4 of WO 00/75348). In some embodiments, the anti-CD40 antibody comprises the heavy chain amino acid sequence shown in SEQ ID NO:1 and the light chain amino acid sequence shown in SEQ ID NO:2, for example anti-CD40 Ab.1.

D. KITS

For use in the applications described or suggested above, kits or articles of manufacture are also provided by the invention. Such kits may comprise at least one reagent specific for detecting expression level of a marker gene described herein, and may further include instructions for carrying out a method described herein.

In some embodiments, the invention provides compositions and kits comprising primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of polynucleotides, such as the polynucleotides corresponding to genes UAP1, BTG2, CD40, VNN2, RGS13, CD22, LMO2, IFITM1, CTSC, CD44, PUS7, BCL6, EPDR1, IGF1R and CD79B, in a sample and as a means for detecting cell expressing proteins encoded by the polynucleotides corresponding to genes UAP1, BTG2, CD40, VNN2, RGS13, CD22, LMO2, IFITM1, CTSC, CD44, PUS7, BCL6, EPDR1, IGF1R and CD79B. As will be understood by the skilled artisan, a great many different primers and probes may be prepared based on the sequences provided herein and used effectively to amplify, clone and/or determine the presence and/or levels of mRNAs.

In some embodiments, the kits comprise reagents for detecting expression levels of at least two, at least three, at least five, at least ten, or fifteen marker genes selected from the group consisting of UAP1, BTG2, CD40, VNN2, RGS13, CD22, LMO2, IFITM1, CTSC, CD44, PUS7, BCL6, EPDR1, IGF1R and CD79B. Kits may also comprise reference samples that are useful as generating reference values. The marker genes include, but are not limited to UAP1, BTG2, CD40, VNN2, RGS13, CD22, LMO2, IFITM1, CTSC, CD44, PUS7, BCL6, EPDR1, IGF1R and CD79B. The reagents for detecting mRNA expression level of a marker gene may comprise at least one pair of primers specific for amplifying the mRNA products of one marker gene. In some embodiments, the pair of primers may target the 3' end of the mRNA sequence (e.g., targeting mRNA at the 3' UTR which is usually shared in common with all transcript variants). In some embodiments, the kits may further comprise a surface or substrate (such as a microarray) for capture probes for detecting of amplified nucleic acids.

In some embodiments, the kits comprise at least one pair of primers and a probe specific for detecting one marker gene expression level using qRT-PCR. Examples of sets of primers and probes that can be used in qRT-PCR are shown in Table 1. For detecting IFITM1, primer and probe sets shown in SEQ ID NOS:27, 28 and 29, SEQ ID NOS:60, 61, and 62, and SEQ ID NOS:93, 94, and 95 may be used. For detecting CD40, primer and probe sets shown in SEQ ID NOS:24, 25, and 26, SEQ ID NOS:57, 58, and 59, SEQ ID NOS:90, 91 and 92 may be used. For detecting RGS13, primer and probe sets shown in SEQ ID NOS:114, 115, and 116, and SEQ ID NOS:126, 127, and 128 may be used. For detecting VNN2, primer and probe sets shown in SEQ ID NOS:30, 31, and 32, SEQ ID NOS:63, 64, and 65, and SEQ ID NOS:96, 97, and 98. For detecting LMO2, primer and probe sets shown in SEQ ID NOS:12, 13, and 14, SEQ ID NOS:45, 46, and 47, and SEQ ID NOS:78, 79, and 80. For detecting CD79B, primer and probe sets shown in SEQ ID NOS:141, 142, and 143, SEQ ID NOS:150, 151, and 152, and SEQ ID NOS:159, 160, and 161. For detecting CD22, primer and probe sets shown in SEQ ID NOS:15, 16, and 17, SEQ ID NOS:48, 49, and 50, and SEQ ID NOS:81, 82, and 83. For detecting BTG2, primer and probe sets shown in SEQ ID NOS:9, 10, and 11, SEQ ID NOS:42, 43, and 44, and SEQ ID NOS:75, 76, and 77. For detecting IGF1R, primer and probe sets shown in SEQ ID NOS:6, 7, and 8, SEQ ID NOS:39, 40, and 41, and SEQ ID NOS:72, 73, and 74. For detecting CD44, primer and probe sets shown in SEQ ID NOS:174, 175, and 176, SEQ ID NOS:180, 181, and 182, and SEQ ID NOS:186, 187, and 188. For detecting CTSC, primer and probe sets shown in SEQ ID NOS:165, 166, and 167, SEQ ID NOS:168, 169, and 170, and SEQ ID NOS:171, 172, and 173. For detecting EPDR1, primer and probe sets shown in SEQ ID NOS:21, 22, and 23, SEQ ID NOS:54, 55, and 56, SEQ ID NOS:87, 88, and 89, SEQ ID NOS:129, 130, and 131, SEQ ID NOS:132, 133, and 134, SEQ ID NOS:135, 136, and 137. For detecting UAP1, primer and probe sets shown in SEQ ID NOS:138, 139, and 140, SEQ ID NOS:147, 148, and 149, and SEQ ID NOS: 156, 157, and 158. For detecting PUS7, primer and probe sets shown in SEQ ID NOS:177, 178, and 179, SEQ ID NOS:183, 184, and 185, and SEQ ID NOS:189, 190, and 191. For detecting BCL6, primer and probe sets shown in SEQ ID NOS:102, 103, and 104, and SEQ ID NOS:108, 109, and 110.

The reagents for detecting the protein expression level of a marker gene may comprise an antibody that specifically binds to the protein encoded by the marker gene.

The kits may further comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for a marker gene. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

The kit can further comprise a set of instructions and materials for preparing a tissue or cell sample and preparing nucleic acids (such as mRNA) from the sample.

The invention provides a variety of compositions suitable for use in performing methods of the invention, which may be used in kits. For example, the invention provides surfaces, such as arrays that can be used in such methods. In some embodiments, an array of the invention comprises individual or collections of nucleic acid molecules useful for detecting mutations of the invention. For instance, an array of the invention may comprises a series of discretely placed individual nucleic acid oligonucleotides or sets of nucleic acid oligonucleotide combinations that are hybridizable to a sample comprising target nucleic acids, whereby such hybridization is indicative of presence or absence of a mutation of the invention.

Several techniques are well-known in the art for attaching nucleic acids to a solid substrate such as a glass slide. One method is to incorporate modified bases or analogs that contain a moiety that is capable of attachment to a solid substrate, such as an amine group, a derivative of an amine group or another group with a positive charge, into nucleic acid molecules that are synthesized. The synthesized product is then contacted with a solid substrate, such as a glass slide, which is coated with an aldehyde or another reactive group which will form a covalent link with the reactive group that is on the amplified product and become covalently attached to the glass slide. Other methods, such as those using amino propryl silican surface chemistry are also known in the art, as disclosed at world wide web at cmt-.corning.com and cmgm.stanford.edu/pbrown1.

Attachment of groups to oligonucleotides which could be later converted to reactive groups is also possible using methods known in the art. Any attachment to nucleotides of oligonucleotides will become part of oligonucleotide, which could then be attached to the solid surface of the microarray. Amplified nucleic acids can be further modified, such as through cleavage into fragments or by attachment of detectable labels, prior to or following attachment to the solid substrate, as required and/or permitted by the techniques used.

The following are examples of the methods and compositions of the invention. It is understood that various other embodiments may be practiced, given the general description provided above.

EXAMPLES

Example 1

Identification of Markers Associated with Responsiveness to Treatment with Anti-CD40 Ab.1 in Clinical Trials Clinical Trial 001 (Phase II)

A multicenter, phase II, open-label study to determine the overall response rate and toxicity profile of anti-CD40 Ab.1 in patients with relapsed DLBCL. Tumor samples were assessed by a central lab for pathology confirmation and CD40 expression. Eligible patients had de novo or a transformed DLBCL at diagnosis and were excluded if there was a prior history of indolent lymphoma. Required prior therapy consisted of combination chemotherapy with rituximab and, if eligible, autologous stem cell transplantation. Patients received 6 IV infusions of anti-CD40 Ab.1 over 5 weeks (Cycle 1) with intra-patient dose loading (1 mg/kg on Day 1; 2 mg/kg on Day 4; 4 mg/kg on Day 8) and 8 mg/kg/wk thereafter. Responding patients and those with SD (stable disease) were eligible to continue therapy until disease progression or up to a maximum of 12 cycles. Tumor tissues were taken from patients before they received treatment with anti-CD40 Ab.1. For example, samples were taken as part of routine lymphoma diagnosis.

Anti-CD40 Ab.1 is a humanized IgG1 monoclonal antibody against CD40. It is produced in and secreted by a genetically engineered Chinese Hamster Ovary (CHO) cell line. The anti-CD40 Ab.1 has the following amino acid sequence:

Heavy Chain (SEQ ID NO: 1). The italicized underlined ASN 294
residue identifies the location of the carbohydrate moiety.

```
EVQLVESGGG LVQPGGSLRL SCAASGYSFT GYYIHWVRQA PGKGLEWVAR      50

VIPNAGGTSY NQKFKGRFTL SVDNSKNTAY LQMNSLRAED TAVYYCAREG     100

IYWWGQGTLV TVSSASTKGP SVFPLAPSSK STSGGTAALG CLVKDYFPEP     150

VTVSWNSGAL TSGVHTFPAV LQSSGLYSLS SVVTVPSSSL GTQTYICNVN     200

HKPSNTKVDK KVEPKSCDKT HTCPPCPAPE LLGGPSVFLF PPKPKDTLMI     250

SRTPEVTCVV VDVSHEDPEV KFNWYVDGVE VHNAKTKPRE EQY*NST*YRVV   300

SVLTVLHQDW LNGKEYKCKV SNKALPAPIE KTISKAKGQP REPQVYTLPP     350

SREEMTKNQV SLTCLVKGFY PSDIAVEWES NGQPENNYKT TPPVLDSDGS     400

FFLYSKLTVD KSRWQQGNVF SCSVMHEALH NHYTQKSLSL SPG            443
```

Light Chain (SEQ ID NO: 2).
```
DIQMTQSPSS LSASVGDRVT ITCRSSQSLV HSNGNTFLHW YQQKPGKAPK      50

LLIYTVSNRF SGVPSRFSGS GSGTDFTLTI SSLQPEDFAT YFCSQTTHVP     100

WTFGQGTKVE IKRTVAAPSV FIFPPSDEQL KSGTASVVCL LNNFYPREAK     150

VQWKVDNALQ SGNSQESVTE QDSKDSTYSL SSTLTLSKAD YEKHKVYACE     200

VTHQGLSSPV TKSFNRGEC                                       219
```

Clinical Trial 002 (Phase I)

Multi-institutional, multi-dose phase I study was conducted to test the safety, pharmacokinetic properties, immunogenicity, and antitumor activity of intravenous anti-CD40 Ab.1 in patients with relapsed NHL. Patients with multiple histologic subtypes of NHL were enrolled on this study, including diffuse large B-cell (DLBCL; 14), follicular (FCL; 9), mantle cell (MCL; 9), marginal zone (MZL; 2) and small lymphocytic (SLL; 1). Patients were treated with a dose-loading schedule: 1 mg/kg of anti-CD40 Ab.1 on day 1 and day 4 and subsequent intra-patient dose-escalation during weeks 2-5 to a maximum dose of 3, 4, 6, or 8 mg/kg over four cohorts. Subsequently, a rapid dose-loading schedule was tested in one cohort (40% increase in total anti-CD40 Ab.1 administered during cycle 1). Responding patients or those with stable disease were eligible for a second cycle, consisting of four consecutive weekly infusions at the cohort-specific maximum dose of anti-CD40 Ab.1. Eight patients with DLBCL completed cycle 1 and received a maximum dose of at least 3 mg/kg anti-CD40 Ab.1 with an objective response rate of 37.5% (i.e. 1 CR and 2 PR) and 2 SD. Additional objective responses were seen in one patient with MCL (CR) and one patient with MZL (PR). The median duration of response for these 5 patients has not yet been reached (range 8-37 weeks). Tumor tissues were taken from patients before they received treatment with anti-Cd40 Ab.1. For example, samples were taken as part of routine lymphoma diagnosis.

Clinical Sample Preparation and qRT-PCR

Formalin Fixed Paraffin Embedded (FFPE) archival tumor tissue from the Phase I and Phase II clinical trials described above was obtained from the clinical investigation sites with appropriate IRB approval and patient consent. 4-6 micron sections derived from the tumor tissue were mounted on glass slides and one slide for each case was subject to H&E staining using standard pathology laboratory protocol. A board certified Pathologist marked the H&E slide for tumor content and was used as a guide to macrodissect the remaining tumor-containing region for RNA extraction using the Ambion RecoverAll™ Total Nucleic Acid Isolation Kit for FFPE Tissues (Cat. No. AM1975; Applied Biosystems/Ambion, Austin, Tex.).

450 ng total RNA per sample was reverse transcribed in a total reaction volume of 20 uL using Applied Biosystems' High Capacity Reverse Transcription cDNA Synthesis kit (Cat. No. 4368814; Applied Biosystems, Foster City, Calif.). Manufacturer's recommendations were followed with the exception of a shortened 60 min RT reaction at 37 degrees. 5 ng total RNA equivalent cDNA (assuming 100% cDNA synthesis efficiency) product was mixed with Applied Biosystems' 2× Universal Master Mix (no UNG) in a volume of 15 uL for each PCR assay well. All amplifications were performed in triplicate in 384-well plates using a 2-step (95 degrees 15 sec, 60 degrees 1 min) PCR amplification procedure. Reactions were carried out to 40 cycles on a validated ABI 7900 real-time PCR system. Sequences of the primers and probes used are shown in Table 1.

TABLE 1

Primers and Probes

| Gene Locus | GenBank Accession No. | Probe Overlap | Forward Primer | Reverse Primer | Probe |
|---|---|---|---|---|---|
| PRKCA | NM_002737.2 | 1 | TGACAAAATGTAGAGGCCATTCA (SEQ ID NO: 3) | CATCCGTCTCCTCTG CGATATAA (SEQ ID NO: 4) | CCGTCAAACACCATTT (SEQ ID NO: 5) |

TABLE 1-continued

Primers and Probes

| Gene Locus | GenBank Accession No. | Probe Overlap | Forward Primer | Reverse Primer | Probe |
|---|---|---|---|---|---|
| IGF1R | NM_000875.3 | 1 | TTGCAAGGAAAGAAATTCAAACAC (SEQ ID NO: 6) | TGCTTGAATCCATTGACTGCTT (SEQ ID NO: 7) | ACAACAGCAGTAAGAAGA (SEQ ID NO: 8) |
| BTG2 | NM_006763.2 | 1 | CAGGTCCCTGCCTTTTTAGAAG (SEQ ID NO: 9) | ATCATAAAGAAGAGAGAGAGACAAGATTAAG (SEQ ID NO: 10) | AGCCTCATGGTCTCAT (SEQ ID NO: 11) |
| LMO2 | NM_005574.2 | 1 | GGCCACAGCCCATCCA (SEQ ID NO: 12) | CTTGCCCCTAAATGTTCCTTTCT (SEQ ID NO: 13) | AGTAACTGACATGATTAGC (SEQ ID NO: 14) |
| CD22 | NM_001771.2 | 1 | TTTGGAAGTGAGGCATTGCA (SEQ ID NO: 15) | CCGGAGTCCCCAGAGTCAA (SEQ ID NO: 16) | AGACGTACGTATCAGCG (SEQ ID NO: 17) |
| SMN1 | NM_000344.2 | 1 | CTGGAATGTGAAGCGTTATAGAAGAT (SEQ ID NO: 18) | CCTTTTTTCTTTCCCAACACTTGA (SEQ ID NO: 19) | CTGGCCTCATTTCT (SEQ ID NO: 20) |
| EPDR1 | NM_017549.3 | 1 | CAGCCTCTCTTGTCCCTGGTT (SEQ ID NO: 21) | TCCCTAGCAATGGACAAACTCA (SEQ ID NO: 22) | CCTTATGTGTTGAATGTGG (SEQ ID NO: 23) |
| CD40 | NM_001250.4 | 1 | GGGATCCTGTTTGCCATCCT (SEQ ID NO: 24) | GCTTCTTGGCCACCTTTTTG (SEQ ID NO: 25) | TTGGTGCTGGTCTTT (SEQ ID NO: 26) |
| IFITM1 | NM_003641.3 | 1 | GGCTTCATAGCATTCGCCTACT (SEQ ID NO: 27) | TCACGTCGCCAACCATCTT (SEQ ID NO: 28) | CGTGAAGTCTAGGGACAG (SEQ ID NO: 29) |
| VNN2 | NM_004665.2 | 1 | GACTTGTATGTATGGGAGTGAGGAGTT (SEQ ID NO: 30) | TCTCTTCAAGGGCACAGCTATG (SEQ ID NO: 31) | CAGGGCCATTGCAA (SEQ ID NO: 32) |
| PRPSAP2 | NM_002767.2 | 1 | GCCAAACTGGAAACATAAGAGTGA (SEQ ID NO: 33) | GCATGACGGTTCCTGTGAAA (SEQ ID NO: 34) | TGCTCGGTGGGATGG (SEQ ID NO: 35) |
| PRKCA | NM_002737.2 | 1 | CGGAGGTTGAGGTTTTTCCTT (SEQ ID NO: 36) | GACGGTTGAATGGCCTCTACA (SEQ ID NO: 37) | TGTATAAGCACCTACTGACAAA (SEQ ID NO: 38) |
| IGF1R | NM_000875.3 | 1 | AGGACTTCTTCATGGGTCTTACAGTT (SEQ ID NO: 39) | AAGTGACATTAAAGACGATGTGTATGC (SEQ ID NO: 40) | TGTTAGACCATGAAACATT (SEQ ID NO: 41) |
| BTG2 | NM_006763.2 | 1 | CAGGCTGTGTTCTTGCATCTTG (SEQ ID NO: 42) | GACCATGAGGCTGCTTCTAAAAA (SEQ ID NO: 43) | CTGCAAACAGGTCCCT (SEQ ID NO: 44) |
| LMO2 | NM_005574.2 | 1 | TTGGACCCAAGGGAAAACTG (SEQ ID NO: 45) | GGTTAAAAGTTGTGGTTTCCATTCTC (SEQ ID NO: 46) | TGGAGACGCATTTCG (SEQ ID NO: 47) |
| CD22 | NM_001771.2 | 1 | GACATCCCCACTCACGAATATTATG (SEQ ID NO: 48) | CTGTCCTTTTCTGGGCTTTCC (SEQ ID NO: 49) | CCAGTTTCTGCCTCTGA (SEQ ID NO: 50) |
| SMN1 | NM_000344.2 | 1 | GGCATAGAGCAGCACTAAATGACA (SEQ ID NO: 51) | TTCTATAACGCTTCACATTCCAGATC (SEQ ID NO: 52) | CACTAAAGAAACGATCAGAC (SEQ ID NO: 53) |
| EPDR1 | NM_017549.3 | 0 | CGCACTTTGGCCTTCCTAGA (SEQ ID NO: 54) | TGGAAGGAGATGCAGAAGTCAGA (SEQ ID NO: 55) | CACTGCTTCATAACCTC (SEQ ID NO: 56) |
| CD40 | NM_001250.4 | 1 | CCTGCCCAGTCGGCTTCT (SEQ ID NO: 57) | GTCCAAGGGTGACATTTTTCG (SEQ ID NO: 58) | CTCCAATGTGTCATCTG (SEQ ID NO: 59) |

TABLE 1-continued

Primers and Probes

| Gene Locus | GenBank Accession No. | Probe Overlap | Forward Primer | Reverse Primer | Probe |
|---|---|---|---|---|---|
| IFITM1 | NM_003641.3 | 1 | GGGTTACTAGTAGCCGCCCATA (SEQ ID NO: 60) | GCAGGGCCAGCATTGC (SEQ ID NO: 61) | CAACCTTTGCACTCCAC (SEQ ID NO: 62) |
| VNN2 | NM_004665.2 | 1 | TGTCCATTTTTTTGGCTACTCTGA (SEQ ID NO: 63) | CCCAAACACCCAGGCTCTT (SEQ ID NO: 64) | CAGTGTGGAACAATG (SEQ ID NO: 65) |
| PRPSAP2 | NM_002767.2 | 0 | GCTCCAGTGCCCCAAGATT (SEQ ID NO: 66) | CGACGGATCGCCTCTGAA (SEQ ID NO: 67) | AAACTGTGGATATCAGCATGA (SEQ ID NO: 68) |
| PRKCA | NM_002737.2 | 0 | TGGGCAACTCAGAAATACTTCGA (SEQ ID NO: 69) | ACGTCAATAGGCACGTTTGCT (SEQ ID NO: 70) | CTCCCAAGATATAAGAGGC (SEQ ID NO: 71) |
| IGF1R | NM_000875.3 | 0 | GTCCACCCTCTCCCCTTTCT (SEQ ID NO: 72) | CACGCACTCTAGTACAAAGCATAAGA (SEQ ID NO: 73) | CTCACTCCAAGAAAC (SEQ ID NO: 74) |
| BTG2 | NM_006763.2 | 0 | CCCAAACCGAATCACCTTAAGA (SEQ ID NO: 75) | CAGGAGGGTGGCCATCCT (SEQ ID NO: 76) | ACAGGGCTAGGGCAT (SEQ ID NO: 77) |
| LMO2 | NM_005574.2 | 0 | TCTCCATGGCATCTTCGTCTT (SEQ ID NO: 78) | ATCCCTTACCCCACCCTCAA (SEQ ID NO: 79) | ACTCTTAGGCACTTTGG (SEQ ID NO: 80) |
| CD22 | NM_001771.2 | 0 | CGGCCTCAGGCACAAGAA (SEQ ID ND: 81) | GCAGCCCATCCAGTGTCAAT (SEQ ID ND: 82) | ATGTGGACTATGTGATCCT (SEQ ID NO: 83) |
| SMN1 | NM_000344.2 | 0 | CATGGTACATGAGTGGCTATCATACTG (SEQ ID NO: 84) | GTGAGCACCTTCCTTCTTTTTGA (SEQ ID NO: 85) | CTATTATATGGGTTTCAGACAAA (SEQ ID NO: 86) |
| EPDR1 | NM_017549.3 | 0 | GACTATTGTCTCCTAAACCCAGGACTA (SEQ ID NO: 87) | CCCAGTGCATTTAATGACCAAA (SEQ ID NO: 88) | AGTTCCCTCGTACTGTC (SEQ ID NO: 89) |
| CD40 | NM_001250.4 | 1 | ATCAATTTTCCCGACGATCTTC (SEQ ID NO: 90) | CGGTTGGCATCCATGTAAAGT (SEQ ID NO: 91) | TGGCTCCAACACTG (SEQ ID NO: 92) |
| IFITM1 | NM_003641.3 | 0 | AGGTCCACCGTGATCAACATC (SEQ ID NO: 93) | CAGGGACCAGACGACATGGT (SEQ ID NO: 94) | ACAGCGAGACCTCCGT (SEQ ID NO: 95) |
| VNN2 | NM_004665.2 | 0 | CAACTTGTGGACGGCCAGTA (SEQ ID NO: 96) | GTGCCACTGAGGGAGAACATTT (SEQ ID NO: 97) | AAACTGCTTCTACAAGATT (SEQ ID NO: 98) |
| PRPSAP2 | NM_002767.2 | 0 | CAGCAGAGACCCTGAAGGAAA (SEQ ID NO: 99) | CAAGCCATGAGTTGCCATCA (SEQ ID NO: 100) | AGGTGCATATAAGATCTT (SEQ ID NO: 101) |
| BCL6 | NM_001706.2 | 1 | CCCATTCTGCGTCATGCTT (SEQ ID NO: 102) | AATGCAGTTTAGACACAGCCAAAC (SEQ ID NO: 103) | TGTTATAACTACTCCGGAGACAG (SEQ ID NO: 104) |
| LRRC8A | NM_019594.2 | 1 | AGTTCAGCCCAGATGGAAGGT (SEQ ID NO: 105) | GCGGCATCGCTAAATAAGGA (SEQ ID NO: 106) | TTCAGGGAAAGGTGGGC (SEQ ID NO: 107) |
| BCL6 | NM_001706.2 | 1 | CACAGGGACTTGAAGTTGTTACTAACTAA (SEQ ID NO: 108) | TGACGCAGAATGGGATGAGA (SEQ ID NO: 109) | CTCTCTTTGGGAATGTT (SEQ ID NO: 110) |
| LRRC8A | NM_019594.2 | 0 | CAAAGCAGCCAGACGTTGAAC (SEQ ID NO: 111) | CACACCAGATCCGGAAGACA (SEQ ID NO: 112) | TTTCCCTGGGCGCAGG (SEQ ID NO: 113) |

TABLE 1-continued

Primers and Probes

| Gene Locus | GenBank Accession No. | Probe Overlap | Forward Primer | Reverse Primer | Probe |
|---|---|---|---|---|---|
| RGS13 | NM_144766.1 | 0 | GGGATTCCTACCCCAGATTTCTA (SEQ ID NO: 114) | CAGAAACTGTTGTTG GACTGCATAG (SEQ ID NO: 115) | AGTCAGAAATGTACCAAAAA (SEQ ID NO: 116) |
| YIPF3 | NM_015388.2 | 1 | TGAGCTGTAGCTGCGTAAGTACCT (SEQ ID NO: 117) | GGCCTTGTGCCTTTC AGAAG (SEQ ID NO: 118) | CTTGATGCCTGTCGGC (SEQ ID NO: 119) |
| YIPF3 | NM_015388.2 | 1 | TGGCTGCCCTACACATGCT (SEQ ID NO: 120) | CAGGATCCCCTCTAC CACTTTG (SEQ ID NO: 121) | CCTGCTCTATCTGCATTT (SEQ ID NO: 122) |
| YIPF3 | NM_015388.2 | 0 | GAGGCTCAGCTGTGATTGACAT (SEQ ID NO: 123) | CACCCATATCCTCGA AGCTAGAG (SEQ ID NO: 124) | AGAACATGGATGATACCTC (SEQ ID NO: 125) |
| RGS13 | NM_144766.1 | 0 | TCCAGCCACAGTCCCCTAGA (SEQ ID NO: 126) | TCCTGAATGTTCCTG ATGATAGTCTCT (SEQ ID NO: 127) | AGATTAACATTGACAGTTCG ACA (SEQ ID NO: 128) |
| EPDR1 | NM_017549.3 | 0 | CGAGAGGAAGGCGCTGATC (SEQ ID NO: 129) | ACATCACTCCATCCT TATACAGCAAA (SEQ ID NO: 130) | CCTGCAAGAGATTATTT (SEQ ID NO: 131) |
| EPDR1 | NM_017549.3 | 0 | GGATCCTCTTGACATTCCTCAAA (SEQ ID NO: 132) | GGCCCCCCGATGGA (SEQ ID NO: 133) | CTCCACCTTTGAAGACC (SEQ ID NO: 134) |
| EPDR1 | NM_017549.3 | 0 | CGAGGGTGTGGCCATATGA (SEQ ID NO: 135) | GAACAGGCATTAGAA ATACCCAAAG (SEQ ID NO: 136) | TGACTAGATGGCTAATATG (SEQ ID NO: 137) |
| UAP1 | NM_003115.4 | 0 | CTACTGCAAGGCATGCTTTGAT (SEQ ID NO: 138) | TGGCCCCCTGCATTG A (SEQ ID NO: 139) | TCCCTTCATCATTGCTG (SEQ ID NO: 140) |
| CD79B | NM_000626.2 | 0 | GCCGGTGCAGTTACACGTT (SEQ ID NO: 141) | CCCCAAACCCGTGAC AAC (SEQ ID NO: 142) | CCTCCAAGGAGCCTC (SEQ ID NO: 143) |
| CLPTM1 | NM_001294.1 | 1 | CAAGGCCCTCAACACATTCA (SEQ ID NO: 144) | GGTACATAACGGGCA TCTTGATG (SEQ ID NO: 145) | ACCTGTTCGCCTTTG (SEQ ID NO: 146) |
| UAP1 | NM_003115.4 | 1 | CCTATGCTGGAGAAGGATTAGAAAGT (SEQ ID NO: 147) | CGATGATTAGAGGTG CATGGAA (SEQ ID NO: 148) | ATGTGGCAGATAAAG (SEQ ID NO: 149) |
| CD79B | NM_000626.2 | 0 | TCTCGCCACCCTCACCAT (SEQ ID NO: 150) | GCTGACAGAAGTAGA TGCCATTGT (SEQ ID NO: 151) | CAAGGCATCCGGTTTG (SEQ ID NO: 152) |
| CLPTM1 | NM_001294.1 | 0 | AAGTCGCCCTGGAACTTCCT (SEQ ID NO: 153) | CACCGAGTCCTGCTC CTCAT (SEQ ID NO: 154) | ATGAGTTGTACGAGCAGTC (SEQ ID NO: 155) |
| UAP1 | NM_003115.4 | 1 | CATGAGCTGGTGAAAAATGGTATTT (SEQ ID NO: 156) | AAAGCTATTCCTATC GTGGCAAA (SEQ ID NO: 157) | AACCAGATACCAAGTTTT (SEQ ID NO: 158) |
| CD79B | NM_000626.2 | 1 | TCCCCAGCTCTTGCCAAAG (SEQ ID NO: 159) | CAGAGAACTCCCTCC AAGTTGCT (SEQ ID NO: 160) | CTGGAGTAGAAGGACAACAG (SEQ ID NO: 161) |
| CLPTM1 | NM_001294.1 | 0 | GGCAGGCCAGGGTTTGT (SEQ ID NO: 162) | CGAGATGGCTGGAAA CACAGA (SEQ ID NO: 163) | AGGCGCTGTCTGTC (SEQ ID NO: 164) |
| CTSC | NM_001814.3 | 1 | GACTCAGCCTCTGGGATGGA (SEQ ID NO: 165) | GGATCCGGAAGTAGC CATTCT (SEQ ID NO: 166) | TGGATTGTTAAAAACAGCTGG (SEQ ID NO: 167) |

TABLE 1-continued

Primers and Probes

| Gene Locus | GenBank Accession No. | Probe Overlap | Forward Primer | Reverse Primer | Probe |
|---|---|---|---|---|---|
| CTSC | NM_001814.3 | 0 | AGGCGGCTTCCCATACCT (SEQ ID NO: 168) | CTTCTTCCACCAGCC CAAAA (SEQ ID NO: 169) | ATTGCAGGAAAGTACGCC (SEQ ID NO: 170) |
| CTSC | NM_001814.3 | 0 | CCCAAACCTGCACCACTGA (SEQ ID NO: 171) | CAAGATGTTGGCAAA TGCAAA (SEQ ID NO: 172) | CTGAAATACAGCAAAAGA (SEQ ID NO: 173) |
| CD44 | NM_000610.3 | 0 | CCTTTGTGGCATTTATTCATCAGT (SEQ ID NO: 174) | GCTTCTATGACAAGC AGCCTTTG (SEQ ID NO: 175) | AGGGTGTCCGATTGG (SEQ ID NO: 176) |
| PUS7 | NM_019042.3 | 0 | CTCTGTAGCACAGGCTGGATTG (SEQ ID NO: 177) | AGGCTGCAGTGCAAG ATTGA (SEQ ID NO: 178) | AGTGCAATCCTGCAATT (SEQ ID NO: 179) |
| CD44 | NM_000610.3 | 0 | CCACTTGGAGGCCTTTCATC (SEQ ID NO: 180) | AGGTTGGCGATCAGG AATACA (SEQ ID NO: 181) | TCGGGTGTGCTATGGA (SEQ ID NO: 182) |
| PUS7 | NM_019042.3 | 0 | CCTTGCCTGGTTTCGATGTT (SEQ ID NO: 183) | GAGCATTTCCCTGTA GGCTTCTT (SEQ ID NO: 184) | CCCAAAGCATAAAATT (SEQ ID NO: 185) |
| CD44 | NM_000610.3 | 0 | CAACCGTTGGAAACATAACCATT (SEQ ID NO: 186) | AACAATCAGTAGCAC ATTGCATCTG (SEQ ID NO: 187) | AGGGAGCTGGGACACT (SEQ ID NO: 188) |
| PUS7 | NM_019042.3 | 0 | TGGACTCACTGAGGCTGACGTA (SEQ ID NO: 189) | GATTCCCGAGAACCC TTGATG (SEQ ID NO: 190) | TCACCAAGTTTGTGAGTTC (SEQ ID NO: 191) |
| RPL22 | NM_000983.3 | 1 | GCTGCCAATTTTGAGCAGTTT (SEQ ID NO: 192) | GTTCCCAGCTTTTCC GTTCA (SEQ ID NO: 193) | TGCAAGAAAGGATCAAA (SEQ ID NO: 194) |
| LOC728179 | XR_015348.1 | 1 | TCTTGCCTGCCCTGTGTTG (SEQ ID NO: 195) | TGCCTTCCCCTTAAT AATGCA (SEQ ID NO: 196) | AAAATGCGGGTCCCTT (SEQ ID NO: 197) |
| SERBP1 | NM_001018067.1 | 1 | CTCCCGCTACACAGAAGTAACAAA (SEQ ID NO: 198) | AAAACATCCCTGCTA CCAATACATT (SEQ ID NO: 199) | ATGGTAGTCAGTTTTGTATT TAG (SEQ ID NO: 200) |
| RPL9 | NM_000661.4 | 1 | TCCGTTACAAGATGAGGTCTGTGT (SEQ ID NO: 201) | CATTCTCCTGGATAA CAACGTTGA (SEQ ID NO: 202) | TGCTCACTTCCCC (SEQ ID NO: 203) |
| CFL1 | NM_005507.2 | 1 | TCCATCCCTTGACGGTTCTG (SEQ ID NO: 204) | AGCCCAAGAGGAATC AAAAGATC (SEQ ID NO: 205) | CCTTCCCAAACTGCTTT (SEQ ID NO: 206) |
| RPL13 | NM_000977.2 | 1 | GAGTCATCACTGAGGAAGAGAAGAA TT (SEQ ID NO: 207) | TGGCACGGGCCATAC G (SEQ ID NO: 208) | CAAAGCCTTCGCTAGTC (SEQ ID NO: 209) |
| FLJ16025 | NM_198505.1 | 1 | CCTACACCCCTTATCCCCATACT (SEQ ID NO: 210) | CCAGGGCTATTGGTT GAATGA (SEQ ID NO: 211) | TTATTATCGAAACCATCAGCC (SEQ ID NO: 212) |
| RPS10 | NM_001014.3 | 1 | CGACCTGCGAGACTCACAAG (SEQ ID NO: 213) | GGCACAGCACTCCGT CTGT (SEQ ID NO: 214) | AAGCTGACAGAGATACC (SEQ ID NO: 215) |
| NPM1 | NM_002520.5 | 1 | TCTGGCTGTCCTTTTTATAATGCA (SEQ ID NO: 216) | CTTGGCAATAGAACC TGGACAAC (SEQ ID NO: 217) | AGTGAGAACTTTCCC (SEQ ID NO: 218) |
| CCDC72 | NM_015933.3 | 1 | GCAAGAAGAAGCCACTGAAACA (SEQ ID NO: 219) | GAAAGCCTTATCTTC CTCGTCCAT (SEQ ID NO: 220) | CCCAAGAAGCAGGCCA (SEQ ID NO: 221) |

TABLE 1-continued

Primers and Probes

| Gene Locus | GenBank Accession No. | Probe Overlap | Forward Primer | Reverse Primer | Probe |
|---|---|---|---|---|---|
| RPS19 | NM_001022.3 | 1 | GGCTGAAAATGGTGGAAAAGG (SEQ ID NO: 222) | CTTTGTCCCTGAGGTGTCAGTTT (SEQ ID NO: 223) | CCAAGATGGCGGCCG (SEQ ID NO: 224) |
| RPS16 | NM_001020.4 | 1 | TGTGGATGAGGCTTCCAAGAA (SEQ ID NO: 225) | CAGCAGGGTCCGGTCATACT (SEQ ID NO: 226) | AGATCAAAGACATCCTCATC (SEQ ID NO: 227) |
| EEF1G | NM_001404.4 | 1 | GGCAGGTGGACTACGAGTCATAC (SEQ ID NO: 228) | GTCTCCTCGCTGCCAGGAT (SEQ ID NO: 229) | CATGGCGGAAACTG (SEQ ID NO: 230) |
| RPS5 | NM_001009.3 | 1 | CCGGAACATTAAGACCATTGC (SEQ ID NO: 231) | CCCTTGGCAGCATTGATGA (SEQ ID NO: 232) | AGTGCCTGGCAGATG (SEQ ID NO: 233) |
| EEF1A1 | NM_001402.5 | 1 | CTGCCACCCCACTCTTAATCA (SEQ ID NO: 234) | GGCCAATTGAAACAAACAGTTCT (SEQ ID NO: 235) | TGGTGGAAGAACGGTC (SEQ ID NO: 236) |
| RPL28 | NM_000991.3 | 1 | GGAAGCCTGCCACCTCCTAT (SEQ ID NO: 237) | TGGCGCGAGCATTCTTG (SEQ ID NO: 238) | TGCGGACCACCATC (SEQ ID NO: 239) |
| ACTG1 | NM_001614.2 | 1 | TGTCCTTGAAGCTTGTATCTGATATCA (SEQ ID NO: 240) | TTCAATACAAGGTCAAAATCAGCAA (SEQ ID NO: 241) | CACTGGATTGTAGAACTT (SEQ ID NO: 242) |
| BTF3 | NM_001037637.1 | 1 | AGCCTCAGATGAAAGAAACAATCA (SEQ ID NO: 243) | CACTTGTGCCTGCAGTTTGG (SEQ ID NO: 244) | AACCAGGAAAAACTC (SEQ ID NO: 245) |
| TMSB4X | NM_021109.2 | 1 | AAGCAGGCGAATCGTAATGAG (SEQ ID NO: 246) | TGCTTGTGGAATGTACAGTGCAT (SEQ ID NO: 247) | CGTGCGCCGCCAA (SEQ ID NO: 248) |
| TPM3 | NM_153649.3 | 1 | CCCTTTTCTGGGTTTGAAGCT (SEQ ID NO: 249) | CTGACTGATACAAAGCACAATTGAGA (SEQ ID NO: 250) | CTGTCTCTAGAAGTGCC (SEQ ID NO: 251) |
| USMG5 | NM_032747.2 | 1 | GCTGTGAAAGCAACATAAATGGAT (SEQ ID NO: 252) | GGCATGGGAACTTAACAGATGAG (SEQ ID NO: 253) | TTAAACTGTCTACGGTTCTT (SEQ ID NO: 254) |
| EIF1 | NM_005801.3 | 1 | CGCTATCCAGAACCTCCACTCT (SEQ ID NO: 255) | CAGGTCATCACCCTTACTTGCA (SEQ ID NO: 256) | TCGACCCCTTTGCTG (SEQ ID NO: 257) |

Data Processing

The raw qRT-PCR as results were pre-processed according to the description below under Normalization, Transformation, and Imputation and the Sensitivity Index was computed as described under Sensitivity Index and Classifier. Spearman's rank correlations were used for correlation estimates and corresponding P-values. For the Multivariate Sensitivity Index, probes were selected and coefficients estimated using the elastic net blend of lasso (L1) and ridge (L2) penalized regression, as described by Zhou et al., Statist. Soc. B. 67:301-320, 2005 and implemented by Friedman, Hastie and Tibshirani, Regularization Paths for Generalized Linear Models via Coordinate Descent. Technical Report, Dept. of Statistics, Stanford University at www-stat.stanford.edu/~hastie/Papers/glmnet.pdf. $X^2$ tests were used to test for associations among categorical variables.

Normalization, Transformation and Imputation

The following are definitions for assay data and model parameters:

DEFINITIONS

Assay Data l=a reference set of samples (e.g. NHL cell lines)
$N_l$=sample size
p=number of probes (not including normalizers)
$N_{lj}^{(Obs)}$=detected sample size for probe j
$N_{lj}^{(N.D)}$=not detected sample size for probe j
$y_{ij}^{(Obs)}$=detected raw assay value for sample i, probe j
$p_i^{(nrm.Obs)}$=number of detected normalizer values for sample i
$y_{ij}^{(nrm.Obs)}$=detected normalizer value for sample i, probe j Model Parameters $\hat{\mu}_{lj}^{(Obs.raw)}$=set l mean of detected $\log_2$ assay values for probe j (un-normalized)

$\hat{\sigma}_{lj}^{(Obs)}$=set l standard deviation of detected log$_2$ assay values for probe j $\gamma_l^{(ND)}$=set l number of standard deviations above the mean For a reference set of samples, such as that used to fit index coefficients and classifier cutoffs, mean and standard deviation model parameters are computed using the reference set data (refer to the formulas for Reference Set Model Parameters below). For new samples, for example a single new sample for which the index and class are to be computed, model parameters must be taken from a reference set, t, which is chosen to be the most representative of the population from which the new sample is drawn. For example, a clinical reference set for each indication and line of therapy in which the assay is used may be maintained. The formulas for calculating reference set model parameters and transformed, normalized assay values are shown below.

Formulas

Reference Set Model Parameters

Intermediate values $$\hat{\mu}_i^{(nrm \cdot Obs)} = \frac{1}{p_i^{(nrm \cdot Obs)}} \sum_{j=1}^{p_i^{(nrm \cdot Obs)}} y_{ij}^{(nrm \cdot Obs)}$$

(sample normalization factor)

$$\hat{\mu}_{lj}^{(Obs)} = \frac{1}{N_{lj}^{(Obs)}} \sum_{i=1}^{N_{lj}^{(Obs)}} [\log_2(y_{ij}^{(Obs)}) - \log_2(\hat{\mu}_i^{(nrm \cdot Obs)})]$$

(normalized mean)

Model parameters $$\hat{\sigma}_{lj}^{(Obs)} = \sqrt{\frac{1}{N_{lj}^{(Obs)}} \sum_{i=1}^{N_{lj}^{(Obs)}} \left(\log_2(y_{ij}^{(Obs)}) - \log_2(\hat{\mu}_i^{(nrm \cdot Obs)}) - \hat{\mu}_{lj}^{(Obs)}\right)^2}$$

$$\hat{\mu}_{lj}^{(Obs \cdot raw)} = \frac{1}{N_{lj}^{(Obs)}} \sum_{i=1}^{N_{lj}^{(Obs)}} \log_2(y_{ij}^{(Obs)})$$

Transformed, Normalized Assay Values

Intermediate values $$\hat{\mu}_i^{(nrm \cdot Obs)} = \frac{1}{p_i^{(nrm \cdot Obs)}} \sum_{j=1}^{p_i^{(nrm \cdot Obs)}} y_{ij}^{(nrm \cdot Obs)}$$

(sample normalization factor)

Transformed, normalized, imputed assay values $$x_{ij}^{(Obs)} = -[\log_2(y_{ij}^{(Obs)}) - \log_2(\hat{\mu}_i^{(nrm \cdot Obs)})], i = 1, \ldots, N_{lj}^{(Obs)}$$

$$x_{ij}^{(ND)} = -[\hat{\mu}_{lj}^{(Obs \cdot raw)} - \log_2(\hat{\mu}_i^{(nrm \cdot Obs)}) + \gamma_l^{(ND)} \hat{\sigma}_{lj}^{(Obs)}], i = 1, \ldots, N_{lj}^{(ND)}$$

The completed $N_l \times p$ matrix of values, $\begin{bmatrix} x_1^{(obs)} & \ldots & x_p^{(Obs)} \\ x_1^{(ND)} & \ldots & x_p^{(ND)} \end{bmatrix}$, is input to the sensitivity index and classifier calculations.

Sensitivity Index and Classifier

The following are definitions for assay data and model parameters:

DEFINITIONS

Assay Data l=a reference set of samples (e.g. NHL cell lines)

$N_l$=sample size p=number of probe pairs $x_{ij}$=transformed, normalized assay value for sample i, probe j $x_{ij'}$=as above with j' the anti-correlated pair probe to probe j Model Parameters $\beta_{lj}$=set l coefficient for probe j $\hat{\mu}_{lj}$=set l mean of transformed normalized assay values for probe j $\hat{\sigma}_{lj}^2$=set l mean of transformed normalized assay values for probe j $C_l$=classification cutpoint The formulas for calculating reference set model parameters and sensitivity index and classifier are shown below.

Formulas

Reference Set Model Parameters

Probe Means and Standard Deviations $$\hat{\mu}_{lj} = \frac{1}{N_l} \sum_{i=1}^{N_l} x_{ij}$$

$$\hat{\sigma}_{lj}^2 = \frac{1}{N_l} \sum_{i=1}^{N_l} (x_{ij} - \hat{\mu}_{lj})^2$$

Index and Classifier

Sensitivity Index $$S_{li} = \sum_{j=1}^{p} \beta_{lj} \frac{x_{ij} - \hat{\mu}_{lj}}{\sqrt{\hat{\sigma}_{lj}^2}} - \beta_{lj'} \frac{x_{ij'} - \hat{\mu}_{lj'}}{\sqrt{\hat{\sigma}_{lj'}^2}}$$

Sensitivity Class $$T_{li} = \begin{cases} 1 \equiv \text{sensitive} & \text{if } S_{li} \geq C_l \\ 0 \equiv \text{resistant} & \text{otherwise} \end{cases}$$

Clinical Trial 001 Results

Table 2 below provides a sample accounting of assayed specimens and clinical samples from Clinical Trial 001. Twenty nine archival FFPE tumor specimens from 24 patients with DLBCL were submitted for qRT-PCR processing. Three patients had multiple specimens and all 24 patients had usable qRT-PCR results for at least one specimen. Of these 24, 21 had tumor sum of the product of diameters (SPD) measurements reported both at baseline and at least one post-baseline visit.

TABLE 2

| Clinical Trial 001 Sample Accounting | | | |
|---|---|---|---|
| Diagnostic Assay | | Clinical Database | |
| Archival FFPE specimens | 29 | Analysis sample size (both qRT-PCR and SPD available) | |
| # of patients (3 with multiple specimens) | 24 | | |
| Specimens qRT-PCR Reported | 27 | | |
| Usable qRT-PCR results | 26 | Patients in clinical database | 46 |

TABLE 2-continued

Clinical Trial 001 Sample Accounting

| Diagnostic Assay | | | Clinical Database | |
|---|---|---|---|---|
| (1 insufficient) qRT-PCR for unique patients (2 patient specimen pairs averaged together) | 24 | 21 | 39 | SPD Change from Baseline Reported |

Table 3 summarizes the pairwise Spearman's rank correlations between the Main and Pair genes that contribute to the sensitivity index. Based on the cell line development samples, genes with low expression in particular groups of patient should be expected to have relatively high expression of the corresponding pair, on average, providing for self-normalization and the interpretation of the Sensitivity Index as a ratio of up- to down-regulated expression pathways (i.e. on a log base 2 scale). The magnitude of the correlations between pairs in this first clinical sample are statistically significant and notable high throughout, with the lower correlation estimate being −0.67 (P=0.0004). These tests alone constitute an independent confirmation that the assay target sequences are expressed in tumor samples from this clinical population in-vitro and that the assay is detecting expression in the archived FFPE tissue samples.

TABLE 3

Main and Pair Gene Anti-correlations (N = 21)

| Main Gene* | Locus Link | Correlation | Pair |
|---|---|---|---|
| IFITM1 | 8519 | −.85 | BTG2 |
| CD40 | 958 | −.84 | IGF1R |
| RGS13 | 6003 | −.70 | CD44 |
| VNN2 | 8875 | −.87 | CTSC |
| LMO2 | 4005 | −.67 | EPDR1 |
| CD79B | 974 | −.75 | UAP1 |
| CD22 | 933 | −.83 | PUS7 |

*CD40, RGS13, VNN2, LMO2, CD22, BTG2, and UAP1 are genes with higher expression in sensitive cell lines.

Table 4 summarizes the associations between the measurements for each probe individually and the largest reduction (or smallest increase) in tumor SPD post-baseline. Since rank correlations are based upon the difference (or ratio) of post-baseline to baseline measurements, positive correlations mean that higher expression of the probe is associated with tumor increases, on average; and the negative correlations mean that higher expression of the probe is associated with tumor decreases on average. Notably, all Main-Pair probe pairs have opposite-direction associations with SPD. The P-values are consistent with a promising trend in this sample. All P-values are below 0.5 (50% expected when there is no true association). All ranges are calculated as bootstrap $95^{th}$ percentile confidence intervals, based upon 5,000 replicates sampled with replacement from the DLBCL patient sample, N=21. Narrower ranges will become available as the sample size increases. Since no model-building or checking was required to produce these results, they comprise a robust trend, which confirms that these qRT-PCR probe measurements are associated, overall, with reduction in tumor SPD in patients treated with anti-CD40 Ab.1.

TABLE 4

Associations between SPD and Individual Probe Measurements (N = 21)

| Main Gene | Rho. | P | Range | Pair Gene | Rho. | P | Range |
|---|---|---|---|---|---|---|---|
| IFITM1 | +0.29 | 0.20 | (−0.13, 0.68) | BTG2 | −0.27 | 0.23 | (−0.70, 0.19) |
| CD40 | −0.16 | 0.49 | (−0.58, 0.30) | IGF1R | +0.33 | 0.15 | (−0.17, 0.73) |
| RGS13 | −0.32 | 0.16 | (−0.66, 0.13) | CD44 | +0.34 | 0.14 | (−0.11, 0.70) |
| VNN2 | −0.26 | 0.26 | (−0.67, 0.21) | CTSC | +0.31 | 0.17 | (−0.17, 0.68) |
| LMO2 | −0.25 | 0.27 | (−0.69, 0.25) | EPDR1 | +0.27 | 0.23 | (−0.22, 0.67) |
| CD79B | +0.22 | 0.34 | (−0.22, 0.61) | UAP1 | −0.22 | 0.35 | (−0.59, 0.22) |
| CD22 | −0.25 | 0.28 | (−0.66, 0.21) | PUS7 | +0.20 | 0.39 | (−0.26, 0.66) |

The multivariate sensitivity index is a weighted average of the probes in Tables 3 and 4. Since weights in cell lines were not expected to reflect optimal weights in patient tumor specimens, the weights in cell lines were restricted to 1 and −1, corresponding to the signed, equal-weighted average, where the signs matched the association between each probe and resistance to anti-CD40 Ab.1 by IC25 in the cell lines. For clinical populations, new weights are required. As a preliminary analysis based upon 21 samples only, we chose to use a penalized, multivariate regression procedure to select and estimate weights for the best 8 of the 14 probes. Those weights (coefficient) are shown in Table 5, and the association between the resulting Sensitivity Index and SPD change from baseline is depicted in FIG. 2. Larger multivariate Sensitivity Index values are associated with SPD decreases post-baseline (Spearman's Rho=−0.58, P=0.006). All ranges in Tables 4, 5, and 6 were calculated as bootstrap 95th percentile confidence intervals, based upon 5,000 replicates sampled with replacement from the DLBCL patient sample, N=21. Narrower ranges will become available as the sample size increases.

TABLE 5

Weights for the Multivariate Sensitivity Index (N = 21)

| Main Gene | Coeff. | Range | Pair Gene | Coeff. | Range |
|---|---|---|---|---|---|
| IFITM1 | −0.08 | (−11.7, 3.7) | BTG2 | −0.62 | (−11.6, 0.0) |
| CD40 | 0 | (−9.5, 8.2) | IGF1R | 0 | (−9.0, 5.6) |
| RGS13 | +1.13 | (−1.9, 8.0) | CD44 | −3.39 | (−11.9, 0.0) |

TABLE 5-continued

Weights for the Multivariate Sensitivity Index (N = 21)

| Main Gene | Coeff. | Range | Pair Gene | Coeff. | Range |
|---|---|---|---|---|---|
| VNN2 | 0 | (−4.1, 4.1) | CTSC | 0 | (−8.8, 2.1) |
| LMO2 | 0 | (−8.5, 2.1) | EPDR1 | −0.74 | (−4.7, 3.6) |
| CD79B | +0.04 | (−3.2, 9.0) | UAP1 | −2.45 | (−15.1, 0.0) |
| CD22 | +0.63 | (−0.0, 12.7) | PUS7 | 0 | (−7.7, 7.3) |

Using 26 samples from Clinical Trail 001, ranges for $\mu_j$ and $\sigma_j$ values obtained are as shown in Table 6.

TABLE 6

$\mu_j$ and $\sigma_j$ ranges based on data from Clinical Trail 001

| $\mu_j$ | IFITM1 | LMO2 | CD40 | VNN2 | IGF1R | BTG2 | CD22 | BCL6 |
|---|---|---|---|---|---|---|---|---|
| lower | −4.89 | −5.09 | −5.09 | −5.10 | −5.12 | −5.02 | −5.03 | −5.07 |
| upper | −4.79 | −5.00 | −5.02 | −5.02 | −5.06 | −4.92 | −4.93 | −4.99 |

| $\mu_j$ | RGS13 | EPDR1 | CD79B | UAP1 | CTSC | CD44 | PUS7 |
|---|---|---|---|---|---|---|---|
| lower | −5.14 | −5.19 | −5.10 | −5.26 | −5.04 | −4.97 | −5.24 |
| upper | −5.00 | −5.12 | −5.04 | −5.18 | −4.95 | −4.87 | −5.16 |

| $\sigma_j$ | IFITM1 | LMO2 | CD40 | VNN2 | IGF1R | BTG2 | CD22 | BCL6 |
|---|---|---|---|---|---|---|---|---|
| lower | 0.10 | 0.09 | 0.07 | 0.08 | 0.06 | 0.09 | 0.09 | 0.08 |
| upper | 0.17 | 0.14 | 0.12 | 0.13 | 0.10 | 0.15 | 0.14 | 0.12 |

| $\sigma_j$ | RGS13 | EPDR1 | CD79B | UAP1 | CTSC | CD44 | PUS7 |
|---|---|---|---|---|---|---|---|
| lower | 0.14 | 0.07 | 0.06 | 0.08 | 0.09 | 0.09 | 0.08 |
| upper | 0.22 | 0.11 | 0.10 | 0.12 | 0.14 | 0.16 | 0.12 |

Clinical Trial 002 Results

Raw qRT-PCR results were successfully generated for 10 patients with archival specimens. For those 10 patients, diagnosis, treatment group, multivariate sensitivity index, clinical response and SPD change from baseline are shown in Table 7. The multivariate sensitivity index weights were taken from the 21 Clinical Trial 001 patients (Table 5), so that these patients constitute a very small validation set. 2 of 4 patients with Sensitivity Index ≥0 exhibited some tumor shrinkage after anti-CD40 Ab.1 exposure and 4 of 6 patients with Sensitivity Index <0 exhibited either tumor increase or a best response of PD (SPD was unavailable for 2 patients, but a best clinical response outcome was available for this patient).

TABLE 7

Summary of diagnosis, treatment group, multivariate sensitivity index, clinical response and SPD change for 6 patients in Clinical Trial 002.

| Samples | Dx. | Treatment Group | Sensitivity Index | Best Response | SPD Percent Change |
|---|---|---|---|---|---|
| 066-0001 | MCL | Pre-2 | +0.01 | PD | +72.48 |
| 066-0015 | MCL | V | −0.87 | PD | +64.07 |
| 066-0009 | DLBCL | III | +1.06 | PR | −78.02 |
| 066-0006 | DLBCL | I | −2.31 | PR | −66.44 |
| 066-0011 | T-Cell-LBCL | IV | −0.46 | SD (PR) | −10.34 |
| 066-0005 | DLBCL | I | −2.99 | PD | +1,208.94 |
| 066-0013 | MCL | IV | −3.67 | PD | +94.59 |
| 066-0019 | DLBCL | V | +0.15 | SD | −32.64 |
| 066-0004 | DLBCL | I | −0.46 | PD | ? |
| 066-0002 | DLBCL | Pre-2 | +0.99 | PD | ? |

Figure 3:
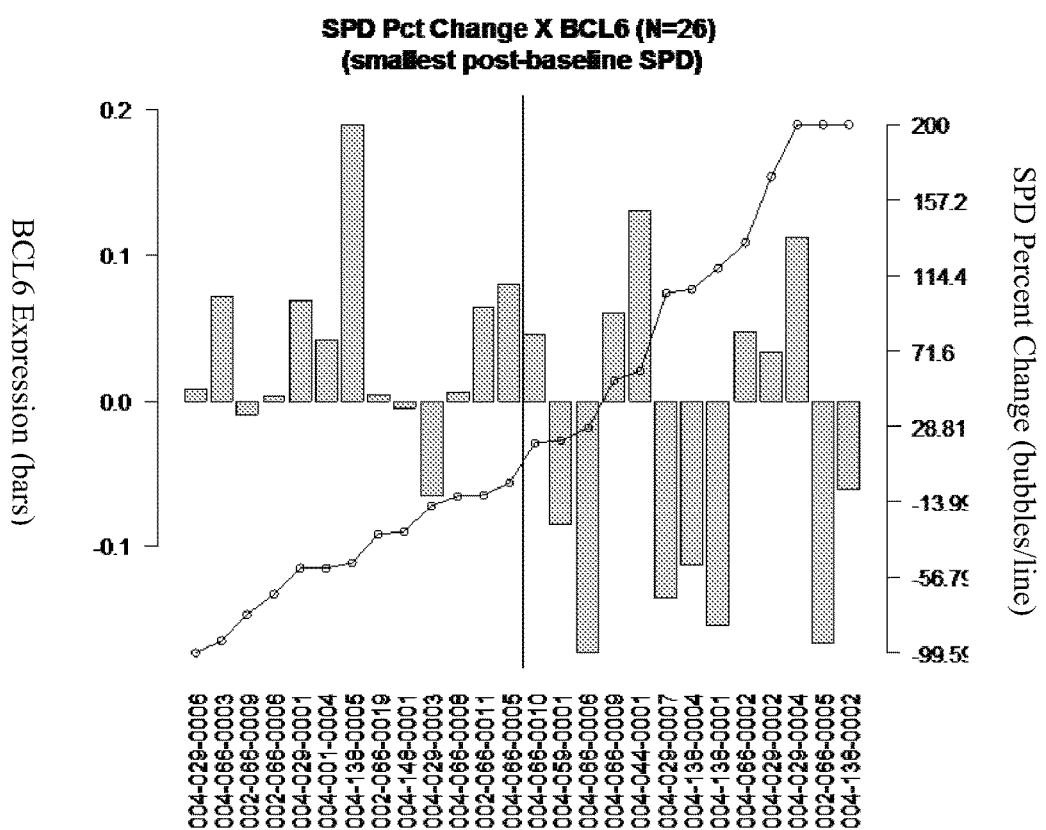
FIG. 3. Association of BCL6 expression and percent change in SPD measurements for 26 patients with DLBCL. SPD percent change was determined by comparing the smallest post-baseline SPD to baseline SPD. Positive change indicates tumor volume increases, and negative change indicates tumor volume decreases.

BCL6. The qRT-PCR assay contains a 15th probe for the BCL6 gene. Though not currently used in the multivariate Sensitivity Index, it was a previously identified potential predictor of response to anti-CD40 Ab.1. As shown in FIG. 3, while not significantly associated with SPD change in the combined DLBCL patient sample (P = 0.25, N = 26), BCL6 trends lower in those with tumor increases (rho = −0.23).

Example 2

Use of 15 Gene Markers to Determine Responsiveness of DLBCL Patients to Treatment with Anti-CD40 Ab.1

Using DLBCL patient samples from Phase I (11 samples) and Phase II (28 samples) clinical trials described in Example 1, a classifier based on qRT-PCT was developed for tumor size reduction of at least 10%, herein defined as anti-CD Ab.1 sensitive, using weighted K-nearest neighbors (KNN), with weights for the 15 markers (UAP1, BTG2, CD40, VNN2, RGS13, CD22, LMO2, IFITM1, CTSC, CD44, PUS7, BCL6, EPDR1, IGF1R and CD79B) determined using penalized regression (GLMNET). Model parameters were determined by cross-validation and robust p-values were computed via permutation tests.

Using weighted K-nearest neighbors (WKNN), a class was assigned for a new sample using the known classes of the K nearest reference samples, where K is an integer between 4 and 13. The nearest reference samples (nearest neighbors) are those with the smallest weighted average of the absolute differences (WAAD) between each of the 15 probe measurements for UAP1, BTG2, CD40, VNN2, RGS13, CD22, LMO2, IFITM1, CTSC, CD44, PUS7, BCL6, EPDR1, IGF1R and CD79B, where the differences are between the probe measurements of new sample to be classified and those from each reference sample. The weights for the WAAD are the absolute values of the coefficients from an elastic net penalized regression of reference sample tumor shrinkage on the 15 probe measurements. The magnitude of the penalty is chosen by 10 fold cross-validation to minimize the WKNN classification error. The optimal K was determined as 5 in the 10-fold cross validation on the training dataset. Note that the weight for some probe measurements may be 0 (zero), so that not all probe measurements necessarily contribute to the classification, and relative contributions depend upon the reference sample probe measurements and their known classes. To determine the predicted class of a new sample, the K nearest reference samples contribute the inverse of their WAAD (i.e. 1 divided by the WAAD) in the manner of a vote for their known class labels. The class label with the largest total inverse WAAD contributions is assigned to the new sample. A prior class weight between 0 and 1, with weights for all classes summing to 1 (one) may used as a multiplier of the normalized inverse WAAD contributions to increase or decrease the proportion of new samples classified to each class. Similar results were obtained using unweighted KNN.

qRT-PCT was performed for all 15 genes using primers and probes described in Example 1 for the patient samples. For a specific sample of 39 DLBCL patients, the weights were determined for each of the 15 marker gene (Table 8).

TABLE 8

| Weights for the Marker Genes | | | | | | |
|---|---|---|---|---|---|---|
| BCL6 | IFITM1 | CD40 | RGS13 | VNN2 | LMO2 | CD79B |
| 1.98010348 | 1.75845322 | 0.00000000 | 0.00000000 | 0.00000000 | 0.00000000 | 0.00000000 |
| CD22 | BTG2 | IGF1R | CD44 | CTSC | EPDR1 | UAP1 | PUS7 |
| 0.05014746 | 0.00000000 | 0.35155187 | 5.33314459 | 0.00000000 | 1.55417748 | 7.13145292 | 0.00000000 |

Figure 4:
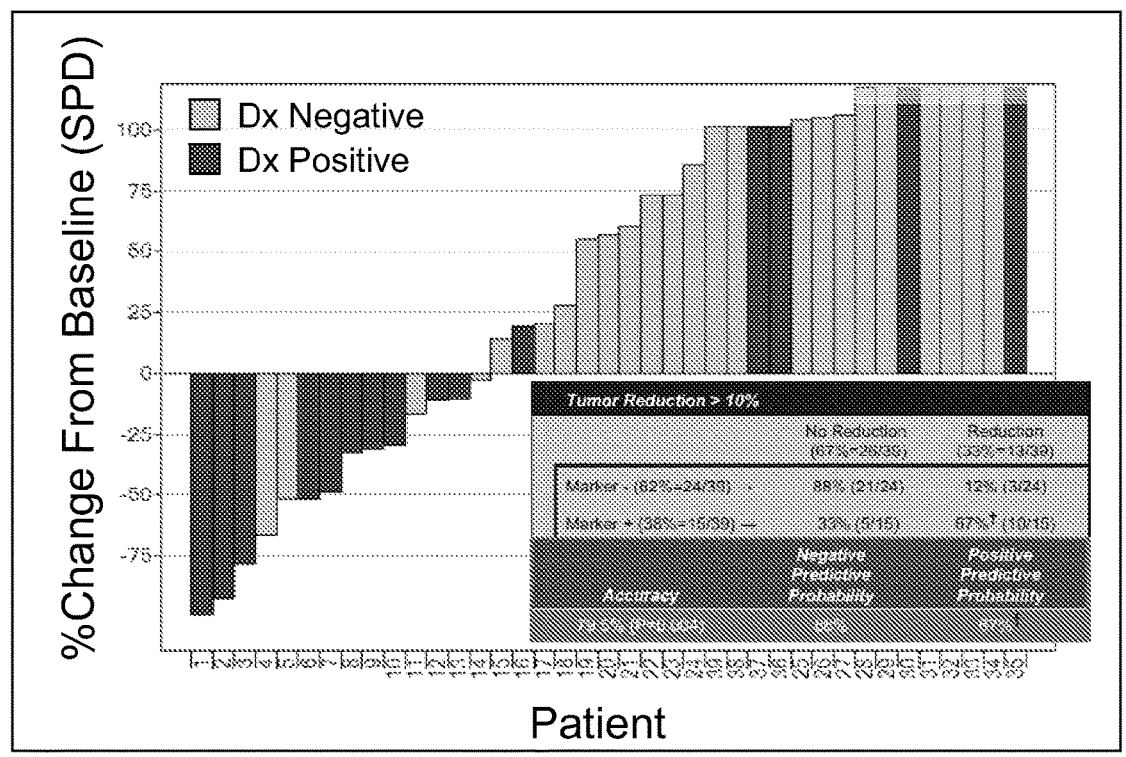
FIG. 4. Use of mRNA expression levels of the marker genes to predict sensitivity to anti-CD40 Ab.1 treatment. SPD percent change was determined by comparing the smallest post-baseline SPD to baseline SPD. Positive change indicates tumor volume increases, and negative change indicates tumor volume decreases.
Figure 5:
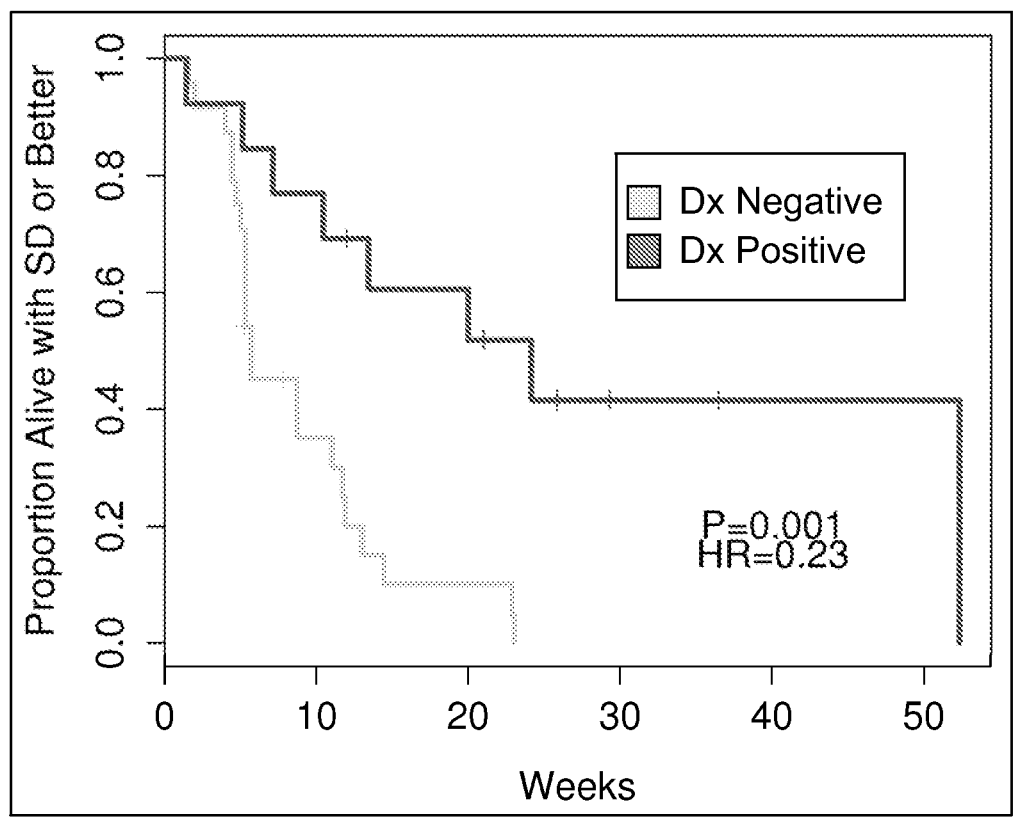
FIG. 5. Progression-free survival for patients that had been classified as being responsive (Dx Positive) to the anti-CD40 Ab.1 treatment or non-responsive (Dx Negative) based on the mRNA expression levels of the marker genes.

Based on the method described above, a sample from the 39 patients was determined as Dx negative (non-responsive to the anti-CD40 Ab.1 treatment) or Dx positive (at least 10% tumor reduction in response to the anti-CD40 Ab.1 treatment). Data shown in FIG. 4 indicate that an overall accuracy for predicting responsiveness to the anti-CD40 Ab.1 treatment are 79.5% (P=0.004). Twenty one of 24 signature negative patients (88%) displayed no measurable tumor shrinkage in response to the anti-CD40 Ab.1 treatment. Ten of 15 signature positive patients (67%) displayed significant tumor shrinkage in response to the anti-CD40 Ab.1 treatment. In addition, as shown in FIG. 5, Dx positive patients had an increased progression free-survival. This is consistent with the observed tumor shrinkage. The progression-free survival (PFS) of the signature positive patients (predicted to respond) was significantly prolonged compared to the signature negative patients, with a median PFS of 169 days vs. 40 days, respectively (p=0.001). These data indicate that a 15-gene qRT-PCR DLBCL tumor signature was effective in predicting outcomes following CD40 pathway stimulation with anti-CD40 Ab.1.

Although the foregoing invention has been described in some detail by way of illustration and example for purposes of clarity of understanding, the descriptions and examples should not be construed as limiting the scope of the invention.

What is claimed is:

1. A method for treating a human subject having B-cell lymphoma, comprising the steps of:
    (a) performing a nucleic acid-based detection assay to detect the expression levels of the RNA transcripts of marker genes in a sample comprising B lymphoma cells obtained from the human subject, wherein said marker genes comprise BCL6, IFITM1, CD40, RGS13, VNN2, LMO2, CD79B, CD22, BTG2, IGF1R, CD44, CTSC, EPDR1, UAP1, and PUS7;
    (b) determining that the human subject is responsive to an anti-CD40 antibody treatment using a K-nearest neighbors analysis based on the expression levels of the RNA transcripts of said marker genes in the B lymphoma cells from the human subject and reference samples with known classes; and
    (c) administering an effective amount of an anti-CD40 antibody to the human subject who has been determined to be responsive using the K-nearest neighbors analysis based on the expression levels of the RNA transcripts of said marker genes in the B lymphoma cells from the human subject and reference samples with known classes, thereby treating B-cell lymphoma in the human subject.

2. The method of claim 1, wherein the expression levels of the RNA transcripts of said marker genes are normalized.

3. The method of claim 1, wherein the reference samples are samples comprising B lymphoma cells obtained from subjects whose responsiveness to the anti-CD40 antibody treatment has been tested.

4. The method of claim 3, wherein the reference samples comprise the same type of B lymphoma cells as the sample from the subject whose responsiveness to the anti-CD40 antibody treatment is predicted.

5. The method of claim 1, wherein determining that the human subject is responsive to an anti-CD40 antibody treatment in step (b) is carried out by (1) determining parameter K; (2) calculating the difference between the measured expression levels of the RNA transcripts of the marker genes in the sample from the subject and the expression levels of the RNA transcripts of the respective marker genes in each reference sample; (3) determining the nearest reference samples by selecting those samples with the smallest weighted average of the absolute differences (WAAD) between the sample from the human subject and the reference sample; and (4) determining the class of the human subject based on the known classes of the K-nearest reference samples.

6. The method of claim 5, wherein parameter K is 4, 5, 6, 7, 8, 9, 10, 11, 12, or 13 in the K-nearest neighbors analysis.

7. The method of claim 1, wherein said anti-CD40 antibody treatment is a treatment with an agonist anti-CD40 antibody.

8. The method of claim 7, wherein the agonist anti-CD40 antibody stimulates CD40 and enhances the interaction between CD40 and CD40 ligand.

9. The method of claim 7, wherein the agonist anti-CD40 antibody comprises the heavy chain amino acid sequence shown in SEQ ID NO:1 and the light chain amino acid sequence shown in SEQ ID NO:2.

10. The method of claim 7, wherein the agonist anti-CD40 antibody stimulates CD40 and does not enhance or inhibits the interaction between CD40 and CD40 ligand.

11. The method of claim 1, wherein said B cell lymphoma is diffuse large B-cell lymphoma (DLBCL).

12. The method of claim 1, wherein said B cell lymphoma is non-Hodgkin's lymphoma.

13. The method of claim 12, wherein said non-Hodgkin's lymphoma is follicular lymphoma, mantle cell lymphoma, marginal zone lymphoma, or small lymphocytic lymphoma.

14. The method of claim 1, wherein the sample is formalin fixed paraffin embedded biopsy sample.

15. The method of claim 1, wherein the expression levels of the RNA transcripts of said marker genes are detected by qRT-PCR.

16. The method of claim 1, wherein the expression levels of the RNA transcripts of said marker genes are detected by microarray.

* * * * *

SEQUENCE LISTING

<160> NUMBER OF SEQ ID NOS: 274

<210> SEQ ID NO 1
<211> LENGTH: 443
<212> TYPE: PRT
<213> ORGANISM: Artificial Sequence
<220> FEATURE:
<223> OTHER INFORMATION: Synthetic construct

```
<400> SEQUENCE: 1

Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Ser Phe Thr Gly Tyr
             20                  25                  30

Tyr Ile His Trp Val Arg Gln Ala Pro Gly Lys Gly Leu Glu Trp Val
         35                  40                  45

Ala Arg Val Ile Pro Asn Ala Gly Gly Thr Ser Tyr Asn Gln Lys Phe
 50                  55                  60

Lys Gly Arg Phe Thr Leu Ser Val Asp Asn Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Tyr Trp Trp Gly Gln Gly Thr Leu Val Thr Val
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415
```

```
Gly Asn Val Phe Ser Cys Ser Val Met His Glu Ala Leu His Asn His
            420                 425                 430

Tyr Thr Gln Lys Ser Leu Ser Leu Ser Pro Gly
        435                 440

<210> SEQ ID NO 2
<211> LENGTH: 219
<212> TYPE: PRT
<213> ORGANISM: Artificial Sequence
<220> FEATURE:
<223> OTHER INFORMATION: Synthetic construct

<400> SEQUENCE: 2

Asp Ile Gln Met Thr Gln Ser Pro Ser Ser Leu Ser Ala Ser Val Gly
  1               5                  10                  15

Asp Arg Val Thr Ile Thr Cys Arg Ser Ser Gln Ser Leu Val His Ser
             20                  25                  30

Asn Gly Asn Thr Phe Leu His Trp Tyr Gln Gln Lys Pro Gly Lys Ala
         35                  40                  45

Pro Lys Leu Leu Ile Tyr Thr Val Ser Asn Arg Phe Ser Gly Val Pro
     50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Phe Cys Ser Gln Thr
                 85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 3
<211> LENGTH: 23
<212> TYPE: DNA
<213> ORGANISM: Artificial Sequence
<220> FEATURE:
<223> OTHER INFORMATION: Synthetic construct

<400> SEQUENCE: 3
tgacaaaatg tagaggccat tca                                              23

<210> SEQ ID NO 4
<211> LENGTH: 23
<212> TYPE: DNA
<213> ORGANISM: Artificial Sequence
<220> FEATURE:
<223> OTHER INFORMATION: Synthetic construct
```

```
<400> SEQUENCE: 4
catccgtctc ctctgcgata taa                                          23

<210> SEQ ID NO 5
<211> LENGTH: 16
<212> TYPE: DNA
<213> ORGANISM: Artificial Sequence
<220> FEATURE:
<223> OTHER INFORMATION: Synthetic construct

<400> SEQUENCE: 5
ccgtcaaaca ccattt                                                  16

<210> SEQ ID NO 6
<211> LENGTH: 24
<212> TYPE: DNA
<213> ORGANISM: Artificial Sequence
<220> FEATURE:
<223> OTHER INFORMATION: Synthetic construct

<400> SEQUENCE: 6
ttgcaaggaa agaaattcaa acac                                         24

<210> SEQ ID NO 7
<211> LENGTH: 22
<212> TYPE: DNA
<213> ORGANISM: Artificial Sequence
<220> FEATURE:
<223> OTHER INFORMATION: Synthetic construct

<400> SEQUENCE: 7
tgcttgaatc cattgactgc tt                                           22

<210> SEQ ID NO 8
<211> LENGTH: 18
<212> TYPE: DNA
<213> ORGANISM: Artificial Sequence
<220> FEATURE:
<223> OTHER INFORMATION: Synthetic construct

<400> SEQUENCE: 8
acaacagcag taagaaga                                                18

<210> SEQ ID NO 9
<211> LENGTH: 22
<212> TYPE: DNA
<213> ORGANISM: Artificial Sequence
<220> FEATURE:
<223> OTHER INFORMATION: Synthetic construct

<400> SEQUENCE: 9
caggtccctg ccttttttaga ag                                          22

<210> SEQ ID NO 10
<211> LENGTH: 32
<212> TYPE: DNA
<213> ORGANISM: Artificial Sequence
<220> FEATURE:
<223> OTHER INFORMATION: Synthetic construct

<400> SEQUENCE: 10
atcataaaga agagaagaga gacaagatta ag                                32

<210> SEQ ID NO 11
<211> LENGTH: 16
```

<212> TYPE: DNA
<213> ORGANISM: Artificial Sequence
<220> FEATURE:
<223> OTHER INFORMATION: Synthetic construct

<400> SEQUENCE: 11
agcctcatgg tctcat                                                    16

<210> SEQ ID NO 12
<211> LENGTH: 16
<212> TYPE: DNA
<213> ORGANISM: Artificial Sequence
<220> FEATURE:
<223> OTHER INFORMATION: Synthetic construct

<400> SEQUENCE: 12
ggccacagcc catcca                                                    16

<210> SEQ ID NO 13
<211> LENGTH: 23
<212> TYPE: DNA
<213> ORGANISM: Artificial Sequence
<220> FEATURE:
<223> OTHER INFORMATION: Synthetic construct

<400> SEQUENCE: 13 cttgcccta aatgttcctt tct                                             23

<210> SEQ ID NO 14
<211> LENGTH: 19
<212> TYPE: DNA
<213> ORGANISM: Artificial Sequence
<220> FEATURE:
<223> OTHER INFORMATION: Synthetic construct

<400> SEQUENCE: 14
agtaactgac atgattagc                                                 19

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
tttggaagtg aggcattgca                                                20

<210> SEQ ID NO 16
<211> LENGTH: 19
<212> TYPE: DNA
<213> ORGANISM: Artificial Sequence
<220> FEATURE:
<223> OTHER INFORMATION: Synthetic construct

<400> SEQUENCE: 16
ccggagtccc cagagtcaa                                                 19

<210> SEQ ID NO 17
<211> LENGTH: 17
<212> TYPE: DNA
<213> ORGANISM: Artificial Sequence
<220> FEATURE:
<223> OTHER INFORMATION: Synthetic construct

<400> SEQUENCE: 17
agacgtacgt atcagcg                                                              17

<210> SEQ ID NO 18
<211> LENGTH: 26
<212> TYPE: DNA
<213> ORGANISM: Artificial Sequence
<220> FEATURE:
<223> OTHER INFORMATION: Synthetic construct

<400> SEQUENCE: 18
ctggaatgtg aagcgttata gaagat                                                    26

<210> SEQ ID NO 19
<211> LENGTH: 24
<212> TYPE: DNA
<213> ORGANISM: Artificial Sequence
<220> FEATURE:
<223> OTHER INFORMATION: Synthetic construct

<400> SEQUENCE: 19
ccttttttct ttcccaacac ttga                                                      24

<210> SEQ ID NO 20
<211> LENGTH: 14
<212> TYPE: DNA
<213> ORGANISM: Artificial Sequence
<220> FEATURE:
<223> OTHER INFORMATION: Synthetic construct

<400> SEQUENCE: 20
ctggcctcat ttct                                                                 14

<210> SEQ ID NO 21
<211> LENGTH: 21
<212> TYPE: DNA
<213> ORGANISM: Artificial Sequence
<220> FEATURE:
<223> OTHER INFORMATION: Synthetic construct

<400> SEQUENCE: 21
cagcctctct tgtccctggt t                                                         21

<210> SEQ ID NO 22
<211> LENGTH: 22
<212> TYPE: DNA
<213> ORGANISM: Artificial Sequence
<220> FEATURE:
<223> OTHER INFORMATION: Synthetic construct

<400> SEQUENCE: 22
tccctagcaa tggacaaact ca                                                        22

<210> SEQ ID NO 23
<211> LENGTH: 19
<212> TYPE: DNA
<213> ORGANISM: Artificial Sequence
<220> FEATURE:
<223> OTHER INFORMATION: Synthetic construct

<400> SEQUENCE: 23
ccttatgtgt tgaatgtgg                                                            19

<210> SEQ ID NO 24
<211> LENGTH: 20
<212> TYPE: DNA
<213> ORGANISM: Artificial Sequence

```
<220> FEATURE:
<223> OTHER INFORMATION: Synthetic construct

<400> SEQUENCE: 24
gggatcctgt ttgccatcct                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic construct

<400> SEQUENCE: 25
gcttcttggc cacctttttg                                              20

<210> SEQ ID NO 26
<211> LENGTH: 15
<212> TYPE: DNA
<213> ORGANISM: Artificial Sequence
<220> FEATURE:
<223> OTHER INFORMATION: Synthetic construct

<400> SEQUENCE: 26
ttggtgctgg tcttt                                                   15

<210> SEQ ID NO 27
<211> LENGTH: 22
<212> TYPE: DNA
<213> ORGANISM: Artificial Sequence
<220> FEATURE:
<223> OTHER INFORMATION: Synthetic construct

<400> SEQUENCE: 27
ggcttcatag cattcgccta ct                                           22

<210> SEQ ID NO 28
<211> LENGTH: 19
<212> TYPE: DNA
<213> ORGANISM: Artificial Sequence
<220> FEATURE:
<223> OTHER INFORMATION: Synthetic construct

<400> SEQUENCE: 28
tcacgtcgcc aaccatctt                                               19

<210> SEQ ID NO 29
<211> LENGTH: 18
<212> TYPE: DNA
<213> ORGANISM: Artificial Sequence
<220> FEATURE:
<223> OTHER INFORMATION: Synthetic construct

<400> SEQUENCE: 29
cgtgaagtct agggacag                                                18

<210> SEQ ID NO 30
<211> LENGTH: 27
<212> TYPE: DNA
<213> ORGANISM: Artificial Sequence
<220> FEATURE:
<223> OTHER INFORMATION: Synthetic construct

<400> SEQUENCE: 30
gacttgtatg tatgggagtg aggagtt                                      27
```

<210> SEQ ID NO 31
<211> LENGTH: 22
<212> TYPE: DNA
<213> ORGANISM: Artificial Sequence
<220> FEATURE:
<223> OTHER INFORMATION: Synthetic construct

<400> SEQUENCE: 31
tctcttcaag ggcacagcta tg                                              22

<210> SEQ ID NO 32
<211> LENGTH: 14
<212> TYPE: DNA
<213> ORGANISM: Artificial Sequence
<220> FEATURE:
<223> OTHER INFORMATION: Synthetic construct

<400> SEQUENCE: 32
cagggccatt gcaa                                                       14

<210> SEQ ID NO 33
<211> LENGTH: 24
<212> TYPE: DNA
<213> ORGANISM: Artificial Sequence
<220> FEATURE:
<223> OTHER INFORMATION: Synthetic construct

<400> SEQUENCE: 33
gccaaactgg aaacataaga gtga                                            24

<210> SEQ ID NO 34
<211> LENGTH: 20
<212> TYPE: DNA
<213> ORGANISM: Artificial Sequence
<220> FEATURE:
<223> OTHER INFORMATION: Synthetic construct

<400> SEQUENCE: 34
gcatgacggt tcctgtgaaa                                                 20

<210> SEQ ID NO 35
<211> LENGTH: 15
<212> TYPE: DNA
<213> ORGANISM: Artificial Sequence
<220> FEATURE:
<223> OTHER INFORMATION: Synthetic construct

<400> SEQUENCE: 35
tgctcggtgg gatgg                                                      15

<210> SEQ ID NO 36
<211> LENGTH: 21
<212> TYPE: DNA
<213> ORGANISM: Artificial Sequence
<220> FEATURE:
<223> OTHER INFORMATION: Synthetic construct

<400> SEQUENCE: 36
cggaggttga ggtttttcct t                                               21

<210> SEQ ID NO 37
<211> LENGTH: 21
<212> TYPE: DNA
<213> ORGANISM: Artificial Sequence
<220> FEATURE:
<223> OTHER INFORMATION: Synthetic construct

<400> SEQUENCE: 37
gacggttgaa tggcctctac a                                    21

<210> SEQ ID NO 38
<211> LENGTH: 22
<212> TYPE: DNA
<213> ORGANISM: Artificial Sequence
<220> FEATURE:
<223> OTHER INFORMATION: Synthetic construct

<400> SEQUENCE: 38
tgtataagca cctactgaca aa                                   22

<210> SEQ ID NO 39
<211> LENGTH: 26
<212> TYPE: DNA
<213> ORGANISM: Artificial Sequence
<220> FEATURE:
<223> OTHER INFORMATION: Synthetic construct

<400> SEQUENCE: 39
aggacttctt catgggtctt acagtt                               26

<210> SEQ ID NO 40
<211> LENGTH: 27
<212> TYPE: DNA
<213> ORGANISM: Artificial Sequence
<220> FEATURE:
<223> OTHER INFORMATION: Synthetic construct

<400> SEQUENCE: 40
aagtgacatt aaagacgatg tgtatgc                              27

<210> SEQ ID NO 41
<211> LENGTH: 19
<212> TYPE: DNA
<213> ORGANISM: Artificial Sequence
<220> FEATURE:
<223> OTHER INFORMATION: Synthetic construct

<400> SEQUENCE: 41
tgttagacca tgaaacatt                                       19

<210> SEQ ID NO 42
<211> LENGTH: 22
<212> TYPE: DNA
<213> ORGANISM: Artificial Sequence
<220> FEATURE:
<223> OTHER INFORMATION: Synthetic construct

<400> SEQUENCE: 42
caggctgtgt tcttgcatct tg                                   22

<210> SEQ ID NO 43
<211> LENGTH: 23
<212> TYPE: DNA
<213> ORGANISM: Artificial Sequence
<220> FEATURE:
<223> OTHER INFORMATION: Synthetic construct

<400> SEQUENCE: 43
gaccatgagg ctgcttctaa aaa                                  23

<210> SEQ ID NO 44

```
<211> LENGTH: 16
<212> TYPE: DNA
<213> ORGANISM: Artificial Sequence
<220> FEATURE:
<223> OTHER INFORMATION: Synthetic construct

<400> SEQUENCE: 44
ctgcaaacag gtccct                                                       16

<210> SEQ ID NO 45
<211> LENGTH: 20
<212> TYPE: DNA
<213> ORGANISM: Artificial Sequence
<220> FEATURE:
<223> OTHER INFORMATION: Synthetic construct

<400> SEQUENCE: 45
ttggacccaa gggaaaactg                                                   20

<210> SEQ ID NO 46
<211> LENGTH: 26
<212> TYPE: DNA
<213> ORGANISM: Artificial Sequence
<220> FEATURE:
<223> OTHER INFORMATION: Synthetic construct

<400> SEQUENCE: 46
ggttaaaagt tgtggtttcc attctc                                            26

<210> SEQ ID NO 47
<211> LENGTH: 15
<212> TYPE: DNA
<213> ORGANISM: Artificial Sequence
<220> FEATURE:
<223> OTHER INFORMATION: Synthetic construct

<400> SEQUENCE: 47
tggagacgca tttcg                                                        15

<210> SEQ ID NO 48
<211> LENGTH: 25
<212> TYPE: DNA
<213> ORGANISM: Artificial Sequence
<220> FEATURE:
<223> OTHER INFORMATION: Synthetic construct

<400> SEQUENCE: 48
gacatcccca ctcacgaata ttatg                                             25

<210> SEQ ID NO 49
<211> LENGTH: 21
<212> TYPE: DNA
<213> ORGANISM: Artificial Sequence
<220> FEATURE:
<223> OTHER INFORMATION: Synthetic construct

<400> SEQUENCE: 49
ctgtcctttt ctgggctttc c                                                 21

<210> SEQ ID NO 50
<211> LENGTH: 17
<212> TYPE: DNA
<213> ORGANISM: Artificial Sequence
<220> FEATURE:
<223> OTHER INFORMATION: Synthetic construct

<400> SEQUENCE: 50
```
ccagtttctg cctctga                                    17

<210> SEQ ID NO 51
<211> LENGTH: 24
<212> TYPE: DNA
<213> ORGANISM: Artificial Sequence
<220> FEATURE:
<223> OTHER INFORMATION: Synthetic construct

<400> SEQUENCE: 51
ggcatagagc agcactaaat gaca                            24

<210> SEQ ID NO 52
<211> LENGTH: 26
<212> TYPE: DNA
<213> ORGANISM: Artificial Sequence
<220> FEATURE:
<223> OTHER INFORMATION: Synthetic construct

<400> SEQUENCE: 52
ttctataacg cttcacattc cagatc                          26

<210> SEQ ID NO 53
<211> LENGTH: 20
<212> TYPE: DNA
<213> ORGANISM: Artificial Sequence
<220> FEATURE:
<223> OTHER INFORMATION: Synthetic construct

<400> SEQUENCE: 53
cactaaagaa acgatcagac                                 20

<210> SEQ ID NO 54
<211> LENGTH: 20
<212> TYPE: DNA
<213> ORGANISM: Artificial Sequence
<220> FEATURE:
<223> OTHER INFORMATION: Synthetic construct

<400> SEQUENCE: 54
cgcactttgg ccttcctaga                                 20

<210> SEQ ID NO 55
<211> LENGTH: 23
<212> TYPE: DNA
<213> ORGANISM: Artificial Sequence
<220> FEATURE:
<223> OTHER INFORMATION: Synthetic construct

<400> SEQUENCE: 55
tggaaggaga tgcagaagtc aga                             23

<210> SEQ ID NO 56
<211> LENGTH: 17
<212> TYPE: DNA
<213> ORGANISM: Artificial Sequence
<220> FEATURE:
<223> OTHER INFORMATION: Synthetic construct

<400> SEQUENCE: 56
cactgcttca taacctc                                    17

<210> SEQ ID NO 57
<211> LENGTH: 18
<212> TYPE: DNA

```
<213> ORGANISM: Artificial Sequence
<220> FEATURE:
<223> OTHER INFORMATION: Synthetic construct

<400> SEQUENCE: 57
cctgcccagt cggcttct                                               18

<210> SEQ ID NO 58
<211> LENGTH: 21
<212> TYPE: DNA
<213> ORGANISM: Artificial Sequence
<220> FEATURE:
<223> OTHER INFORMATION: Synthetic construct

<400> SEQUENCE: 58
gtccaagggt gacatttttc g                                           21

<210> SEQ ID NO 59
<211> LENGTH: 17
<212> TYPE: DNA
<213> ORGANISM: Artificial Sequence
<220> FEATURE:
<223> OTHER INFORMATION: Synthetic construct

<400> SEQUENCE: 59
ctccaatgtg tcatctg                                                17

<210> SEQ ID NO 60
<211> LENGTH: 22
<212> TYPE: DNA
<213> ORGANISM: Artificial Sequence
<220> FEATURE:
<223> OTHER INFORMATION: Synthetic construct

<400> SEQUENCE: 60
gggttactag tagccgccca ta                                          22

<210> SEQ ID NO 61
<211> LENGTH: 16
<212> TYPE: DNA
<213> ORGANISM: Artificial Sequence
<220> FEATURE:
<223> OTHER INFORMATION: Synthetic construct

<400> SEQUENCE: 61
gcagggccag cattgc                                                 16

<210> SEQ ID NO 62
<211> LENGTH: 17
<212> TYPE: DNA
<213> ORGANISM: Artificial Sequence
<220> FEATURE:
<223> OTHER INFORMATION: Synthetic construct

<400> SEQUENCE: 62
caacctttgc actccac                                                17

<210> SEQ ID NO 63
<211> LENGTH: 24
<212> TYPE: DNA
<213> ORGANISM: Artificial Sequence
<220> FEATURE:
<223> OTHER INFORMATION: Synthetic construct

<400> SEQUENCE: 63
tgtccatttt tttggctact ctga                                        24
```

<210> SEQ ID NO 64
<211> LENGTH: 19
<212> TYPE: DNA
<213> ORGANISM: Artificial Sequence
<220> FEATURE:
<223> OTHER INFORMATION: Synthetic construct

<400> SEQUENCE: 64
cccaaacacc caggctctt                                                  19

<210> SEQ ID NO 65
<211> LENGTH: 15
<212> TYPE: DNA
<213> ORGANISM: Artificial Sequence
<220> FEATURE:
<223> OTHER INFORMATION: Synthetic construct

<400> SEQUENCE: 65
cagtgtggaa caatg                                                      15

<210> SEQ ID NO 66
<211> LENGTH: 19
<212> TYPE: DNA
<213> ORGANISM: Artificial Sequence
<220> FEATURE:
<223> OTHER INFORMATION: Synthetic construct

<400> SEQUENCE: 66
gctccagtgc cccaagatt                                                  19

<210> SEQ ID NO 67
<211> LENGTH: 18
<212> TYPE: DNA
<213> ORGANISM: Artificial Sequence
<220> FEATURE:
<223> OTHER INFORMATION: Synthetic construct

<400> SEQUENCE: 67
cgacggatcg cctctgaa                                                   18

<210> SEQ ID NO 68
<211> LENGTH: 21
<212> TYPE: DNA
<213> ORGANISM: Artificial Sequence
<220> FEATURE:
<223> OTHER INFORMATION: Synthetic construct

<400> SEQUENCE: 68
aaactgtgga tatcagcatg a                                               21

<210> SEQ ID NO 69
<211> LENGTH: 23
<212> TYPE: DNA
<213> ORGANISM: Artificial Sequence
<220> FEATURE:
<223> OTHER INFORMATION: Synthetic construct

<400> SEQUENCE: 69
tgggcaactc agaaatactt cga                                             23

<210> SEQ ID NO 70
<211> LENGTH: 21
<212> TYPE: DNA
<213> ORGANISM: Artificial Sequence
<220> FEATURE:

<223> OTHER INFORMATION: Synthetic construct

<400> SEQUENCE: 70
acgtcaatag gcacgtttgc t                                              21

<210> SEQ ID NO 71
<211> LENGTH: 19
<212> TYPE: DNA
<213> ORGANISM: Artificial Sequence
<220> FEATURE:
<223> OTHER INFORMATION: Synthetic construct

<400> SEQUENCE: 71
ctcccaagat ataagaggc                                                 19

<210> SEQ ID NO 72
<211> LENGTH: 20
<212> TYPE: DNA
<213> ORGANISM: Artificial Sequence
<220> FEATURE:
<223> OTHER INFORMATION: Synthetic construct

<400> SEQUENCE: 72
gtccaccctc tcccttttct                                                20

<210> SEQ ID NO 73
<211> LENGTH: 26
<212> TYPE: DNA
<213> ORGANISM: Artificial Sequence
<220> FEATURE:
<223> OTHER INFORMATION: Synthetic construct

<400> SEQUENCE: 73
cacgcactct agtacaaagc ataaga                                         26

<210> SEQ ID NO 74
<211> LENGTH: 15
<212> TYPE: DNA
<213> ORGANISM: Artificial Sequence
<220> FEATURE:
<223> OTHER INFORMATION: Synthetic construct

<400> SEQUENCE: 74
ctcactccaa gaaac                                                     15

<210> SEQ ID NO 75
<211> LENGTH: 22
<212> TYPE: DNA
<213> ORGANISM: Artificial Sequence
<220> FEATURE:
<223> OTHER INFORMATION: Synthetic construct

<400> SEQUENCE: 75
cccaaaccga atcaccttaa ga                                             22

<210> SEQ ID NO 76
<211> LENGTH: 18
<212> TYPE: DNA
<213> ORGANISM: Artificial Sequence
<220> FEATURE:
<223> OTHER INFORMATION: Synthetic construct

<400> SEQUENCE: 76
caggagggtg gccatcct                                                  18

```
<210> SEQ ID NO 77
<211> LENGTH: 15
<212> TYPE: DNA
<213> ORGANISM: Artificial Sequence
<220> FEATURE:
<223> OTHER INFORMATION: Synthetic construct

<400> SEQUENCE: 77
acagggctag ggcat                                                          15

<210> SEQ ID NO 78
<211> LENGTH: 21
<212> TYPE: DNA
<213> ORGANISM: Artificial Sequence
<220> FEATURE:
<223> OTHER INFORMATION: Synthetic construct

<400> SEQUENCE: 78
tctccatggc atcttcgtct t                                                   21

<210> SEQ ID NO 79
<211> LENGTH: 20
<212> TYPE: DNA
<213> ORGANISM: Artificial Sequence
<220> FEATURE:
<223> OTHER INFORMATION: Synthetic construct

<400> SEQUENCE: 79
atcccttacc ccaccctcaa                                                     20

<210> SEQ ID NO 80
<211> LENGTH: 17
<212> TYPE: DNA
<213> ORGANISM: Artificial Sequence
<220> FEATURE:
<223> OTHER INFORMATION: Synthetic construct

<400> SEQUENCE: 80
actcttaggc actttgg                                                        17

<210> SEQ ID NO 81
<211> LENGTH: 18
<212> TYPE: DNA
<213> ORGANISM: Artificial Sequence
<220> FEATURE:
<223> OTHER INFORMATION: Synthetic construct

<400> SEQUENCE: 81
cggcctcagg cacaagaa                                                       18

<210> SEQ ID NO 82
<211> LENGTH: 20
<212> TYPE: DNA
<213> ORGANISM: Artificial Sequence
<220> FEATURE:
<223> OTHER INFORMATION: Synthetic construct

<400> SEQUENCE: 82
gcagcccatc cagtgtcaat                                                     20

<210> SEQ ID NO 83
<211> LENGTH: 19
<212> TYPE: DNA
<213> ORGANISM: Artificial Sequence
<220> FEATURE:
<223> OTHER INFORMATION: Synthetic construct
```

<400> SEQUENCE: 83
atgtggacta tgtgatcct                                                19

<210> SEQ ID NO 84
<211> LENGTH: 27
<212> TYPE: DNA
<213> ORGANISM: Artificial Sequence
<220> FEATURE:
<223> OTHER INFORMATION: Synthetic construct

<400> SEQUENCE: 84
catggtacat gagtggctat catactg                                       27

<210> SEQ ID NO 85
<211> LENGTH: 23
<212> TYPE: DNA
<213> ORGANISM: Artificial Sequence
<220> FEATURE:
<223> OTHER INFORMATION: Synthetic construct

<400> SEQUENCE: 85
gtgagcacct tccttctttt tga                                           23

<210> SEQ ID NO 86
<211> LENGTH: 23
<212> TYPE: DNA
<213> ORGANISM: Artificial Sequence
<220> FEATURE:
<223> OTHER INFORMATION: Synthetic construct

<400> SEQUENCE: 86
ctattatatg ggtttcagac aaa                                           23

<210> SEQ ID NO 87
<211> LENGTH: 27
<212> TYPE: DNA
<213> ORGANISM: Artificial Sequence
<220> FEATURE:
<223> OTHER INFORMATION: Synthetic construct

<400> SEQUENCE: 87
gactattgtc tcctaaaccc aggacta                                       27

<210> SEQ ID NO 88
<211> LENGTH: 22
<212> TYPE: DNA
<213> ORGANISM: Artificial Sequence
<220> FEATURE:
<223> OTHER INFORMATION: Synthetic construct

<400> SEQUENCE: 88
cccagtgcat ttaatgacca aa                                            22

<210> SEQ ID NO 89
<211> LENGTH: 17
<212> TYPE: DNA
<213> ORGANISM: Artificial Sequence
<220> FEATURE:
<223> OTHER INFORMATION: Synthetic construct

<400> SEQUENCE: 89
agttccctcg tactgtc                                                  17

<210> SEQ ID NO 90
<211> LENGTH: 22

```
<212> TYPE: DNA
<213> ORGANISM: Artificial Sequence
<220> FEATURE:
<223> OTHER INFORMATION: Synthetic construct

<400> SEQUENCE: 90
atcaattttc ccgacgatct tc                                              22

<210> SEQ ID NO 91
<211> LENGTH: 21
<212> TYPE: DNA
<213> ORGANISM: Artificial Sequence
<220> FEATURE:
<223> OTHER INFORMATION: Synthetic construct

<400> SEQUENCE: 91
cggttggcat ccatgtaaag t                                               21

<210> SEQ ID NO 92
<211> LENGTH: 14
<212> TYPE: DNA
<213> ORGANISM: Artificial Sequence
<220> FEATURE:
<223> OTHER INFORMATION: Synthetic construct

<400> SEQUENCE: 92
tggctccaac actg                                                       14

<210> SEQ ID NO 93
<211> LENGTH: 21
<212> TYPE: DNA
<213> ORGANISM: Artificial Sequence
<220> FEATURE:
<223> OTHER INFORMATION: Synthetic construct

<400> SEQUENCE: 93
aggtccaccg tgatcaacat c                                               21

<210> SEQ ID NO 94
<211> LENGTH: 20
<212> TYPE: DNA
<213> ORGANISM: Artificial Sequence
<220> FEATURE:
<223> OTHER INFORMATION: Synthetic construct

<400> SEQUENCE: 94
cagggaccag acgacatggt                                                 20

<210> SEQ ID NO 95
<211> LENGTH: 16
<212> TYPE: DNA
<213> ORGANISM: Artificial Sequence
<220> FEATURE:
<223> OTHER INFORMATION: Synthetic construct

<400> SEQUENCE: 95
acagcgagac ctccgt                                                     16

<210> SEQ ID NO 96
<211> LENGTH: 20
<212> TYPE: DNA
<213> ORGANISM: Artificial Sequence
<220> FEATURE:
<223> OTHER INFORMATION: Synthetic construct

<400> SEQUENCE: 96
```
caacttgtgg acggccagta                                                      20

<210> SEQ ID NO 97
<211> LENGTH: 22
<212> TYPE: DNA
<213> ORGANISM: Artificial Sequence
<220> FEATURE:
<223> OTHER INFORMATION: Synthetic construct

<400> SEQUENCE: 97
gtgccactga gggagaacat tt                                                   22

<210> SEQ ID NO 98
<211> LENGTH: 19
<212> TYPE: DNA
<213> ORGANISM: Artificial Sequence
<220> FEATURE:
<223> OTHER INFORMATION: Synthetic construct

<400> SEQUENCE: 98
aaactgcttc tacaagatt                                                       19

<210> SEQ ID NO 99
<211> LENGTH: 21
<212> TYPE: DNA
<213> ORGANISM: Artificial Sequence
<220> FEATURE:
<223> OTHER INFORMATION: Synthetic construct

<400> SEQUENCE: 99
cagcagagac cctgaaggaa a                                                    21

<210> SEQ ID NO 100
<211> LENGTH: 20
<212> TYPE: DNA
<213> ORGANISM: Artificial Sequence
<220> FEATURE:
<223> OTHER INFORMATION: Synthetic construct

<400> SEQUENCE: 100
caagccatga gttgccatca                                                      20

<210> SEQ ID NO 101
<211> LENGTH: 18
<212> TYPE: DNA
<213> ORGANISM: Artificial Sequence
<220> FEATURE:
<223> OTHER INFORMATION: Synthetic construct

<400> SEQUENCE: 101
aggtgcatat aagatctt                                                        18

<210> SEQ ID NO 102
<211> LENGTH: 19
<212> TYPE: DNA
<213> ORGANISM: Artificial Sequence
<220> FEATURE:
<223> OTHER INFORMATION: Synthetic construct

<400> SEQUENCE: 102
cccattctgc gtcatgctt                                                       19

<210> SEQ ID NO 103
<211> LENGTH: 24
<212> TYPE: DNA
<213> ORGANISM: Artificial Sequence

```
<220> FEATURE:
<223> OTHER INFORMATION: Synthetic construct

<400> SEQUENCE: 103
aatgcagttt agacacagcc aaac                                              24

<210> SEQ ID NO 104
<211> LENGTH: 23
<212> TYPE: DNA
<213> ORGANISM: Artificial Sequence
<220> FEATURE:
<223> OTHER INFORMATION: Synthetic construct

<400> SEQUENCE: 104
tgttataact actccggaga cag                                               23

<210> SEQ ID NO 105
<211> LENGTH: 21
<212> TYPE: DNA
<213> ORGANISM: Artificial Sequence
<220> FEATURE:
<223> OTHER INFORMATION: Synthetic construct

<400> SEQUENCE: 105
agttcagccc agatggaagg t                                                 21

<210> SEQ ID NO 106
<211> LENGTH: 20
<212> TYPE: DNA
<213> ORGANISM: Artificial Sequence
<220> FEATURE:
<223> OTHER INFORMATION: Synthetic construct

<400> SEQUENCE: 106
gcggcatcgc taaataagga                                                   20

<210> SEQ ID NO 107
<211> LENGTH: 17
<212> TYPE: DNA
<213> ORGANISM: Artificial Sequence
<220> FEATURE:
<223> OTHER INFORMATION: Synthetic construct

<400> SEQUENCE: 107
ttcagggaaa ggtgggc                                                      17

<210> SEQ ID NO 108
<211> LENGTH: 29
<212> TYPE: DNA
<213> ORGANISM: Artificial Sequence
<220> FEATURE:
<223> OTHER INFORMATION: Synthetic construct

<400> SEQUENCE: 108
cacagggact tgaagttgtt actaactaa                                         29

<210> SEQ ID NO 109
<211> LENGTH: 20
<212> TYPE: DNA
<213> ORGANISM: Artificial Sequence
<220> FEATURE:
<223> OTHER INFORMATION: Synthetic construct

<400> SEQUENCE: 109
tgacgcagaa tgggatgaga                                                   20
```

```
<210> SEQ ID NO 110
<211> LENGTH: 17
<212> TYPE: DNA
<213> ORGANISM: Artificial Sequence
<220> FEATURE:
<223> OTHER INFORMATION: Synthetic construct

<400> SEQUENCE: 110
ctctctttgg gaatgtt                                                  17

<210> SEQ ID NO 111
<211> LENGTH: 21
<212> TYPE: DNA
<213> ORGANISM: Artificial Sequence
<220> FEATURE:
<223> OTHER INFORMATION: Synthetic construct

<400> SEQUENCE: 111
caaagcagcc agacgttgaa c                                             21

<210> SEQ ID NO 112
<211> LENGTH: 20
<212> TYPE: DNA
<213> ORGANISM: Artificial Sequence
<220> FEATURE:
<223> OTHER INFORMATION: Synthetic construct

<400> SEQUENCE: 112
cacaccagat ccggaagaca                                               20

<210> SEQ ID NO 113
<211> LENGTH: 16
<212> TYPE: DNA
<213> ORGANISM: Artificial Sequence
<220> FEATURE:
<223> OTHER INFORMATION: Synthetic construct

<400> SEQUENCE: 113
tttccctggg cgcagg                                                   16

<210> SEQ ID NO 114
<211> LENGTH: 23
<212> TYPE: DNA
<213> ORGANISM: Artificial Sequence
<220> FEATURE:
<223> OTHER INFORMATION: Synthetic construct

<400> SEQUENCE: 114
gggattccta ccccagattt cta                                           23

<210> SEQ ID NO 115
<211> LENGTH: 25
<212> TYPE: DNA
<213> ORGANISM: Artificial Sequence
<220> FEATURE:
<223> OTHER INFORMATION: Synthetic construct

<400> SEQUENCE: 115
cagaaactgt tgttggactg catag                                         25

<210> SEQ ID NO 116
<211> LENGTH: 20
<212> TYPE: DNA
<213> ORGANISM: Artificial Sequence
<220> FEATURE:
<223> OTHER INFORMATION: Synthetic construct
```

```
<400> SEQUENCE: 116
agtcagaaat gtaccaaaaa                                              20

<210> SEQ ID NO 117
<211> LENGTH: 24
<212> TYPE: DNA
<213> ORGANISM: Artificial Sequence
<220> FEATURE:
<223> OTHER INFORMATION: Synthetic construct

<400> SEQUENCE: 117
tgagctgtag ctgcgtaagt acct                                         24

<210> SEQ ID NO 118
<211> LENGTH: 20
<212> TYPE: DNA
<213> ORGANISM: Artificial Sequence
<220> FEATURE:
<223> OTHER INFORMATION: Synthetic construct

<400> SEQUENCE: 118
ggccttgtgc ctttcagaag                                              20

<210> SEQ ID NO 119
<211> LENGTH: 16
<212> TYPE: DNA
<213> ORGANISM: Artificial Sequence
<220> FEATURE:
<223> OTHER INFORMATION: Synthetic construct

<400> SEQUENCE: 119
cttgatgcct gtcggc                                                  16

<210> SEQ ID NO 120
<211> LENGTH: 19
<212> TYPE: DNA
<213> ORGANISM: Artificial Sequence
<220> FEATURE:
<223> OTHER INFORMATION: Synthetic construct

<400> SEQUENCE: 120
tggctgccct acacatgct                                               19

<210> SEQ ID NO 121
<211> LENGTH: 22
<212> TYPE: DNA
<213> ORGANISM: Artificial Sequence
<220> FEATURE:
<223> OTHER INFORMATION: Synthetic construct

<400> SEQUENCE: 121
caggatcccc tctaccactt tg                                           22

<210> SEQ ID NO 122
<211> LENGTH: 18
<212> TYPE: DNA
<213> ORGANISM: Artificial Sequence
<220> FEATURE:
<223> OTHER INFORMATION: Synthetic construct

<400> SEQUENCE: 122
cctgctctat ctgcattt                                                18

<210> SEQ ID NO 123
```

```
<211> LENGTH: 22
<212> TYPE: DNA
<213> ORGANISM: Artificial Sequence
<220> FEATURE:
<223> OTHER INFORMATION: Synthetic construct

<400> SEQUENCE: 123
gaggctcagc tgtgattgac at                                              22

<210> SEQ ID NO 124
<211> LENGTH: 23
<212> TYPE: DNA
<213> ORGANISM: Artificial Sequence
<220> FEATURE:
<223> OTHER INFORMATION: Synthetic construct

<400> SEQUENCE: 124
cacccatatc ctcgaagcta gag                                             23

<210> SEQ ID NO 125
<211> LENGTH: 19
<212> TYPE: DNA
<213> ORGANISM: Artificial Sequence
<220> FEATURE:
<223> OTHER INFORMATION: Synthetic construct

<400> SEQUENCE: 125
agaacatgga tgatacctc                                                  19

<210> SEQ ID NO 126
<211> LENGTH: 20
<212> TYPE: DNA
<213> ORGANISM: Artificial Sequence
<220> FEATURE:
<223> OTHER INFORMATION: Synthetic construct

<400> SEQUENCE: 126
tccagccaca gtcccctaga                                                 20

<210> SEQ ID NO 127
<211> LENGTH: 27
<212> TYPE: DNA
<213> ORGANISM: Artificial Sequence
<220> FEATURE:
<223> OTHER INFORMATION: Synthetic construct

<400> SEQUENCE: 127
tcctgaatgt tcctgatgat agtctct                                         27

<210> SEQ ID NO 128
<211> LENGTH: 23
<212> TYPE: DNA
<213> ORGANISM: Artificial Sequence
<220> FEATURE:
<223> OTHER INFORMATION: Synthetic construct

<400> SEQUENCE: 128
agattaacat tgacagttcg aca                                             23

<210> SEQ ID NO 129
<211> LENGTH: 19
<212> TYPE: DNA
<213> ORGANISM: Artificial Sequence
<220> FEATURE:
<223> OTHER INFORMATION: Synthetic construct

<400> SEQUENCE: 129
```
cgagaggaag gcgctgatc                                              19

<210> SEQ ID NO 130
<211> LENGTH: 26
<212> TYPE: DNA
<213> ORGANISM: Artificial Sequence
<220> FEATURE:
<223> OTHER INFORMATION: Synthetic construct

<400> SEQUENCE: 130
acatcactcc atccttatac agcaaa                                      26

<210> SEQ ID NO 131
<211> LENGTH: 17
<212> TYPE: DNA
<213> ORGANISM: Artificial Sequence
<220> FEATURE:
<223> OTHER INFORMATION: Synthetic construct

<400> SEQUENCE: 131
cctgcaagag attattt                                                17

<210> SEQ ID NO 132
<211> LENGTH: 23
<212> TYPE: DNA
<213> ORGANISM: Artificial Sequence
<220> FEATURE:
<223> OTHER INFORMATION: Synthetic construct

<400> SEQUENCE: 132
ggatcctctt gacattcctc aaa                                         23

<210> SEQ ID NO 133
<211> LENGTH: 14
<212> TYPE: DNA
<213> ORGANISM: Artificial Sequence
<220> FEATURE:
<223> OTHER INFORMATION: Synthetic construct

<400> SEQUENCE: 133 ggcccccga tgga                                                    14

<210> SEQ ID NO 134
<211> LENGTH: 17
<212> TYPE: DNA
<213> ORGANISM: Artificial Sequence
<220> FEATURE:
<223> OTHER INFORMATION: Synthetic construct

<400> SEQUENCE: 134
ctccaccttt gaagacc                                                17

<210> SEQ ID NO 135
<211> LENGTH: 19
<212> TYPE: DNA
<213> ORGANISM: Artificial Sequence
<220> FEATURE:
<223> OTHER INFORMATION: Synthetic construct

<400> SEQUENCE: 135
cgagggtgtg gccatatga                                              19

<210> SEQ ID NO 136
<211> LENGTH: 25
<212> TYPE: DNA

```
<213> ORGANISM: Artificial Sequence
<220> FEATURE:
<223> OTHER INFORMATION: Synthetic construct

<400> SEQUENCE: 136
gaacaggcat tagaaatacc caaag                                              25

<210> SEQ ID NO 137
<211> LENGTH: 19
<212> TYPE: DNA
<213> ORGANISM: Artificial Sequence
<220> FEATURE:
<223> OTHER INFORMATION: Synthetic construct

<400> SEQUENCE: 137
tgactagatg gctaatatg                                                     19

<210> SEQ ID NO 138
<211> LENGTH: 22
<212> TYPE: DNA
<213> ORGANISM: Artificial Sequence
<220> FEATURE:
<223> OTHER INFORMATION: Synthetic construct

<400> SEQUENCE: 138
ctactgcaag gcatgctttg at                                                 22

<210> SEQ ID NO 139
<211> LENGTH: 16
<212> TYPE: DNA
<213> ORGANISM: Artificial Sequence
<220> FEATURE:
<223> OTHER INFORMATION: Synthetic construct

<400> SEQUENCE: 139
tggccccctg cattga                                                        16

<210> SEQ ID NO 140
<211> LENGTH: 17
<212> TYPE: DNA
<213> ORGANISM: Artificial Sequence
<220> FEATURE:
<223> OTHER INFORMATION: Synthetic construct

<400> SEQUENCE: 140
tcccttcatc attgctg                                                       17

<210> SEQ ID NO 141
<211> LENGTH: 19
<212> TYPE: DNA
<213> ORGANISM: Artificial Sequence
<220> FEATURE:
<223> OTHER INFORMATION: Synthetic construct

<400> SEQUENCE: 141
gccggtgcag ttacacgtt                                                     19

<210> SEQ ID NO 142
<211> LENGTH: 18
<212> TYPE: DNA
<213> ORGANISM: Artificial Sequence
<220> FEATURE:
<223> OTHER INFORMATION: Synthetic construct

<400> SEQUENCE: 142
ccccaaaccc gtgacaac                                                      18
```

<210> SEQ ID NO 143
<211> LENGTH: 15
<212> TYPE: DNA
<213> ORGANISM: Artificial Sequence
<220> FEATURE:
<223> OTHER INFORMATION: Synthetic construct

<400> SEQUENCE: 143
cctccaagga gcctc                                                          15

<210> SEQ ID NO 144
<211> LENGTH: 20
<212> TYPE: DNA
<213> ORGANISM: Artificial Sequence
<220> FEATURE:
<223> OTHER INFORMATION: Synthetic construct

<400> SEQUENCE: 144
caaggccctc aacacattca                                                     20

<210> SEQ ID NO 145
<211> LENGTH: 23
<212> TYPE: DNA
<213> ORGANISM: Artificial Sequence
<220> FEATURE:
<223> OTHER INFORMATION: Synthetic construct

<400> SEQUENCE: 145
ggtacataac gggcatcttg atg                                                 23

<210> SEQ ID NO 146
<211> LENGTH: 15
<212> TYPE: DNA
<213> ORGANISM: Artificial Sequence
<220> FEATURE:
<223> OTHER INFORMATION: Synthetic construct

<400> SEQUENCE: 146
acctgttcgc ctttg                                                          15

<210> SEQ ID NO 147
<211> LENGTH: 26
<212> TYPE: DNA
<213> ORGANISM: Artificial Sequence
<220> FEATURE:
<223> OTHER INFORMATION: Synthetic construct

<400> SEQUENCE: 147
cctatgctgg agaaggatta gaaagt                                              26

<210> SEQ ID NO 148
<211> LENGTH: 22
<212> TYPE: DNA
<213> ORGANISM: Artificial Sequence
<220> FEATURE:
<223> OTHER INFORMATION: Synthetic construct

<400> SEQUENCE: 148
cgatgattag aggtgcatgg aa                                                  22

<210> SEQ ID NO 149
<211> LENGTH: 15
<212> TYPE: DNA
<213> ORGANISM: Artificial Sequence
<220> FEATURE:

<223> OTHER INFORMATION: Synthetic construct

<400> SEQUENCE: 149
atgtggcaga taaag                                                    15

<210> SEQ ID NO 150
<211> LENGTH: 18
<212> TYPE: DNA
<213> ORGANISM: Artificial Sequence
<220> FEATURE:
<223> OTHER INFORMATION: Synthetic construct

<400> SEQUENCE: 150
tctcgccacc ctcaccat                                                 18

<210> SEQ ID NO 151
<211> LENGTH: 24
<212> TYPE: DNA
<213> ORGANISM: Artificial Sequence
<220> FEATURE:
<223> OTHER INFORMATION: Synthetic construct

<400> SEQUENCE: 151
gctgacagaa gtagatgcca ttgt                                          24

<210> SEQ ID NO 152
<211> LENGTH: 16
<212> TYPE: DNA
<213> ORGANISM: Artificial Sequence
<220> FEATURE:
<223> OTHER INFORMATION: Synthetic construct

<400> SEQUENCE: 152
caaggcatcc ggtttg                                                   16

<210> SEQ ID NO 153
<211> LENGTH: 20
<212> TYPE: DNA
<213> ORGANISM: Artificial Sequence
<220> FEATURE:
<223> OTHER INFORMATION: Synthetic construct

<400> SEQUENCE: 153
aagtcgccct ggaacttcct                                               20

<210> SEQ ID NO 154
<211> LENGTH: 20
<212> TYPE: DNA
<213> ORGANISM: Artificial Sequence
<220> FEATURE:
<223> OTHER INFORMATION: Synthetic construct

<400> SEQUENCE: 154
caccgagtcc tgctcctcat                                               20

<210> SEQ ID NO 155
<211> LENGTH: 19
<212> TYPE: DNA
<213> ORGANISM: Artificial Sequence
<220> FEATURE:
<223> OTHER INFORMATION: Synthetic construct

<400> SEQUENCE: 155
atgagttgta cgagcagtc                                                19

<210> SEQ ID NO 156
<211> LENGTH: 25
<212> TYPE: DNA
<213> ORGANISM: Artificial Sequence
<220> FEATURE:
<223> OTHER INFORMATION: Synthetic construct

<400> SEQUENCE: 156
catgagctgg tgaaaaatgg tattt                                  25

<210> SEQ ID NO 157
<211> LENGTH: 23
<212> TYPE: DNA
<213> ORGANISM: Artificial Sequence
<220> FEATURE:
<223> OTHER INFORMATION: Synthetic construct

<400> SEQUENCE: 157
aaagctattc ctatcgtggc aaa                                    23

<210> SEQ ID NO 158
<211> LENGTH: 18
<212> TYPE: DNA
<213> ORGANISM: Artificial Sequence
<220> FEATURE:
<223> OTHER INFORMATION: Synthetic construct

<400> SEQUENCE: 158
aaccagatac caagtttt                                          18

<210> SEQ ID NO 159
<211> LENGTH: 19
<212> TYPE: DNA
<213> ORGANISM: Artificial Sequence
<220> FEATURE:
<223> OTHER INFORMATION: Synthetic construct

<400> SEQUENCE: 159
tccccagctc ttgccaaag                                         19

<210> SEQ ID NO 160
<211> LENGTH: 23
<212> TYPE: DNA
<213> ORGANISM: Artificial Sequence
<220> FEATURE:
<223> OTHER INFORMATION: Synthetic construct

<400> SEQUENCE: 160
cagagaactc cctccaagtt gct                                    23

<210> SEQ ID NO 161
<211> LENGTH: 20
<212> TYPE: DNA
<213> ORGANISM: Artificial Sequence
<220> FEATURE:
<223> OTHER INFORMATION: Synthetic construct

<400> SEQUENCE: 161
ctggagtaga aggacaacag                                        20

<210> SEQ ID NO 162
<211> LENGTH: 17
<212> TYPE: DNA
<213> ORGANISM: Artificial Sequence
<220> FEATURE:
<223> OTHER INFORMATION: Synthetic construct

```
<400> SEQUENCE: 162
ggcaggccag ggtttgt                                                    17

<210> SEQ ID NO 163
<211> LENGTH: 21
<212> TYPE: DNA
<213> ORGANISM: Artificial Sequence
<220> FEATURE:
<223> OTHER INFORMATION: Synthetic construct

<400> SEQUENCE: 163
cgagatggct ggaaacacag a                                               21

<210> SEQ ID NO 164
<211> LENGTH: 14
<212> TYPE: DNA
<213> ORGANISM: Artificial Sequence
<220> FEATURE:
<223> OTHER INFORMATION: Synthetic construct

<400> SEQUENCE: 164
aggcgctgtc tgtc                                                       14

<210> SEQ ID NO 165
<211> LENGTH: 20
<212> TYPE: DNA
<213> ORGANISM: Artificial Sequence
<220> FEATURE:
<223> OTHER INFORMATION: Synthetic construct

<400> SEQUENCE: 165
gactcagcct ctgggatgga                                                 20

<210> SEQ ID NO 166
<211> LENGTH: 21
<212> TYPE: DNA
<213> ORGANISM: Artificial Sequence
<220> FEATURE:
<223> OTHER INFORMATION: Synthetic construct

<400> SEQUENCE: 166
ggatccggaa gtagccattc t                                               21

<210> SEQ ID NO 167
<211> LENGTH: 21
<212> TYPE: DNA
<213> ORGANISM: Artificial Sequence
<220> FEATURE:
<223> OTHER INFORMATION: Synthetic construct

<400> SEQUENCE: 167
tggattgtta aaaacagctg g                                               21

<210> SEQ ID NO 168
<211> LENGTH: 18
<212> TYPE: DNA
<213> ORGANISM: Artificial Sequence
<220> FEATURE:
<223> OTHER INFORMATION: Synthetic construct

<400> SEQUENCE: 168
aggcggcttc ccatacct                                                   18

<210> SEQ ID NO 169
<211> LENGTH: 20
```

```
<212> TYPE: DNA
<213> ORGANISM: Artificial Sequence
<220> FEATURE:
<223> OTHER INFORMATION: Synthetic construct

<400> SEQUENCE: 169
cttcttccac cagcccaaaa                                                  20

<210> SEQ ID NO 170
<211> LENGTH: 18
<212> TYPE: DNA
<213> ORGANISM: Artificial Sequence
<220> FEATURE:
<223> OTHER INFORMATION: Synthetic construct

<400> SEQUENCE: 170
attgcaggaa agtacgcc                                                    18

<210> SEQ ID NO 171
<211> LENGTH: 19
<212> TYPE: DNA
<213> ORGANISM: Artificial Sequence
<220> FEATURE:
<223> OTHER INFORMATION: Synthetic construct

<400> SEQUENCE: 171
cccaaacctg caccactga                                                   19

<210> SEQ ID NO 172
<211> LENGTH: 21
<212> TYPE: DNA
<213> ORGANISM: Artificial Sequence
<220> FEATURE:
<223> OTHER INFORMATION: Synthetic construct

<400> SEQUENCE: 172
caagatgttg gcaaatgcaa a                                                21

<210> SEQ ID NO 173
<211> LENGTH: 18
<212> TYPE: DNA
<213> ORGANISM: Artificial Sequence
<220> FEATURE:
<223> OTHER INFORMATION: Synthetic construct

<400> SEQUENCE: 173
ctgaaataca gcaaaaga                                                    18

<210> SEQ ID NO 174
<211> LENGTH: 24
<212> TYPE: DNA
<213> ORGANISM: Artificial Sequence
<220> FEATURE:
<223> OTHER INFORMATION: Synthetic construct

<400> SEQUENCE: 174
cctttgtggc atttattcat cagt                                             24

<210> SEQ ID NO 175
<211> LENGTH: 23
<212> TYPE: DNA
<213> ORGANISM: Artificial Sequence
<220> FEATURE:
<223> OTHER INFORMATION: Synthetic construct

<400> SEQUENCE: 175
```

```
gcttctatga caagcagcct ttg                                        23

<210> SEQ ID NO 176
<211> LENGTH: 15
<212> TYPE: DNA
<213> ORGANISM: Artificial Sequence
<220> FEATURE:
<223> OTHER INFORMATION: Synthetic construct

<400> SEQUENCE: 176
agggtgtccg attgg                                                 15

<210> SEQ ID NO 177
<211> LENGTH: 22
<212> TYPE: DNA
<213> ORGANISM: Artificial Sequence
<220> FEATURE:
<223> OTHER INFORMATION: Synthetic construct

<400> SEQUENCE: 177
ctctgtagca caggctggat tg                                         22

<210> SEQ ID NO 178
<211> LENGTH: 20
<212> TYPE: DNA
<213> ORGANISM: Artificial Sequence
<220> FEATURE:
<223> OTHER INFORMATION: Synthetic construct

<400> SEQUENCE: 178
aggctgcagt gcaagattga                                            20

<210> SEQ ID NO 179
<211> LENGTH: 17
<212> TYPE: DNA
<213> ORGANISM: Artificial Sequence
<220> FEATURE:
<223> OTHER INFORMATION: Synthetic construct

<400> SEQUENCE: 179
agtgcaatcc tgcaatt                                               17

<210> SEQ ID NO 180
<211> LENGTH: 20
<212> TYPE: DNA
<213> ORGANISM: Artificial Sequence
<220> FEATURE:
<223> OTHER INFORMATION: Synthetic construct

<400> SEQUENCE: 180
ccacttggag gcctttcatc                                            20

<210> SEQ ID NO 181
<211> LENGTH: 21
<212> TYPE: DNA
<213> ORGANISM: Artificial Sequence
<220> FEATURE:
<223> OTHER INFORMATION: Synthetic construct

<400> SEQUENCE: 181
aggttggcga tcaggaatac a                                          21

<210> SEQ ID NO 182
<211> LENGTH: 16
<212> TYPE: DNA
<213> ORGANISM: Artificial Sequence
```

```
<220> FEATURE:
<223> OTHER INFORMATION: Synthetic construct

<400> SEQUENCE: 182
tcgggtgtgc tatgga                                                           16

<210> SEQ ID NO 183
<211> LENGTH: 20
<212> TYPE: DNA
<213> ORGANISM: Artificial Sequence
<220> FEATURE:
<223> OTHER INFORMATION: Synthetic construct

<400> SEQUENCE: 183
ccttgcctgg tttcgatgtt                                                       20

<210> SEQ ID NO 184
<211> LENGTH: 23
<212> TYPE: DNA
<213> ORGANISM: Artificial Sequence
<220> FEATURE:
<223> OTHER INFORMATION: Synthetic construct

<400> SEQUENCE: 184
gagcatttcc ctgtaggctt ctt                                                   23

<210> SEQ ID NO 185
<211> LENGTH: 16
<212> TYPE: DNA
<213> ORGANISM: Artificial Sequence
<220> FEATURE:
<223> OTHER INFORMATION: Synthetic construct

<400> SEQUENCE: 185
cccaaagcat aaaatt                                                           16

<210> SEQ ID NO 186
<211> LENGTH: 23
<212> TYPE: DNA
<213> ORGANISM: Artificial Sequence
<220> FEATURE:
<223> OTHER INFORMATION: Synthetic construct

<400> SEQUENCE: 186
caaccgttgg aaacataacc att                                                   23

<210> SEQ ID NO 187
<211> LENGTH: 25
<212> TYPE: DNA
<213> ORGANISM: Artificial Sequence
<220> FEATURE:
<223> OTHER INFORMATION: Synthetic construct

<400> SEQUENCE: 187
aacaatcagt agcacattgc atctg                                                 25

<210> SEQ ID NO 188
<211> LENGTH: 16
<212> TYPE: DNA
<213> ORGANISM: Artificial Sequence
<220> FEATURE:
<223> OTHER INFORMATION: Synthetic construct

<400> SEQUENCE: 188
agggagctgg gacact                                                           16
```

<210> SEQ ID NO 189
<211> LENGTH: 22
<212> TYPE: DNA
<213> ORGANISM: Artificial Sequence
<220> FEATURE:
<223> OTHER INFORMATION: Synthetic construct

<400> SEQUENCE: 189
tggactcact gaggctgacg ta                                              22

<210> SEQ ID NO 190
<211> LENGTH: 21
<212> TYPE: DNA
<213> ORGANISM: Artificial Sequence
<220> FEATURE:
<223> OTHER INFORMATION: Synthetic construct

<400> SEQUENCE: 190
gattcccgag aacccttgat g                                               21

<210> SEQ ID NO 191
<211> LENGTH: 19
<212> TYPE: DNA
<213> ORGANISM: Artificial Sequence
<220> FEATURE:
<223> OTHER INFORMATION: Synthetic construct

<400> SEQUENCE: 191
tcaccaagtt tgtgagttc                                                  19

<210> SEQ ID NO 192
<211> LENGTH: 21
<212> TYPE: DNA
<213> ORGANISM: Artificial Sequence
<220> FEATURE:
<223> OTHER INFORMATION: Synthetic construct

<400> SEQUENCE: 192
gctgccaatt ttgagcagtt t                                               21

<210> SEQ ID NO 193
<211> LENGTH: 20
<212> TYPE: DNA
<213> ORGANISM: Artificial Sequence
<220> FEATURE:
<223> OTHER INFORMATION: Synthetic construct

<400> SEQUENCE: 193
gttcccagct tttccgttca                                                 20

<210> SEQ ID NO 194
<211> LENGTH: 17
<212> TYPE: DNA
<213> ORGANISM: Artificial Sequence
<220> FEATURE:
<223> OTHER INFORMATION: Synthetic construct

<400> SEQUENCE: 194
tgcaagaaag gatcaaa                                                    17

<210> SEQ ID NO 195
<211> LENGTH: 19
<212> TYPE: DNA
<213> ORGANISM: Artificial Sequence
<220> FEATURE:
<223> OTHER INFORMATION: Synthetic construct

```
<400> SEQUENCE: 195
tcttgcctgc cctgtgttg                                              19

<210> SEQ ID NO 196
<211> LENGTH: 21
<212> TYPE: DNA
<213> ORGANISM: Artificial Sequence
<220> FEATURE:
<223> OTHER INFORMATION: Synthetic construct

<400> SEQUENCE: 196
tgccttcccc ttaataatgc a                                           21

<210> SEQ ID NO 197
<211> LENGTH: 16
<212> TYPE: DNA
<213> ORGANISM: Artificial Sequence
<220> FEATURE:
<223> OTHER INFORMATION: Synthetic construct

<400> SEQUENCE: 197
aaaatgcggg tccctt                                                 16

<210> SEQ ID NO 198
<211> LENGTH: 24
<212> TYPE: DNA
<213> ORGANISM: Artificial Sequence
<220> FEATURE:
<223> OTHER INFORMATION: Synthetic construct

<400> SEQUENCE: 198
ctcccgctac acagaagtaa caaa                                        24

<210> SEQ ID NO 199
<211> LENGTH: 25
<212> TYPE: DNA
<213> ORGANISM: Artificial Sequence
<220> FEATURE:
<223> OTHER INFORMATION: Synthetic construct

<400> SEQUENCE: 199
aaaacatccc tgctaccaat acatt                                       25

<210> SEQ ID NO 200
<211> LENGTH: 23
<212> TYPE: DNA
<213> ORGANISM: Artificial Sequence
<220> FEATURE:
<223> OTHER INFORMATION: Synthetic construct

<400> SEQUENCE: 200
atggtagtca gttttgtatt tag                                         23

<210> SEQ ID NO 201
<211> LENGTH: 24
<212> TYPE: DNA
<213> ORGANISM: Artificial Sequence
<220> FEATURE:
<223> OTHER INFORMATION: Synthetic construct

<400> SEQUENCE: 201
tccgttacaa gatgaggtct gtgt                                        24

<210> SEQ ID NO 202
```

```
<211> LENGTH: 24
<212> TYPE: DNA
<213> ORGANISM: Artificial Sequence
<220> FEATURE:
<223> OTHER INFORMATION: Synthetic construct

<400> SEQUENCE: 202
cattctcctg gataacaacg ttga                                          24

<210> SEQ ID NO 203
<211> LENGTH: 13
<212> TYPE: DNA
<213> ORGANISM: Artificial Sequence
<220> FEATURE:
<223> OTHER INFORMATION: Synthetic construct

<400> SEQUENCE: 203
tgctcacttc ccc                                                      13

<210> SEQ ID NO 204
<211> LENGTH: 20
<212> TYPE: DNA
<213> ORGANISM: Artificial Sequence
<220> FEATURE:
<223> OTHER INFORMATION: Synthetic construct

<400> SEQUENCE: 204
tccatccctt gacggttctg                                               20

<210> SEQ ID NO 205
<211> LENGTH: 23
<212> TYPE: DNA
<213> ORGANISM: Artificial Sequence
<220> FEATURE:
<223> OTHER INFORMATION: Synthetic construct

<400> SEQUENCE: 205
agcccaagag gaatcaaaag atc                                           23

<210> SEQ ID NO 206
<211> LENGTH: 17
<212> TYPE: DNA
<213> ORGANISM: Artificial Sequence
<220> FEATURE:
<223> OTHER INFORMATION: Synthetic construct

<400> SEQUENCE: 206
ccttcccaaa ctgctttt                                                 17

<210> SEQ ID NO 207
<211> LENGTH: 27
<212> TYPE: DNA
<213> ORGANISM: Artificial Sequence
<220> FEATURE:
<223> OTHER INFORMATION: Synthetic construct

<400> SEQUENCE: 207
gagtcatcac tgaggaagag aagaatt                                       27

<210> SEQ ID NO 208
<211> LENGTH: 16
<212> TYPE: DNA
<213> ORGANISM: Artificial Sequence
<220> FEATURE:
<223> OTHER INFORMATION: Synthetic construct

<400> SEQUENCE: 208
```
tggcacgggc catacg                                                  16

<210> SEQ ID NO 209
<211> LENGTH: 17
<212> TYPE: DNA
<213> ORGANISM: Artificial Sequence
<220> FEATURE:
<223> OTHER INFORMATION: Synthetic construct

<400> SEQUENCE: 209
caaagccttc gctagtc                                                 17

<210> SEQ ID NO 210
<211> LENGTH: 23
<212> TYPE: DNA
<213> ORGANISM: Artificial Sequence
<220> FEATURE:
<223> OTHER INFORMATION: Synthetic construct

<400> SEQUENCE: 210
cctacacccc ttatccccat act                                          23

<210> SEQ ID NO 211
<211> LENGTH: 21
<212> TYPE: DNA
<213> ORGANISM: Artificial Sequence
<220> FEATURE:
<223> OTHER INFORMATION: Synthetic construct

<400> SEQUENCE: 211
ccagggctat tggttgaatg a                                            21

<210> SEQ ID NO 212
<211> LENGTH: 21
<212> TYPE: DNA
<213> ORGANISM: Artificial Sequence
<220> FEATURE:
<223> OTHER INFORMATION: Synthetic construct

<400> SEQUENCE: 212
ttattatcga aaccatcagc c                                            21

<210> SEQ ID NO 213
<211> LENGTH: 20
<212> TYPE: DNA
<213> ORGANISM: Artificial Sequence
<220> FEATURE:
<223> OTHER INFORMATION: Synthetic construct

<400> SEQUENCE: 213
cgacctgcga gactcacaag                                              20

<210> SEQ ID NO 214
<211> LENGTH: 19
<212> TYPE: DNA
<213> ORGANISM: Artificial Sequence
<220> FEATURE:
<223> OTHER INFORMATION: Synthetic construct

<400> SEQUENCE: 214
ggcacagcac tccgtctgt                                               19

<210> SEQ ID NO 215
<211> LENGTH: 17
<212> TYPE: DNA

<213> ORGANISM: Artificial Sequence
<220> FEATURE:
<223> OTHER INFORMATION: Synthetic construct

<400> SEQUENCE: 215
aagctgacag agatacc                                                          17

<210> SEQ ID NO 216
<211> LENGTH: 24
<212> TYPE: DNA
<213> ORGANISM: Artificial Sequence
<220> FEATURE:
<223> OTHER INFORMATION: Synthetic construct

<400> SEQUENCE: 216
tctggctgtc cttttttataa tgca                                                 24

<210> SEQ ID NO 217
<211> LENGTH: 23
<212> TYPE: DNA
<213> ORGANISM: Artificial Sequence
<220> FEATURE:
<223> OTHER INFORMATION: Synthetic construct

<400> SEQUENCE: 217
cttggcaata gaacctggac aac                                                   23

<210> SEQ ID NO 218
<211> LENGTH: 15
<212> TYPE: DNA
<213> ORGANISM: Artificial Sequence
<220> FEATURE:
<223> OTHER INFORMATION: Synthetic construct

<400> SEQUENCE: 218
agtgagaact ttccc                                                            15

<210> SEQ ID NO 219
<211> LENGTH: 22
<212> TYPE: DNA
<213> ORGANISM: Artificial Sequence
<220> FEATURE:
<223> OTHER INFORMATION: Synthetic construct

<400> SEQUENCE: 219
gcaagaagaa gccactgaaa ca                                                    22

<210> SEQ ID NO 220
<211> LENGTH: 24
<212> TYPE: DNA
<213> ORGANISM: Artificial Sequence
<220> FEATURE:
<223> OTHER INFORMATION: Synthetic construct

<400> SEQUENCE: 220
gaaagcctta tcttcctcgt ccat                                                  24

<210> SEQ ID NO 221
<211> LENGTH: 16
<212> TYPE: DNA
<213> ORGANISM: Artificial Sequence
<220> FEATURE:
<223> OTHER INFORMATION: Synthetic construct

<400> SEQUENCE: 221
cccaagaagc aggcca                                                           16

<210> SEQ ID NO 222
<211> LENGTH: 21
<212> TYPE: DNA
<213> ORGANISM: Artificial Sequence
<220> FEATURE:
<223> OTHER INFORMATION: Synthetic construct

<400> SEQUENCE: 222
ggctgaaaat ggtggaaaag g                                    21

<210> SEQ ID NO 223
<211> LENGTH: 23
<212> TYPE: DNA
<213> ORGANISM: Artificial Sequence
<220> FEATURE:
<223> OTHER INFORMATION: Synthetic construct

<400> SEQUENCE: 223
ctttgtccct gaggtgtcag ttt                                  23

<210> SEQ ID NO 224
<211> LENGTH: 15
<212> TYPE: DNA
<213> ORGANISM: Artificial Sequence
<220> FEATURE:
<223> OTHER INFORMATION: Synthetic construct

<400> SEQUENCE: 224
ccaagatggc ggccg                                           15

<210> SEQ ID NO 225
<211> LENGTH: 21
<212> TYPE: DNA
<213> ORGANISM: Artificial Sequence
<220> FEATURE:
<223> OTHER INFORMATION: Synthetic construct

<400> SEQUENCE: 225
tgtggatgag gcttccaaga a                                    21

<210> SEQ ID NO 226
<211> LENGTH: 20
<212> TYPE: DNA
<213> ORGANISM: Artificial Sequence
<220> FEATURE:
<223> OTHER INFORMATION: Synthetic construct

<400> SEQUENCE: 226
cagcagggtc cggtcatact                                      20

<210> SEQ ID NO 227
<211> LENGTH: 20
<212> TYPE: DNA
<213> ORGANISM: Artificial Sequence
<220> FEATURE:
<223> OTHER INFORMATION: Synthetic construct

<400> SEQUENCE: 227
agatcaaaga catcctcatc                                      20

<210> SEQ ID NO 228
<211> LENGTH: 23
<212> TYPE: DNA
<213> ORGANISM: Artificial Sequence
<220> FEATURE:

<223> OTHER INFORMATION: Synthetic construct

<400> SEQUENCE: 228
ggcaggtgga ctacgagtca tac                                            23

<210> SEQ ID NO 229
<211> LENGTH: 19
<212> TYPE: DNA
<213> ORGANISM: Artificial Sequence
<220> FEATURE:
<223> OTHER INFORMATION: Synthetic construct

<400> SEQUENCE: 229
gtctcctcgc tgccaggat                                                 19

<210> SEQ ID NO 230
<211> LENGTH: 14
<212> TYPE: DNA
<213> ORGANISM: Artificial Sequence
<220> FEATURE:
<223> OTHER INFORMATION: Synthetic construct

<400> SEQUENCE: 230
catggcggaa actg                                                      14

<210> SEQ ID NO 231
<211> LENGTH: 21
<212> TYPE: DNA
<213> ORGANISM: Artificial Sequence
<220> FEATURE:
<223> OTHER INFORMATION: Synthetic construct

<400> SEQUENCE: 231
ccggaacatt aagaccattg c                                              21

<210> SEQ ID NO 232
<211> LENGTH: 19
<212> TYPE: DNA
<213> ORGANISM: Artificial Sequence
<220> FEATURE:
<223> OTHER INFORMATION: Synthetic construct

<400> SEQUENCE: 232
cccttggcag cattgatga                                                 19

<210> SEQ ID NO 233
<211> LENGTH: 15
<212> TYPE: DNA
<213> ORGANISM: Artificial Sequence
<220> FEATURE:
<223> OTHER INFORMATION: Synthetic construct

<400> SEQUENCE: 233
agtgcctggc agatg                                                     15

<210> SEQ ID NO 234
<211> LENGTH: 21
<212> TYPE: DNA
<213> ORGANISM: Artificial Sequence
<220> FEATURE:
<223> OTHER INFORMATION: Synthetic construct

<400> SEQUENCE: 234
ctgccacccc actcttaatc a                                              21

```
<210> SEQ ID NO 235
<211> LENGTH: 23
<212> TYPE: DNA
<213> ORGANISM: Artificial Sequence
<220> FEATURE:
<223> OTHER INFORMATION: Synthetic construct

<400> SEQUENCE: 235
ggccaattga aacaaacagt tct                                            23

<210> SEQ ID NO 236
<211> LENGTH: 16
<212> TYPE: DNA
<213> ORGANISM: Artificial Sequence
<220> FEATURE:
<223> OTHER INFORMATION: Synthetic construct

<400> SEQUENCE: 236
tggtggaaga acggtc                                                    16

<210> SEQ ID NO 237
<211> LENGTH: 20
<212> TYPE: DNA
<213> ORGANISM: Artificial Sequence
<220> FEATURE:
<223> OTHER INFORMATION: Synthetic construct

<400> SEQUENCE: 237
ggaagcctgc cacctcctat                                                20

<210> SEQ ID NO 238
<211> LENGTH: 17
<212> TYPE: DNA
<213> ORGANISM: Artificial Sequence
<220> FEATURE:
<223> OTHER INFORMATION: Synthetic construct

<400> SEQUENCE: 238
tggcgcgagc attcttg                                                   17

<210> SEQ ID NO 239
<211> LENGTH: 14
<212> TYPE: DNA
<213> ORGANISM: Artificial Sequence
<220> FEATURE:
<223> OTHER INFORMATION: Synthetic construct

<400> SEQUENCE: 239
tgcggaccac catc                                                      14

<210> SEQ ID NO 240
<211> LENGTH: 27
<212> TYPE: DNA
<213> ORGANISM: Artificial Sequence
<220> FEATURE:
<223> OTHER INFORMATION: Synthetic construct

<400> SEQUENCE: 240
tgtccttgaa gcttgtatct gatatca                                        27

<210> SEQ ID NO 241
<211> LENGTH: 25
<212> TYPE: DNA
<213> ORGANISM: Artificial Sequence
<220> FEATURE:
<223> OTHER INFORMATION: Synthetic construct
```

```
<400> SEQUENCE: 241
ttcaatacaa ggtcaaaatc agcaa                                      25

<210> SEQ ID NO 242
<211> LENGTH: 18
<212> TYPE: DNA
<213> ORGANISM: Artificial Sequence
<220> FEATURE:
<223> OTHER INFORMATION: Synthetic construct

<400> SEQUENCE: 242
cactggattg tagaactt                                              18

<210> SEQ ID NO 243
<211> LENGTH: 24
<212> TYPE: DNA
<213> ORGANISM: Artificial Sequence
<220> FEATURE:
<223> OTHER INFORMATION: Synthetic construct

<400> SEQUENCE: 243
agcctcagat gaaagaaaca atca                                       24

<210> SEQ ID NO 244
<211> LENGTH: 20
<212> TYPE: DNA
<213> ORGANISM: Artificial Sequence
<220> FEATURE:
<223> OTHER INFORMATION: Synthetic construct

<400> SEQUENCE: 244
cacttgtgcc tgcagtttgg                                            20

<210> SEQ ID NO 245
<211> LENGTH: 15
<212> TYPE: DNA
<213> ORGANISM: Artificial Sequence
<220> FEATURE:
<223> OTHER INFORMATION: Synthetic construct

<400> SEQUENCE: 245
aaccaggaaa aactc                                                 15

<210> SEQ ID NO 246
<211> LENGTH: 21
<212> TYPE: DNA
<213> ORGANISM: Artificial Sequence
<220> FEATURE:
<223> OTHER INFORMATION: Synthetic construct

<400> SEQUENCE: 246
aagcaggcga atcgtaatga g                                          21

<210> SEQ ID NO 247
<211> LENGTH: 23
<212> TYPE: DNA
<213> ORGANISM: Artificial Sequence
<220> FEATURE:
<223> OTHER INFORMATION: Synthetic construct

<400> SEQUENCE: 247
tgcttgtgga atgtacagtg cat                                        23

<210> SEQ ID NO 248
<211> LENGTH: 13
```

```
<212> TYPE: DNA
<213> ORGANISM: Artificial Sequence
<220> FEATURE:
<223> OTHER INFORMATION: Synthetic construct

<400> SEQUENCE: 248
cgtgcgccgc caa                                                            13

<210> SEQ ID NO 249
<211> LENGTH: 21
<212> TYPE: DNA
<213> ORGANISM: Artificial Sequence
<220> FEATURE:
<223> OTHER INFORMATION: Synthetic construct

<400> SEQUENCE: 249 ccctttttctg ggtttgaagc t                                                  21

<210> SEQ ID NO 250
<211> LENGTH: 26
<212> TYPE: DNA
<213> ORGANISM: Artificial Sequence
<220> FEATURE:
<223> OTHER INFORMATION: Synthetic construct

<400> SEQUENCE: 250
ctgactgata caaagcacaa ttgaga                                              26

<210> SEQ ID NO 251
<211> LENGTH: 17
<212> TYPE: DNA
<213> ORGANISM: Artificial Sequence
<220> FEATURE:
<223> OTHER INFORMATION: Synthetic construct

<400> SEQUENCE: 251
ctgtctctag aagtgcc                                                        17

<210> SEQ ID NO 252
<211> LENGTH: 24
<212> TYPE: DNA
<213> ORGANISM: Artificial Sequence
<220> FEATURE:
<223> OTHER INFORMATION: Synthetic construct

<400> SEQUENCE: 252
gctgtgaaag caacataaat ggat                                                24

<210> SEQ ID NO 253
<211> LENGTH: 23
<212> TYPE: DNA
<213> ORGANISM: Artificial Sequence
<220> FEATURE:
<223> OTHER INFORMATION: Synthetic construct

<400> SEQUENCE: 253
ggcatgggaa cttaacagat gag                                                 23

<210> SEQ ID NO 254
<211> LENGTH: 20
<212> TYPE: DNA
<213> ORGANISM: Artificial Sequence
<220> FEATURE:
<223> OTHER INFORMATION: Synthetic construct

<400> SEQUENCE: 254
```
ttaaactgtc tacggttctt                                                    20

<210> SEQ ID NO 255
<211> LENGTH: 22
<212> TYPE: DNA
<213> ORGANISM: Artificial Sequence
<220> FEATURE:
<223> OTHER INFORMATION: Synthetic construct

<400> SEQUENCE: 255
cgctatccag aacctccact ct                                                 22

<210> SEQ ID NO 256
<211> LENGTH: 22
<212> TYPE: DNA
<213> ORGANISM: Artificial Sequence
<220> FEATURE:
<223> OTHER INFORMATION: Synthetic construct

<400> SEQUENCE: 256
caggtcatca cccttacttg ca                                                 22

<210> SEQ ID NO 257
<211> LENGTH: 15
<212> TYPE: DNA
<213> ORGANISM: Artificial Sequence
<220> FEATURE:
<223> OTHER INFORMATION: Synthetic construct

<400> SEQUENCE: 257
tcgacccctt tgctg                                                         15

<210> SEQ ID NO 258
<211> LENGTH: 2034
<212> TYPE: DNA
<213> ORGANISM: Homo sapiens

<400> SEQUENCE: 258
aaaccttggc catggtcact tcctcttttc caatctctgt ggcagttttt gccctaataa         60
ccctgcaggt tggtactcag gacagtttta tagctgcagt gtatgaacat gctgtcattt        120
tgccaaataa aacagaaaca ccagtttctc aggaggatgc cttgaatctc atgaacgaga        180
atatagacat tctggagaca gcgatcaagc aggcagctga gcagggtgct cgaatcattg        240
tgactccaga agatgcactt tatggatgga aatttaccag ggaaactgtt ttcccttatc        300
tggaggatat cccagaccct caggtgaact ggattccgtg tcaagacccc cacagatttg        360
gtcacacacc agtacaagca agactcagct gcctggccaa ggacaactct atctatgtct        420
tgcaaatttt gggggacaaa aagccatgta attcccgtga ctccacatgt cctcctaatg        480
gctactttca atacaatacc aatgtggtgt ataatacaga aggaaaactc gtggcacgtt        540
accataagta ccacctgtac tctgagcctc agtttaatgt ccctgaaaag ccggagttgg        600
tgactttcaa caccgcattt ggaaggtttg gcatttttcac gtgctttgat atattcttct        660
atgatcctgg tgttacccctg gtgaaagatt ccatgtggga caccatactg tttcccacag        720
cttggatgaa cgttttgccc cttttgacag ctattgaatt ccattcagct tgggcaatgg        780
gaatgggagt taatcttctt gtggccaaca cacatcatgt cagcctaaat atgacaggaa        840
gtggtattta tgcaccaaat ggtcccaaag tgtatcatta tgacatgaag acagagttgg        900
gaaaacttct ccttttcagag gtggattcac atccccctatc ctcgcttgcc tacccaacag        960
ctgttaattg gaatgcctac gccaccacca tcaaaccatt tccagtacag aaaaacactt       1020

-continued

```
tcaggggatt tatttccagg gatgggttca acttcacaga acttttttgaa aatgcaggaa      1080 accttacagt ctgtcaaaag gagctttgct gtcatttaag ctacagaatg ttacaaaaag      1140
aagagaatga agtatacgtt ctaggagctt ttacaggatt acatggccga aggagaagag      1200
agtactggca ggtctgcaca atgctgaagt gcaaaactac taatttgaca acttgtggac      1260
ggccagtaga aactgcttct acaagatttg aaatgttctc cctcagtggc acatttggaa      1320
cagagtatgt ttttcctgaa gtgctactta ccgaaattca tctgtcacct ggaaaatttg      1380
aggtgctgaa agatgggcgt ttggtaaaca agaatggatc atctgggcct atactaacag      1440
tgtcactctt tgggaggtgg tacacaaagg actcacttta cagctcatgt gggaccagca      1500
attcagcaat aacttacctg ctaatattca tattattaat gatcatagct ttgcaaaata      1560
ttgtaatgtt atagggcgtc tctttatcac tcagcttctg catcatatgc ttggctgaat      1620
gtgtttatcg gcttcccaag tttactaaga aactttgaag ggctatttca gtagtataga      1680
ccagtgagtc ctaaatattt tttctcatca ataattattt tttaagtatt atgataatgt      1740
tgtccatttt tttggctact ctgaaatgtt gcagtgtgga acaatggaaa gagcctgggt      1800
gtttgggtca gataaatgaa gatcaaactc cagctccagc ctcatttgct tgagactttg      1860
tgtgtatggg ggacttgtat gtatgggagt gaggagtttc agggccattg caaacatagc      1920
tgtgcccttg aagagaatag taatgatggg aatttagagg tttatgactg aattcccttt      1980
gacattaaag actatttgaa ttcaaaaaaa aaaaaaaaaa aaaaaaaaaa aaaa            2034
```

<210> SEQ ID NO 259
<211> LENGTH: 1498
<212> TYPE: DNA
<213> ORGANISM: Homo sapiens

<400> SEQUENCE: 259

```
gaggccagag tgccatcgaa ggtaattata gagacagtaa aatcctttta ctctgggaaa        60
aataaaatgc tgggtgtctc acaaaatttc agaacctgat ttcaaacgga tcataacaaa       120
gaggagatca aatttagcat ggtggactgc tcgacaggat atatttgtca atggaatgtt       180
tccacatatt ataccaccaa catgagaaaa aaatgatcat tgtttatttg aagcttgatg       240
atattctaac gctgcctttt ctcttctcat tttagagaaa aatgagcagg cggaattgtt       300
ggatttgtaa gatgtgcaga gatgaatcta agaggcccccc ttcaaacctt actttggagg      360
aagtattaca gtgggcccag tcttttgaaa atttaatggc tacaaaatat ggtccagtag       420
tctatgcagc atatttaaaa atggagcaca gtgacgagaa tattcaattc tggatggcat       480
gtgaaaccta taagaaaatt gcctcacggt ggagcagaat ttctagggca aagaagcttt       540
ataagattta catccagcca cagtcccta gagagattaa cattgacagt tcgacaagag        600
agactatcat caggaacatt caggaaccca ctgaaacatg ttttgaagaa gctcagaaaa       660
tagtctatat gcatatggaa agggattcct accccagatt tctaaagtca gaaatgtacc       720
aaaaactttt gaaaactatg cagtccaaca acagtttctg actacaactc aaaagtttaa      780
atagaaaaca gtatattgaa agtggtgggt ttgatctttt tatttagaaa cccacaaaat      840
cagaaacaca gtacaaataa aacagaaatc aaactataag ttgacttta gttcctaaaa       900 agaaacatat ttcaaaagca atggaatcta gaattcttat aacatgaata acaaaatgta      960
cagcaagcct atgtagttca attaatatat aaggaaaagg aaggtctttc ttcatgatac      1020
aagcattata aagttttac tgtagtagtc aattaatgga tatttccttg ttaataaaat      1080
```

| | |
|---|---|
| tttgtgtcat aatttacaaa ttagttcttt aaaaattgtt gttatatgaa ttgtgtttct | 1140 |
| agcatgaatg ttctatagag tactctaaat aacttgaatt tatagacaaa tgctactcac | 1200 |
| agtacaatca attgtattat accatgagaa aatcaaaaag gtgttcttca gagacatttt | 1260 |
| atctataaaa ttttcctact attatgttca ttaacaaact tctttatcac atgtatcttc | 1320 |
| tacatgtaaa acatttctga tgattttta acaaaaaata tatgaatttc ttcatttgct | 1380 |
| cttgcatcta cattgctata aggatataaa atgtggtttc tatattttga gatgttttt | 1440 |
| ccttacaatg tgaactcatc gtgatcttgg aaatcaataa agtcaaatat caactaaa | 1498 |

<210> SEQ ID NO 260
<211> LENGTH: 3260
<212> TYPE: DNA
<213> ORGANISM: Homo sapiens

<400> SEQUENCE: 260

| | |
|---|---|
| ccatcccata gtgagggaag acacgcggaa acaggcttgc acccagacac gacaccatgc | 60 |
| atctcctcgg cccctggctc ctgctcctgg ttctagaata cttggctttc tctgactcaa | 120 |
| gtaaatgggt ttttgagcac cctgaaaccc tctacgcctg gaggggggcc tgcgtctgga | 180 |
| tcccctgcac ctacagagcc ctagatggtg acctggaaag cttcatcctg ttccacaatc | 240 |
| ctgagtataa caagaacacc tcgaagtttg atgggacaag actctatgaa agcacaaagg | 300 |
| atgggaaggt tccttctgag cagaaaaggg tgcaattcct gggagacaag aataagaact | 360 |
| gcacactgag tatccacccg gtgcacctca atgacagtgg tcagctgggg ctgaggatgg | 420 |
| agtccaagac tgagaaatgg atggaacgaa tacacctcaa tgtctctgaa aggccttttc | 480 |
| cacctcatat ccagctccct ccagaaaattc aagagtccca ggaagtcact ctgacctgct | 540 |
| tgctgaattt ctcctgctat gggtatccga tccaattgca gtggctccta gaggggttc | 600 |
| caatgaggca ggctgctgtc acctcgacct ccttgaccat caagtctgtc ttcacccgga | 660 |
| gcgagctcaa gttctcccca cagtggagtc accatgggaa gattgtgacc tgccagcttc | 720 |
| aggatgcaga tgggaagttc ctctccaatg acacggtgca gctgaacgtg aagcacaccc | 780 |
| cgaagttgga gatcaaggtc actcccagtg atgccatagt gagggagggg gactctgtga | 840 |
| ccatgacctg cgaggtcagc agcagcaacc ggagtacac gacggtatcc tggctcaagg | 900 |
| atgggaccct gctgaagaag cagaatacat tcacgctaaa cctgcgcgaa gtgaccaagg | 960 |
| accagagtgg gaagtactgc tgtcaggtct ccaatgacgt gggcccggga aggtcggaag | 1020 |
| aagtgttcct gcaagtgcag tatgccccgg aaccttccac ggttcagatc ctccactcac | 1080 |
| cggctgtgga gggaagtcaa gtcgagtttt tttgcatgtc actggccaat cctcttccaa | 1140 |
| caaattacac gtggtaccac aatgggaaag aaatgcaggg aaggacagag gagaaagtcc | 1200 |
| acatcccaaa gatcctcccc tggcacgctg ggactattc ctgtgtggca gaaaacattc | 1260 |
| ttggtactgg acagagggc ccgggagctg agctggatgt ccagtatcct cccaagaagg | 1320 |
| tgaccacagt gattcaaaac cccatgccga ttcgagaagg agacacagtg acccttcct | 1380 |
| gtaactacaa ttccagtaac cccagtgtta cccggtatga atggaaaccc catggcgcct | 1440 |
| gggaggagcc atcgcttggg gtgctgaaga tccaaaacgt tggctggac aacacaacca | 1500 |
| tcgcctgcgc acgttgtaat agttggtgct cgtgggcctc cctgtcgcc ctgaatgtcc | 1560 |
| agtatgcccc ccgagacgtg agggtccgga aaatcaagcc cctttccgag attcactctg | 1620 |
| gaaactcggt cagcctccaa tgtgacttct caagcagcca ccccaaagaa gtccagttct | 1680 |
| tctgggagaa aaatggcagg cttctgggga aagaaagcca gctgaatttt gactccatct | 1740 |

```
ccccagaaga tgctgggagt tacagctgct gggtgaacaa ctccatagga cagacagcgt   1800
ccaaggcctg gacacttgaa gtgctgtatg cacccaggag gctgcgtgtg tccatgagcc   1860
cgggggacca agtgatggag gggaagagtg caaccctgac ctgtgagagt gacgccaacc   1920
ctcccgtctc ccactacacc tggtttgact ggaataacca aagcctcccc cacccacagcc   1980 agaagctgag attggagccg gtgaaggtcc agcactcggg tgcctactgg tgccagggga   2040
ccaacagtgt gggcaagggc cgttcgcctc tcagcaccct tactgtctac tatagcccgg   2100
agaccatcgg caggcgagtg gctgtgggac tcgggtcctg cctcgccatc ctcatcctgg   2160
caatctgtgg gctcaagctc cagcgacgtt ggaagaggac acagagccag cagggcttc   2220 aggagaattc cagcggccag agcttctttg tgaggaataa aaaggttaga agggcccccc   2280
tctctgaagg cccccactcc ctgggatgct acaatccaat gatggaagat ggcattagct   2340
acaccaccct gcgctttccc gagatgaaca taccacgaac tggagatgca gagtcctcag   2400
agatgcagag acctcccgg acctgcgatg acacggtcac ttattcagca ttgcacaagc   2460
gccaagtggg cgactatgag aacgtcattc agattttcc agaagatgag gggattcatt   2520
actcagagct gatccagttt ggggtcgggg agcggcctca ggcacaagaa atgtggact   2580 atgtgatcct caaacattga cactggatgg gctgcagcag aggcactggg ggcagcgggg   2640
gccagggaag tccccgagtt tccccagaca ccgccacatg gcttcctcct gcgtgcatgt   2700
gcgcacacac acacacacac gcacacacac acacacacac tcactgcgga gaaccttgtg   2760
cctggctcag agccagtctt tttggtgagg gtaaccccaa acctccaaaa ctcctgcccc   2820
tgttctcttc cactctcctt gctacccaga aatcatctaa atacctgccc tgacatgcac   2880
acctcccctg ccccaccagc ccactggcca tctccacccg gagctgctgt gtcctctgga   2940
tctgctcgtc attttccttc ccttctccat ctctctggcc ctctacccct gatctgacat   3000
ccccactcac gaatattatg cccagtttct gcctctgagg gaaagcccag aaaaggacag   3060
aaacgaagta gaaaggggcc cagtcctggc ctggcttctc ctttggaagt gaggcattgc   3120
acggggagac gtacgtatca gcggcccctt gactctgggg actccgggtt tgagatggac   3180
acactggtgt ggattaacct gccagggaga cagagctcac aataaaaatg gctcagatgc   3240
cacttcaaag aaaaaaaaaa                                                3260
```

<210> SEQ ID NO 261
<211> LENGTH: 1616
<212> TYPE: DNA
<213> ORGANISM: Homo sapiens

<400> SEQUENCE: 261

```
gccaaggctg gggcagggga gtcagcagag gcctcgctcg ggcgcccagt ggtcctgccg     60
cctggtctca cctcgctatg gttcgtctgc ctctgcagtg cgtcctctgg ggctgcttgc    120
tgaccgctgt ccatccagaa ccacccactg catgcagaga aaaacagtac ctaataaaca    180
gtcagtgctg ttctttgtgc cagccaggac agaaactggt gagtgactgc acagagttca    240
ctgaaacgga atgccttcct tgcggtgaaa gcgaattcct agacacctgg aacagagaga    300
cacactgcca ccagcacaaa tactgcgacc ccaacctagg gcttcgggtc cagcagaagg    360
gcacctcaga aacagacacc atctgcacct gtgaagaagg ctggcactgt acgagtgagg    420
cctgtgagag ctgtgtcctg caccgctcat gctcgcccgg ctttgggtc aagcagattg    480 ctacagggt ttctgatacc atctgcgagc cctgcccagt cggcttcttc tccaatgtgt    540
```

```
catctgcttt cgaaaaatgt cacccttgga caagctgtga gaccaaagac ctggttgtgc      600
aacaggcagg cacaaacaag actgatgttg tctgtggtcc ccaggatcgg ctgagagccc      660
tggtggtgat ccccatcatc ttcgggatcc tgtttgccat cctcttggtg ctggtcttta      720
tcaaaaaggt ggccaagaag ccaaccaata aggcccccca ccccaagcag aaccccagg       780
agatcaattt tcccgacgat cttcctggct ccaacactgc tgctccagtg caggagactt      840
tacatggatg ccaaccggtc acccaggagg atggcaaaga gagtcgcatc tcagtgcagg      900
agagacagtg aggctgcacc cacccaggag tgtggccacg tgggcaaaca ggcagttggc      960
cagagagcct ggtgctgctg ctgctgtggc gtgagggtga ggggctggca ctgactgggc      1020
atagctcccc gcttctgcct gcaccccctgc agtttgagac aggagacctg gcactggatg     1080
cagaaacagt tcaccttgaa gaacctctca cttcaccctg gagcccatcc agtctcccaa      1140
cttgtattaa agacagaggc agaagtttgg tggtggtggt gttggggtat ggtttagtaa      1200
tatccaccag accttccgat ccagcagttt ggtgccagag aggcatcat ggtggcttcc       1260
ctgcgcccag gaagccatat acacagatgc ccattgcagc attgtttgtg atagtgaaca     1320
actggaagct gcttaactgt ccatcagcag gagactggct aaataaaatt agaatatatt      1380
tatacaacag aatctcaaaa acactgttga gtaaggaaaa aaaggcatgc tgctgaatga      1440
tgggtatgga actttttaaa aaagtacatg cttttatgta tgtatattgc ctatggatat      1500
atgtataaat acaatatgca tcatatattg atataacaag ggttctggaa gggtacacag      1560
aaaacccaca gctcgaagag tggtgacgtc tggggtgggg aagaagggtc tgggg           1616
```

<210> SEQ ID NO 262
<211> LENGTH: 733
<212> TYPE: DNA
<213> ORGANISM: Homo sapiens

<400> SEQUENCE: 262

```
aaacagcagg aaatagaaac ttaagagaaa tacacacttc tgagaaactg aaacgacagg       60
ggaaaggagg tctcactgag caccgtccca gcatccggac accacagcgg cccttcgctc      120
cacgcagaaa accacacttc tcaaaccttc actcaacact tccttcccca agccagaag       180
atgcacaagg aggaacatga ggtggctgtg ctggggcac cccccagcac catccttcca      240
aggtccaccg tgatcaacat ccacagcgag acctccgtgc ccgaccatgt cgtctggtcc      300
ctgttcaaca ccctcttctt gaactggtgc tgtctgggct tcatagcatt cgcctactcc      360
gtgaagtcta gggacaggaa gatggttggc gacgtgaccg gggcccaggc ctatgcctcc      420
accgccaagt gcctgaacat ctgggccctg attctgggca tcctcatgac cattggattc      480
atcctgttac tggtattcgg ctctgtgaca gtctaccata ttatgttaca gataatacag      540
gaaaaacggg gttactagta gccgcccata gcctgcaacc tttgcactcc actgtgcaat      600
gctggccctg cacgctgggg ctgttgcccc tgccccttg gtcctgcccc tagatacagc       660
agtttatacc cacacacctg tctacagtgt cattcaataa agtgcacgtg cttgtgaaaa      720
aaaaaaaaaa aaa                                                         733
```

<210> SEQ ID NO 263
<211> LENGTH: 3537
<212> TYPE: DNA
<213> ORGANISM: Homo sapiens

<400> SEQUENCE: 263

```
ggcccctcga gcctcgaacc ggaacctcca aatccgagac gctctgctta tgaggacctc       60
```

-continued

```
gaaatatgcc ggccagtgaa aaaatcttgt ggcttttgagg gcttttggtt ggccaggggc     120
agtaaaaatc tcggagagct gacaccaagt cctcccctgc cacgtagcag tggtaaagtc     180
cgaagctcaa attccgagaa ttgagctctg ttgattctta gaactggggt tcttagaagt     240
ggtgatgcaa gaagtttcta ggaaaggccg gacaccaggt tttgagcaaa attttggact     300
gtgaagcaag gcattggtga agacaaaatg gcctcgccgg ctgacagctg tatccagttc     360
acccgccatg ccagtgatgt tcttctcaac cttaatcgtc tccggagtcg agacatcttg     420
actgatgttg tcattgttgt gagccgtgag cagtttagag cccataaaac ggtcctcatg     480
gcctgcagtg gcctgttcta tagcatcttt acagaccagt tgaaatgcaa ccttagtgtg     540
atcaatctag atcctgagat caaccctgag ggattctgca tcctcctgga cttcatgtac     600
acatctcggc tcaatttgcg ggagggcaac atcatggctg tgatggccac ggctatgtac     660
ctgcagatgg agcatgttgt ggacacttgc cggaagttta ttaaggccag tgaagcagag     720
atggtttctg ccatcaagcc tcctcgtgaa gagttcctca acagccggat gctgatgccc     780
caagacatca tggcctatcg gggtcgtgag gtggtggaga caacctgcc actgaggagc     840
gccctgggt gtgagagcag agcctttgcc cccagcctgt acagtggcct gtccacaccg     900
ccagcctctt attccatgta cagccacctc cctgtcagca gcctcctctt ctccgatgag     960
gagtttcggg atgtccggat gcctgtggcc aaccccttcc ccaaggagcg ggcactccca    1020
tgtgatagtg ccaggccagt ccctggtgag tacagccggc cgactttgga ggtgtccccc    1080
aatgtgtgcc acagcaatat ctattcaccc aaggaaacaa tcccagaaga ggcacgaagt    1140
gatatgcact acagtgtggc tgagggcctc aaacctgctg cccctcagc ccgaaatgcc    1200
ccctacttcc cttgtgacaa ggccagcaaa aagaagagaa gaccctcctc ggaagatgag    1260
attgccctgc atttcgagcc ccccaatgca cccctgaacc ggaagggtct ggttagtcca    1320
cagagccccc agaaatctga ctgccagccc aactcgccca cagagtcctg cagcagtaag    1380
aatgcctgca tcctccaggc ttctggctcc cctccagcca agagccccac tgaccccaaa    1440
gcctgcaact ggaagaaata caagttcatc gtgctcaaca gcctcaacca gaatgccaaa    1500
ccagagggc ctgagcaggc tgagctgggc cgccttttcc cacgagccta cacggcccca    1560
cctgcctgcc agccaccat ggagcctgag aaccttgacc tccagtcccc aaccaagctg    1620
agtgccagcg gggaggactc caccatccca caagccagcg ggctcaataa catcgttaac    1680
aggtccatga cgggctctcc ccgcagcagc agcgagagcc actcaccact ctacatgcac    1740
cccccgaagt gcacgtcctg cggctctcag tccccacagc atgcagagat gtgcctccac    1800
accgctggcc ccacgttccc tgaggagatg ggagagaccc agtctgagta ctcagattct    1860
agctgtgaga cgggccctt cttctgcaat gagtgtgact gccgcttctc tgaggaggcc    1920
tcactcaaga ggcacacgct gcagacccac agtgacaaac cctacaagtg tgaccgctgc    1980
caggcctcct tccgctacaa gggcaacctc gccagccaca agaccgtcca taccggtgag    2040
aaaccctatc gttgcaacat ctgtggggcc cagttcaacc ggccagccaa cctgaaaacc    2100
cacactcgaa ttcactctgg agagaagccc tacaaatgcg aaacctgcgg agccagattt    2160
gtacaggtgg cccacctccg tgcccatgtg cttatccaca ctggtgagaa gccctatccc    2220
tgtgaaatct gtggcacccg tttccggcac cttcagactc tgaagagcca cctgcgaatc    2280
cacacaggag agaaacctta ccattgtgag aagtgtaacc tgcatttccg tcacaaaagc    2340
cagctgcgac ttcacttgcg ccagaagcat ggcgccatca ccaacaccaa ggtgcaatac    2400
```

| | | | | |
|---|---|---|---|---|
| cgcgtgtcag | ccactgacct | gcctccggag | ctccccaaag | cctgctgaag catggagtgt | 2460 |
| tgatgctttc | gtctccagcc | ccttctcaga | atctacccaa | aggatactgt aacactttac | 2520 |
| aatgttcatc | ccatgatgta | gtgcctcttt | catccactag | tgcaaatcat agctggggt | 2580 |
| tgggggtggt | gggggtcggg | gcctggggga | ctgggagccg | cagcagctcc cctcccccca | 2640 |
| ctgccataaa | acattaagaa | aatcatattg | cttcttctcc | tatgtgtaag gtgaaccatg | 2700 |
| tcagcaaaaa | gcaaaatcat | tttatatgtc | aaagcagggg | agtatgcaaa agttctgact | 2760 |
| tgactttagt | ctgcaaaatg | aggaatgtat | atgttttgtg | ggaacagatg tttcttttgt | 2820 |
| atgtaaatgt | gcattctttt | aaaagacaag | acttcagtat | gttgtcaaag agagggcttt | 2880 |
| aattttttta | accaaaggtg | aaggaatata | tggcagagtt | gtaaatatat aaatatatat | 2940 |
| atatataaaa | taaatatata | taaacctaac | aaagatatat | taaaaatata aaactgcgtt | 3000 |
| aaaggctcga | ttttgtatct | gcaggcagac | acggatctga | aatctttat tgagaaagag | 3060 |
| cacttaagag | aatattttaa | gtattgcatc | tgtataagta | agaaaatatt ttgtctaaaa | 3120 |
| tgcctcagtg | tatttgtatt | tttttgcaag | tgaaggttta | caatttacaa agtgtgtatt | 3180 |
| aaaaaaaaca | aaaagaacaa | aaaaatctgc | agaaggaaaa | atgtgtaatt ttgttctagt | 3240 |
| tttcagtttg | tatatacccg | tacaacgtgt | cctcacggtg | cctttttca cggaagtttt | 3300 |
| caatgatggg | cgagcgtgca | ccatcccttt | ttgaagtgta | ggcagacaca gggacttgaa | 3360 |
| gttgttacta | actaaactct | ctttgggaat | gtttgtctca | tcccattctg cgtcatgctt | 3420 |
| gtgttataac | tactccggag | acagggtttg | gctgtgtcta | aactgcatta ccgcgttgta | 3480 |
| aaatatagct | gtacaaatat | aagaataaaa | tgttgaaaag | tcaaactgga aaaaaa | 3537 |

<210> SEQ ID NO 264
<211> LENGTH: 2613
<212> TYPE: DNA
<213> ORGANISM: Homo sapiens

<400> SEQUENCE: 264

| | | | | |
|---|---|---|---|---|
| tcccccctct | taaaacacga | tgcctcccag | gatgctagtg | gcaccactgc cactgcattt | 60 |
| cctgttggca | gcagtgagca | gtgaaaaccg | aagcggcaga | aggcagtggc agcaggcagt | 120 |
| ggcagcaggc | agtggcccag | gcagaaatag | ctcccgcgcg | attcactgga gccttccccg | 180 |
| ggccctggtc | ccggctaccg | ggactcgcgc | gtccggatct | caaaagcggc agaggccacc | 240 |
| gaagggacag | gaagcacttt | ggtccagacc | acactcccgg | cacagtgcgg aaagagccgg | 300 |
| cgggagccac | tctgatcccg | gacgcctcag | cgcccccttg | gcttgggct tgccctcggg | 360 |
| ccggggaagg | ctgaccgcga | tgccaggacg | cgctcccctc | cgcaccgtcc cgggcgccct | 420 |
| gggtgcctgg | ctgctgggcg | gcctctgggc | ctggaccctg | tgcggcctgt gcagcctggg | 480 |
| ggcggtggga | gccccgcgcc | cgtgccaggc | gccgcagcag | tgggagggc gccaggttat | 540 |
| gtaccagcaa | agtagcgggc | gcaacagccg | cgccctgctc | tcctacgacg ggctcaacca | 600 |
| gcgcgtgcgg | gtgctggacg | agaggaaggc | gctgatcccc | tgcaagagat tatttgaata | 660 |
| tattttgctg | tataaggatg | gagtgatgtt | tcagattgac | caagccacca agcagtgctc | 720 |
| aaagatgacc | ctgacacagc | cctgggatcc | tcttgacatt | cctcaaaact ccacctttga | 780 |
| agaccagtac | tccatcgggg | ggcctcagga | gcagatcacc | gtccaggagt ggtcggacag | 840 |
| aaagtcagct | agatcctatg | aaacctggat | tggcatctat | acagtcaagg attgctatcc | 900 |
| tgtccaggaa | acctttacca | taaactacag | tgtgatattg | tctacgcggt tttttgacat | 960 |
| ccagctgggt | attaaagacc | cctcggtgtt | taccccctcca | agcacgtgcc agatggccca | 1020 |

```
actggagaag atgagcgaag actgctcctg gtgagcctgt gcatagggaa gcggcagcat    1080
cggatgtcag ccccctgcgg ccccagctgg agatggatat gagactagtc aagatgtgaa    1140
tgctaattgg agagaaatat aattttagga agatgcacat tgatgtgggg ttttgatgtg    1200
tctgattttg actactcaag ctctgtttac agaagaaaat tgaatggcga gggtgtggcc    1260
atatgaactg actagatggc taatatggac actttgggta tttctaatgc ctgttcaggg    1320
ctggttttct gcatgcacgg gtatacacat aatgcagtgc catgcacata gggaagggtc    1380
agtaagagaa gtttgccttg gcagcaagta tttattgttg acattattca gaattagtga    1440
taataaaaag cagagtgatt ttggtcaatt ttattattaa ttcttaaatt ccctgcagag    1500
aatgccccct ttattgctgc accagggttg gcattgctcc cactgagccc tactccaccc    1560
tgtccctgca ctcccttggt tgccaaaaaa atgataactt aaatcccttc cagacttaag    1620
aattttatgg catggcccaa ttgatataaa catttagaag gaaatgaaaa gctaaaatag    1680
gaagtaatta ttcctctaaa gaaacatttt gagcaaggca gtttagagaa tcctaatgtc    1740
tacactggca tagcacgagc catgtaagct tcttttttt ctatgcaaga gtattgatgt    1800
atgtgctgaa tcttcacaga cttgtcaata cacaggcagt attctaaaat agcactgaac    1860
agggagtcag gagactattg tctcctaaac ccaggactag agttccctcg tactgtcact    1920
cctttggtca ttaaatgcac tgggcttgcc cgcactttgg ccttcctaga acactgcttc    1980
ataacctctc tgtctgactt ctgcatctcc ttccaggtca gctcattcac aagagttgct    2040
cccaagcctg gatgagttgc accttgcatc ttgagcatgc atttctcaca ataattatta    2100
agctgtgtga taatttctgc tttcaggaca ctcatccatt atcttggctg tgagctcctt    2160
gggtacgggt accttgtatg tttacttta tatccctagc acaaagcaag tgcctggcac    2220
atagtcagtg ccctaagtat tcgtagagtg aagaatgcca gcctctcttg tccctggttt    2280
ccttatgtgt tgaatgtggt tgagtttgtc cattgctagg gagagacttc cagtaataaa    2340
atttactatt ctagatgctt ctactgttat gttttatctg cccatttatc tttcttagtt    2400
accaggagaa atgtgtgaca cctatattat aatgaaaaca atctcattac ttatagttta    2460
tctatattaa acaaatttaa ttgcatttta aagcattctt tgatactgtt gcttttgcaa    2520
taaatatgga taatcttggt tataagggag ttaaaacaat gctgtaataa ataaagtgct    2580
tcatgtgatc aaaatcaaaa aaaaaaaaaa aaa    2613

<210> SEQ ID NO 265
<211> LENGTH: 11242
<212> TYPE: DNA
<213> ORGANISM: Homo sapiens

<400> SEQUENCE: 265 ttttttttt tttttttga gaaagggaa tttcatccca aataaaagga atgaagtctg      60
gctccggagg agggtccccg acctcgctgt ggggctcct gtttctctcc gccgcgctct    120
cgctctggcc gacgagtgga gaaatctgcg ggccaggcat cgacatccgc aacgactatc    180
agcagctgaa gcgcctggag aactgcacgg tgatcgaggg ctacctccac atcctgctca    240
tctccaaggc cgaggactac cgcagctacc gcttccccaa gctcacggtc attaccgagt    300
acttgctgct gttccgagtg gctggcctcg agagcctcgg agacctcttc cccaacctca    360
cggtcatccg cggctggaaa ctcttctaca actacgccct ggtcatcttc gagatgacca    420
atctcaagga tattgggctt tacaacctga ggaacattac tcggggggcc atcaggattg    480
```

```
agaaaaatgc tgacctctgt tacctctcca ctgtggactg gtccctgatc ctggatgcgg    540
tgtccaataa ctacattgtg gggaataagc ccccaaagga atgtggggac ctgtgtccag    600
ggaccatgga ggagaagccg atgtgtgaga agaccaccat caacaatgag tacaactacc    660
gctgctggac cacaaaccgc tgccagaaaa tgtgcccaag cacgtgtggg aagcgggcgt    720
gcaccgagaa caatgagtgc tgccaccccg agtgcctggg cagctgcagc gcgcctgaca    780
acgacacggc tgtgtagct tgccgccact actactatgc cggtgtctgt gtgcctgcct     840
gcccgcccaa cacctacagg tttgagggct ggcgctgtgt ggaccgtgac ttctgcgcca    900
acatcctcag cgccgagagc agcgactccg aggggtttgt gatccacgac ggcgagtgca    960
tgcaggagtg cccctcgggc ttcatccgca acggcagcca gagcatgtac tgcatcccTt   1020
gtgaaggtcc ttgcccgaag gtctgtgagg aagaaaagaa aacaaagacc attgattctg   1080
ttacttctgc tcagatgctc caaggatgca ccatcttcaa gggcaatttg ctcattaaca   1140
tccgacgggg gaataacatt gcttcagagc tggagaactt catggggctc atcgaggtgg   1200
tgacgggcta cgtgaagatc cgccattctc atgccttggt ctccttgtcc ttcctaaaaa   1260
accttcgcct catcctagga gaggagcagc tagaagggaa ttactccttc tacgtcctcg   1320
acaaccagaa cttgcagcaa ctgtgggact gggaccaccg caacctgacc atcaaagcag   1380
ggaaaatgta ctttgctttc aatcccaaat tatgtgtttc gaaatttac cgcatggagg    1440 aagtgacggg gactaagggg cgccaaagca aggggacat aaaaccagg aacaacgggg      1500 agagagcctc ctgtgaaagt gacgtcctgc atttcacctc caccaccacg tcgaagaatc   1560
gcatcatcat aacctggcac cggtaccggc cccctgacta cagggatctc atcagcttca   1620
ccgtttacta caaggaagca cccttTaaga atgtcacaga gtatgatggg caggatgcct   1680
gcggctccaa cagctggaac atggtggacg tggacctccc gcccaacaag gacgtggagc   1740
ccggcatctt actacatggg ctgaagccct ggactcagta cgccgtttac gtcaaggctg   1800
tgaccctcac catggtggag aacgaccata tccgtggggc caagagtgag atcttgtaca   1860
ttcgcaccaa tgcttcagtt ccttccattc ccttggacgt tctttcagca tcgaactcct   1920
cttctcagtt aatcgtgaag tggaaccctc cctctctgcc caacggcaac ctgagttact   1980
acattgtgcg ctggcagcgg cagcctcagg acggctacct ttaccggcac aattactgct   2040
ccaaagacaa aatccccatc aggaagtatg ccgacggcac catcgacatt gaggaggtca   2100
cagagaaccc caagactgag gtgtgtggtg gggagaaagg gccttgctgc gcctgcccca   2160
aaactgaagc cgaaagcag gccgagaagg aggaggctga ataccgcaaa gtctttgaga   2220
atttcctgca caactccatc ttcgtgccca gacctgaaag gaagcggaga gatgtcatgc   2280
aagtggccaa caccaccatg tccagccgaa gcaggaacac cacggccgca gacacctaca   2340
acatcaccga cccggaagag ctggagacag agtaccctt ctttgagagc agagtggata   2400
acaaggagag aactgtcatt tctaaccttc ggcctttcac attgtaccgc atcgatatcc   2460
acagctgcaa ccacgaggct gagaagctgg gctgcagcgc ctccaacttc gtcttTgcaa   2520
ggactatgcc cgcagaagga gcagatgaca ttcctgggcc agtgacctgg agccaaggc    2580 ctgaaaactc catctttTa aagtggccgg aacctgagaa tcccaatgga ttgattctaa   2640
tgtatgaaat aaaatacgga tcacaagttg aggatcagcg agaatgtgtg tccagacagg   2700
aatacaggaa gtatggaggg gccaagctaa accggctaaa cccggggaac tacacagccc   2760
ggattcaggc cacatctctc tctgggaatg gtcgtggac agatcctgtg ttcttctatg    2820
tccaggccaa aacaggatat gaaaacttca tccatctgat catcgctctg cccgtcgctg   2880
```

```
tcctgttgat cgtgggaggg ttggtgatta tgctgtacgt cttccataga aagagaaata   2940
acagcaggct ggggaatgga gtgctgtatg cctctgtgaa cccggagtac ttcagcgctg   3000
ctgatgtgta cgttcctgat gagtgggagg tggctcggga aagatcacc atgagccggg    3060 aacttgggca ggggtcgttt gggatggtct atgaaggagt tgccaagggt gtggtgaaag   3120
atgaacctga aaccagagtg gccattaaaa cagtgaacga ggccgcaagc atgcgtgaga   3180
ggattgagtt tctcaacgaa gcttctgtga tgaaggagtt caattgtcac catgtggtgc   3240
gattgctggg tgtggtgtcc caaggccagc caacactggt catcatggaa ctgatgacac   3300
ggggcgatct caaaagttat ctccggtctc tgaggccaga aatggagaat aatccagtcc   3360
tagcacctcc aagcctgagc aagatgattc agatggccgg agagattgca gacggcatgg   3420
catacctcaa cgccaataag ttcgtccaca gagaccttgc tgcccggaat tgcatggtag   3480
ccgaagattt cacagtcaaa atcggagatt ttggtatgac gcgagatatc tatgagacag   3540
actattaccg gaaaggaggg aaagggctgc tgcccgtgcg ctggatgtct cctgagtccc   3600
tcaaggatgg agtcttcacc acttactcgg acgtctggtc cttcggggtc gtcctctggg   3660
agatcgccac actggccgag cagccctacc agggcttgtc caacgagcaa gtccttcgct   3720
tcgtcatgga gggcggcctt ctggacaagc cagacaactg tcctgacatg ctgtttgaac   3780
tgatgcgcat gtgctggcag tataacccca agatgaggcc ttccttcctg agatcatca   3840 gcagcatcaa agaggagatg gagcctggct ccgggaggt ctccttctac tacagcgagg    3900
agaacaagct gcccgagccg gaggagctgg acctggagcc agagaacatg gagagcgtcc   3960
ccctggaccc ctcggcctcc tcgtcctccc tgccactgcc cgacagacac tcaggacaca   4020
aggccgagaa cggccccggc cctggggtgc tggtcctccg cgccagcttc gacgagagac   4080
agccttacgc ccacatgaac gggggccgca agaacgagcg ggccttgccg ctgccccagt   4140
cttcgacctg ctgatccttg gatcctgaat ctgtgcaaac agtaacgtgt gcgcacgcgc   4200
agcggggtgg gggggagag agagttttaa caatccattc acaagcctcc tgtacctcag   4260
tggatcttca gaactgccct tgctgcccgc gggagacagc ttctctgcag taaaacacat   4320
ttgggatgtt cctttttca atatgcaagc agcttttat tccctgccca aacccttaac    4380
tgacatgggc ctttaagaac cttaatgaca acacttaata gcaacagagc acttgagaac   4440
cagtctcctc actctgtccc tgtccttccc tgttctcct ttctctctcc tctctgcttc    4500
ataacggaaa ataattgcc acaagtccag ctgggaagcc ctttttatca gtttgaggaa    4560
gtggctgtcc ctgtggcccc atccaaccac tgtacacacc cgcctgacac cgtgggtcat   4620
tacaaaaaaa cacgtggaga tggaaatttt tacctttatc tttcacctttt ctagggacat   4680 gaaatttaca aagggccatc gttcatccaa ggctgttacc attttaacgc tgcctaattt    4740
tgccaaaatc ctgaactttc tccctcatcg gcccggcgct gattcctcgt gtccggaggc   4800
atgggtgagc atggcagctg gttgctccat ttgagagaca cgctggcgac acactccgtc   4860
catccgactg cccctgctgt gctgctcaag gccacaggca cacaggtctc attgcttctg   4920
actagattat tatttggggg aactggacac aataggtctt tctctcagtg aaggtgggga   4980
gaagctgaac cggcttccct gcctgcctc cccagccccc tgcccaaccc ccaagaatct    5040
ggtggccatg ggccccgaag cagcctggcg acaggcttg gagtcaaggg gccccatgcc    5100
tgcttctctc ccagccccag ctcccccgcc cgccccaag gacacagatg ggaagggggtt   5160 tccagggact cagcccccact gttgatgcag gtttgcaagg aaagaaattc aaacaccaca   5220
```

```
acagcagtaa gaagaaaagc agtcaatgga ttcaagcatt ctaagctttg ttgacatttt    5280
ctctgttcct aggacttctt catgggtctt acagttctat gttagaccat gaaacatttg    5340
catacacatc gtctttaatg tcacttttat aactttttta cggttcagat attcatctat    5400
acgtctgtac agaaaaaaaa aagctgctat ttttttttgtt cttgatcttt gtggatttaa    5460
tctatgaaaa ccttcaggtc caccctctcc cctttctgct cactccaaga aacttcttat    5520
gctttgtact agagtgcgtg actttcttcc tcttttcccg gtaatggata cttctatcac    5580
ataatttgcc atgaactgtt ggatgccttt ttataaatac atcccccatc cctgctccca    5640 cctgccccctt tagttgtttt ctaacccgta ggctctctgg gcacgaggca gaaagcaggc    5700
cgggcaccca tcctgagagg gccgcgctcc tctccccagc ctgccctcac agcattggag    5760
cctgttacag tgcaagacat gatacaaact caggtcagaa aaacaaaggt taaatatttc    5820
acacgtcttt gttcagtgtt tccactcacc gtggttgaga agcctcaccc tctctttccc    5880
ttgcctttgc ttaggttgtg acacacatat atatatattt ttttaattct tgggtacaac    5940
agcagtgtta accgcagaca ctaggcattt ggattactat ttttcttaat ggctatttaa    6000
tccttccatc ccacgaaaaa cagctgctga gtccaaggga gcagcagagc gtggtccggc    6060
agggcctgtt gtggccctcg ccaccccccct caccggaccg actgacctgt ctttggaacc    6120
agaacatccc aagggaactc cttcgcactg gcgttgagtg ggaccccggg atccaggctg    6180
gcccagggcg gcaccctcag ggctgtgccc gctggagtgc taggtggagg cagcacagac    6240
gccacggtgg cccaagagcc cctttgcttc ttgctgggggg accagggctg tggtgctggc    6300
ccactttccc tcggccagga atccaggtcc ttggggccca ggggtcttgt cttgtttcat    6360
ttttagcact tctcaccaga gagatgacag cacaagagtt gcttctggga tagaaatgtt    6420
taggagtaag aacaaagctg ggatacggtg attgctagtt gtgactgaag attcaacaca    6480
gaaaagaaag tttatacggc ttttttgctg gtcagcagtt tgtcccactg ctttctctag    6540
tctctatccc atagcgtgtt ccctttaaaa aaaaaaaaaa ggtattatat gtaggagttt    6600
tcttttaatt tattttgtga taaattacca gtttcaatca ctgtagaaaa gccccattat    6660
gaatttaaat ttcaaggaaa gggtgtgtgt gtgtgtatgt gtggggtgtg tgtgtgtgag    6720
agtgatggga cagttcttga ttttttgggt ttttttttccc ccaaacatttt atctacctca    6780 ctcttatttt ttatatgtgt atatagacaa aagaatacat ctcacctttc tcagcacctg    6840
acaataggcc gttgatactg gtaacctcat ccacgccaca ggcgccacac ccaggtgatg    6900 caggggggaag ccaggctgta ttccggggtc aaagcaacac taactcacct ctctgctcat    6960
ttcagacagc ttgcctttttt ctgagatgtc ctgttttgtg ttgcttttttt tgttttgttt    7020 tctatcttgg tttccaccaa ggtgttagat ttctcctcct cctagccagg tggccctgtg    7080
aggccaacga gggcaccaga gcacacctgg gggagccacc aggctgtccc tggctggttg    7140
tctttggaac aaaactgcttc tgtgcagatg gaatgaccaa cacatttcgt ccttaagaga    7200
gcagtggttc ctcaggttct gaggagagga aggtgtccag gcagcaccat ctctgtgcga    7260
atccccaggg taaaggcgtg gggcattggg tttgctcccc ttgctgctgc tccatccctg    7320
caggaggctc gcgctgaggc aggaccgtgc ggccatggct gctgcattca ttgagcacaa    7380
aggtgcagct gcagcagcag ctggagagca agagtcaccc agcctgtgcg ccagaatgca    7440
gaggctcctg acctcacagc cagtccctga tagaacacac gcaggagcag agtcccctcc    7500
ccctccaggc tgccctctca acttctccct cacctccttc cctaggggta gacagagatg    7560
taccaaacct tccggctgga aagcccagtg gccggcgccg aggctcgtgg cgtcacgccc    7620
```

```
cccccgccag ggctgtacct ccgtctccct ggtcctgctg ctcacaggac agacggctcg   7680
ctcccctctt ccagcagctg ctcttacagg cactgatgat ttcgctggga agtgtggcgg   7740
gcagctttgc ctaagcgtgg atggctcctc ggcaattcca gcctaagtga aggcgctcag   7800
gagcctcctg ctggaacgcg acccatctct cccaggaccc cggggatctt aaggtcattg   7860
agaaatactg ttggatcagg gttttgttct tccacactgt aggtgacccc ttggaataac   7920
ggcctctcct ctcgtgcaca tacctaccgg tttccacaac tggatttcta cagatcattc   7980
agctggttat aagggttttg tttaaactgt ccgagttact gatgtcattt tgttttttgtt   8040 ttatgtaggt agcttttaag tagaaaacac taacagtgta gtgcccatca tagcaaatgc   8100
ttcagaaaca cctcaataaa agagaaaact tggcttgtgt gatggtgcag tcactttact   8160
ggaccaaccc acccaccttg actataccaa ggcatcatct atccacagtt ctagcctaac   8220
ttcatgctga tttctctgcc tcttgatttt tctctgtgtg ttccaaataa tcttaagctg   8280
agttgtggca ttttccatgc aacctccttc tgccagcagc tcacactgct tgaagtcata   8340
tgaaccactg aggcacatca tggaattgat gtgagcatta agacgttctc ccacacagcc   8400
cttccctgag gcagcaggag ctggtgtgta ctggagacac tgttgaactt gatcaagacc   8460
cagaccaccc caggtctcct tcgtgggatg tcatgacgtt tgacatacct ttggaacgag   8520
cctcctcctt ggaagatgga agaccgtgtt cgtggccgac ctggcctctc ctggcctgtt   8580
tcttaagatg cggagtcaca tttcaatggt acgaaaagtg gcttcgtaaa atagaagagc   8640
agtcactgtg gaactaccaa atggcgagat gctcggtgca cattggggtg ctttgggata   8700
aaagatttat gagccaacta ttctctggca ccagattcta ggccagtttg ttccactgaa   8760
gcttttccca cagcagtcca cctctgcagg ctggcagccg aatggcttgc cagtggctct   8820
gtggcaagat cacactgaga tcgatgggtg agaaggctag gatgcttgtc tagtgttctt   8880
agctgtcacg ttggctcctt ccagggtggc cagacggtgt tggccactcc cttctaaaac   8940
acaggcgccc tcctggtgac agtgacccgc cgtggtatgc cttggcccat tccagcagtc   9000
ccagttatgc atttcaagtt tggggtttgt tcttttcgtt aatgttcctc tgtgttgtca   9060
gctgtcttca tttcctgggc taagcagcat tgggagatgg ggaccagaga tccactcctt   9120
aagaaccagt ggcgaaagac actttctttc ttcactctga agtagctggt ggtacaaatg   9180
agaacttcaa gagaggatgt tatttagact gaacctctgt tgccagagat gctgaagata   9240
cagaccttgg acaggtcaga gggtttcatt tttggccttc atcttagatg actggttgcg   9300
tcatttggaa aagtgagtgc tccttgatgg tggaatgacc gggtggtggg tacagaacca   9360
ttgtcacagg gatcctggca cagagaagag ttacgagcag cagggtgcag ggcttggaag   9420
gaatgtgggc aaggttttga acttgattgt tcttgaagct atcagaccac atcgaggctc   9480
agcagtcatc cgtgggcatt tggtttcaac aaagaaacct aacatcctac tctggaaact   9540
gatctcggag ttaaggcgaa ttgttcaaga acacaaacta catcgcactc gtcagttgtc   9600
agttctgggg catgacttta gcgttttgtt tctgcgagaa cataacgatc actcattttt   9660
atgtcccacg tgtgtgtgtc cgcatctttc tggtcaacat tgttttaact agtcactcat   9720
tagcgttttc aatagggctc ttaagtccag tagattacgg gtagtcagtt gacgaagatc   9780
tggtttacaa gaactaatta aatgtttcat tgcattttg taagaacaga ataatttat   9840 aaaatgtttg tagtttataa ttgccgaaaa taatttaaag acacttttt tttctctgtg   9900 tgtgcaaatg tgtgtttgtg atccattttt ttttttttttt tttaggacac ctgtttacta   9960
```

| | |
|---|---|
| gctagcttta caatatgcca aaaaaggatt tctccctgac cccatccgtg gttcaccctc | 10020 |
| ttttccccc atgctttttg ccctagttta taacaaagga atgatgatga tttaaaaagt | 10080 |
| agttctgtat cttcagtatc ttggtcttcc agaaccctct ggttgggaag gggatcattt | 10140 |
| tttactggtc atttcccttt ggagtgtagc tactttaaca gatggaaaga acctcattgg | 10200 |
| ccatggaaac agccgaggtg ttggagccca gcagtgcatg gcaccgttcg gcatctggct | 10260 |
| tgattggtct ggctgccgtc attgtcagca cagtgccatg gacatgggaa gacttgactg | 10320 |
| cacagccaat ggttttcatg atgattacag catacacagt gatcacataa acgatgacag | 10380 |
| ctatggggca cacaggccat ttgcttacat gcctcgtatc atgactgatt actgctttgt | 10440 |
| tagaacacag aagagaccct attttattta aggcagaacc ccgaagatac gtatttccaa | 10500 |
| tacagaaaag aattttttaat aaaaactata acatacacaa aaattggttt taaagttgac | 10560 |
| tccacttcct ctaactccag tggattgttg gccatgtctc cccaactcca caatatctct | 10620 |
| atcatgggaa acacctgggg ttttgcgct acataggaga aagatctgga aactatttgg | 10680 |
| gttttgtttt caacttttca tttggatgtt tggcgttgca cacacacatc caccggtgga | 10740 |
| agagacgccc ggtgaaaaca cctgtctgct ttctaagcca gtgaggttga ggtgagaggt | 10800 |
| ttgccagagt ttgtctacct ctgggtatcc ctttgtctgg gataaaaaaa atcaaaccag | 10860 |
| aaggcgggat ggaatggatg caccgcaaat aatgcatttt ctgagttttc ttgttaaaaa | 10920 |
| aaaatttttt taagtaagaa aaaaaaaggt aataacatgg ccaatttgtt acataaaatg | 10980 |
| actttctgtg tataaattat tcctaaaaaa tcctgtttat ataaaaaatc agtagatgaa | 11040 |
| aaaaatttca aaatgttttt gtatattctg ttgtaagaat ttattcctgt tattgcgata | 11100 |
| tactctggat tctttacata atggaaaaaa gaaactgtct attttgaatg gctgaagcta | 11160 |
| aggcaacgtt agtttctctt actctgcttt tttctagtaa agtactacat ggtttaagtt | 11220 |
| aaataaaata attctgtatg ca | 11242 |

<210> SEQ ID NO 266
<211> LENGTH: 2718
<212> TYPE: DNA
<213> ORGANISM: Homo sapiens

<400> SEQUENCE: 266

| | |
|---|---|
| cagggtaacg ctgtcttgtg gacccgcact tcccacccga gacctctcac tgagcccgag | 60 |
| ccgcgcgcga catgagccac gggaagggaa ccgacatgct cccggagatc gccgccgccg | 120 |
| tgggcttcct ctccagcctc ctgaggaccc ggggctgcgt gagcgagcag aggcttaagg | 180 |
| tcttcagcgg ggcgctccag gaggcactca cagagcacta caaacaccac tggtttcccg | 240 |
| aaaagccgtc caagggctcc ggctaccgct gcattcgcat caaccacaag atggacccca | 300 |
| tcatcagcag ggtggccagc cagatcggac tcagccagcc ccagctgcac cagctgctgc | 360 |
| ccagcgagct gacccgtgg gtggacccct atgaggtgtc ctaccgcatt ggggaggacg | 420 |
| gctccatctg cgtcttgtac gaggaggccc cactggccgc ctcctgtggg ctcctcacct | 480 |
| gcaagaacca agtgctgctg ggccggagca gcccctccaa gaactacgtg atggcagtct | 540 |
| ccagctaggc ccttccgccc ccgccctggg cgccgccgtg tcatgctgcc cgtgacaaca | 600 |
| ggccaccaca tacctcaacc tggggaactg tatttttaaa tgaagagcta tttatatata | 660 |
| ttattttttt ttaagaaagg aggaaaagaa accaaaagtt ttttttaaga aaaaaaatcc | 720 |
| ttcaaggag ctgcttggaa gtggcctccc caggtgcctt tggagagaac tgttgcgtgc | 780 |
| ttgagtctgt gagccagtgt ctgcctatag gagggggagc tgttaggggg tagacctagc | 840 |

```
caaggagaag tgggagacgt ttggctagca ccccaggaag atgtgagagg gagcaagcaa      900
ggttagcaac tgtgaacaga gaggtcggga tttgccctgg gggaggaaga gaggccaagt      960
tcagagctct ctgtctcccc cagccagaca cctgcatccc tggctcctct attactcagg     1020
ggcattcatg cctggactta aacaatacta tgttatcttt tcttttattt ttctaatgag     1080
gtcctgggca gagagtgaaa aggcctctcc tgattcctac tgtcctaagc tgcttttctt     1140
gaaatcatga cttgtttcta attctaccct caggggcctg tagatgttgc tttccagcca     1200
ggaatctaaa gctttgggtt ttctgagggg ggggaggagg gaactggagg ttattggggt     1260
taggatggaa gggaactctg cacaaaacct ttgctttgct agtgctgctt tgtgtgtatg     1320
tgtggcaaat aatttggggg tgatttgcaa tgaaattttg ggacccaaag agtatccact     1380
ggggatgttt tttggccaaa actcttcctt ttggaaccac atgaaagtct tgatgctgct     1440
gccatgatcc ctttgagagg tggctcaaaa gctacaggga actccaggtc ctttattact     1500
gccttctttt caaaagcaca actctcctct aaccctcccc tccccttcc cttctggtcg     1560 ggtcatagag ctaccgtatt ttctaggaca agagttctca gtcactgtgc aatatgcccc     1620
ctgggtccca ggagggtctg gaggaaaact ggctatcaga acctcctgat gccctggtgg     1680
gcttagggaa ccatctctcc tgctctcctt gggatgatgg ctggctagtc agccttgcat     1740
gtattccttg gctgaatggg agagtgcccc atgttctgca agactacttg gtattcttgt     1800
agggccgaca ctaaataaaa gccaaacctt gggcactgtt ttttctccct ggtgctcaga     1860
gcacctgtgg gaaaggttgc tgtctgtctc agtacaatcc aaatttgtcg tagacttgtg     1920
caatatatac tgttgtgggt tggagaaaag tggaaagcta cactgggaag aaactccctt     1980
ccttcaattt ctcagtgaca ttgatgaggg gtcctcaaaa gacctcgagt ttcccaaacc     2040
gaatcacctt aagaaggaca gggctagggc atttggccag gatggccacc ctcctgctgt     2100
tgccccttag tgaggaatct tcaccccact tcctctaccc ccaggttctc ctccccacag     2160
ccagtcccct ttcctggatt tctaaactgc tcaattttga ctcaaaggtg ctatttacca     2220
aacactctcc ctaccattc ctgccagctc tgcctccttt tcaactctcc acattttgta     2280
ttgccttccc agacctgctt ccagtcttta ttgctttaaa gttcactttg ggcccacaga     2340
cccaagagct aattttctgg tttgtgggtt gaaacaaagc tgtgaatcac tgcaggctgt     2400
gttcttgcat cttgtctgca aacaggtccc tgccttttta gaagcagcct catggtctca     2460
tgcttaatct tgtctctctt ctcttcttta tgatgttcac tttaaaaaca acaaaacccc     2520
tgagctggac tgttgagcag gcctgtctct cctattaagt aaaaataaat agtagtagta     2580
tgtttgtaag ctattctgac agaaaagaca aaggttacta attgtatgat agtgtttta     2640 tatggaagaa tgtacagctt atggacaaat gtacacctt tgttactttt aataaaaatg     2700
tagtaggata aaaaaaaa                                                  2718
```

<210> SEQ ID NO 267
<211> LENGTH: 2304
<212> TYPE: DNA
<213> ORGANISM: Homo sapiens

<400> SEQUENCE: 267

```
gaattcgtcc aaactgagga tcacaagtct ccacattctg agtaggagga tgagggtctg       60
agttaggatt tgggtcctgc agggcttgct aaggaatccc ctgatggcct aggattccac      120
gcagagcaca tctggtgtga gagagctcgc tgcaagggtg aaggctccgc cctatcagat      180
```

```
agacaaccag gccaccaaga ggcccagccc tccaaaccct ggatttgcaa catcctcaaa    240
gaacagcaac gggccttgag cagaattgag aaggaaatac ccccacctgc cctcagccgt    300
taagtgggct ttgctattca caagggcctc tgggtgtcct ggcagagagg ggagatggca    360
caggcaccag gtgctagggt gccagggcct cccgagaagg aacaggtgca aagcaggcaa    420
ttagcccaga aggtatccgt ggggcaggca gcctagatct gatgggggaa gccaccagga    480
ttacatcatc tgctgtaaca actgctctga aaagaagata tttttcaacc tgaacttgca    540
gtagctagtg gagaggcagg aaaaaggaaa tgaaacagag acagagggaa gcctgagcca    600
aaatagacct tcccgagaga ggaggaagcc cggagagaga cgcacggtcc cctccccgcc    660
cctaggccgc cgccccctct ctgccctcgg cggcgagcag ggcgccgcga cccggggccg    720
gaaaggtgcc aggggctccg ggcggccggg cgggcgcaca ccatccccgc gggcggcgcg    780
gagccggcga cagcgcgcga gagggaccgg gcggtggcgg cggcgggacc gggatggaag    840
ggagcgcggt gactgtcctt gagcgcggag gggcgagctc gccggcggag gccgagcaag    900
cggaggcagg agcggcggcg acggcggcgg cggcggcggc gcccgagcac ccgaggggggt    960 ccgagccccg gcagccggcc agccccgcgc acaaagggga gcgcccccgc cgcccggcac   1020
cccgcctccc tccccaatgt cctcggccat cgaaaggaag agcctggacc cttcaggga    1080 accagtggat gaggtgctgc agatccccc atccctgctg acatgcggcg gctgccagca    1140
gaacatcggg gaccgctact tcctgaaggc catcgaccag tactggcacg aggactgcct    1200
gagctgcgac ctctgtggct gccggctggg tgaggtgggg cggcgcctct actacaaact    1260
gggccggaag ctctgccgga gagactatct caggcttttt gggcaagacg gtctctgcgc    1320
atcctgtgac aagcggattc gtgcctatga gatgacaatg cgggtgaaag acaaagtgta    1380
tcacctggaa tgtttcaagt gcgccgcctg tcagaagcat ttctgtgtag gtgacagata   1440
cctcctcatc aactctgaca tagtgtgcga acaggacatc tacgagtgga ctaagatcaa   1500
tgggatgata taggcccgag tccccgggca tctttgggga ggtgttcact gaagacgccg    1560
tctccatggc atcttcgtct tcactcttag gcactttggg ggtttgaggg tggggtaagg   1620
gatttcttag gggatggtag acctttattg ggtatcaaga catagcatcc aagtggcata   1680
attcaggggc tgacacttca aggtgacaga aggaccagcc cttgagggag aacttatggc   1740
cacagcccat ccatagtaac tgacatgatt agcagaagaa aggaacattt aggggcaagc    1800
aggcgctgtg ctatcatgat ggaatttcat atctacagat agagagttgt tgtgtacaga   1860
cttgttgtga ctttgacgct tgcgaactag agatgtgcaa ttgatttctt ttcttcctgg   1920
ctttttaact cccctgtttc aatcactgtc ctccacacaa gggaaggaca gaaaggagag    1980
tggccattct ttttttcttg gcccccttcc caaggcctta agcttggac ccaagggaaa   2040 actgcatgga gacgcatttc ggttgagaat ggaaaccaca acttttaacc aaacaattat    2100
ttaaagcaat gctgatgaat cactgttttt agacaccttc attttgaggg gaggagttcc   2160
acagattgtt tctatacaaa tataaatctt aaaaagttgt tcaactattt tattatccta   2220
gattatatca aagtatttgt cgtgtgtaga aaaaaaaaac agctctgcag gcttaataaa   2280
aatgacagac tgaaaaaaaa aaaa                                         2304
```

<210> SEQ ID NO 268
<211> LENGTH: 1300
<212> TYPE: DNA
<213> ORGANISM: Homo sapiens

<400> SEQUENCE: 268

```
ctgcagccgg tgcagttaca cgttttcctc caaggagcct cggacgttgt cacgggtttg      60
gggtcgggga cagagcggtg accatggcca ggctggcgtt gtctcctgtg cccagccact     120
ggatggtggc gttgctgctg ctgctctcag ctgagccagt accagcagcc agatcggagg     180
accggtaccg gaatcccaaa ggtagtgctt gttcgcggat ctggcagagc ccacgtttca     240
tagccaggaa acgggcttc acggtgaaaa tgcactgcta catgaacagc gcctccggca      300
atgtgagctg gctctggaag caggagatgg acgagaatcc ccagcagctg aagctggaaa     360
agggccgcat ggaagagtcc cagaacgaat ctctcgccac cctcaccatc caaggcatcc     420
ggtttgagga caatggcatc tacttctgtc agcagaagtg caacaacacc tcggaggtct     480
accagggctg cggcacagag ctgcgagtca tgggattcag caccttggca cagctgaagc     540
agaggaacac gctgaaggat ggtatcatca tgatccagac gctgctgatc atcctcttca     600
tcatcgtgcc tatcttcctg ctgctggaca aggatgacag caaggctggc atggaggaag     660
atcacaccta cgagggcctg gacattgacc agacagccac ctatgaggac atagtgacgc     720
tgcggacagg ggaagtgaag tggtctgtag gtgagcaccc aggccaggag tgagagccag     780
gtcgccccat gacctgggtg caggctccct ggcctcagtg actgcttcgg agctgcctgg     840
ctcatggccc aacccctttc ctggaccccc cagctggcct ctgaagctgg cccaccagag     900
ctgccatttg tctccagccc ctggtcccca gctcttgcca aagggcctgg agtagaagga     960
caacagggca gcaacttgga gggagttctc tggggatgga cgggacccag ccttctgggg    1020
gtgctatgag gtgatccgtc cccacacatg ggatggggga ggcagagact ggtccagagc    1080
ccgcaaatgg actcggagcc gagggcctcc cagcagagct tgggaagggc catggaccca    1140
actgggcccc agaagagcca caggaacatc attcctctcc cgcaaccact cccaccccag    1200
ggaggccctg gcctccagtg ccttcccccg tggaataaac ggtgtgtcct gagaaaccac    1260
aaaaaaaaaa aaaaaaaaaa aaaaaaaaaa aaaaaaaaaa                          1300
```

<210> SEQ ID NO 269
<211> LENGTH: 5748
<212> TYPE: DNA
<213> ORGANISM: Homo sapiens

<400> SEQUENCE: 269

```
gagaagaaag ccagtgcgtc tctgggcgca ggggccagtg gggctcggag gcacaggcac      60
cccgcgacac tccaggttcc ccgacccacg tccctggcag ccccgattat ttacagcctc     120
agcagagcac ggggcggggg cagaggggcc cgcccgggag ggctgctact tcttaaaacc     180
tctgcgggct gcttagtcac agccccccctt gcttgggtgt gtccttcgct cgctccctcc     240
ctccgtctta ggtcactgtt ttcaacctcg aataaaaact gcagccaact tccgaggcag     300
cctcattgcc cagcggaccc cagcctctgc caggttcggt ccgccatcct cgtcccgtcc     360
tccgccggcc cctgccccgc gcccagggat cctccagctc ctttcgcccg cgccctccgt     420
tcgctccgga caccatggac aagtttttggt ggcacgcagc ctgggactc tgcctcgtgc     480 cgctgagcct ggcgcagatc gatttgaata aacctgccg cttttgcaggt gtattccacg     540 tggagaaaaa tggtcgctac agcatctctc ggacggaggc cgctgacctc tgcaaggctt     600
tcaatagcac cttgcccaca atggcccaga tggagaaagc tctgagcatc ggatttgaga     660
cctgcaggta tgggttcata gaagggcacg tggtgattcc ccggatccac cccaactcca     720
tctgtgcagc aaacaacaca ggggtgtaca tcctcacatc caacacctcc cagtatgaca     780
```

```
catattgctt caatgcttca gctccacctg aagaagattg tacatcagtc acagacctgc      840
ccaatgcctt tgatggacca attaccataa ctattgttaa ccgtgatggc acccgctatg      900
tccagaaagg agaatacaga acgaatcctg aagacatcta ccccagcaac cctactgatg      960
atgacgtgag cagcggctcc tccagtgaaa ggagcagcac ttcaggaggt tacatctttt     1020
acaccttttc tactgtacac cccatcccag acgaagacag tccctggatc accgacagca     1080
cagacagaat ccctgctacc actttgatga gcactagtgc tacagcaact gagacagcaa     1140
ccaagaggca agaaacctgg gattggtttt catggttgtt tctaccatca gagtcaaaga     1200
atcatcttca cacaacaaca caaatggctg gtacgtcttc aaataccatc tcagcaggct     1260
gggagccaaa tgaagaaaat gaagatgaaa gagacagaca cctcagtttt tctggatcag     1320
gcattgatga tgatgaagat tttatctcca gcaccatttc aaccacacca cgggcttttg     1380
accacacaaa acagaaccag gactggaccc agtggaaccc aagccattca aatccggaag     1440
tgctacttca gacaaccaca aggatgacta atgtagacag aaatggcacc actgcttatg     1500
aaggaaactg gaacccagaa gcacaccctc ccctcattca ccatgagcat catgaggaag     1560
aagagacccc acattctaca agcacaatcc aggcaactcc tagtagtaca acggaagaaa     1620
cagctaccca gaaggaacag tggtttggca acagatggca tgagggatat cgccaaacac     1680
ccaaagaaga ctcccattcg acaacaggga cagctgcagc ctcagctcat accagccatc     1740
caatgcaagg aaggacaaca ccaagcccag aggacagttc ctggactgat ttcttcaacc     1800
caatctcaca ccccatggga cgaggtcatc aagcaggaag aaggatggat atggactcca     1860
gtcatagtat aacgcttcag cctactgcaa atccaaacac aggtttggtg aagatttgg      1920 acaggacagg acctctttca atgacaacgc agcagagtaa ttctcagagc ttctctacat     1980
cacatgaagg cttggaagaa gataaagacc atccaacaac ttctactctg acatcaagca     2040
ataggaatga tgtcacaggt ggaagaagag acccaaatca ttctgaaggc tcaactactt     2100
tactggaagg ttatacctct cattacccac acacgaagga aagcaggacc ttcatcccag     2160
tgacctcagc taagactggg tcctttggag ttactgcagt tactgttgga gattccaact     2220
ctaatgtcaa tcgttcctta tcaggagacc aagacacatt ccaccccagt gggggtccc      2280 ataccactca tggatctgaa tcagatggac actcacatgg gagtcaagaa ggtggagcaa     2340
acacaacctc tggtcctata aggacacccc aaattccaga atggctgatc atcttggcat     2400
ccctcttggc cttggctttg attcttgcag tttgcattgc agtcaacagt cgaagaaggt     2460
gtgggcagaa gaaaaagcta gtgatcaaca gtggcaatgg agctgtggag acagaaagc      2520 caagtggact caacggagag gccagcaagt ctcaggaaat ggtgcatttg tgaacaagg      2580 agtcgtcaga aactccagac cagtttatga cagctgatga gacaaggaac ctgcagaatg     2640
tggacatgaa gattggggtg taacacctac accattatct tggaaagaaa caaccgttgg     2700
aaacataacc attacaggga gctgggacac ttaacagatg caatgtgcta ctgattgttt     2760
cattgcgaat ctttttagc ataaaattt ctactctttt tgttttttgt gttttgttct      2820
ttaaagtcag gtccaatttg taaaaacagc attgctttct gaaattaggg cccaattaat     2880
aatcagcaag aatttgatcg ttccagttcc cacttggagg cctttcatcc ctcgggtgtg     2940
ctatggatgg cttctaacaa aaactacaca tatgtattcc tgatcgccaa ccttcccccc     3000
accagctaag gacatttccc agggttaata gggcctggtc cctgggagga aatttgaatg     3060
ggtccatttt gcccttccat agcctaatcc ctgggcattg ctttccactg aggttggggg     3120
ttggggtgta ctagttacac atcttcaaca gacccccttct agaaattttt cagatgcttc    3180
```

```
tgggagacac ccaaagggtg aagctattta tctgtagtaa actatttatc tgtgttttg    3240
aaatattaaa ccctggatca gtcctttgat cagtataatt ttttaaagtt actttgtcag    3300
aggcacaaaa gggtttaaac tgattcataa taaatatctg tacttcttcg atcttcacct    3360
tttgtgctgt gattcttcag tttctaaacc agcactgtct gggtccctac aatgtatcag    3420
gaagagctga gaatggtaag gagactcttc taagtcttca tctcagagac cctgagttcc    3480
cactcagacc cactcagcca aatctcatgg aagaccaagg agggcagcac tgttttgtt    3540
ttttgttttt tgttttttt ttttgacact gtccaaaggt tttccatcct gtcctggaat    3600
cagagttgga agctgaggag cttcagcctc ttttatggtt taatggccac ctgttctctc    3660
ctgtgaaagg ctttgcaaag tcacattaag tttgcatgac ctgttatccc tggggcccta    3720
tttcatagag gctggcccta ttagtgattt ccaaaaacaa tatggaagtg cctttgatg    3780
tcttacaata agagaagaag ccaatggaaa tgaaagagat tggcaaaggg gaaggatgat    3840
gccatgtaga tcctgtttga cattttatg gctgtatttg taaacttaaa cacaccagtg    3900
tctgttcttg atgcagttgc tatttaggat gagttaagtg cctggggagt ccctcaaaag    3960
gttaaaggga ttcccatcat tggaatctta tcaccagata ggcaagttta tgaccaaaca    4020
agagagtact ggctttatcc tctaacctca tattttctcc cacttggcaa gtcctttgtg    4080
gcatttattc atcagtcagg gtgtccgatt ggtcctagaa cttccaaagg ctgcttgtca    4140
tagaagccat tgcatctata aagcaacggc tcctgttaaa tggtatctcc tttctgaggc    4200
tcctactaaa agtcatttgt tacctaaact tatgtgctta acaggcaatg cttctcagac    4260
cacaaagcag aaagaagaag aaaagctcct gactaaatca gggctgggct tagacagagt    4320
tgatctgtag aatatcttta aaggagagat gtcaactttc tgcactattc ccagcctctg    4380
ctcctccctg tctaccctct ccctccctc tctccctcca cttcacccca caatcttgaa    4440
aaacttcctt tctcttctgt gaacatcatt ggccagatcc attttcagtg gtctggattt    4500
ctttttattt tcttttcaac ttgaaagaaa ctggacatta ggccactatg tgttgttact    4560
gccactagtg ttcaagtgcc tcttgttttc ccagagattt cctgggtctg ccagaggccc    4620
agacaggctc actcaagctc tttaactgaa aagcaacaag ccactccagg acaaggttca    4680
aaatggttac aacagcctct acctgtcgcc ccagggagaa aggggtagtg atacaagtct    4740
catagccaga gatggttttc cactccttct agatattccc aaaaagaggc tgagacagga    4800
ggttattttc aattttattt tggaattaaa tacttttttc cctttattac tgttgtagtc    4860
cctcacttgg atatacctct gttttcacga tagaaataag ggaggtctag agcttctatt    4920
ccttggccat tgtcaacgga gagctggcca gtcttcaca aacccttgca acattgcctg    4980
aagtttatgg aataagatgt attctcactc ccttgatctc aagggcgtaa ctctggaagc    5040
acagcttgac tacacgtcat ttttaccaat gattttcagg tgacctgggc taagtcattt    5100
aaactgggtc tttataaaag taaaaggcca acatttaatt attttgcaaa gcaacctaag    5160
agctaaagat gtaattttc ttgcaattgt aaatctttg tgtctcctga agacttccct    5220
taaaattagc tctgagtgaa aaatcaaaag agacaaaaga catcttcgaa tccatatttc    5280
aagcctggta gaattggctt ttctagcaga acctttccaa aagtttttata ttgagattca    5340
taacaacacc aagaattgat tttgtagcca acattcattc aatactgtta tatcagagga    5400
gtaggagaga ggaaacattt gacttatctg gaaaagcaaa atgtacttaa gaataagaat    5460
aacatggtcc attcaccttt atgttataga tatgtctttg tgtaaatcat tgttttgag    5520
```

-continued

| | |
|---|---|
| ttttcaaaga atagcccatt gttcattctt gtgctgtaca atgaccactg ttattgttac | 5580 |
| tttgactttt cagagcacac ccttcctctg gtttttgtat atttattgat ggatcaataa | 5640 |
| taatgaggaa agcatgatat gtatattgct gagttgaaag cacttattgg aaaatattaa | 5700 |
| aaggctaaca ttaaaagact aaaggaaaca gaaaaaaaaa aaaaaaaa | 5748 |

<210> SEQ ID NO 270
<211> LENGTH: 1924
<212> TYPE: DNA
<213> ORGANISM: Homo sapiens

<400> SEQUENCE: 270

| | |
|---|---|
| cgtagctatt tcaaggcgcg cgcctcgtgg tggactcacc gctagcccgc agcgctcggc | 60 |
| ttcctggtaa ttcttcacct cttttctcag ctccctgcag catgggtgct gggccctcct | 120 |
| tgctgctcgc cgccctcctg ctgcttctct ccggcgacgg cgccgtgcgc tgcgacacac | 180 |
| ctgccaactg cacctatctt gacctgctgg gcacctgggt cttccaggtg gctccagcg | 240 |
| gttcccagcg cgatgtcaac tgctcggtta tgggaccaca agaaaaaaaa gtagtggtgt | 300 |
| accttcagaa gctggataca gcatatgatg accttggcaa ttctggccat ttcaccatca | 360 |
| tttacaacca aggctttgag attgtgttga atgactacaa gtggtttgcc ttttttaagt | 420 |
| ataaagaaga gggcagcaag gtgaccactt actgcaacga cacaatgact gggtgggtgc | 480 |
| atgatgtgtt gggccggaac tgggcttgtt tcaccgaaaa aaggtggga actgcctctg | 540 |
| agaatgtgta tgtcaacata gcacacctta agaattctca ggaaaagtat tctaataggc | 600 |
| tctacaagta tgatcacaac tttgtgaaag ctatcaatgc cattcagaag tcttggactg | 660 |
| caactacata catggaatat gagactctta ccctgggaga tatgattagg agaagtggtg | 720 |
| gccacagtcg aaaaatccca aggcccaaac ctgcaccact gactgctgaa atacagcaaa | 780 |
| agattttgca tttgccaaca tcttgggact ggagaaatgt tcatggtatc aattttgtca | 840 |
| gtcctgttcg aaaccaagca tcctgtggca gctgctactc atttgcttct atgggtatgc | 900 |
| tagaagcgag aatccgtata ctaaccaaca attctcagac cccaatccta agccctcagg | 960 |
| aggttgtgtc ttgtagccag tatgctcaag gctgtgaagg cggcttccca taccttattg | 1020 |
| caggaaagta cgcccaagat tttgggctgg tggaagaagc ttgcttcccc tacacaggca | 1080 |
| ctgattctcc atgcaaaatg aaggaagact gctttcgtta ttactcctct gagtaccact | 1140 |
| atgtaggagg tttctatgga ggctgcaatg aagccctgat gaagcttgag ttggtccatc | 1200 |
| atgggcccat ggcagttgct tttgaagtat atgatgactt cctccactac aaaaagggga | 1260 |
| tctaccacca cactggtcta agagacccctt tcaaccccctt tgagctgact aatcatgctg | 1320 |
| ttctgcttgt gggctatggc actgactcag cctctgggat ggattactgg attgttaaaa | 1380 |
| acagctgggg caccggctgg ggtgagaatg gctacttccg gatccgcaga ggaactgatg | 1440 |
| agtgtgcaat tgagagcata gcagtggcag ccacaccaat tcctaaattg tagggtatgc | 1500 |
| cttccagtat ttcataatga tctgcatcag ttgtaaaggg gaattggtat attcacagac | 1560 |
| tgtagacttt cagcagcaat ctcagaagct tacaaataga tttccatgaa gatatttgtc | 1620 |
| ttcagaatta aaactgccct taattttaat ataccttttca atcggccact ggccattttt | 1680 |
| ttctaagtat tcaattaagt gggaattttc tggaagatgg tcagctatga agtaatagag | 1740 |
| tttgcttaat catttgtaat tcaaacatgc tatattttt aaaatcaatg tgaaaacata | 1800 |
| gacttatttt taaattgtac caatcacaag aaaataatgg caataattat caaaactttt | 1860 |
| aaaatagatg ctcatatttt taaaataaag ttttaaaaat aactgcaaaa aaaaaaaaaa | 1920 | aaaa                                                                    1924

<210> SEQ ID NO 271
<211> LENGTH: 2344
<212> TYPE: DNA
<213> ORGANISM: Homo sapiens

<400> SEQUENCE: 271

| | | | | | |
|---|---|---|---|---|---|
| cggccgcctc | cgcgtccgcg | tcgtcgtctg | tgctcccggc | gctgacgtgt | ctgggcggtc     60 |
| ggcttccact | ccttcaggcg | tcggcagcca | ctagtcgtgg | cgagaggggc | ggggtggccg    120 |
| gggctggcgc | tccacttggc | ccccgctccc | ggcccgcccc | gccgccgcgg | ccccccggat    180 |
| gagggtatat | attcggagcg | agcgcgggac | gccgatgagt | ggccgcgcgg | aaggagctgg    240 |
| agacggtcgt | agctgcggtc | gcgccgagaa | aggtttacag | gtacatacat | tacacccta     300 |
| tttctacaaa | gcttggctat | tagagcatta | tgaacattaa | tgacctcaaa | ctcacgttgt    360 |
| ccaaagctgg | gcaagagcac | ctactacgtt | tctggaatga | gcttgaagaa | gcccaacagg    420 |
| tagaacttta | tgcagagctc | caggccatga | actttgagga | gctgaacttc | ttttccaaa     480 |
| aggccattga | aggttttaac | cagtcttctc | accaaaagaa | tgtggatgca | cgaatggaac    540 |
| ctgtgcctcg | agaggtatta | ggcagtgcta | caagggatca | agatcagctc | caggcctggg    600 |
| aaagtgaagg | acttttccag | atttctcaga | ataaagtagc | agttcttctt | ctagctggtg    660 |
| ggcaggggac | aagactcggc | gttgcatatc | ctaagggat | gtatgatgtt | ggtttgccat    720 |
| cccgtaagac | acttttcag | attcaagcag | agcgtatcct | gaagctacag | caggttgctg    780 |
| aaaaatatta | tggcaacaaa | tgcattattc | catggtatat | aatgaccagt | ggcagaacaa    840 |
| tggaatctac | aaaggagttc | ttcaccaagc | acaagtactt | tggtttaaaa | aaagagaatg    900 |
| taatcttttt | tcagcaagga | atgctccccg | ccatgagttt | tgatgggaaa | attattttgg    960 |
| aagagaagaa | caaagtttct | atggctccag | atgggaatgg | tggtctttat | cgggcacttg   1020 |
| cagcccagaa | tattgtggag | gatatggagc | aaagaggcat | ttggagcatt | catgtctatt   1080 |
| gtgttgacaa | catattagta | aaagtggcag | acccacggtt | cattggattt | tgcattcaga   1140 |
| aaggagcaga | ctgtggagca | aaggtggtag | agaaaacgaa | ccctacagaa | ccagttggag   1200 |
| tggtttgccg | agtggatgga | gtttaccagg | tggtagaata | tagtgagatt | tccctggcaa   1260 |
| cagctcaaaa | acgaagctca | gacggacgac | tgctgttcaa | tgcggggaac | attgccaacc   1320 |
| atttcttcac | tgtaccattt | ctgagagatg | ttgtcaatgt | ttatgaacct | cagttgcagc   1380 |
| accatgtggc | tcaaaagaag | attccttatg | tggataccca | aggacagtta | attaagccag   1440 |
| acaaacccaa | tggaataaag | atggaaaaat | ttgtctttga | catcttccag | tttgcaaaga   1500 |
| agtttgtggt | atatgaagta | ttgcgagaag | atgagttttc | cccactaaag | aatgctgata   1560 |
| gtcagaatgg | gaaagacaac | cctactactg | caaggcatgc | tttgatgtcc | cttcatcatt   1620 |
| gctgggtcct | caatgcaggg | ggccatttca | tagatgaaaa | tggctctcgc | cttccagcaa   1680 |
| ttccccgctt | gaaggatgcc | aatgatgtac | caatccaatg | tgaaatctct | cctcttatct   1740 |
| cctatgctgg | agaaggatta | gaaagttatg | tggcagataa | agaattccat | gcacctctaa   1800 |
| tcatcgatga | gaatggagtt | catgagctgg | tgaaaaatgg | tatttgaacc | agataccaag   1860 |
| ttttgtttgc | cacgatagga | atagctttta | ttttgatag | accaactgtg | aacctacaag   1920 |
| acgtcttgga | caactgaagt | ttaaatatcc | acagggtttt | attttgcttg | ttgaactctt   1980 |
| agagctattg | caaacttccc | aagatccaga | tgactgaatt | tcagatagca | tttttatgat   2040 |

| | |
|---|---|
| tcccaactca ttgaaggtct tatttatata attttttcca agccaaggag accattggcc | 2100 |
| atccaggaaa tttcgtacag ctgaaatata ggcaggatgt tcaacatcag tttacttgca | 2160 |
| gctggaagca tttgtttttg aagttgtaca tagtaataat atgtcattgt acatgttgaa | 2220 |
| aggtttctat ggtactaaaa gtttgtttta ttttatcaaa cattaagctt ttttaagaaa | 2280 |
| ataattgggc agtgaaataa atgtatcttc ttgtctctgg agtgtcaaaa aaaaaaaaaa | 2340 |
| aaaa | 2344 |

<210> SEQ ID NO 272
<211> LENGTH: 3484
<212> TYPE: DNA
<213> ORGANISM: Homo sapiens

<400> SEQUENCE: 272

| | |
|---|---|
| gtgcgagccc ggccgccggt gagtcggctg gagcgcatct ggtcctccgc gcggaaagcg | 60 |
| ctgcttttgc ctggccgccc tagccgctgg ctcatccaag tggccttcgc cgctctcttg | 120 |
| cgtcccaacc agagcgctgg ccacctcgcc gcccagctca cgccgcgccc gcgctcccag | 180 |
| gctccgggtt ttcttaaatg ttttcttgga gccttaaaga tggagatgac agaaatgact | 240 |
| ggtgtgtcgc tgaaacgtgg ggcactggtt gtcgaagata tgacagtgg agtcccagtt | 300 |
| gaagagacaa aaaacagaa gctgtcggaa tgcagtctaa ccaaaggtca agatgggcta | 360 |
| cagaatgact ttctgtccat cagtgaagac gtgcctcggc ctcctgacac tgtcagtact | 420 |
| gggaaaggtg aaagaattc tgaggctcag ttggaagatg aggaagaaga ggaggaagat | 480 |
| ggactttcag aggagtgcga ggaggaggaa tcagagagtt ttgcagacat gatgaagcat | 540 |
| ggactcactg aggctgacgt aggcatcacc aagtttgtga gttctcatca agggttctcg | 600 |
| ggaatcttaa agaaagata ctccgacttc gttgttcatg aaataggaaa agatggacgg | 660 |
| atcagccatt tgaatgactt gtccattcca gtggatgagg aggacccttc agaagacata | 720 |
| tttacagttt tgacagctga agaaaagcag cgattggaag agctccagct gttcaaaaat | 780 |
| aaggaaacca gtgttgccat tgaggttatc gaggacacca agagaaaag aaccatcatc | 840 |
| catcaggcta tcaaatctct gtttccagga ttagagacaa aaacagagga tagggagggg | 900 |
| aagaaataca ttgtagccta ccacgcagct gggaaaaagg ctttggcaaa tccaagaaaa | 960 |
| cattcttggc caaatctag gggaagttac tgccacttcg tactatataa ggaaaacaaa | 1020 |
| gacaccatgg atgctattaa tgtactctcc aaatacttaa gagtcaagcc aaatatattc | 1080 |
| tcctacatgg gaaccaaaga taaagggct ataacagttc aagaaattgc tgttctcaaa | 1140 |
| ataactgcac aaagacttgc ccacctgaat aagtgcttga tgaactttaa gctagggaat | 1200 |
| ttcagctatc aaaaaaccc actgaaattg ggagagcttc aaggaaacca cttcactgtt | 1260 |
| gttctcagaa atataacagg aactgatgac caagtacagc aagctatgaa ctctctcaag | 1320 |
| gagattggat ttattaacta ctatggaatg caaagatttg gaaccacagc tgtccctacg | 1380 |
| tatcaggttg gaagagctat actacaaaat tcctggacag aagtcatgga tttaatattg | 1440 |
| aaacccgct ctggagctga aaagggctac ttggttaaat gcagagaaga atgggcaaag | 1500 |
| accaaagacc caactgctgc cctcagaaaa ctacctgtca aaggtgtgt ggaagggcag | 1560 |
| ctgcttcgag gactttcaaa atatggaatg aagaatatag tctctgcatt tggcataata | 1620 |
| cccagaaata tcgcttaat gtatattcat agctaccaaa gctatgtgtg aataacatg | 1680 |
| gtaagcaaga ggatagaaga ctatggacta aaacctgttc caggggacct cgttctcaaa | 1740 |
| ggagccacag ccacctatat tgaggaagat gatgttaata attactctat ccatgatgtg | 1800 |

| | |
|---|---|
| gtaatgccct tgcctggttt cgatgttatc tacccaaagc ataaaattca agaagcctac | 1860 |
| agggaaatgc tcacagctga caatcttgat attgacaaca tgagacacaa aattcgagat | 1920 |
| tattccttgt caggggccta ccgaaagatc attattcgtc ctcagaatgt tagctgggaa | 1980 |
| gtcgttgcat atgatgatcc caaaattcca cttttcaaca cagatgtgga caacctagaa | 2040 |
| gggaagacac caccagtttt tgcttctgaa ggcaaataca gggctctgaa atggattttt | 2100 |
| tctctacccc cttctactta cgccaccatg gccattcgag aagtgctaaa aatggatacc | 2160 |
| agtatcaaga accagacgca gctgaataca acctggcttc gctgagcagt accttgtcca | 2220 |
| cagattagaa aacgtacaca agtgtttgct tcctggctcc ctgtgcattt ttgtcttagt | 2280 |
| tcagactcat atatggattt caaatctttg taataaaaat tatttgtatt tttaagtttt | 2340 |
| tattagctta aagaaataat ttgcaatatt tgtacatgta cacaaatcct gaggttctta | 2400 |
| attttagctc agaatataaa ttagtcaaaa tacacttcag gtgcttaaat cagagtaaaa | 2460 |
| tgtcagcttt acaataataa aaaaaggact ttggtttaaa gtagcaggtt taggttttgc | 2520 |
| tacattctca aaagacagca ggagtatttg acacatctgt gatggagtat acaacaatgc | 2580 |
| attttaagag caaatgcaac aaaacaaatc tggactatgg ataaataatt tgagagctgc | 2640 |
| cacccacaaa tataaataca gtactcatgc tgactgaaat aataagacat ctacaaattt | 2700 |
| ataaacaaaa agtgattgtc attatcctgc ttatgtacta gattcaggca agcattatag | 2760 |
| acttttggt tgcggtggct tttgcattta tattatcaat gccttgcagg aacgttgcat | 2820 |
| tgataggccc atttattttt tttatttttt ttttcgagac aggatctcac tctgtagcac | 2880 |
| aggctggatt gcagtgcaat cctgcaattc tcaatcttgc actgcagcct cgacctccca | 2940 |
| ggctccagtg actctcccac ctcagcctcc taagtagctg ggagtacagg cgcgcaccac | 3000 |
| cacgcctagc tgattttttgt attttttttgt agagacgggg gtttggccat gttgccgagg | 3060 |
| ctaactcctg ggattacagg catgagctgt gctggccggg tttttttttc ttgatgtaaa | 3120 |
| cgtgtacagc tgttttatta gttaaggtct aattttttact ctaggtgcct tttatgttca | 3180 |
| gaactctttc cactggactg gtatttgctc aaaaataaat aatggtagag aagaaaacta | 3240 |
| taaaaatgga caaggctttc ttctatcagt agcgtttacc ctttgtcacc agtggctttg | 3300 |
| gtatttccat gtctggcatt gcataaactt ctctggtgtg aaaggataaa tatgcctttc | 3360 |
| taaagttgta tatcaaaatt gtatcaattt ttattttcta tgatttctag aaacaaatgt | 3420 |
| aataaatatt tttaaaatct cctttctact ggttatgtaa ataaatcaaa taaatatatc | 3480 |
| aaaa | 3484 |

<210> SEQ ID NO 273
<211> LENGTH: 3293
<212> TYPE: DNA
<213> ORGANISM: Homo sapiens

<400> SEQUENCE: 273

| | |
|---|---|
| cttttgctct cagatgctgc cagggtccct gaagagggaa gacacgcgga aacaggcttg | 60 |
| cacccagaca cgacaccatg catctcctcg gcccctggct cctgctcctg gttctagaat | 120 |
| acttggcttt ctctgactca agtaaatggg tttttgagca ccctgaaacc ctctacgcct | 180 |
| gggaggggc ctgcgtctgg atcccctgca cctacagagc cctagatggt gacctggaaa | 240 |
| gcttcatcct gttccacaat cctgagtata acaagaacac ctcgaagttt gatgggacaa | 300 |
| gactctatga aagcacaaag gatgggaagg ttccttctga gcagaaaagg gtgcaattcc | 360 |

```
tgggagacaa gaataagaac tgcacactga gtatccaccc ggtgcacctc aatgacagtg    420
gtcagctggg gctgaggatg gagtccaaga ctgagaaatg gatggaacga atacacctca    480
atgtctctga aaggccttt tccacctcata tccagctccc tccagaaatt caagagtccc    540
aggaagtcac tctgacctgc ttgctgaatt tctcctgcta tgggtatccg atccaattgc    600
agtggctcct agagggggtt ccaatgaggc aggctgctgt cacctcgacc tccttgacca    660
tcaagtctgt cttcacccgg agcgagctca agttctcccc acagtggagt caccatggga    720
agattgtgac ctgccagctt caggatgcag atgggaagtt cctctccaat gacacggtgc    780
agctgaacgt gaagcacacc ccgaagttgg agatcaaggt cactcccagt gatgccatag    840
tgagggaggg ggactctgtg accatgacct gcgaggtcag cagcagcaac ccggagtaca    900
cgacggtatc ctggctcaag gatgggacct cgctgaagaa gcagaataca ttcacgctaa    960
acctgcgcga agtgaccaag gaccagagtg ggaagtactg ctgtcaggtc tccaatgacg   1020
tgggcccggg aagtcggaa gaagtgttcc tgcaagtgca gtatgccccg gaaccttcca   1080
cggttcagat cctccactca ccggctgtgg agggaagtca agtcgagttt ctttgcatgt   1140
cactggccaa tcctcttcca acaaattaca cgtggtacca caatgggaaa gaaatgcagg   1200
gaaggacaga ggagaaagtc cacatcccaa agatcctccc ctggcacgct gggacttatt   1260
cctgtgtggc agaaaacatt cttggtactg gacagagggg cccggagct gagctggatg   1320 tccagtatcc tccaagaag gtgaccacag tgattcaaaa ccccatgccg attcgagaag   1380
gagacacagt gaccctttcc tgtaactaca attccagtaa ccccagtgtt acccggtatg   1440 aatgaaacc ccatggcgcc tgggaggagc atcgcttgg ggtgctgaag atccaaaacg   1500
ttggctggga caacacaacc atcgcctgcg cagcttgtaa tagttggtgc tcgtgggcct   1560
cccctgtcgc cctgaatgtc cagtatgccc cccgagacgt gagggtccgg aaaatcaagc   1620 cccttttccga gattcactct ggaaactcgg tcagcctcca atgtgacttc tcaagcagcc   1680
accccaaaga agtccagttc ttctgggaga aaaatggcag gcttctgggg aaagaaagcc   1740
agctgaattt tgactccatc tccccagaag atgctgggag ttacagctgc tgggtgaaca   1800
actccatagg acagacagcg tccaaggcct ggacacttga agtgctgtat gcacccagga   1860
ggctgcgtgt gtccatgagc ccgggggacc aagtgatgga ggggaagagt gcaaccctga   1920
cctgtgagag cgacgccaac cctcccgtct cccactacac ctggtttgac tggaataacc   1980
aaagcctccc ctaccacagc cagaagctga gattggagcc ggtgaaggtc cagcactcgg   2040
gtgcctactg gtgccagggg accaacagtg tgggcaaggg ccgttcgcct ctcagcaccc   2100
tcaccgtcta ctatagcccg gagaccatcg gcaggcgagt ggctgtggga ctcgggtcct   2160
gcctcgccat cctcatcctg gcaatctgtg gctcaagct ccagcgacgt tggaagagga   2220
cacagagcca gcagggcctt caggagaatt ccagcggcca gagcttcttt gtgaggaata   2280
aaaaggttag aagggccccc ctctctgaag gcccccactc cctgggatgc tacaatccaa   2340
tgatggaaga tggcattagc tacaccaccc tgcgcttttcc cgagatgaac ataccacgaa   2400
ctggagatgc agagtcctca gagatgcaga gacctccccc ggactgcgat gacacggtca   2460
cttattcagc attgcacaag cgccaagtgg gcgactatga aacgtcatt ccagattttc   2520 cagaagatga ggggattcat tactcagagc tgatccagtt tgggtcggg gagcggcctc   2580 aggcacaaga aaatgtggac tatgtgatcc tcaaacattg acactggatg ggctgcagca   2640
gaggcactgg gggcagcggg ggccagggaa gtccccgagt tccccagac accgccacat   2700 ggcttcctcc tgcgcgcatg tgcgcacaca cacacacaca cgcacacaca cacacacaca   2760
```

```
ctcactgcgg agaaccttgt gcctggctca gagccagtct ttttggtgag ggtaacccca    2820
aacctccaaa actcctgccc ctgttctctt ccactctcct tgctacccag aaatccatct    2880
aaatacctgc cctgacatgc acacctcccc ctgcccccac cacggccact ggccatctcc    2940
accccagct gcttgtgtcc ctcctgggat ctgctcgtca tcattttcc ttcccttctc    3000
catctctctg gccctctacc cctgatctga catccccact cacgaatatt atgcccagtt    3060
tctgcctctg agggaaagcc cagaaaagga cagaaacgaa gtagaaaggg gcccagtcct    3120
ggcctggctt ctcctttgga agtgaggcat tgcacgggga gacgtacgta tcagcggccc    3180
cttgactctg gggactccgg gtttgagatg gacacactgg tgtggattaa cctgccaggg    3240
agacagagct cacaataaaa atggctcaga tgccacttca aagaaaaaaa aaa          3293

<210> SEQ ID NO 274
<211> LENGTH: 1458
<212> TYPE: DNA
<213> ORGANISM: Homo sapiens

<400> SEQUENCE: 274
gaggccagag tgccatcgaa ggtaattata gagacagtaa aatccttta ctctgggaaa      60
aataaaatgc tgggtgtctc acaaaatttc agaacctgat ttcaaacgga tcataacaaa    120
gaggagatca aatttagcat ggtggactgc tcgacaggat atatttgtca atggaatgtt    180
tccacatatt ataccaccaa catgagaaaa aaatgatcat tgtttatttg aagcttgaaa    240
aatgagcagg cggaattgtt ggatttgtaa gatgtgcaga gatgaatcta agaggccccc    300
ttcaaacctt actttggagg aagtattaca gtgggcccag tcttttgaaa atttaatggc    360
tacaaaatat ggtccagtag tctatgcagc atatttaaaa atggagcaca gtgacgagaa    420
tattcaattc tggatggcat gtgaaaccta aagaaaatt gcctcacggt ggagcagaat    480
ttctagggca aagaagcttt ataagattta catccagcca cagtccccta gagagattaa    540
cattgacagt tcgacaagag agactatcat caggaacatt caggaaccca ctgaaacatg    600
ttttgaagaa gctcagaaaa tagtctatat gcatatggaa agggattcct accccagatt    660
tctaaagtca gaaatgtacc aaaaactttt gaaaactatg cagtccaaca acagtttctg    720
actacaactc aaaagtttaa atagaaaaca gtatattgaa agtggtgggt ttgatctttt    780
tatttagaaa cccacaaaat cagaaacaca gtacaaataa aacagaaatc aaactataag    840
ttgactttta gttcctaaaa agaaacatat ttcaaaagca atggaatcta gaattcttat    900
aacatgaata acaaaatgta cagcaagcct atgtagttca attaatatat aaggaaaagg    960
aaggtctttc ttcatgatac aagcattata aagttttac tgtagtagtc aattaatgga   1020
tatttccttg ttaataaaat tttgtgtcat aatttacaaa ttagttcttt aaaaattgtt   1080
gttatatgaa ttgtgtttct agcatgaatg ttctatagag tactctaaat aacttgaatt   1140
tatagacaaa tgctactcac agtacaatca attgtattat accatgagaa atcaaaaag   1200
gtgttcttca gagacatttt atctataaaa ttttcctact attatgttca ttaacaaact   1260
tctttatcac atgtatcttc tacatgtaaa acatttctga tgatttttta acaaaaata    1320
tatgaatttc ttcatttgct cttgcatcta cattgctata aggatataaa atgtggttc    1380
tatattttga gatgtttttt ccttacaatg tgaactcatc gtgatcttgg aaatcaataa   1440
agtcaaatat caactaaa                                                   1458
```